(12) United States Patent
Tabar et al.

(10) Patent No.: US 10,526,341 B2
(45) Date of Patent: Jan. 7, 2020

(54) THIENOPYRIMIDINES AND USES THEREOF

(71) Applicant: Memorial Sloan-Kettering Cancer Center, New York, NY (US)

(72) Inventors: Viviane Tabar, New York, NY (US); Kosuke Funato, Astoria, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 15/527,982

(22) PCT Filed: Nov. 19, 2015

(86) PCT No.: PCT/US2015/061594
§ 371 (c)(1),
(2) Date: May 18, 2017

(87) PCT Pub. No.: WO2016/081732
PCT Pub. Date: May 26, 2016

(65) Prior Publication Data
US 2017/0355711 A1 Dec. 14, 2017

Related U.S. Application Data

(60) Provisional application No. 62/081,984, filed on Nov. 19, 2014.

(51) Int. Cl.
| C07D 495/04 | (2006.01) |
| A61K 31/519 | (2006.01) |
| A61P 35/00 | (2006.01) |
| C12N 5/0797 | (2010.01) |
| G01N 33/50 | (2006.01) |

(52) U.S. Cl.
CPC .......... C07D 495/04 (2013.01); A61K 31/519 (2013.01); A61P 35/00 (2018.01); C12N 5/0623 (2013.01); G01N 33/5011 (2013.01); *C12N 2503/02* (2013.01); *C12N 2510/00* (2013.01)

(58) Field of Classification Search
CPC ...... C07D 495/04; A61K 31/519; A61P 35/00
USPC ...................................... 544/278; 514/260.1
See application file for complete search history.

(56) References Cited

U.S. PATENT DOCUMENTS

| 5,654,183 | A |  | 8/1997 | Anderson et al. |
| 8,993,552 | B2 | * | 3/2015 | Grembecka .......... A61K 31/519 514/183 |
| 9,216,993 | B2 | * | 12/2015 | Grembecka .......... C07D 495/04 |
| 9,505,782 | B2 | * | 11/2016 | Grembecka .......... C07D 495/04 |
| 2009/0181917 | A1 |  | 7/2009 | Hua et al. |
| 2011/0065690 | A1 | * | 3/2011 | Grembecka .......... A61K 31/519 514/218 |
| 2014/0275070 | A1 |  | 9/2014 | Grembecka et al. |

FOREIGN PATENT DOCUMENTS

| WO | WO 2007/139970 A2 | 12/2007 |
| WO | WO 2008/070303 A2 | 6/2008 |
| WO | WO 2011/029054 A1 | 3/2011 |
| WO | WO 2014/053581 A1 | 4/2014 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cancer Drug Design and Discovery Neidle, Stephen, ed. (Elsevier/Academic Press, 2008) pp. 427-431.*
International Search Report and Written Opinion for PCT/US2015/061594, dated Jan. 22, 2016.
International Preliminary Report on Patentability for PCT/US2015/061594, dated Jun. 1, 2017.
Caslini et al., Interaction of MLL amino terminal sequences with menin is required for transformation. Cancer Res. Aug. 1, 2007;67(15):7275-83.
Chan et al., The histone H3.3K27M mutation in pediatric glioma reprograms H3K27 methylation and gene expression. Genes Dev. May 1, 2013;27(9):985-90. doi: 10.1101/gad.217778.113. Epub Apr. 19, 2013.
Cierpicki et al., Challenges and opportunities in targeting the menin-MLL interaction. Future Med Chem. Mar. 2014;6(4):447-62. doi: 10.4155/fmc.13.214.
Grembecka et al., Menin-MLL inhibitors reverse oncogenic activity of MLL fusion proteins in leukemia. Nat Chem Biol. Jan. 29, 2012; 8(3): 277-284.
Grembecka et al., Molecular basis of the mixed lineage leukemia-menin interaction:implications for targeting mixed lineage leukemias. J Biol Chem. Dec. 24, 2010; 285(52): 40690-40698.
He et al., High-Affinity Small-Molecule Inhibitors of the Menin-Mixed Lineage Leukemia (MLL) Interaction Closely Mimic acNatural Protein-Protein Interaction. J Med Chem. Feb. 27, 2014; 57(4): 1543-1556.
Khuong-Quang et al., K27M mutation in histone H3.3 defines clinically and biologically distinct subgroups of pediatlic diffuse intlinsic pontine gliomas. Acta Neuropathol. Sep. 2012;124(3):439-47. doi: 10.1007/s00401-012-0998-0. Epub Jun. 3, 2012.
Lewis et al., Inhibition of PRC2 activity by a gain-of-function H3 mutation found in pediatric glioblastoma. Science. May 17, 2013;340(6134):857-61. doi: 10.1126/science.1232245. Epub Mar. 28, 2013.

(Continued)

*Primary Examiner* — Venkataraman Balasubramanian
(74) *Attorney, Agent, or Firm* — Wolf, Greenfield & Sacks, P.C.

(57) ABSTRACT

Described herein are thienopyrimidine compounds of Formula (I), and pharmaceutically acceptable salts, and pharmaceutical compositions thereof. Also provided are methods and kits involving the thienopyrimidine compounds or compositions for treating or preventing proliferative diseases such as cancers (e.g., brain tumors such as DIPGs) in a subject. The invention further provides an embryonic stem cell-based tumor cell model, which can be used for drug screening and disease target identification.

17 Claims, 116 Drawing Sheets

(56) References Cited

OTHER PUBLICATIONS

Lewis et al., Poisoning the "histone code" in pediatric gliomagenesis. Cell Cycle. Oct. 15, 2013;12(20):3241-2. doi: 10.4161/cc.26356. Epub Sep. 13, 2013.

Li et al., Discovery of two aminoglycoside antibiotics as inhibitors targeting the menin-mixed lineage leukaemia interface. Bioorg Med Chem Lett. May 1, 2014;24(9):2090-3. doi: 10.1016/j.bmcl.2014.03.055. Epub Mar. 26, 2014.

McCarthy, Leukaemia: Targeting menin. Nat Rev Cancer. Feb. 16, 2012;12(3):154. doi: 10.1038/nrc3231.

Milne, et al., Menin and MLL cooperatively regulate expression of cyclindependent kinase inhibitors. Proc Natl Acad Sci U S A. Jan. 18, 2005;102(3):749-54. Epub Jan. 7, 2005.

Murai et al., Crystal Structure of Menin Reveals Binding Site for Mixed Lineage Leukemia (MLL) Protein. J Biol Chem. Sep. 9, 2011;286(36):31742-8. doi: 10.1074/jbc.M111.258186. Epub Jul. 13, 2011.

Schwartzentruber et al., Driver mutations in histone H3.3 and chromatin remodelling genes in paediatlic glioblastoma. Nature. Jan. 29, 2012;482(7384):226-31. doi: 10.1038/nature10833.

Shi et al., Stmctural insights into inhibition of the bivalent menin-MLL interaction by small molecules in leukemia. Blood. Nov. 29, 2012;120(23):4461-9. doi: 10.1182/blood-2012-05-429274. Epub Aug. 30, 2012.

Sturm et al., Hotspot Mutations in H3F3A and IDH1 Define Distinct Epigenetic and Biological Subgroups of Glioblastoma. Cancer Cell. Oct. 16, 2012;22(4):425-37. doi: 10.1016/j.ccr.2012.08.024.

Thiel et al., The trithorax protein partner menin acts in tandem with EZH2 to suppress C/EBPa and differentiation in MLL-AF9 leukemia. Haematologica. Jun. 2013;98(6):918-27. doi: 10.3324/haematol.2012.074195. Epub Jan. 24, 2013.

Wu et al., Menin represses tumorigenesis via repressing cell proliferation. Am J Cancer Res. 2011;1(6):726-39. Epub May 16, 2011.

Wu et al., Somatic histone H3 alterations in pediatric diffuse intlinsic pontine gliomas and nonbrainstem glioblastomas. Nat Genet. Jan. 29, 2012;44(3):251-3. doi: 10.1038/ng.1102.

Yokoyama et al., The menin tumor suppressor protein is an essential oncogenic cofactor for MLL-associated leukemogenesis. Cell. Oct. 21, 2005;123(2):207-18.

Zhang et al., Menin expression is regulated by transforming growth factor beta signaling in leukemia cells. Chinese Medical Journal 2011;124(10):1556-62.

\* cited by examiner

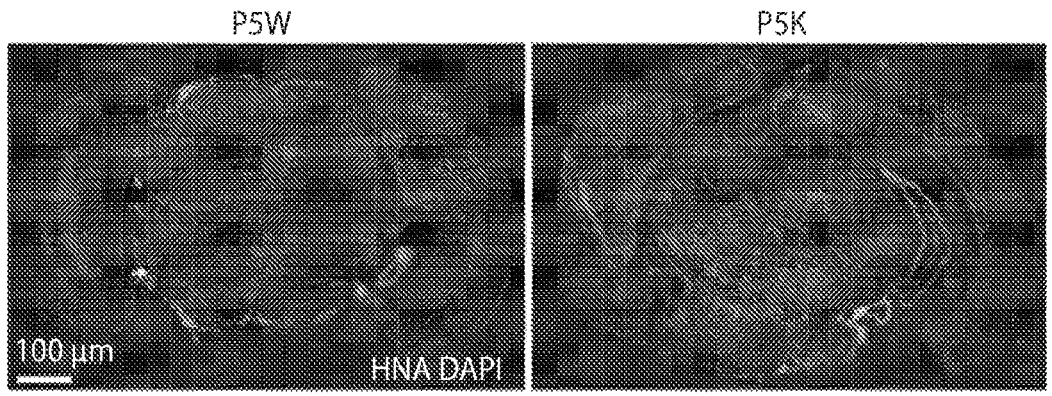
Fig. 2I
|  | # of cells injected | Tumor formation |
|---|---|---|
| Mock | $1.0 \times 10^5$ | 0/4 |
| P5W | $1.0 \times 10^5$ | 1/8 |
| P5K | $1.0 \times 10^5$ | 8/15 |
Fig. 2J
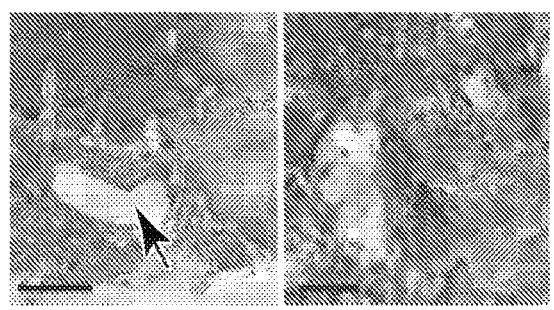
Fig. 2K

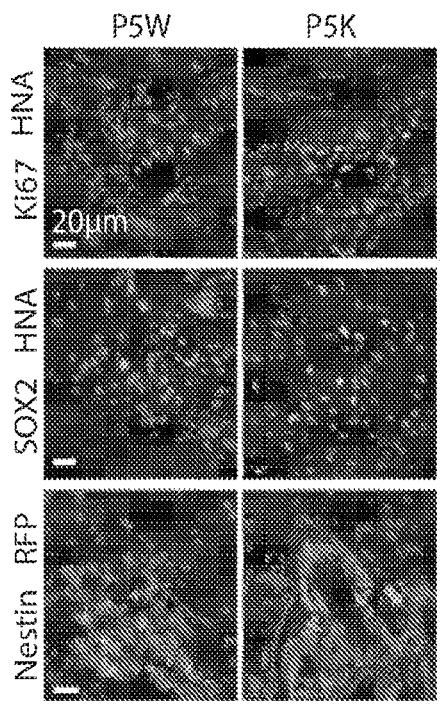
Fig. 2L
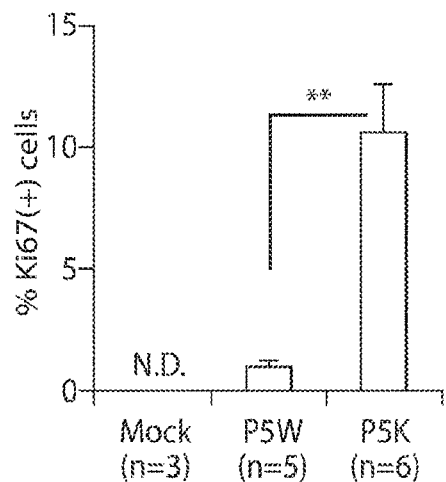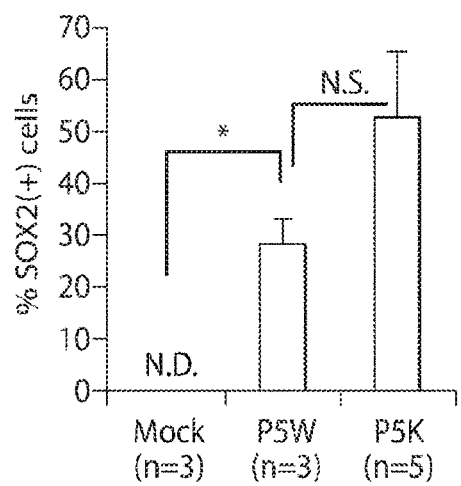
Fig. 2M                Fig. 2N

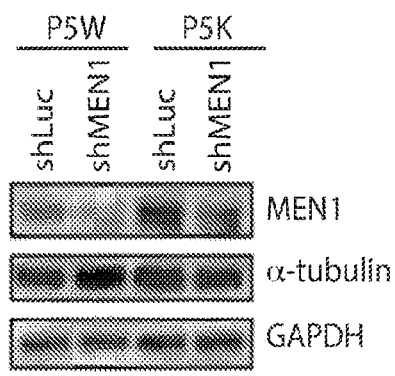
Fig. 4G
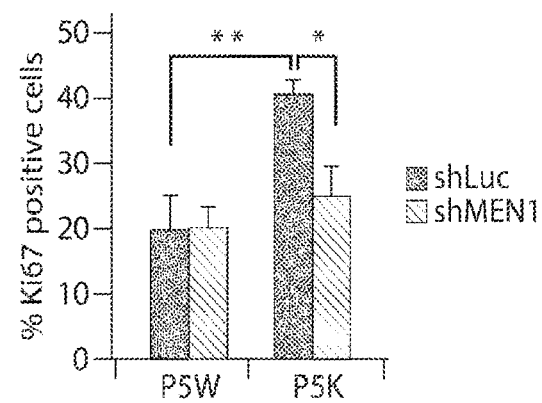
Fig. 4H
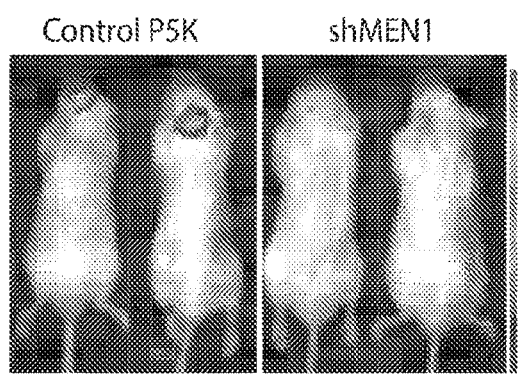
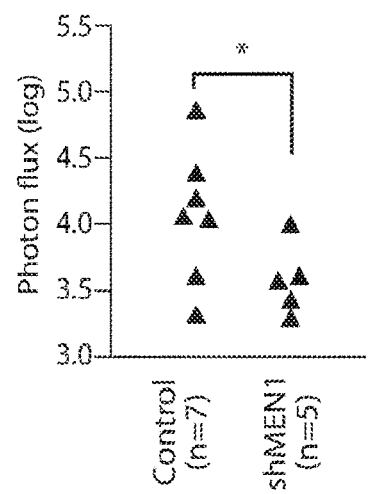
Fig. 4I

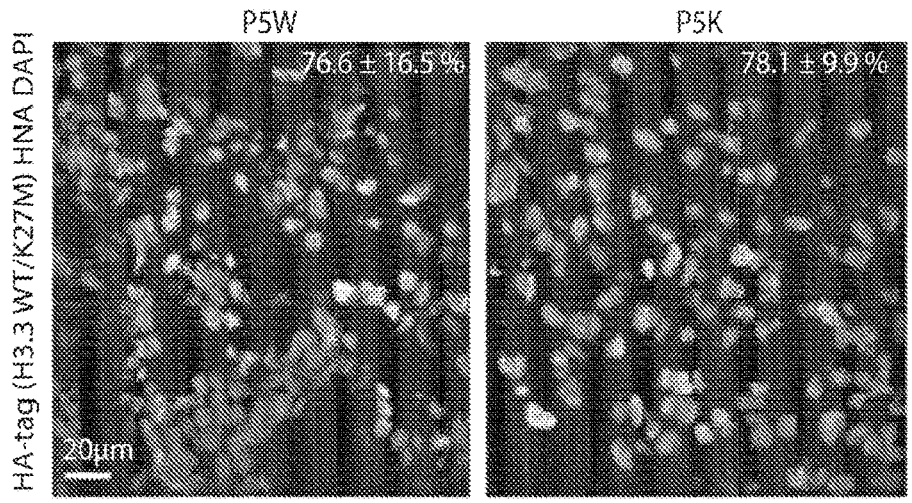
Fig. 10A
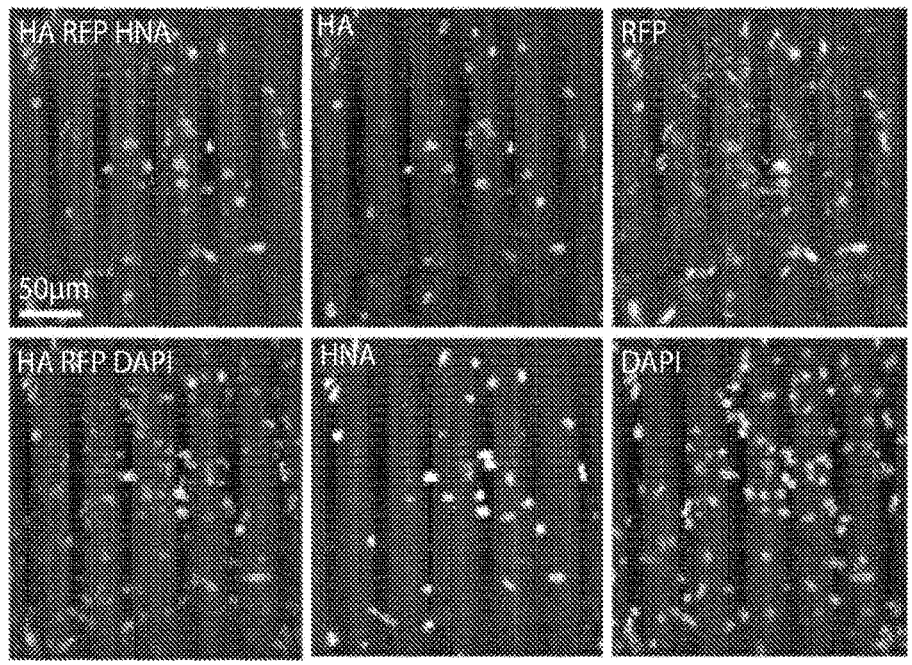
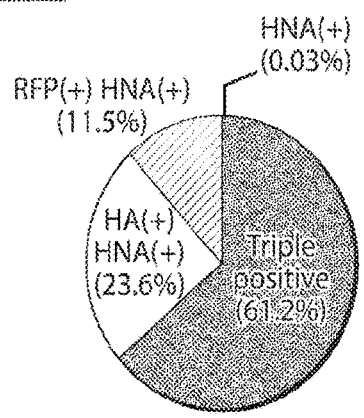
Fig. 10B

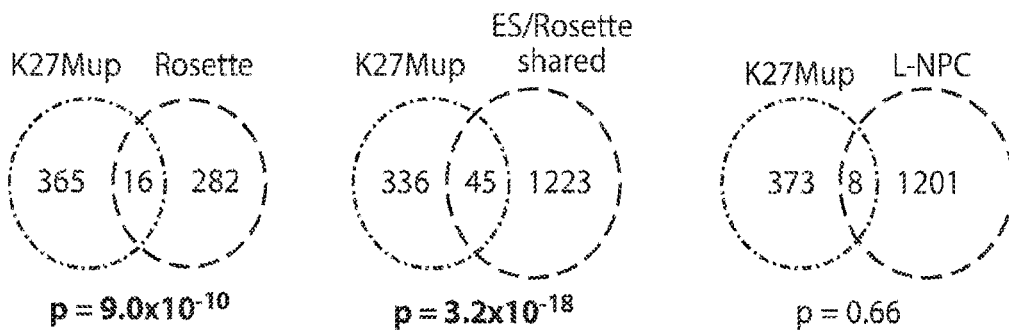
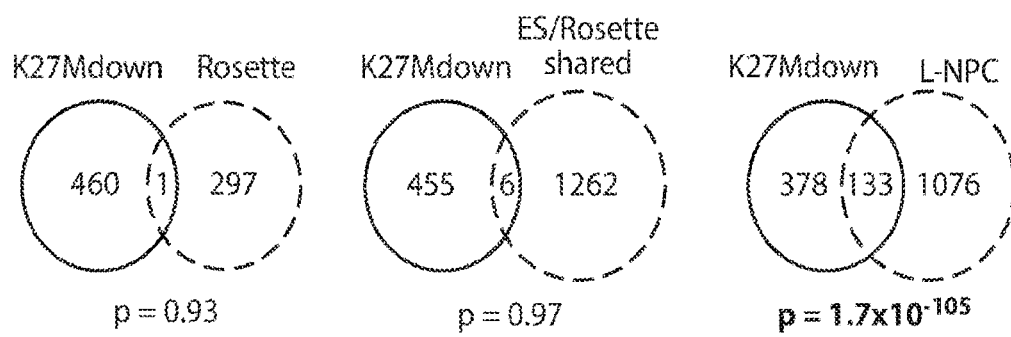
Fig. 11A
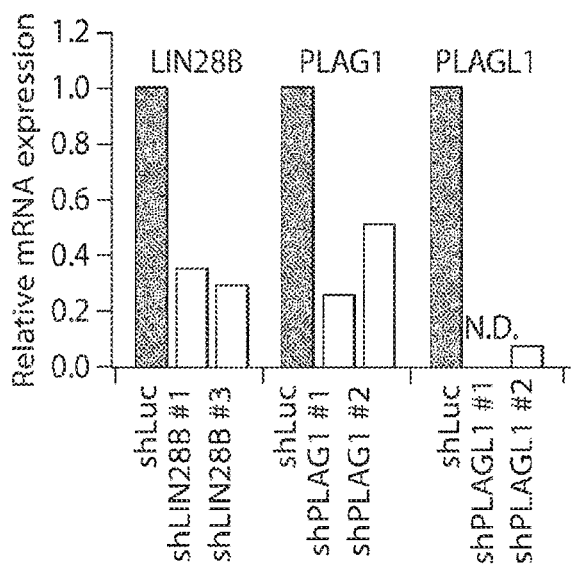
Fig. 11B
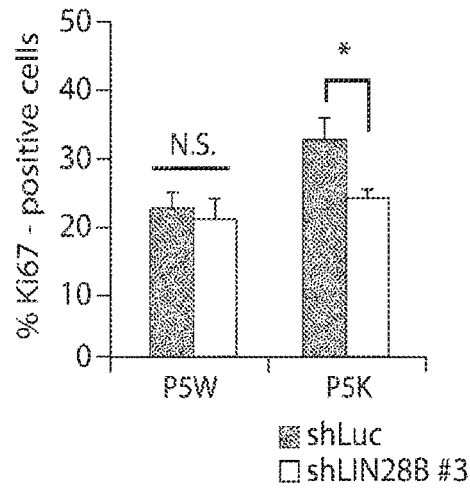
Fig. 11C

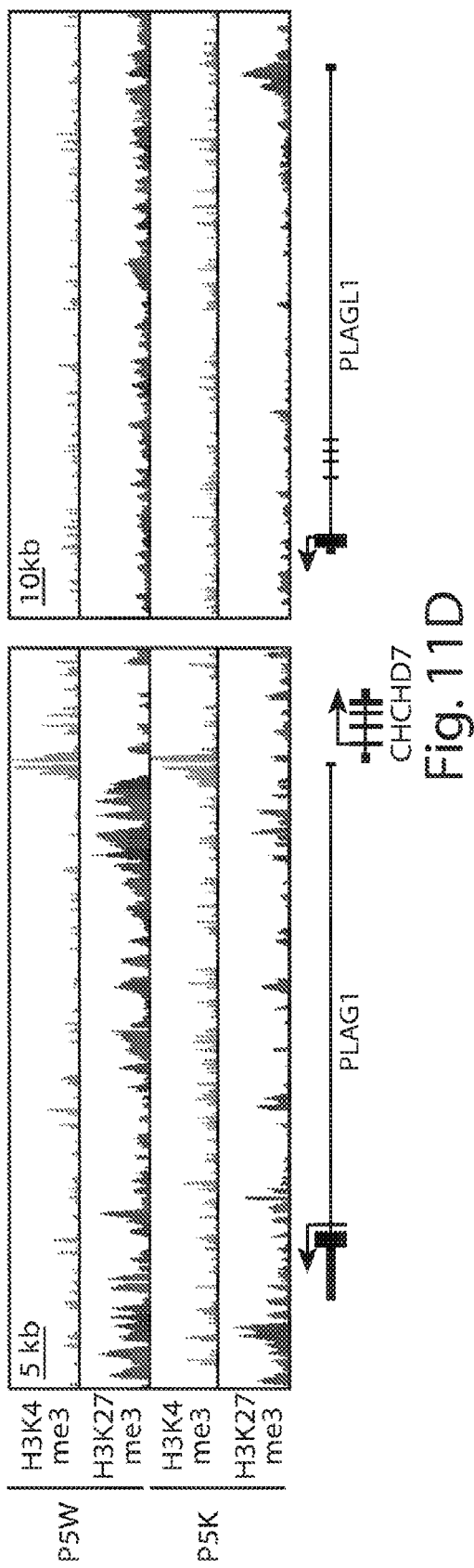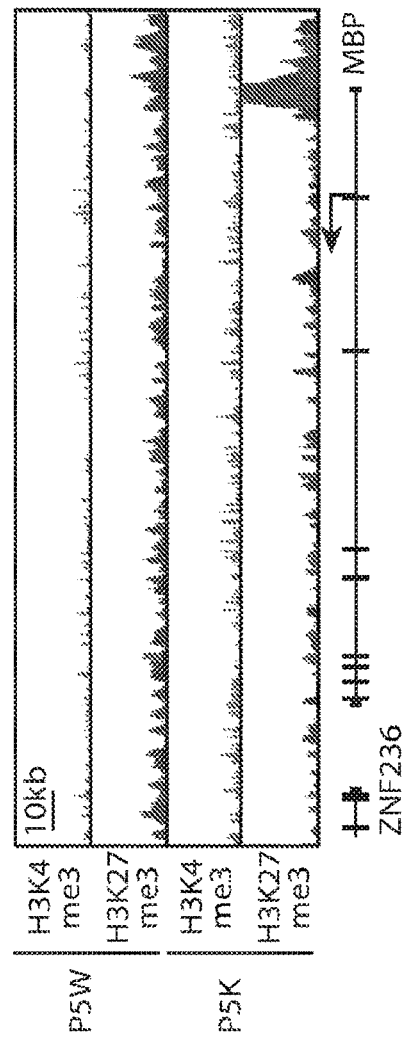
Fig. 11D
Fig. 11E

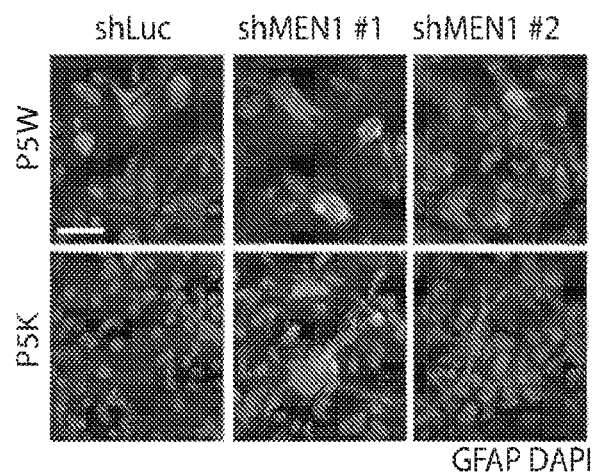
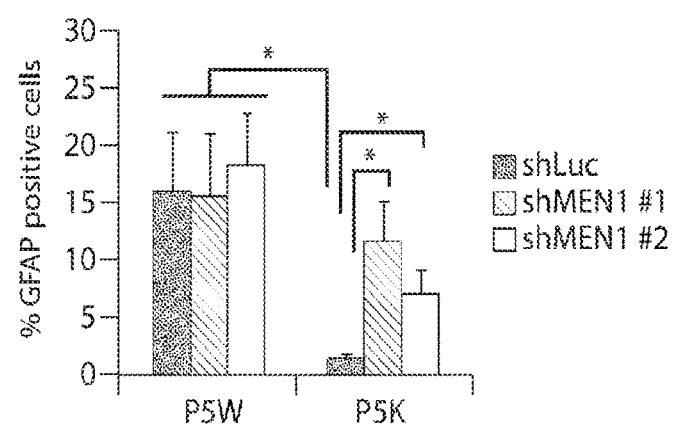
Fig. 12E

| Rank | Gene ID (Affymetrix) | Gene Description | Score (Signal-to-noise ratio) |
|---|---|---|---|
| 1 | 232231_at | runt-related transcription factor 2, RUNX2 | 9.73 |
| 2 | 205229_s_at | coagulation factor C homolog, cochlin (Limulus polyphemus), COCH | 8.15 |
| 3 | 1554242_a_at | coagulation factor C homolog, cochlin (Limulus polyphemus), COCH | 7.49 |
| 4 | 222392_x_at | PERP, TP53 apoptosis effector, PERP | 6.70 |
| 5 | 218499_at | serine/threonine protein kinase MST4, MST4 | 6.63 |
| 6 | 243356_at | | 6.52 |
| 7 | 222701_s_at | coiled-coil-helix-coiled-coil-helix domain containing 7, CHCHD7 | 6.39 |
| 8 | 206023_at | neuromedin U, NMU | 5.87 |
| 9 | 217744_s_at | PERP, TP53 apoptosis effector, PERP | 5.74 |
| 10 | 204984_at | glypican 4, GPC4 | 5.73 |
| 11 | 205372_at | pleiomorphic adenoma gene 1, PLAG1 | 5.72 |
| 12 | 223038_s_at | family with sequence similarity 60, member A, FAM60A | 5.66 |
| 13 | 219523_s_at | odz, odd Oz/ten-m homolog 3 (Drosophila), ODZ3 | 5.22 |
| 14 | 218872_at | tescalcin, TESC | 4.95 |
| 15 | 229349_at | lin-28 homolog B (C. elegans), LIN28B | 4.87 |
| 16 | 229385_s_at | placenta-specific 2 (non-protein coding), PLAC2 | 4.65 |
| 17 | 220147_s_at | family with sequence similarity 60, member A, FAM60A | 4.60 |
| 18 | 233814_at | ephrin-A5, EFNA5 | 4.51 |
| 19 | 228107_at | hypothetical protein LOC100127983, LOC100127983 | 4.41 |
| 20 | 205190_at | plastin 1, PLS1 | 4.40 |
| 21 | 205201_at | GLI family zinc finger 3, GLI3 | 4.36 |
| 22 | 1559266_s_at | chromosome 10 open reading frame 140, C10orf140 | 4.26 |
| 23 | 209763_at | chordin-like 1, CHRDL1 | 4.25 |
| 24 | 227307_at | tetraspanin 18, TSPAN18 | 4.21 |
| 25 | 1559360_at | | 4.16 |
| 26 | 227623_at | calcium channel, voltage-dependent, alpha 2/delta subunit 1, CACNA2D1 | 4.15 |
| 27 | 238865_at | poly(A) binding protein, cytoplasmic 4-like, PABPC4L | 4.13 |
| 28 | 227955_s_at | ephrin-A5, EFNA5 | 4.11 |
| 29 | 207943_x_at | pleiomorphic adenoma gene-like 1, PLAGL1 | 4.10 |
| 30 | 206953_s_at | latrophilin 2, LPHN2 | 4.06 |
| 31 | 231310_at | | 4.02 |
| 32 | 214785_at | vacuolar protein sorting 13 homolog A (S. cerevisiae), VPS13A | 3.98 |
| 33 | 222900_at | nuclear receptor interacting protein 3, NRIP3 | 3.97 |
| 34 | 233257_at | | 3.94 |
| 35 | 217809_at | basic leucine zipper and W2 domains 2, BZW2 | 3.93 |
| 36 | 214036_at | ephrin-A5, EFNA5 | 3.92 |
| 37 | 209212_s_at | Kruppel-like factor 5 (intestinal), KLF5 | 3.92 |

Fig. 13

| 38 | 207002_s_at | pleiomorphic adenoma gene-like 1, PLAGL1 | 3.83 |
|---|---|---|---|
| 39 | 209318_x_at | pleiomorphic adenoma gene-like 1, PLAGL1 | 3.83 |
| 40 | 1560652_at | | 3.80 |
| 41 | 1569652_at | mixed-lineage leukemia (trithorax homolog); translocated to, 3, MLLT3 | 3.79 |
| 42 | 219778_at | zinc finger protein, multitype 2, ZFPM2 | 3.79 |
| 43 | 221760_at | mannosidase, alpha, class 1A, member 1, MAN1A1 | 3.78 |
| 44 | 233002_at | protein phosphatase 4, regulatory subunit 4, PPP4R4 | 3.78 |
| 45 | 226117_at | TRAF-interacting protein with forkhead-associated domain, TIFA | 3.76 |
| 46 | 220987_s_at | chromosome 11 open reading frame 17 /// NUAK2 | 3.72 |
| 47 | 225177_at | RAB11 family interacting protein 1 (class I), RAB11FIP1 | 3.71 |
| 48 | 204983_s_at | glypican 4, GPC4 | 3.68 |
| 49 | 225051_at | erythrocyte membrane protein band 4.1 (elliptocytosis 1, RH-linked), EPB41 | 3.68 |
| 50 | 227415_at | hypothetical protein LOC283508, LOC283508 | 3.67 |

Fig. 13 (Continued)

| Rank | Gene ID (Affymetrix) | Gene Description | Score (Signal-to-noise ratio) |
|---|---|---|---|
| 1 | 235562_at | chromosome 3 open reading frame 70, C3orf70 | -7.45276 |
| 2 | 242447_at | chromosome 3 open reading frame 70, C3orf70 | -7.12643 |
| 3 | 227055_at | methyltransferase like 7B, METTL7B | -6.85883 |
| 4 | 240242_at |  | -6.79264 |
| 5 | 206306_at | ryanodine receptor 3, RYR3 | -6.59394 |
| 6 | 207981_s_at | estrogen-related receptor gamma, ESRRG | -6.33449 |
| 7 | 204916_at | receptor (G protein-coupled) activity modifying protein 1, RAMP1 | -6.06627 |
| 8 | 203908_at | solute carrier family 4, sodium bicarbonate cotransporter, member 4, SLC4A4 | -6.05743 |
| 9 | 229382_at | chromosome 1 open reading frame 183, C1orf183 | -6.01959 |
| 10 | 229266_at | shisa homolog 6 (Xenopus laevis), SHISA6 | -5.9745 |
| 11 | 213543_at | sarcoglycan, delta (35kDa dystrophin-associated glycoprotein), SGCD | -5.82467 |
| 12 | 1552626_a_at | transmembrane protein 163, TMEM163 | -5.65298 |
| 13 | 207093_s_at | oligodendrocyte myelin glycoprotein, OMG | -5.35129 |
| 14 | 227148_at | pleckstrin homology domain containing, family H member 2, PLEKHH2 | -5.34979 |
| 15 | 200953_s_at | cyclin D2, CCND2 | -5.31529 |
| 16 | 207789_s_at | dipeptidyl-peptidase 6, DPP6 | -5.30983 |
| 17 | 231001_at | fin bud initiation factor homolog (zebrafish), FIBIN | -5.24142 |
| 18 | 226769_at | fin bud initiation factor homolog (zebrafish), FIBIN | -5.13636 |
| 19 | 228546_at | dipeptidyl-peptidase 6, DPP6 | -5.1138 |
| 20 | 213832_at | potassium voltage-gated channel, Shal-related subfamily, member 3, KCND3 | -5.0929 |
| 21 | 220761_s_at | TAO kinase 3, TAOK3 | -5.06633 |
| 22 | 231098_at |  | -5.05854 |
| 23 | 241706_at | copine VIII, CPNE8 | -5.04386 |
| 24 | 233129_at |  | -5.03761 |
| 25 | 232377_at | neurexophilin 1, NXPH1 | -4.91254 |
| 26 | 218807_at | vav 3 guanine nucleotide exchange factor, VAV3 | -4.91059 |
| 27 | 206462_s_at | neurotrophic tyrosine kinase, receptor, type 3, NTRK3 | -4.89773 |
| 28 | 212098_at | mannosyl (α-1,6-)-glycoprotein beta-1,6-N-acetyl-glucosaminyltransferase, MGAT5 | -4.88847 |
| 29 | 223923_at | chromosome 21 open reading frame 62, C21orf62 | -4.84926 |
| 30 | 239221_at | G protein-coupled receptor 123, GPR123 | -4.84522 |
| 31 | 206915_at | NK2 homeobox 2, NKX2-2 | -4.84372 |
| 32 | 223503_at | transmembrane protein 163, TMEM163 | -4.77141 |
| 33 | 212190_at | serpin peptidase inhibitor, clade E (nexin), member 2, | -4.75121 |
| 34 | 223468_s_at | RGM domain family, member A, RGMA | -4.70716 |

Fig. 14

| 35 | 206243_at | TIMP metallopeptidase inhibitor 4, TIMP4 | -4.68817 |
|---|---|---|---|
| 36 | 219564_at | potassium inwardly-rectifying channel, subfamily J, member 16, KCNJ16 | -4.67798 |
| 37 | 219049_at | chondroitin sulfate N-acetylgalactosaminyltransferase 1, CSGALNACT1 | -4.62745 |
| 38 | 229759_s_at | ventricular zone expressed PH domain homolog 1 (zebrafish), VEPH1 | -4.62055 |
| 39 | 202242_at | tetraspanin 7, TSPAN7 | -4.59022 |
| 40 | 205475_at | stimulator of chondrogenesis 1, SCRG1 | -4.55727 |
| 41 | 238003_at | hepatocyte cell adhesion molecule, HEPACAM | -4.55185 |
| 42 | 220543_at | chromosome 21 open reading frame 62, C21orf62 | -4.55149 |
| 43 | 215014_at | potassium voltage-gated channel, Shal-related subfamily, member 3, KCND3 | -4.52529 |
| 44 | 217033_x_at | neurotrophic tyrosine kinase, receptor, type 3, NTRK3 | -4.51016 |
| 45 | 232235_at | dermatan sulfate epimerase-like, DSEL | -4.46631 |
| 46 | 240458_at |  | -4.44163 |
| 47 | 236599_at |  | -4.4402 |
| 48 | 1557143_at | CUB and Sushi multiple domains 2, CSMD2 | -4.42817 |
| 49 | 213618_at | ArfGAP with RhoGAP domain, ankyrin repeat and PH domain 2, ARAP2 | -4.39381 |
| 50 | 209356_x_at | EGF-containing fibulin-like extracellular matrix protein 2, EFEMP2 | -4.38892 |

Fig. 14 (Continued)

| K4me3 | K27me3 |
|---|---|
| >1.0 | >0.6 |
| >2.0 | >1.0 |
| >3.0 | >2.0 |

| Genes upregulated by K27M | | | | |
|---|---|---|---|---|
| Name | P5W | | P5K | |
| | K4me3 | K27me3 | K4me3 | K27me3 |
| Runx2 | 0.87 | 0.34 | 0.93 | 0.14 |
| COCH | 1.32 | 0.48 | 1.02 | 0.34 |
| PERP | 0.63 | 0.55 | 0.40 | 1.00 |
| CHCHD7 | 1.97 | 0.11 | 1.79 | 0.54 |
| NMU | 0.58 | 0.70 | 0.77 | 0.37 |
| MST4 | 0.63 | 0.57 | 1.37 | 0.66 |
| GPC4 | 2.21 | 0.43 | 1.47 | 0.29 |
| PLAG1 | 1.97 | 0.11 | 1.88 | 0.51 |
| FAM60A | 1.50 | 0.30 | 1.12 | 0.46 |
| TESC | 0.34 | 0.39 | 0.56 | 0.37 |
| LIN28B | 0.55 | 0.95 | 0.91 | 1.46 |
| EFNA5 | 0.97 | 0.30 | 1.00 | 0.66 |
| PLS1 | 1.74 | 0.52 | 0.93 | 0.29 |
| GLI3 | 2.13 | 0.27 | 0.88 | 0.20 |
| CHRDL1 | 1.11 | 0.43 | 0.93 | 0.29 |
| TSPAN18 | 0.63 | 0.61 | 0.53 | 0.20 |
| CACNA2D1 | 1.71 | 0.14 | 0.95 | 0.34 |
| PABPC4L | 0.95 | 0.43 | 0.65 | 0.23 |
| PLAGL1 | 0.53 | 0.50 | 0.44 | 1.89 |
| LPHN2 | 1.39 | 0.32 | 1.00 | 0.31 |
| VPS13A | 1.24 | 0.45 | 0.74 | 0.46 |
| BZW2 | 2.37 | 0.43 | 1.35 | 0.40 |
| KLF5 | 1.66 | 0.34 | 0.98 | 0.40 |
| MLLT3 | 1.79 | 0.20 | 0.74 | 0.14 |
| ZFPM2 | 1.03 | 0.27 | 0.63 | 0.54 |
| MAN1A1 | 3.11 | 0.18 | 1.88 | 0.80 |
| PPP4R4 | 0.82 | 0.27 | 0.88 | 0.37 |
| TIFA | 0.68 | 0.43 | 0.79 | 0.20 |
| NUAK2 | 1.26 | 0.32 | 1.23 | 0.46 |
| CDH8 | 0.47 | 0.82 | 0.70 | 1.03 |
| BCL11A | 1.32 | 0.14 | 0.58 | 0.57 |

Fig. 15-1

| | | | | |
|---|---|---|---|---|
| RBPMS | 2.05 | 0.23 | 1.26 | 0.40 |
| NRIP3 | 0.87 | 0.41 | 0.49 | 0.57 |
| DACH1 | 1.50 | 0.27 | 0.79 | 1.66 |
| CDKN1C | 0.39 | 0.18 | 0.63 | 0.20 |
| RGS10 | 0.71 | 0.27 | 0.74 | 0.80 |
| CTSC | 1.89 | 0.41 | 1.51 | 0.31 |
| PAK1 | 0.47 | 0.09 | 0.70 | 0.11 |
| SNAI2 | 1.05 | 0.27 | 0.77 | 0.29 |
| DPYD | 2.47 | 0.45 | 1.02 | 0.49 |
| MAML3 | 1.47 | 0.18 | 0.79 | 0.14 |
| BSG | 1.92 | 0.25 | 0.95 | 0.46 |
| H1FX | 1.87 | 0.43 | 0.74 | 0.43 |
| CDH6 | 1.21 | 0.41 | 1.09 | 0.51 |
| STXBP6 | 0.92 | 0.27 | 0.60 | 0.37 |
| SSX2IP | 1.61 | 0.20 | 0.98 | 0.37 |
| SLC44A1 | 1.58 | 0.34 | 0.60 | 0.29 |
| SMC4 | 4.50 | 0.34 | 2.09 | 0.80 |
| H1F0 | 0.47 | 0.36 | 0.40 | 1.91 |
| RUNX1T1 | 1.45 | 0.52 | 0.72 | 0.46 |
| SLC35F2 | 0.84 | 0.45 | 1.02 | 0.26 |
| NID1 | 1.18 | 0.25 | 1.12 | 0.43 |
| GJA3 | 0.32 | 0.34 | 0.28 | 3.37 |
| KLF10 | 2.05 | 0.16 | 1.07 | 0.51 |
| VGLL3 | 1.74 | 0.34 | 1.42 | 0.69 |
| DDIT4L | 1.29 | 0.39 | 1.14 | 0.29 |
| MEF2C | 2.26 | 0.34 | 1.21 | 0.69 |
| SLC6A15 | 1.03 | 0.82 | 0.93 | 0.60 |
| PHIP | 2.97 | 0.23 | 1.35 | 0.51 |
| SFRP2 | 0.79 | 0.73 | 0.72 | 0.63 |
| CALB1 | 0.71 | 0.57 | 0.88 | 0.43 |
| RRAS2 | 0.89 | 0.55 | 1.23 | 0.83 |
| NEK2 | 1.50 | 0.36 | 0.95 | 0.29 |
| PHLDB2 | 0.45 | 0.36 | 0.56 | 0.63 |
| PPL | 0.03 | 0.32 | 0.30 | 0.83 |
| SEMA3A | 3.37 | 0.89 | 1.98 | 2.37 |
| TIAM1 | 2.53 | 0.36 | 1.65 | 0.46 |
| GABRA5 | 0.63 | 0.20 | 0.42 | 0.31 |
| SNCA | 0.53 | 0.57 | 1.12 | 0.54 |
| KLHL14 | 0.18 | 0.61 | 0.42 | 0.80 |
| CDC14B | 1.00 | 0.23 | 0.51 | 0.29 |
| ARL4C | 1.00 | 0.16 | 0.53 | 0.26 |
| TMEM38B | 1.21 | 0.48 | 0.86 | 1.74 |
| TLE4 | 1.11 | 0.23 | 0.65 | 0.26 |
| ADAMTS3 | 2.50 | 0.16 | 1.60 | 0.23 |

Fig. 15-2

| | | | | |
|---|---|---|---|---|
| STX3 | 0.74 | 0.41 | 1.02 | 0.49 |
| PRTG | 2.82 | 0.23 | 1.40 | 0.20 |
| SHB | 0.74 | 0.16 | 0.72 | 0.66 |
| MSI2 | 0.50 | 0.23 | 0.44 | 0.34 |
| TXNIP | 2.55 | 0.18 | 1.42 | 0.31 |
| HDAC9 | 0.89 | 0.50 | 0.93 | 0.09 |
| SCEL | 0.37 | 0.41 | 0.47 | 0.37 |
| CPS1 | 1.39 | 0.25 | 0.84 | 0.29 |
| TRIM36 | 1.45 | 0.16 | 0.88 | 1.94 |
| PDK4 | 1.34 | 0.27 | 1.05 | 0.23 |
| TPBG | 0.79 | 0.75 | 0.44 | 1.29 |
| EMB | 0.87 | 0.45 | 0.86 | 0.40 |
| FOXG1 | 0.11 | 0.16 | 0.28 | 0.54 |
| OTX2 | 0.71 | 0.64 | 1.12 | 1.97 |
| LIN7A | 1.42 | 0.32 | 0.95 | 0.31 |
| HSPB1 | 1.13 | 0.45 | 0.60 | 0.74 |

| Genes downregulated by K27M | | | | |
|---|---|---|---|---|
| Name | P5W | | P5K | |
| | K4me3 | K27me3 | K4me3 | K27me3 |
| AQP4 | 1.16 | 0.23 | 0.47 | 0.43 |
| RYR3 | 1.39 | 0.25 | 1.02 | 0.49 |
| NKX2-2 | 0.92 | 0.18 | 0.40 | 3.97 |
| CCND2 | 1.66 | 0.43 | 0.67 | 4.40 |
| ESRRG-P1 | 1.03 | 0.80 | 0.37 | 1.91 |
| ESRRG-P2 | 0.53 | 0.70 | 0.28 | 8.43 |
| DPP6 | 0.71 | 0.18 | 0.33 | 1.31 |
| VAV3 | 1.39 | 0.18 | 0.56 | 0.43 |
| PI3KR1 | 2.42 | 0.27 | 1.60 | 0.66 |
| KAT7 | 2.63 | 0.39 | 1.44 | 0.54 |
| TMEM163 | 0.71 | 0.48 | 0.44 | 1.89 |
| CSMD2 | 1.18 | 0.14 | 0.72 | 1.09 |
| SNRPN | 0.34 | 0.48 | 0.33 | 0.71 |
| TRAF4 | 1.39 | 0.14 | 0.67 | 0.34 |
| FEZ1 | 1.34 | 0.34 | 0.49 | 0.40 |
| GSTT1 | 0.87 | 0.18 | 0.33 | 0.26 |
| KAT2B | 1.05 | 0.02 | 1.26 | 0.29 |
| BAI3 | 1.97 | 0.11 | 1.40 | 0.20 |
| IQSEC1 | 0.39 | 0.05 | 0.33 | 0.14 |
| SLC4A4 | 2.42 | 0.20 | 1.53 | 0.37 |
| MAPK10 | 1.58 | 0.45 | 0.54 | 0.34 |

Fig. 15-3

| | | | | |
|---|---|---|---|---|
| SLC6A1 | 1.03 | 0.23 | 0.30 | 1.63 |
| INPP4B | 1.79 | 0.41 | 1.28 | 0.23 |
| BLM | 3.05 | 0.43 | 1.37 | 0.31 |
| C3orf70 | 0.71 | 0.14 | 0.63 | 0.34 |
| SHISA6 | 0.63 | 0.09 | 0.05 | 0.83 |
| SGCD | 0.63 | 0.45 | 0.19 | 0.51 |
| PLEKHH2 | 2.08 | 0.27 | 0.93 | 0.54 |
| FIBIN | 0.45 | 0.34 | 0.95 | 0.23 |
| KCND3 | 1.37 | 0.16 | 0.58 | 0.29 |
| TAOK3 | 3.76 | 0.20 | 1.51 | 0.29 |
| CPNE8 | 2.68 | 0.43 | 0.91 | 0.80 |
| NXPH1 | 1.45 | 0.36 | 0.49 | 1.60 |
| NTRK3 | 2.34 | 0.23 | 0.56 | 0.37 |
| GPR123 | 0.55 | 0.39 | 0.44 | 0.40 |
| SERPINE2 | 2.08 | 0.25 | 1.40 | 0.17 |
| RGMA | 1.24 | 0.39 | 0.63 | 0.83 |
| VEPH1 | 0.21 | 0.41 | 0.81 | 0.20 |
| SCRG1 | 1.21 | 0.50 | 0.53 | 0.80 |
| DSEL | 2.95 | 0.39 | 1.72 | 0.51 |
| ARAP2 | 2.08 | 0.32 | 1.40 | 0.46 |
| RASSF2 | 1.66 | 0.20 | 0.74 | 0.43 |
| NLGN3 | 0.97 | 0.39 | 0.53 | 0.37 |
| CDH10 | 2.39 | 0.16 | 1.12 | 0.14 |
| LRRK2 | 0.68 | 0.30 | 0.49 | 0.43 |
| DOCK10 | 1.26 | 0.48 | 0.65 | 0.60 |
| SRI | 2.08 | 0.25 | 1.05 | 0.31 |
| SLC6A11 | 1.05 | 0.25 | 0.40 | 1.63 |
| SLC6A1 | 1.03 | 0.23 | 0.30 | 1.63 |
| ITPR2 | 2.26 | 0.48 | 0.56 | 0.46 |
| DLC1 | 0.66 | 0.45 | 0.53 | 0.66 |
| GRIA1 | 2.82 | 0.55 | 0.84 | 0.37 |
| NPAS3 | 1.79 | 0.77 | 1.21 | 1.34 |
| MYO5C | 0.97 | 0.20 | 0.72 | 0.26 |
| DMD | 0.82 | 0.39 | 0.47 | 0.40 |
| TRIL | 0.84 | 0.32 | 0.77 | 0.66 |
| ZEB1 | 3.16 | 0.11 | 1.70 | 0.31 |
| ZCCHC24 | 0.66 | 0.27 | 0.30 | 0.23 |
| TCF12-P1 | 1.53 | 0.23 | 1.07 | 0.31 |
| TCF12-P2 | 1.29 | 0.25 | 0.53 | 0.17 |
| PCYT1B | 1.24 | 0.27 | 0.56 | 0.31 |
| SALL1 | 2.47 | 0.32 | 0.79 | 4.31 |
| VSTM2A | 0.84 | 0.27 | 0.56 | 0.83 |
| SNTB1 | 1.18 | 0.45 | 0.58 | 1.29 |
| CST3 | 1.08 | 0.25 | 0.67 | 0.29 |

Fig. 15-4

| | | | | |
|---|---|---|---|---|
| PLD5 | 1.05 | 0.27 | 0.74 | 1.09 |
| CTH | 2.63 | 0.41 | 1.53 | 0.31 |
| SMOC1 | 1.21 | 0.30 | 0.58 | 0.46 |
| SLC15A2 | 1.29 | 0.23 | 0.72 | 0.34 |
| RGS6 | 1.32 | 0.30 | 0.47 | 0.66 |
| PLA2G16 | 1.37 | 0.18 | 0.74 | 0.09 |
| IGSF11 | 2.66 | 0.30 | 1.07 | 0.83 |
| SPOCK2 | 0.82 | 0.25 | 0.26 | 0.31 |
| RIT2 | 1.32 | 0.34 | 0.51 | 0.37 |
| TRIM9 | 1.13 | 0.45 | 0.77 | 0.29 |
| ZMAT4 | 1.08 | 0.45 | 0.40 | 0.34 |
| PHEX | 0.16 | 0.57 | 0.56 | 0.74 |
| STAMBPL1 | 1.32 | 0.61 | 1.14 | 0.54 |
| PTPRE | 1.50 | 0.20 | 0.77 | 0.17 |
| SYNE1 | 0.61 | 0.55 | 0.86 | 1.23 |
| CNKSR2 | 2.45 | 0.27 | 0.98 | 0.46 |
| ZNF93 | 2.03 | 0.16 | 0.95 | 0.34 |

Fig. 15-5

| (A) P5W H3K27me3 target | (B) P5K H3K27me3 target | (C) P5K-specific H3K27me3 target | (D) Benporath_ESC H3K27me3 target | (E) Benporath_ESC PRC2 target | (C) AND (D) shared | (C) AND (E) shared |
|---|---|---|---|---|---|---|
| AATF | A4GALT | A4GALT | AATF | ABCC8 | ACAN | ADAMTS18 |
| ACCSL | AARS2 | AARS2 | ABCC3 | ABTB2 | ACTL6B | ADAP2 |
| ACSM4 | AATF | ABCE1 | ABCC8 | ADAMTS15 | ADAMTS18 | ADARB2 |
| ACTBL2 | ABCE1 | ACAD9 | ABCG4 | ADAMTS18 | ADAP2 | ADCY8 |
| ADCY4 | ACAD9 | ACAN | ABTB2 | ADAP2 | ADARB2 | ADCYAP1 |
| ADORA3 | ACAN | ACHE | ACADL | ADARB2 | ADCY8 | ADRA1A |
| AGBL5 | ACHE | ACIN1 | ACAN | ADCY4 | ADCYAP1 | ADRB1 |
| AGPAT5 | ACIN1 | ACOT13 | ACCN2 | ADCY8 | ADRA1A | ADRB3 |
| AHCYL1 | ACOT13 | ACOXL | ACTL6B | ADCYAP1 | ADRB1 | AGPAT9 |
| AHCYL2 | ACOXL | ACRV1 | ADAM15 | ADRA1A | ADRB3 | ALOX15 |
| ALDH1A2 | ACRV1 | ACSL1 | ADAM22 | ADRA2A | AGPAT9 | ALX3 |
| AMER3 | ACSL1 | ACSL5 | ADAMTS15 | ADRB1 | AIM1 | ALX4 |
| AMPD1 | ACSL5 | ACSM1 | ADAMTS17 | ADRB3 | ALOX15 | ANKRD18A |
| ANKRD1 | ACSM1 | ACSS1 | ADAMTS18 | AGPAT9 | ALX3 | ANKRD18B |
| ANO2 | ACSS1 | ACTA1 | ADAP2 | ALOX15 | ALX4 | ANKRD19P |
| ANO6 | ACTA1 | ACTL6A | ADARB2 | ALX3 | ANKRD18A | ANKRD27 |
| ANXA2P1 | ACTL6A | ACTL6B | ADC | ALX4 | ANKRD18B | ASCL2 |
| ARSF | ACTL6B | ACVR1C | ADCY4 | ANKRD18A | ANKRD19P | ASTN2 |
| ARSH | ACVR1C | ADAM8 | ADCY8 | ANKRD18B | ANKRD27 | ATF3 |
| ASB17 | ADAM8 | ADAMTS18 | ADCYAP1 | ANKRD19P | ARID3C | ATOH8 |
| ASCL5 | ADAMTS18 | ADAMTS2 | ADRA1A | ANKRD20A1 | ARNTL | BARHL1 |
| ASTL | ADAMTS2 | ADAMTS20 | ADRA2A | ANKRD20A2 | ASCL2 | BARHL2 |
| ATOH1 | ADAMTS20 | ADAMTS8 | ADRB1 | ANKRD20A3 | ASCL4 | BARX2 |
| ATP8B4 | ADAMTS8 | ADAMTSL3 | ADRB3 | ANKRD20A5P | ASTN2 | BATF3 |
| ATXN7L2 | ADAMTSL3 | ADAP2 | ADRBK2 | ANKRD20A8P | ATF3 | BHLHE23 |
| B4GALNT2 | ADAP2 | ADARB2 | AGAP2 | ANKRD27 | ATOH8 | C17orf102 |
| BARX1 | ADARB2 | ADCY8 | AGPAT9 | AQP5 | BARHL1 | C17orf82 |
| BASP1 | ADCY4 | ADCYAP1 | AIM1 | ARHGAP20 | BARHL2 | C1orf194 |
| BCL6 | ADCY8 | ADM | ALOX15 | ARL9 | BARX2 | C1orf213 |
| BCL9 | ADCYAP1 | ADORA2A-AS1 | ALOXE3 | ASCL1 | BATF3 | C2CD4A |
| BHLHE22 | ADM | ADPGK | ALX3 | ASCL2 | BHLHE23 | CA10 |
| BMF | ADORA2A-AS1 | ADRA1A | ALX4 | ASTN1 | BMP6 | CACNA1B |
| BMP4 | ADPGK | ADRB1 | AMELX | ASTN2 | C14orf132 | CACNA1D |
| BNC1 | ADRA1A | ADRB3 | AMN | ATF3 | C17orf102 | CACNA1E |
| BPIFA1 | ADRB1 | AFAP1L2 | AMPH | ATOH1 | C17orf82 | CACNA1G |
| BPIFA4P | ADRB3 | AFF3 | ANKRD18A | ATOH8 | C1orf194 | CAMK2N1 |
| BPIFB4 | AFAP1L2 | AFM | ANKRD18B | B4GALNT1 | C1orf213 | CBLN1 |
| BSND | AFF3 | AGBL4 | ANKRD19P | B4GALNT2 | C1orf94 | CD34 |
| BTAF1 | AFM | AGPAT9 | ANKRD20A1 | BARHL1 | C1QL1 | CD70 |
| BTBD11 | AGBL4 | AHSA2 | ANKRD20A2 | BARHL2 | C2CD4A | CD8A |

Fig. 16-1

| | | | | | | |
|---|---|---|---|---|---|---|
| C10orf11 | AGBL5 | AHSP | ANKRD20A3 | BARX1 | CA10 | CDH7 |
| C10orf126 | AGPAT5 | AIFM1 | ANKRD20A5P | BARX2 | CA7 | CDK5R2 |
| C12orf57 | AGPAT9 | AIM1 | ANKRD20A8P | BATF3 | CACNA1A | CDKN2C |
| C14orf23 | AHSA2 | AJAP1 | ANKRD27 | BCL2 | CACNA1B | CDX2 |
| C14orf39 | AHSP | AK5 | ANKRD35 | BHLHE22 | CACNA1D | CH25H |
| C16orf95 | AIFM1 | ALDH1A3 | ANKRD43 | BHLHE23 | CACNA1E | CHRDL2 |
| C17orf47 | AIM1 | ALOX15 | AP8A1 | BHLHE41 | CACNA1G | CHST8 |
| C1orf185 | AJAP1 | ALOX15P1 | AQP5 | BMP8A | CACNG3 | CLSTN2 |
| C1QTNF1-AS1 | AK5 | ALOX5 | ARHGAP20 | BNC1 | CALCR | COL27A1 |
| C1QTNF6 | ALDH1A2 | ALPL | ARHGEF38 | BTG2 | CAMK2N1 | COL2A1 |
| C21orf49 | ALDH1A3 | ALX1 | ARHGEF7 | C13orf15 | CBLN1 | COLEC12 |
| C21orf90 | ALOX15 | ALX3 | ARID3C | C17orf102 | CBX4 | COMP |
| C2CD4B | ALOX15P1 | ALX4 | ARID5B | C17orf82 | CCNA1 | CRLF1 |
| C2orf71 | ALOX5 | AMZ1 | ARL10 | C1orf194 | CD34 | CRTAC1 |
| C2orf78 | ALPL | ANAPC10 | ARL5C | C1orf213 | CD38 | CRYBA2 |
| C3 | ALX1 | ANAPC15 | ARL9 | C20orf103 | CD70 | CSMD1 |
| C4BPA | ALX3 | ANAPC1P1 | ARNTL | C21orf63 | CD8A | CSMD3 |
| C7orf50 | ALX4 | ANG | ASCL1 | C2CD4A | CDC20B | CXCL16 |
| C7orf71 | AMER3 | ANGEL1 | ASCL2 | C3orf15 | CDH7 | CYP26A1 |
| C9orf53 | AMZ1 | ANK1 | ASCL4 | C4orf49 | CDK5R2 | CYP26B1 |
| CACNG2 | ANAPC10 | ANKH | ASTN1 | C5orf39 | CDKN2C | CYP27B1 |
| CALCA | ANAPC15 | ANKRD18A | ASTN2 | C8orf47 | CDX2 | DACH1 |
| CALHM2 | ANAPC1P1 | ANKRD18B | ATF3 | CA10 | CERKL | DACH2 |
| CAMK4 | ANG | ANKRD18DP | ATOH1 | CACNA1B | CH25H | DCC |
| CAPN14 | ANGEL1 | ANKRD19P | ATOH8 | CACNA1D | CHD5 | DGKG |
| CASC4 | ANK1 | ANKRD27 | ATP1A3 | CACNA1E | CHN2 | DIO3 |
| CASP8 | ANKH | ANKRD29 | AVPR1B | CACNA1G | CHRDL2 | DKK1 |
| CCDC112 | ANKRD18A | ANKRD34B | B4GALNT1 | CALCA | CHST8 | DKK2 |
| CCDC140 | ANKRD18B | ANKRD34C | B4GALNT2 | CAMK2N1 | CLIC5 | DLL4 |
| CCL11 | ANKRD18DP | ANKRD6 | BAI2 | CASZ1 | CLSTN2 | DLX1 |
| CCL20 | ANKRD19P | ANKS1B | BARHL1 | CBLN1 | CNTNAP5 | DLX2 |
| CCL27 | ANKRD27 | ANP32A-IT1 | BARHL2 | CBLN4 | COL12A1 | DLX3 |
| CCR6 | ANKRD29 | ANP32E | BARX1 | CBR3 | COL27A1 | DLX4 |
| CD160 | ANKRD34B | ANXA2 | BARX2 | CBX8 | COL2A1 | DMRT1 |
| CD300LB | ANKRD34C | ANXA2R | BATF3 | CCDC140 | COLEC12 | DMRT2 |
| CELF2 | ANKRD6 | AP1M2 | BCAN | CD34 | COMP | DMRT3 |
| CEP85 | ANKS1B | AP2B1 | BCL2 | CD70 | CR2 | DPF3 |
| CES3 | ANO2 | AP3B1 | BHLHE22 | CD6A | CRLF1 | DRD5 |
| CHRNA3 | ANP32A-IT1 | APCDD1L | BHLHE23 | CDH23 | CRTAC1 | DSC3 |
| CHRNB3 | ANP32E | APCDD1L-AS1 | BHLHE41 | CDH7 | CRYBA2 | DSCAML1 |
| CLDN5 | ANXA2 | APOBEC3G | BLVRB | CDK5R2 | CSMD1 | DUOX1 |
| CLEC1B | ANXA2R | ARC | BMP6 | CDKN2C | CSMD2 | DUOXA1 |
| CNIH3 | AP1M2 | ARHGAP12 | BMP8A | CDX2 | CSMD3 | ECEL1 |
| COL20A1 | AP2B1 | ARHGAP22 | BMX | CGB7 | CWH43 | EGFL6 |
| COL25A1 | AP3B1 | ARHGAP27 | BNC1 | CGB8 | CXCL16 | EGR4 |

Fig. 16-2

| COL4A3 | APCDD1L | ARHGAP30 | BTG2 | CH25H | CYP26A1 | ELMOD1 |
| COL4A4 | APCDD1L-AS1 | ARHGAP6 | C11orf45 | CHODL | CYP26B1 | EN1 |
| COL6A5 | APOBEC3G | ARHGAP9 | C13orf15 | CHRD | CYP27B1 | EN2 |
| COX16 | ARC | ARHGEF15 | C14orf132 | CHRDL2 | CYP2A13 | EPAS1 |
| CPO | ARHGAP12 | ARID3C | C17orf100 | CHST8 | DACH1 | EPHA5 |
| CRH | ARHGAP22 | ARIH1 | C17orf102 | CIDEA | DACH2 | ESPN |
| CRHR2 | ARHGAP27 | ARL15 | C17orf82 | CITED1 | DCC | ESX1 |
| CRISP3 | ARHGAP30 | ARNTL | C1orf115 | CLCN5 | DCX | FAM163A |
| CSH1 | ARHGAP6 | ARPP21 | C1orf194 | CLEC14A | DGKG | FAM19A4 |
| CSTA | ARHGAP9 | ARSG | C1orf213 | CLSTN2 | DIO3 | FAM43B |
| CTRB2 | ARHGEF15 | ARX | C1orf51 | CMTM2 | DKK1 | FAM89A |
| CWC25 | ARID3C | ASCL2 | C1orf94 | CNNM1 | DKK2 | FBLN7 |
| CXorf28 | ARIH1 | ASCL3 | C1QL1 | CNRIP1 | DLK1 | FBXL8 |
| CXXC4 | ARL15 | ASCL4 | C1QTNF5 | CNTFR | DLL4 | FEZF2 |
| CYMP | ARNTL | ASIC2 | C20orf103 | COL24A1 | DLX1 | FGF3 |
| CYP1B1 | ARPP21 | ASTN2 | C21orf63 | COL25A1 | DLX2 | FGF5 |
| CYP24A1 | ARSG | ATF2 | C2CD4A | COL27A1 | DLX3 | FGF9 |
| CYP2A6 | ARX | ATF3 | C3orf15 | COL2A1 | DLX4 | FIGLA |
| CYP2C9 | ASCL2 | ATG5 | C3orf54 | COL4A5 | DLX5 | FLI1 |
| CYP2F1 | ASCL3 | ATG9B | C4orf49 | COL4A6 | DMRT1 | FLRT2 |
| CYP2S1 | ASCL4 | ATN1 | C5orf39 | COL9A2 | DMRT2 | FOXB1 |
| DCAKD | ASIC2 | ATOH8 | C8orf47 | COLEC12 | DMRT3 | FOXD3 |
| DDC | ASTN2 | ATP12A | CA10 | COMP | DPF3 | FOXD4L3 |
| DDX4 | ATF2 | ATP2A3 | CA7 | CORO6 | DPP6 | FOXD4L4 |
| DEFA1 | ATF3 | ATP2B1 | CACNA1A | CRHR1 | DRD5 | FOXE1 |
| DEFA1B | ATG5 | ATP2C2 | CACNA1B | CRLF1 | DSC3 | FOXF1 |
| DEFA3 | ATG9B | ATP5G3 | CACNA1D | CRTAC1 | DSCAML1 | FOXG1 |
| DEFB104A | ATN1 | ATP5J | CACNA1E | CRYBA2 | DUOX1 | FOXL1 |
| DEFB104B | ATOH1 | ATP6V1C2 | CACNA1G | CSMD1 | DUOXA1 | FOXL2 |
| DEFB107A | ATOH8 | ATP8B1 | CACNB3 | CSMD3 | EBF1 | FRMD3 |
| DEFB107B | ATP12A | ATPIF1 | CACNB4 | CTNND2 | EBF3 | FZD10 |
| DEFB124 | ATP2A3 | AVPR1A | CACNG3 | CXCL14 | ECEL1 | GABRA2 |
| DEFB136 | ATP2B1 | AVPR2 | CACNG8 | CXCL16 | EGFL6 | GABRA4 |
| DISC2 | ATP2C2 | B3GNT1 | CADM4 | CYP24A1 | EGFLAM | GAD2 |
| DLX6-AS1 | ATP5G3 | B3GNT3 | CALCA | CYP26A1 | EGR4 | GALR2 |
| DMKN | ATP5J | B3GNT4 | CALCR | CYP26B1 | EIF4E3 | GATA3 |
| DNM1P35 | ATP6V1C2 | B3GNT7 | CAMK2B | CYP26C1 | ELAVL2 | GATA4 |
| DNMT3L | ATP8B1 | BAG3 | CAMK2N1 | CYP27B1 | ELMOD1 | GATA6 |
| DOCK2 | ATPIF1 | BAG4 | CAMK2N2 | DACH1 | ELOVL3 | GBX2 |
| DRP2 | ATXN7L2 | BAIAP3 | CASZ1 | DACH2 | EN1 | GDF6 |
| DUOX2 | AVPR1A | BAMBI | CBLN1 | DCC | EN2 | GDF7 |
| DUOXA2 | AVPR2 | BANCR | CBLN4 | DCHS2 | EPAS1 | GHR |
| DYSF | B3GNT1 | BARHL1 | CBR3 | DCLK2 | EPHA10 | GHSR |
| ECRP | B3GNT3 | BARHL2 | CBX4 | DDAH1 | EPHA3 | GJB2 |
| EDIL3 | B3GNT4 | BARX2 | CBX8 | DGKG | EPHA5 | GJD2 |

Fig. 16-3

| | | | | | | |
|---|---|---|---|---|---|---|
| EOMES | B3GNT7 | BATF3 | CCDC140 | DGKI | ESPN | GPR101 |
| ERICH1-AS1 | B4GALNT2 | BAZ2A | CCDC50 | DHH | ESR1 | GPR88 |
| ESRRG | BAG3 | BCL2L11 | CCDC96 | DIO3 | ESX1 | GRIA2 |
| EVA1A | BAG4 | BCL7A | CCNA1 | DKK1 | FAM163A | GRID1 |
| EVX1 | BAIAP3 | BDNF | CD34 | DKK2 | FAM19A4 | GRIK3 |
| EXOC3L2 | BAMBI | BEAN1 | CD38 | DLL4 | FAM43B | GRM7 |
| FABP4 | BANCR | BEGAIN | CD47 | DLX1 | FAM89A | GSC |
| FAHD1 | BARHL1 | BEND4 | CD70 | DLX2 | FBLN7 | GSC2 |
| FAIM | BARHL2 | BEST2 | CD8A | DLX3 | FBXL8 | GSX1 |
| FAM138A | BARX1 | BHLHE23 | CDC20B | DLX4 | FERD3L | HAND2 |
| FAM138B | BARX2 | BHMT | CDH23 | DMRT1 | FEZF2 | HES2 |
| FAM138C | BASP1 | BLACE | CDH4 | DMRT2 | FGF3 | HHEX |
| FAM138F | BATF3 | BLK | CDH6 | DMRT3 | FGF5 | HLX |
| FAM150A | BAZ2A | BLOC1S1 | CDH7 | DNAJC22 | FGF8 | HMX2 |
| FAM159B | BCL2L11 | BLOC1S1-RDH5 | CDK5R2 | DOK6 | FGF9 | HMX3 |
| FAM172BP | BCL7A | BMP2 | CDKN2C | DPF3 | FIGLA | HOXB3 |
| FAM177B | BCL9 | BMP3 | CDX1 | DPY19L2 | FLI1 | HOXB7 |
| FAM180A | BDNF | BMP6 | CDX2 | DPY19L2P2 | FLRT2 | HOXB8 |
| FAM194B | BEAN1 | BMP8B | CERKL | DRD5 | FNDC1 | HOXC6 |
| FAM72D | BEGAIN | BMPER | CGB7 | DSC3 | FOXB1 | HOXD13 |
| FAM99B | BEND4 | BNC2 | CGB8 | DSCAML1 | FOXC1 | HOXD8 |
| FBXL21 | BEST2 | BNIP2 | CH25H | DUOX1 | FOXD3 | HOXD9 |
| FBXO31 | BHLHE22 | BOD1L1 | CHAD | DUOX2 | FOXD4L3 | HPSE2 |
| FCGR1C | BHLHE23 | BRDT | CHD5 | DUOXA1 | FOXD4L4 | HRK |
| FCGR2A | BHMT | BRE | CHDH | DUOXA2 | FOXE1 | HS3ST3B1 |
| FCGR3A | BLACE | BRINP2 | CHN2 | DUSP4 | FOXE3 | HS6ST3 |
| FEV | BLK | BRINP3 | CHODL | ECEL1 | FOXF1 | HSF4 |
| FFAR1 | BLOC1S1 | BRIX1 | CHRD | EFNA1 | FOXF2 | HTR1A |
| FGF4 | BLOC1S1-RDH5 | BRWD3 | CHRDL1 | EFNA3 | FOXG1 | ICAM5 |
| FLI1-AS1 | BMP2 | BSPRY | CHRDL2 | EGFL6 | FOXL1 | IGF2-AS |
| FLJ23867 | BMP3 | BSX | CHST8 | EGR3 | FOXL2 | IKZF3 |
| FLJ36000 | BMP4 | BTBD1 | CIDEA | EGR4 | FOXQ1 | IL1RAPL2 |
| FMO5 | BMP6 | BTG4 | CITED1 | ELMOD1 | FRMD3 | IL7 |
| FOLR1 | BMP8B | BTN1A1 | CLCN5 | EN1 | FRMPD1 | INSRR |
| FOXA2 | BMPER | BTNL9 | CLEC14A | EN2 | FXYD7 | IRX3 |
| FOXD2 | BNC1 | BUB3 | CLEC4G | EOMES | FZD10 | IRX5 |
| FOXD4L1 | BNC2 | C10orf131 | CLIC5 | EPAS1 | GAB3 | ISL1 |
| GABRA1 | BNIP2 | C10orf32 | CLIP4 | EPB41L4A | GABRA2 | ITGA4 |
| GAL3ST1 | BOD1L1 | C10orf32-AS3MT | CLSTN2 | EPHA5 | GABRA4 | ITPKA |
| GALNTL6 | BRDT | C10orf55 | CMTM2 | EPHB1 | GABRB2 | KCNA1 |
| GATA2 | BRE | C10orf67 | CNNM1 | EPHB3 | GAD2 | KCNAB1 |
| GBA | BRINP2 | C10orf88 | CNNM2 | ERBB4 | GALR2 | KCNC4 |
| GBA3 | BRINP3 | C11orf44 | CNRIP1 | ESAM | GATA3 | KCNK12 |
| GDNF | BRIX1 | C11orf70 | CNTFR | ESPN | GATA4 | KCNK13 |

Fig. 16-4

| | | | | | | |
|---|---|---|---|---|---|---|
| GDNF-AS1 | BRWD3 | C11orf74 | CNTN2 | ESX1 | GATA6 | KCNK2 |
| GFI1 | BSND | C11orf88 | CNTNAP5 | F2R | GBX2 | KCNK4 |
| GFOD1 | BSPRY | C14orf119 | COL12A1 | FAM150A | GCM2 | KCNMA1 |
| GIPC2 | BSX | C14orf132 | COL24A1 | FAM163A | GDF6 | KCNQ3 |
| GJA4 | BTAF1 | C16orf11 | COL25A1 | FAM19A4 | GDF7 | KCNV1 |
| GKN2 | BTBD1 | C16orf13 | COL27A1 | FAM43B | GHR | KIAA1324 |
| GLIS1 | BTBD11 | C17orf102 | COL2A1 | FAM5B | GHSR | KIRREL3 |
| GLOD5 | BTG4 | C17orf82 | COL4A5 | FAM5C | GJB2F | KL |
| GLUD2 | BTN1A1 | C18orf42 | COL4A6 | AM81A | GJD2 | KLF4 |
| GPR4 | BTNL9 | C19orf33 | COL8A1 | FAM84A | GPR101 | KLHL35 |
| GPR68 | BUB3 | C19orf59 | COL9A2 | FAM89A | GPR26 | LBX1 |
| GPR83 | C10orf131 | C1orf110 | COLEC12 | FBLN7 | GPR88 | LGR5 |
| GPRIN2 | C10orf32 | C1orf170 | COMMD3 | FBN2 | GRIA2 | LHX2 |
| GRHL3 | C10orf32-AS3MT | C1orf172 | COMP | FBP1 | GRID1 | LHX4 |
| GRIN3A | C10orf55 | C1orf194 | CORO6 | FBXL8 | GRIK3 | LHX5 |
| GRM4 | C10orf67 | C1orf200 | COX6B2 | FBXO3 | GRIN1 | LMX1B |
| GSN | C10orf88 | C1orf210 | CPM | FEV | GRM6 | LOC153684 |
| GSN-AS1 | C11orf44 | C1orf213 | CR2 | FEZ1 | GRM7 | LONRF3 |
| GSX2 | C11orf70 | C1orf27 | CRH | FEZF2 | GSC | LPL |
| GUCY1A3 | C11orf74 | C1orf53 | CRHR1 | FGF20 | GSC2 | LRRC71 |
| GZMA | C11orf88 | C1orf61 | CRIP1 | FGF3 | GSX1 | LTBP2 |
| H1FOO | C14orf119 | C1orf74 | CRLF1 | FGF5 | HAND1 | LTK |
| H2AFX | C14orf132 | C1orf94 | CRMP1 | FGF9 | HAND2 | LYSMD2 |
| HAGH | C14orf23 | C1QC | CRTAC1 | FIGLA | HCN4 | MAB21L1 |
| HBA1 | C14orf39 | C1QL1 | CRYBA2 | FLI1 | HES2 | MAB21L2 |
| HBA2 | C16orf11 | C1QL2 | CRYL1 | FLJ11235 | HES3 | MAFB |
| HCG11 | C16orf13 | C1QL3 | CSF1 | FLJ32063 | HHEX | MAL |
| HCK | C16orf95 | C1QL4 | CSMD1 | FLJ45983 | HLX | MCOLN3 |
| HEMGN | C17orf102 | C1QTNF1 | CSMD2 | FLJ46347 | HMX2 | MESP1 |
| HEPHL1 | C17orf82 | C20orf166 | CSMD3 | FLRT2 | HMX3 | MKX |
| HES5 | C18orf42 | C20orf166-AS1 | CTNND2 | FOXA2 | HOXA1 | MSC |
| HHIPL1 | C19orf33 | C20orf201 | CWH43 | FOXB1 | HOXA2 | MSX1 |
| HIGD1B | C19orf59 | C2CD4A | CXCL14 | FOXD2 | HOXA4 | MT1A |
| HIST1H1A | C1orf110 | C3orf58 | CXCL16 | FOXD3 | HOXA6 | MT1B |
| HIST1H1D | C1orf170 | C3orf72 | CYP24A1 | FOXD4L1 | HOXB3 | MT1DP |
| HIST1H4H | C1orf172 | C3orf80 | CYP26A1 | FOXD4L3 | HOXB7 | MT1H |
| HIST2H2AA3 | C1orf194 | C3orf84 | CYP26B1 | FOXD4L4 | HOXB8 | MT1M |
| HIST2H2AA4 | C1orf200 | C4orf19 | CYP26C1 | FOXE1 | HOXC6 | MYO5B |
| HIST2H2BC | C1orf210 | C4orf32 | CYP27B1 | FOXF1 | HOXD13 | MYOD1 |
| HMBOX1 | C1orf213 | C5orf38 | CYP2A13 | FOXG1 | HOXD8 | NAG5 |
| HMGCLL1 | C1orf27 | C7orf43 | CYP2A6 | FOXJ1 | HOXD9 | NEFL |
| HNF1B | C1orf53 | C8orf31 | CYP2A7 | FOXL1 | HPSE | NELL1 |
| HNRNPCP5 | C1orf61 | C8orf37 | CYP2J2 | FOXL2 | HPSE2 | NEUROD2 |
| HOMER1 | C1orf74 | C9orf3 | CYP39A1 | FRMD3 | HR | NEUROG1 |
| HOTAIR | C1orf94 | C9orf66 | DACH1 | FRMPD4 | HRK | NEUROG2 |

Fig. 16-5

| | | | | | | |
|---|---|---|---|---|---|---|
| HOTTIP | C1QC | CA1 | DACH2 | FUT4 | HS3ST2 | NEUROG3 |
| HOXA10 | C1QL1 | CA10 | DCC | FZD10 | HS3ST3B1 | NKX2-1 |
| HOXA10-HOXA9 | C1QL2 | CA14 | DCHS2 | FZD2 | HS3ST4 | NKX2-2 |
| HOXA11 | C1QL3 | CA4 | DCLK1 | GABRA2 | HS6ST3 | NKX2-3 |
| HOXA13 | C1QL4 | CA7 | DCLK2 | GABRA4 | HSF4 | NKX2-8 |
| HOXA3 | C1QTNF1 | CA8 | DCX | GAD2 | HTR1A | NKX3-1 |
| HOXA7 | C20orf166 | CABLES1 | DDAH1 | GALNTL4 | HTR6 | NKX3-2 |
| HOXA9 | C20orf166-AS1 | CABP7 | DDX25 | GALR2 | ICAM5 | NKX6-1 |
| HOXA-AS3 | C20orf201 | CACNA1A | DGKG | GATA2 | IGF2-AS | NKX6-2 |
| HOXA-AS4 | C21orf49 | CACNA1B | DGKI | GATA3 | IGFBP3 | NPAS1 |
| HOXB1 | C2CD4A | CACNA1D | DHH | GATA4 | IHH | NPAS4 |
| HOXB13 | C2CD4B | CACNA1E | DIO3 | GATA6 | IKZF3 | NPNT |
| HOXB2 | C2orf78 | CACNA1G | DKK1 | GBX2 | IL10RA | NPR3 |
| HOXB4 | C3orf58 | CACNA1G-AS1 | DKK2 | GDF6 | IL1RAPL2 | NPTX1 |
| HOXB5 | C3orf72 | CACNA2D3 | DLK1 | GDF7 | IL7 | NR2F2 |
| HOXB6 | C3orf80 | CACNG3 | DLK2 | GDNF | INSRR | NRG2 |
| HOXB-AS1 | C3orf84 | CACNG6 | DLL4 | GHR | IRX1 | NTNG2 |
| HOXB-AS3 | C4orf19 | CALCR | DLX1 | GHSR | IRX3 | NTRK1 |
| HOXC11 | C4orf32 | CALM1 | DLX2 | GIMAP5 | IRX5 | OLIG2 |
| HOXC12 | C5orf38 | CALN1 | DLX3 | GJB2 | ISL1 | ONECUT1 |
| HOXC13 | C7orf43 | CALY | DLX4 | GJD2 | ITGA4 | ONECUT2 |
| HOXC4 | C8orf31 | CAMK2N1 | DLX5 | GLT25D2 | ITIH5 | OPRD1 |
| HOXC5 | C8orf37 | CAMP | DMRT1 | GNA14 | ITPKA | OSR1 |
| HOXC8 | C9orf3 | CAMTA1 | DMRT2 | GPC5 | KCNA1 | OTOP1 |
| HOXC-AS2 | C9orf53 | CAND1.11 | DMRT3 | GPM6B | KCNA5 | OTOP2 |
| HOXC-AS5 | C9orf66 | CARTPT | DNAJC22 | GPR101 | KCNAB1 | OTOP3 |
| HOXD1 | CA1 | CASR | DNER | GPR12 | KCNC4 | OTP |
| HOXD10 | CA10 | CAST | DOK6 | GPR88 | KCNIP4 | OTX1 |
| HOXD12 | CA14 | CBLN1 | DPF3 | GRIA2 | KCNK12 | OTX2 |
| HOXD3 | CA4 | CBWD1 | DPP6 | GRID1 | KCNK13 | PABPC1L2A |
| HOXD4 | CA7 | CBWD2 | DPY19L2 | GRIK1 | KCNK17 | PAPPA |
| HPGDS | CA8 | CBWD3 | DPY19L2P2 | GRIK3 | KCNK2 | PAX1 |
| HS3ST1 | CABLES1 | CBWD5 | DPYSL5 | GRIN3A | KCNK4 | PAX2 |
| HSPA5 | CABP7 | CBWD6 | DRD4 | GRM7 | KCNMA1 | PAX8 |
| HSPA6 | CACNA1A | CBX4 | DRD5 | GSC | KCNQ1 | PAX9 |
| HTR2C | CACNA1B | CCBE1 | DSC3 | GSC2 | KCNQ3 | PCDH8 |
| HYLS1 | CACNA1D | CCDC108 | DSCAML1 | GSX1 | KCNS2 | PDGFRA |
| ICAM2 | CACNA1E | CCDC129 | DTNB | GSX2 | KCNS3 | PDX1 |
| ICAM4 | CACNA1G | CCDC17 | DUOX1 | GUCY1A3 | KCNV1 | PENK |
| IFNK | CACNA1G-AS1 | CCDC3 | DUOX2 | GUCY2D | KIAA1324 | PGM5 |
| IGF2 | CACNA2D3 | CCDC59 | DUOXA1 | HAND2 | KIRREL3 | PGR |
| IGFN1 | CACNG2 | CCDC64B | DUOXA2 | HBA1 | KIRREL3-AS3 | PHOX2A |
| IGLL5 | CACNG3 | CCDC68 | DUSP15 | HBA2 | KISS1R | PITX3 |
| IGSF21 | CACNG6 | CCDC71 | DUSP4 | HES2 | KL | PMP22 |
| IL21R | CALCA | CCDC84 | DUSP6 | HES7 | KLF4 | POU3F4 |

Fig. 16-6

| | | | | | | |
|---|---|---|---|---|---|---|
| IL23A | CALCR | CCK | DUSP8 | HEY1 | KLHL35 | POU4F1 |
| IL32 | CALM1 | CCL4 | DYNC1I1 | HHAT | KLK4 | POU4F2 |
| INTS9 | CALN1 | CCNA1 | EBF1 | HHEX | LAMB1 | POU4F3 |
| IQCF4 | CALY | CCND2 | EBF3 | HHIP | LBX1 | PRDM12 |
| IRF4 | CAMK2N1 | CCNO | ECEL1 | HLX | LEF1 | PRLHR |
| IRX4 | CAMP | CCNYL1 | EFCAB1 | HMX2 | LGI3 | PROK2 |
| ISL2 | CAMTA1 | CCT6B | EFNA1 | HMX3 | LGR5 | PTF1A |
| ITGB2 | CAND1.11 | CCZ1B | EFNA3 | HNF1B | LHFPL3 | PTGDR |
| KDR | CARTPT | CD1D | EGFL6 | HOXB1 | LHX2 | PTGER2 |
| KIAA1217 | CASC4 | CD200R1L | EGFLAM | HOXB13 | LHX3 | PTGER3 |
| KIAA1239 | CASR | CD24 | EGR2 | HOXB2 | LHX4 | PTGER4 |
| KIR3DX1 | CAST | CD300LF | EGR3 | HOXB3 | LHX5 | PTH2 |
| KISS1 | CBLN1 | CD302 | EGR4 | HOXB6 | LMX1B | PTHLH |
| KLF14 | CBWD1 | CD34 | EIF4E3 | HOXB7 | LOC153684 | PTPRT |
| KNCN | CBWD2 | CD38 | ELAVL2 | HOXB8 | LONRF3 | PYY |
| KPNA2 | CBWD3 | CD4 | ELAVL3 | HOXC11 | LPL | RAB6C |
| KRT12 | CBWD5 | CD44 | ELMOD1 | HOXC12 | LRRC71 | RASGRF1 |
| KRT34 | CBWD6 | CD70 | ELOVL2 | HOXC4 | LTBP2 | RASSF5 |
| KRT76 | CBX4 | CD8A | ELOVL3 | HOXC5 | LTK | RAX |
| KRTAP13-2 | CCBE1 | CD8B | EN1 | HOXC6 | LYSMD2 | RBP4 |
| KRTAP4-2 | CCDC108 | CDA | EN2 | HOXC8 | MAB21L1 | RGS10 |
| L1TD1 | CCDC129 | CDC20B | ENTPD2 | HOXD1 | MAB21L2 | RGS9BP |
| LAMA3 | CCDC140 | CDC5L | ENTPD3 | HOXD12 | MAFB | RIPK3 |
| LBX2 | CCDC17 | CDCA5 | EOMES | HOXD13 | MAL | RSPO2 |
| LEUTX | CCDC3 | CDCP1 | EPAS1 | HOXD3 | MCOLN3 | SCTR |
| LHX6 | CCDC59 | CDH13 | EPB41L4A | HOXD4 | MECOM | SFRP1 |
| LHX8 | CCDC64B | CDH15 | EPHA10 | HOXD8 | MEIS1 | SFRP5 |
| LILRA5 | CCDC68 | CDH22 | EPHA3 | HOXD9 | MEOX2 | SGPP2 |
| LILRB2 | CCDC71 | CDH7 | EPHA4 | HPCAL4 | MESP1 | SHH |
| LINC00111 | CCDC84 | CDK5R2 | EPHA5 | HPSE2 | MFSD4 | SHISA6 |
| LINC00489 | CCK | CDKN2A | EPHB1 | HRK | MICB | SHOX |
| LINC00554 | CCL11 | CDKN2B | EPHB3 | HS3ST3B1 | MKX | SHOX2 |
| LINC00861 | CCL4 | CDKN2B-AS1 | ERBB4 | HS6ST1P1 | MLPH | SIDT1 |
| LINC00900 | CCNA1 | CDKN2C | ERO1LB | HS6ST3 | MLXIPL | SIM2 |
| LINC00910 | CCND2 | CDX2 | ESAM | HSF4 | MSC | SIX1 |
| LINC00942 | CCNO | CEACAM19 | ESPN | HSPA6 | MSX1 | SIX2 |
| LINC01020 | CCNYL1 | CEP192 | ESR1 | HTR1A | MSX2 | SIX3 |
| LINC01056 | CCT6B | CEP85L | ESX1 | HTR2C | MT1A | SLC1A2 |
| LIPC | CCZ1B | CERKL | ETV7 | HTR7 | MT1B | SLC24A4 |
| LMF1 | CD1D | CFTR | EVX1 | ICAM5 | MT1DP | SLC30A2 |
| LOC100128239 | CD200R1L | CH25H | EXOC3L2 | IGF2-AS | MT1H | SLC30A3 |
| LOC100132174 | CD24 | CHAT | EYA4 | IGSF21 | MT1M | SLC32A1 |
| LOC100289473 | CD300LF | CHD5 | F2R | IKZF3 | MYO5B | SLC35F3 |
| LOC100506178 | CD302 | CHN2 | FAMa115C | IL1RAPL2 | MYOD1 | SLC6A1 |
| LOC100506241 | CD34 | CHRDL2 | FAM123A | IL7 | NAGS | SLC6A3 |

Fig. 16-7

| | | | | | | |
|---|---|---|---|---|---|---|
| LOC100506730 | CD38 | CHRM2 | FAM129A | ILDR2 | NCCRP1 | SLC6A5 |
| LOC100507003 | CD4 | CHST13 | FAM150A | INA | NDRG1 | SLC9A2 |
| LOC100507489 | CD44 | CHST8 | FAM159A | INSM2 | NEFH | SLC9A3 |
| LOC100652768 | CD70 | CISTR-ACT | FAM163A | INSRR | NEFL | SLCO5A1 |
| LOC100996758 | CD8A | CKMT1A | FAM167A | IRX3 | NELL1 | SLFN11 |
| LOC148696 | CD8B | CLDN14 | FAM19A4 | IRX4 | NEUROD2 | SLITRK3 |
| LOC150622 | CDA | CLDN7 | FAM43B | IRX5 | NEUROG1 | SORCS1 |
| LOC152586 | CDC20B | CLEC2L | FAM5B | ISL1 | NEUROG2 | SORCS3 |
| LOC284757 | CDC5L | CLEC4GP1 | FAM5C | ISL2 | NEUROG3 | SOX14 |
| LOC285696 | CDCA5 | CLIC5 | FAM70B | ITGA4 | NGF | SOX17 |
| LOC286094 | CDCP1 | CLIC6 | FAM78A | ITPKA | NGFR | SOX7 |
| LOC286297 | CDH13 | CLNS1A | FAM81A | JUN | NKX2-1 | SPAG6 |
| LOC286437 | CDH15 | CLOCK | FAM84A | KAZALD1 | NKX2-2 | SPON1 |
| LOC339240 | CDH22 | CLSTN2 | FAM89A | KCNA1 | NKX2-3 | SRD5A2 |
| LOC340073 | CDH7 | CLTC | FBLN5 | KCNA3 | NKX2-5 | SSTR2 |
| LOC389033 | CDK5R2 | CLVS2 | FBLN7 | KCNAB1 | NKX2-8 | STMN2 |
| LOC641515 | CDKN2A | CMA1 | FBN1 | KCNC2 | NKX3-1 | SUSD4 |
| LOC643802 | CDKN2B | CMTM7 | FBN2 | KCNC4 | NKX3-2 | SV2B |
| LOC727924 | CDKN2B-AS1 | CMTR1 | FBP1 | KCND3 | NKX6-1 | TBR1 |
| LOC729218 | CDKN2C | CNGA3 | FBXL14 | KCNH1 | NKX6-2 | TBX1 |
| LOC729737 | CDX2 | CNOT2 | FBXL8 | KCNH3 | NOTUM | TBX2 |
| LPAR3 | CEACAM19 | CNPY1 | FBXO25 | KCNK12 | NPAS1 | TBX3 |
| LRRC26 | CELF2 | CNTNAP5 | FBXO3 | KCNK13 | NPAS4 | THBD |
| LRRC72 | CEP192 | COL12A1 | FERD3L | KCNK2 | NPNT | TLL1 |
| LRTM1 | CEP85 | COL14A1 | FEV | KCNK4 | NPR1 | TLX1 |
| LRTM2 | CEP85L | COL15A1 | FEZ1 | KCNMA1 | NPR3 | TLX2 |
| LTBP1 | CERKL | COL21A1 | FEZF2 | KCNQ3 | NPTX1 | TMEM132E |
| LTF | CFTR | COL27A1 | FGF11 | KCNV1 | NPY5R | TMEM30B |
| LYZL6 | CH25H | COL2A1 | FGF20 | KIAA1199 | NR2E1 | TMEM59L |
| LZTS1-AS1 | CHAT | COL5A3 | FGF3 | KIAA1324 | NR2F2 | TMOD2 |
| MALL | CHD5 | COLEC12 | FGF5 | KIRREL3 | NRG2 | TP73 |
| MAPRE3 | CHN2 | COMMD4 | FGF8 | KL | NRIP3 | TRADD |
| MAST4 | CHRDL2 | COMP | FGF9 | KLF4 | NRN1 | TRH |
| MEP1A | CHRM2 | COPS7A | FIGLA | KLHL35 | NRXN1 | TRIM36 |
| MIR10A | CHRNA3 | CPAMD8 | FLI1 | KY | NTNG2 | TRIM67 |
| MIR10B | CHST13 | CPLX2 | FLJ11235 | LAYN | NTRK1 | TRPC5 |
| MIR1-1 | CHST8 | CPNE1 | FLJ32063 | LBX1 | NXPH4 | TSLP |
| MIR1252 | CISTR-ACT | CPNE7 | FLJ39739 | LGALS3 | OLIG2 | UCN |
| MIR1258 | CKMT1A | CPT1A | FLJ45983 | LGR5 | OLIG3 | UCP1 |
| MIR196A1 | CLDN14 | CPXM2 | FLJ46347 | LHX2 | ONECUT1 | UNC5C |
| MIR196A2 | CLDN7 | CPZ | FLRT2 | LHX4 | ONECUT2 | USH1G |
| MIR196B | CLEC2L | CR1 | FNDC1 | LHX5 | OPRD1 | VAX1 |
| MIR200B | CLEC4GP1 | CR2 | FNDC5 | LHX6 | OSR1 | VAX2 |
| MIR206 | CLIC5 | CRABP1 | FOXA2 | LHX8 | OSR2 | VDR |
| MIR3131 | CLIC6 | CRB3 | FOXB1 | LINC00268 | OTOP1 | WNT1 |

Fig. 16-8

| | | | | | | |
|---|---|---|---|---|---|---|
| MIR3185 | CLN5IA | CREB3L2 | FOXC1 | LMX1B | OTOP2 | WNT10A |
| MIR3646 | CLOCK | CREG2 | FOXD2 | LOC153684 | OTOP3 | WNT11 |
| MIR3907 | CLSTN2 | CRHBP | FOXD3 | LONRF3 | OTP | WNT2 |
| MIR4276 | CLTC | CRIM1 | FOXD4L1 | LPHN3 | OTX1 | WNT3A |
| MIR4420 | CLVS2 | CRLF1 | FOXD4L3 | LPL | OTX2 | WNT6 |
| MIR4423 | CMA1 | CRNDE | FOXD4L4 | LPPR1 | OVOL1 | WNT7A |
| MIR4461 | CMTM7 | CRTAC1 | FOXE1 | LRCH2 | PABPC1L2A | WRAP73 |
| MIR4493 | CMTR1 | CRYBA2 | FOXE3 | LRFN5 | PADI2 | ZCCHC16 |
| MIR4713 | CNGA3 | CRYM | FOXF1 | LRP2 | PAPPA | ZFHX3 |
| MIR4727 | CNIH3 | CSE1L | FOXF2 | LRRC71 | PAX1 | ZFYVE28 |
| MIR4730 | CNOT2 | CSGALNACT1 | FOXG1 | LRRTM1 | PAX2 | ZIC1 |
| MIR4778 | CNPY1 | CSMD1 | FOXJ1 | LTBP2 | PAX8 | ZIC4 |
| MIR4801 | CNTNAP5 | CSMD2 | FOXL1 | LTK | PAX9 | ZMYND15 |
| MIR5092 | COL12A1 | CSMD3 | FOXL2 | LYSMD2 | PCDH8 | ZNF436 |
| MIR5093 | COL14A1 | CSRNP2 | FOXQ1 | MAB21L1 | PCSK2 | ZNF503 |
| MIR5188 | COL15A1 | CSRP2 | FRAT1 | MAB21L2 | PDGFRA | |
| MIR518B | COL21A1 | CTAGE11P | FRMD3 | MAFB | PDX1 | |
| MIR520C | COL25A1 | CTDSP1 | FRMPD1 | MAL | PENK | |
| MIR520G | COL27A1 | CTSE | FRMPD4 | MAPK4 | PGM5 | |
| MIR520H | COL2A1 | CUX2 | FUCA1 | MAPT | PGR | |
| MIR663A | COL4A3 | CWC15 | FUT4 | MCOLN3 | PHOX2A | |
| MIR888 | COL4A4 | CWH43 | FUT9 | MESP1 | PITX3 | |
| MIR890 | COL5A3 | CXCL12 | FXYD7 | METRNL | PMP22 | |
| MIR891A | COL6A5 | CXCL16 | FZD1 | MGC39545 | POMC | |
| MNX1 | COLEC12 | CXCL6 | FZD10 | MIR137HG | POU3F4 | |
| MRGPRX4 | COMMD4 | CYB5R2 | FZD2 | MKX | POU4F1 | |
| MROH5 | COMP | CYP11B1 | GAB3 | MLLT3 | POU4F2 | |
| MS4A10 | COPS7A | CYP26A1 | GABBR2 | MNX1 | POU4F3 | |
| MSGN1 | COX16 | CYP26B1 | GABRA2 | MSC | PPP1R14C | |
| MSX2P1 | CPAMD8 | CYP27B1 | GABRA4 | MSX1 | PRDM12 | |
| MT1G | CPLX2 | CYP2A13 | GABRB2 | MT1A | PRDM13 | |
| MT1L | CPNE1 | CYP4F2 | GABRG3 | MT1B | PRKCB | |
| MTFR1 | CPNE7 | CYP4X1 | GAD2 | MT1DP | PRKCH | |
| MTHFSD | CPT1A | CYS1 | GALNTL1 | MT1H | PRLHR | |
| MTRNR2L7 | CPXM2 | DACH1 | GALNTL4 | MT1M | PROK2 | |
| MUC12 | CPZ | DACH2 | GALR2 | MYF6 | PRUNE2 | |
| MUC13 | CR1 | DACT1 | GAST | MYO5B | PSD2 | |
| MYH4 | CR2 | DBX1 | GATA2 | MYOD1 | PTF1A | |
| MYL3 | CRABP1 | DBX2 | GATA3 | NAGS | PTGDR | |
| MYOM2 | CRB3 | DCC | GATA4 | NAV2 | PTGER2 | |
| MYOT | CREB3L2 | DCX | GATA6 | NBPF11 | PTGER3 | |
| NAA30 | CREG2 | DDX17 | GBX2 | NCAM1 | PTGER4 | |
| NASP | CRHBP | DDX51 | GCC1 | NDUFA4L2 | PTH2 | |
| NDRG4 | CRHR2 | DEFB119 | GCM2 | NEFL | PTHLH | |
| NEBL | CRIM1 | DEGS2 | GDF6 | NEFM | PTPRT | |

Fig. 16-9

| | | | | | |
|---|---|---|---|---|---|
| NEUROD1 | CRLF1 | DENND6A | GDF7 | NELL1 | PYY |
| NEUROD4 | CRNDE | DGKG | GDNF | NEUROD1 | RAB6C |
| NFIX | CRTAC1 | DGKK | GHR | NEUROD2 | RASGRF1 |
| NFS1 | CRYBA2 | DHDDS | GHSR | NEUROG1 | RASSF5 |
| NMT1 | CRYM | DHDH | GIMAP5 | NEUROG2 | RAX |
| NOTO | CSE1L | DIO3 | GJB2 | NEUROG3 | RBP4 |
| NPAS3 | CSGALNACT1 | DKFZP434I0714 | GJD2 | NFIX | RBP7 |
| NPFFR1 | CSMD1 | DKFZp686K1684 | GKAP1 | | REEP1 |
| NPY4R | CSMD2 | DKK1 | GLB1L2 | NKX2-2 | RFX6 |
| NR2F1 | CSMD3 | DKK2 | GLIPR2 | NKX2-3 | RGS10 |
| NR2F1-AS1 | CSRNP2 | DLK1 | GLT25D2 | NKX2-8 | RGS9BP |
| NSG1 | CSRP2 | DLL1 | GNA14 | NKX3-1 | RIPK3 |
| NUBPL | CTAGE11P | DLL4 | GNAO1 | NKX3-2 | RSPO2 |
| NXPE2 | CTDSP1 | DLX1 | GPC3 | NKX6-1 | RSPO3 |
| OAZ3 | CTSE | DLX2 | GPC5 | NKX6-2 | RTBDN |
| OCA2 | CUX2 | DLX3 | GPD1L | NOL4 | SAMD11 |
| OLFM3 | CWC15 | DLX4 | GPM6B | NPAS1 | SCTR |
| OLFM4 | CWC25 | DLX5 | GPR101 | NPAS4 | SEZ6 |
| OPALIN | CWH43 | DLX6 | GPR12 | NPNT | SFRP1 |
| OR10J1 | CXCL12 | DMBT1 | GPR124 | NPR3 | SFRP5 |
| OR11H6 | CXCL16 | DMRT1 | GPR150 | NPTX1 | SFTPC |
| OR13C8 | CXCL6 | DMRT2 | GPR174 | NPY1R | SGPP2 |
| OR1I1 | CXXC4 | DMRT3 | GPR26 | NR2F2 | SH3GL2 |
| OR1J4 | CYB5R2 | DMRTA2 | GPR6 | NR4A3 | SHH |
| OR1L3 | CYP11B1 | DNAH11 | GPR62 | NRG1 | SHISA6 |
| OR1N1 | CYP1B1 | DNAJB11 | GPR88 | NRG2 | SHOX |
| OR2A5 | CYP24A1 | DNTT | GRB10 | NT5C1A | SHOX2 |
| OR4B1 | CYP26A1 | DOC2B | GRHL3 | NTN1 | SIDT1 |
| OR4C3 | CYP26B1 | DOCK10 | GRIA2 | NTNG2 | SIM2 |
| OR4C6 | CYP27B1 | DOCK3 | GRID1 | NTRK1 | SIX1 |
| OR4F16 | CYP2A13 | DOCK8 | GRIK1 | NTRK2 | SIX2 |
| OR4F29 | CYP2S1 | DPF3 | GRIK3 | O3FAR1 | SIX3 |
| OR4F3 | CYP4F2 | DPP10 | GRIN1 | OAF | SKAP1 |
| OR4F5 | CYP4X1 | DPP6 | GRIN2D | OCA2 | SLC17A6 |
| OR4L1 | CYS1 | DPP9 | GRIN3A | OLFML2B | SLC17A7 |
| OR4N3P | DACH1 | DPRX | GRK5 | OLIG2 | SLC1A2 |
| OR51E1 | DACH2 | DPY19L2P1 | GRM6 | ONECUT1 | SLC24A4 |
| OR52E6 | DACT1 | DPYSL2 | GRM7 | ONECUT2 | SLC26A5 |
| OR52W1 | DBX1 | DRD1 | GSC | OPRD1 | SLC30A2 |
| OR56B1 | DBX2 | DRD2 | GSC2 | OSR1 | SLC30A3 |
| OR5B17 | DCC | DRD5 | GSN | OTOP1 | SLC32A1 |
| OR5H14 | DCX | DRGX | GSX1 | OTOP2 | SLC35D3 |
| OR6P1 | DDC | DSC3 | GSX2 | OTOP3 | SLC35F3 |
| OR6X1 | DDX17 | DSCAM-IT1 | GUCY1A3 | OTP | SLC6A1 |

Fig. 16-10

| | | | | | |
|---|---|---|---|---|---|
| OR8D1 | DDX51 | DSCAML1 | GUCY2D | OTX1 | SLC6A11 |
| OR8G1 | DEFB119 | DSP | HAND1 | OTX2 | SLC6A3 |
| OR8G2 | DEGS2 | DTL | HAND2 | OXCT2 | SLC6A5 |
| OR8G5 | DENND6A | DUOX1 | HBA1 | PABPC1L2A | SLC9A2 |
| OR9Q2 | DGKG | DUOXA1 | HBA2 | PAPPA | SLC9A3 |
| OTOA | DGKK | DUSP1 | HCG9 | PARM1 | SLCO5A1 |
| OTX2-AS1 | DHDDS | DUSP5P1 | HCN4 | PAX1 | SLFN11 |
| OVOL2 | DHDH | DUX2 | HES2 | PAX2 | SLIT3 |
| PABPC4L | DIO3 | DUX4 | HES3 | PAX3 | SLITRK3 |
| PADI6 | DKFZP434I0714 | DUX4L2 | HES5 | PAX6 | SMOC2 |
| PAK7 | DKFZp686K1684 | DUX4L3 | HES7 | PAX7 | SNTB1 |
| PALLD | DKK1 | DUX4L5 | HEY1 | PAX8 | SORCS1 |
| PAMR1 | DKK2 | DUX4L6 | HEYL | PAX9 | SORCS3 |
| PAPL | DLK1 | DUX4L7 | HHAT | PCDH17 | SOX14 |
| PAPPA-AS1 | DLL1 | EBF1 | HHEX | PCDH8 | SOX17 |
| PATL2 | DLL4 | EBF2 | HHIP | PDE4DIP | SOX7 |
| PAX3 | DLX1 | EBF3 | HIC1 | PDGFRA | SPAG6 |
| PAX5 | DLX2 | ECEL1 | HLA-A | PDX1 | SPON1 |
| PAX6 | DLX3 | ECEL1P2 | HLA-B | PDZD2 | SPON2 |
| PAX7 | DLX4 | EDA | HLA-C | PENK | SRD5A2 |
| PAXBP1 | DLX5 | EDN3 | HLA-F | PGM5 | SSTR2 |
| PDCL | DLX6 | EEF1A1 | HLX | PGR | ST8SIA5 |
| PDCL2 | DLX6-AS1 | EEF2 | HMX2 | PHOX2A | STC2 |
| PDE1B | DMBT1 | EFCAB6 | HMX3 | PHOX2B | STMN2 |
| PDE4A | DMKN | EFCC1 | HNF1B | PIGZ | SUSD4 |
| PDE4DIP | DMRT1 | EFNA5 | HOXA1 | PIP5K1B | SV2B |
| PDIA4 | DMRT2 | EGFL6 | HOXA10 | PIR | SYNE1 |
| PDPR | DMRT3 | EGFLAM | HOXA13 | PITX1 | SYT6 |
| PEG3-AS1 | DMRTA2 | EGR4 | HOXA2 | PITX2 | T |
| PER4 | DNAH11 | EHD1 | HOXA3 | PITX3 | TACR1 |
| PF4V1 | DNAJB11 | EIF3E | HOXA4 | PKNOX2 | TBR1 |
| PGLYRP4 | DNTT | EIF3M | HOXA6 | PKP1 | TBX1 |
| PGM5-AS1 | DOC2B | EIF4E3 | HOXA7 | PLEC | TBX2 |
| PGPEP1L | DOCK10 | ELAVL2 | HOXA9 | PLXNA2 | TBX20 |
| PGRMC2 | DOCK3 | ELMOD1 | HOXB1 | PMP22 | TBX3 |
| PHACTR3 | DOCK8 | ELOVL3 | HOXB13 | PODN | TGFA |
| PHLDA1 | DPF3 | ELOVL7 | HOXB2 | POLE | THBD |
| PHOX2B | DPP10 | ELP3 | HOXB3 | POU3F1 | TLL1 |
| PI16 | DPP6 | EMC1 | HOXB6 | POU3F4 | TLX1 |
| PIK3IP1 | DPP9 | EMILIN2 | HOXB7 | POU4F1 | TLX2 |
| PITX1 | DPRX | EMX1 | HOXB8 | POU4F2 | TLX3 |
| PITX2 | DPY19L2P1 | EMX2 | HOXC11 | POU4F3 | TMEM132E |
| PKD2L1 | DPYSL2 | EMX2OS | HOXC12 | PPM1E | TMEM163 |
| PLA2G7 | DRD1 | EN1 | HOXC4 | PRAC | TMEM30B |

Fig. 16-11

| | | | | | |
|---|---|---|---|---|---|
| PLXNC1 | DRD2 | EN2 | HOXC5 | PRDM12 | TMEM59L |
| PNLIP | DRD5 | ENTHD1 | HOXC6 | PRKCE | TMOD2 |
| PNPLA8 | DRGX | ENTPD6 | HOXC8 | PRKG1 | TNFSF9 |
| PPEF2 | DSC3 | EPAS1 | HOXD1 | PRLHR | TP73 |
| PPIP5K1 | DSCAM-IT1 | EPB41L3 | HOXD12 | PROK2 | TRADD |
| PPP1R26-AS1 | DSCAML1 | EPB42 | HOXD13 | PTF1A | TRH |
| PPP2R2C | DSP | EPHA10 | HOXD3 | PTGDR | TRIM36 |
| PRAC2 | DTL | EPHA2 | HOXD4 | PTGER2 | TRIM67 |
| PRAMEF10 | DUOX1 | EPHA3 | HOXD8 | PTGER3 | TRPC5 |
| PRAMEF2 | DUOX2 | EPHA5 | HOXD9 | PTGER4 | TSLP |
| PRDM14 | DUOXA1 | EPHA8 | HPCAL4 | PTGFR | TWIST1 |
| PRG3 | DUOXA2 | EPO | HPSE | PTH2 | UCN |
| PRICKLE2-AS2 | DUSP1 | EPPIN | HPSE2 | PTHLH | UCP1 |
| PRKCZ | DUSP5P1 | EPPIN-WFDC6 | HR | PTPRT | ULBP1 |
| PRR9 | DUX2 | ERAP1 | HRK | PTPRU | ULBP2 |
| PRSS16 | DUX4 | ERG | HS3ST2 | PXMP2 | UNC5C |
| PRSS22 | DUX4L2 | ERVMER34-1 | HS3ST3B1 | PYY | USH1G |
| PRSS3 | DUX4L3 | ESPN | HS3ST4 | RAB6C | VAX1 |
| PRSS30P | DUX4L5 | ESPNL | HS6ST1P1 | RASGRF1 | VAX2 |
| PTPRD | DUX4L6 | ESR1 | HS6ST3 | RASL10A | VDR |
| PVALB | DUX4L7 | ESRP1 | HSF4 | RASSF5 | WNT1 |
| RAB7L1 | DYSF | ESX1 | HSPA1A | RAX | WNT10A |
| RAPGEF5 | EBF1 | ESYT3 | HSPA1B | RBP4 | WNT11 |
| RBP2 | EBF2 | ETS1 | HSPA1L | REPS2 | WNT2 |
| REXO1L1 | EBF3 | EVX2 | HSPA6 | RGS10 | WNT3A |
| REXO1L2P | ECEL1 | EXOSC9 | HTR1A | RGS20 | WNT6 |
| RGS3 | ECEL1P2 | EYA2 | HTR2C | RGS9BP | WNT7A |
| RNASE7 | EDA | F11R | HTR6 | RIMBP3 | WRAP73 |
| RNF128 | EDIL3 | F13A1 | HTR7 | RIMBP3B | ZACN |
| RNPS1 | EDN3 | FADS6 | HTRA3 | RIMBP3C | ZCCHC16 |
| ROBO1 | EEF1A1 | FAM118B | ICAM4 | RIMKLA | ZFHX3 |
| ROBO3 | EEF2 | FAM135B | ICAM5 | RIPK3 | ZFYVE28 |
| ROMO1 | EFCAB6 | FAM150B | IGF2-AS | RNF128 | ZIC1 |
| RPL24 | EFCC1 | FAM155B | IGFBP1 | ROBO3 | ZIC4 |
| RPSAP52 | EFNA5 | FAM161A | IGFBP3 | RPRML | ZMYND15 |
| RRAD | EGFL6 | FAM163A | IGSF21 | RPS6KA6 | ZNF436 |
| RSPO1 | EGFLAM | FAM189A2 | IHH | RSPO1 | ZNF503 |
| RSPO4 | EGR4 | FAM196A | IKZF3 | RSPO2 | |
| S100A6 | EHD1 | FAM19A4 | IL10RA | RTN4RL2 | |
| SAMD7 | EIF3E | FAM201A | IL11 | RYR3 | |
| SATB2 | EIF3M | FAM210A | IL17D | SCD5 | |
| SCARNA6 | EIF4E3 | FAM212A | IL17RB | SCN4B | |
| SELL | ELAVL2 | FAM21A | IL1RAPL2 | SCNN1G | |
| SEMA3A | ELMOD1 | FAM21C | IL7 | SCTR | |
| SERPINB13 | ELOVL3 | FAM32A | ILDR2 | SEMA6D | |

Fig. 16-12

| | | | | |
|---|---|---|---|---|
| SERTAD1 | ELOVL7 | FAM43B | IMPDH1 | SERTM1 |
| SIM1 | ELP3 | FAM69C | INA | SFRP1 |
| SIRPB1 | EMC1 | FAM78B | INSM2 | SFRP5 |
| SIX6 | EMILIN2 | FAM83F | INSRR | SGPP2 |
| SKOR2 | EMX1 | FAM83H | INTS4L1 | SHC4 |
| SLC13A4 | EMX2 | FAM89A | IRF4 | SHH |
| SLC14A2 | EMX2OS | FAM95C | IRX1 | SHISA6 |
| SLC18A2 | EN1 | FASTK | IRX3 | SHOX |
| SLC22A9 | EN2 | FBLN7 | IRX4 | SHOX2 |
| SLC26A4 | ENTHD1 | FBXL16 | IRX5 | SIDT1 |
| SLC27A6 | ENTPD6 | FBXL20 | ISL1 | SIM2 |
| SLC28A3 | EOMES | FBXL8 | ISL2 | SIX1 |
| SLC4A11 | EPAS1 | FBXW2 | ITGA4 | SIX2 |
| SLC5A7 | EPB41L3 | FBXW7 | ITIH5 | SIX3 |
| SLC6A12 | EPB42 | FCER1G | ITPKA | SIX6 |
| SLC6A2 | EPHA10 | FCER2 | JUN | SLC10A4 |
| SLC6A20 | EPHA2 | FCHSD2 | KAZALD1 | SLC1A2 |
| SLC6A7 | EPHA3 | FCRL6 | KCNA1 | SLC1A4 |
| SLPI | EPHA5 | FCRLB | KCNA3 | SLC24A4 |
| SMC5 | EPHA8 | FENDRR | KCNA5 | SLC26A4 |
| SMC5-AS1 | EPO | FERD3L | KCNAB1 | SLC27A2 |
| SMUG1 | EPPIN | FEZF1 | KCNC2 | SLC30A2 |
| SNAR-A1 | EPPIN-WFDC6 | FEZF1-AS1 | KCNC4 | SLC30A3 |
| SNAR-A10 | ERAP1 | FEZF2 | KCND3 | SLC30A4 |
| SNAR-A11 | ERG | FFAR4 | KCNF1 | SLC32A1 |
| SNAR-A12 | ERICH1-AS1 | FGD2 | KCNH1 | SLC35F3 |
| SNAR-A13 | ERVMER34-1 | FGF1 | KCNH3 | SLC6A1 |
| SNAR-A14 | ESPN | FGF10 | KCNH7 | SLC6A3 |
| SNAR-A2 | ESPNL | FGF14 | KCNIP2 | SLC6A5 |
| SNAR-A3 | ESR1 | FGF17 | KCNIP4 | SLC9A2 |
| SNAR-A4 | ESRP1 | FGF19 | KCNJ10 | SLC9A3 |
| SNAR-A5 | ESRRG | FGF23 | KCNJ3 | SLCO2A1 |
| SNAR-A6 | ESX1 | FGF3 | KCNJ4 | SLCO5A1 |
| SNAR-A7 | ESYT3 | FGF5 | KCNJ9 | SLFN11 |
| SNAR-A8 | ETS1 | FGF7 | KCNK12 | SLIT1 |
| SNAR-A9 | EVA1A | FGF8 | KCNK13 | SLIT2 |
| SNAR-C1 | EVX1 | FGF9 | KCNK17 | SLITRK1 |
| SNAR-C2 | EVX2 | FGFR2 | KCNK2 | SLITRK3 |
| SNAR-C4 | EXOC3L2 | FGL2 | KCNK3 | SORCS1 |
| SNAR-C5 | EXOSC9 | FIBCD1 | KCNK4 | SORCS3 |
| SNHG7 | EYA2 | FIGLA | KCNMA1 | SOX14 |
| SNORA45 | F11R | FLI1 | KCNQ1 | SOX17 |
| SNORD113-6 | F13A1 | FLJ12825 | KCNQ3 | SOX7 |
| SNRPA1 | FADS6 | FLJ20518 | KCNQ5 | SPAG6 |
| SNX16 | FAHD1 | FLJ31813 | KCNS2 | SPOCK3 |

Fig. 16-13

| | | | | |
|---|---|---|---|---|
| SNX29P1 | FAIM | FLJ44511 | KCNS3 | SPON1 |
| SOX18 | FAM118B | FLRT2 | KCNV1 | SRD5A2 |
| SOX5 | FAM135B | FLT1 | KIAA1191 | SSTR1 |
| SOX8 | FAM150A | FLT3 | KIAA1199 | SSTR2 |
| SP6 | FAM150B | FLT4 | KIAA1324 | ST8SIA2 |
| SP8 | FAM155B | FNDC1 | KIRREL3 | STK32B |
| SPDEF | FAM159B | FNIP1 | KIRREL3-AS3 | STMN2 |
| SPDYE3 | FAM161A | FOXA1 | KISS1R | STXBP6 |
| SPERT | FAM163A | FOXA3 | KL | SUSD4 |
| SPINK8 | FAM189A2 | FOXB1 | KLF4 | SV2B |
| SPOCK3 | FAM196A | FOXB2 | KLHL1 | SYT12 |
| SRP9 | FAM19A4 | FOXC1 | KLHL13 | TAL1 |
| SRSF7 | FAM201A | FOXC2 | KLHL14 | TBR1 |
| SSTR1 | FAM210A | FOXD1 | KLHL17 | TBX1 |
| SSTR5 | FAM212A | FOXD2-AS1 | KLHL35 | TBX2 |
| ST14 | FAM21A | FOXD3 | KLK4 | TBX21 |
| ST5 | FAM21C | FOXD4 | KY | TBX3 |
| STX6 | FAM32A | FOXD4L2 | LAMB1 | TBX5 |
| SYCP1 | FAM43B | FOXD4L3 | LAYN | TCEA3 |
| TAAR1 | FAM69C | FOXD4L4 | LBX1 | TET2 |
| TAC1 | FAM78B | FOXD4L5 | LEF1 | TFAP2E |
| TAGAP | FAM83F | FOXD4L6 | LEKR1 | THBD |
| TAL1 | FAM83H | FOXE1 | LGALS3 | TLL1 |
| TARBP1 | FAM89A | FOXE3 | LGI3 | TLX1 |
| TAS2R39 | FAM95C | FOXF1 | LGR5 | TLX2 |
| TBC1D3 | FASTK | FOXF2 | LHFPL3 | TMEFF2 |
| TBC1D3C | FBLN7 | FOXG1 | LHX2 | TMEM132E |
| TBC1D3F | FBXL16 | FOXI2 | LHX3 | TMEM27 |
| TBC1D3H | FBXL20 | FOXI3 | LHX4 | TMEM30B |
| TBC1D3P5 | FBXL21 | FOXL1 | LHX5 | TMEM59L |
| TBX15 | FBXL8 | FOXL2 | LHX6 | TMEM88 |
| TBX4 | FBXW2 | FOXO3 | LHX8 | TMOD2 |
| TBX5 | FBXW7 | FOXP2 | LINC00268 | TP73 |
| TBX5-AS1 | FCER1G | FOXQ1 | LMO1 | TPPP3 |
| TCF21 | FCER2 | FREM3 | LMOD1 | TRADD |
| TES | FCGR1C | FRG2B | LMX1B | TRH |
| TFAP2A | FCHSD2 | FRG2C | LOC100131554 | TRIM36 |
| TFAP2B | FCRL6 | FRMD3 | LOC153684 | TRIM67 |
| TFAP2D | FCRLB | FRMD4B | LOC154761 | TRIM9 |
| TGM5 | FENDRR | FRMPD1 | LOC84931 | TRPC5 |
| TGM6 | FERD3L | FSHR | LONRF3 | TSLP |
| TIGD2 | FEV | FSIP2 | LPHN3 | TTYH1 |
| TMEM132B | FEZF1 | FST | LPL | UCN |
| TMEM174 | FEZF1-AS1 | FSTL4 | LPPR1 | UCP1 |
| TMEM45B | FEZF2 | FTCDNL1 | LRAT | UNC5C |

Fig. 16-14

| | | | | |
|---|---|---|---|---|
| TNFAIP2 | FFAR4 | FUOM | LRBA | USH1G |
| TNFSF11 | FGD2 | FUS | LRCH2 | VASH1 |
| TNS4 | FGF1 | FXYD2 | LRFN2 | VAX1 |
| TOB1 | FGF10 | FXYD5 | LRFN5 | VAX2 |
| TPI1P3 | FGF14 | FXYD7 | LRP2 | VDR |
| TPM3 | FGF17 | FZD10 | LRRC71 | VSX1 |
| TREML4 | FGF19 | FZD10-AS1 | LRRTM1 | VSX2 |
| TRPA1 | FGF23 | GAB3 | LTBP2 | WNT1 |
| UBC | FGF3 | GABPA | LTK | WNT10A |
| UCA1 | FGF4 | GABRA2 | LY6H | WNT10B |
| UPK1A-AS1 | FGF5 | GABRA4 | LYSMD2 | WNT11 |
| UPK3A | FGF7 | GABRB2 | MAB21L1 | WNT16 |
| USHBP1 | FGF8 | GABRE | MAB21L2 | WNT2 |
| USP16 | FGF9 | GAD2 | MADCAM1 | WNT3A |
| USP44 | FGFR2 | GADD45G | MAFB | WNT6 |
| USP46 | FGL2 | GAGE12F | MAL | WNT7A |
| USPL1 | FIBCD1 | GAGE12I | MAN1C1 | WRAP73 |
| VGLL2 | FIGLA | GAGE2A | MAP6 | WT1 |
| VSIG10L | FLI1 | GAGE2B | MAPK4 | WT1-AS |
| VSX1 | FLI1-AS1 | GAGE2C | MAPK8IP2 | ZADH2 |
| VSX2 | FLJ12825 | GAGE2E | MAPT | ZBTB16 |
| VTCN1 | FLJ20518 | GAGE4 | MAST4 | ZCCHC16 |
| WDR72 | FLJ31813 | GAGE5 | MCOLN3 | ZEB2 |
| WIPF3 | FLJ36000 | GAGE7 | MECOM | ZFHX3 |
| WNT10B | FLJ44511 | GAGE8 | MED31 | ZFYVE28 |
| WNT16 | FLRT2 | GAL | MEIS1 | ZIC1 |
| WNT8B | FLT1 | GALNT3 | MEOX2 | ZIC4 |
| WT1 | FLT3 | GALNT6 | MESP1 | ZMYND15 |
| WT1-AS | FLT4 | GALNT9 | METRNL | ZNF436 |
| XDH | FNDC1 | GALR1 | MFSD4 | ZNF503 |
| ZAN | FNIP1 | GALR2 | MGC39545 | |
| ZMYM3 | FOXA1 | GAN | MICB | |
| ZMYM4 | FOXA2 | GAP43 | MIR137HG | |
| ZNF260 | FOXA3 | GAS2 | MKX | |
| ZNF280A | FOXB1 | GATA3 | MLLT3 | |
| ZNF420 | FOXB2 | GATA3-AS1 | MLPH | |
| ZNF462 | FOXC1 | GATA4 | MLXIPL | |
| ZNF503-AS1 | FOXC2 | GATA5 | MMD2 | |
| ZNF534 | FOXD1 | GATA6 | MMP2 | |
| ZNF555 | FOXD2 | GATA6-AS1 | MNX1 | |
| ZNF676 | FOXD2-AS1 | GBX1 | MSC | |
| ZPBP2 | FOXD3 | GBX2 | MSX1 | |
| | FOXD4 | GCGR | MSX2 | |
| | FOXD4L1 | GCM2 | MT1A | |
| | FOXD4L2 | GDE1 | MT1B | |

Fig. 16-15

| | | | | | |
|---|---|---|---|---|---|
| FOXD4L3 | GDF6 | MT1DP | GAGE2A | GRIA2 | NKX6-2 |
| FOXD4L4 | GDF7 | MT1H | GAGE2B | GRID1 | NOC2L |
| FOXD4L5 | GET4 | MT1M | GAGE2C | GRIK3 | NOL4 |
| FOXD4L6 | GFI1B | MT3 | GAGE2E | GRIN1 | NOTUM |
| FOXE1 | GFRA1 | MXRA7 | GAGE4 | GRIN2C | NOVA2 |
| FOXE3 | GFRA4 | MYB | GAGE5 | GRIN3B | NOXO1 |
| FOXF1 | GGT8P | MYF6 | GAGE7 | GRM1 | NPAS1 |
| FOXF2 | GHR | MYO5B | GAGE8 | GRM6 | NPAS2 |
| FOXG1 | GHRL | MYOD1 | GAL | GRM7 | NPAS4 |
| FOXI2 | GHSR | NAGS | GALNT3 | GRM8 | NPNT |
| FOXI3 | GIMAP4 | NAV2 | GALNT6 | GRP | NPR1 |
| FOXL1 | GINS3 | NBL1 | GALNT9 | GSC | NPR3 |
| FOXL2 | GIPC1 | NBPF11 | GALR1 | GSC2 | NPTX1 |
| FOXO3 | GJA3 | NCAM1 | GALR2 | GSDMC | NPY1R |
| FOXP2 | GJB2 | NCCRP1 | GAN | GSG1L | NPY5R |
| FOXQ1 | GJB3 | NDRG1 | GAP43 | GSG2 | NR2E1 |
| FREM3 | GJB4 | NDUFA4L2 | GAS2 | GSTA3 | NR2F2 |
| FRG2B | GJB6 | NEFH | GATA2 | GSTZ1 | NR4A3 |
| FRG2C | GJD2 | NEFL | GATA3 | GSX1 | NRG1 |
| FRMD3 | GLB1L | NEFM | GATA3-AS1 | H1F0 | NRG2 |
| FRMD4B | GLB1L3 | NEGR1 | GATA4 | H1FX | NRGN |
| FRMPD1 | GLP1R | NELL1 | GATA5 | H1FX-AS1 | NRIP3 |
| FSHR | GLYAT | NEURL | GATA6 | H3F3B | NRN1 |
| FSIP2 | GMFB | NEUROD1 | GATA6-AS1 | HAND1 | NRXN1 |
| FST | GNAL | NEUROD2 | GBA | HAND2 | NT5C1A |
| FSTL4 | GNAS | NEUROG1 | GBX1 | HAND2-AS1 | NTN1 |
| FTCDNL1 | GNE | NEUROG2 | GBX2 | HAP1 | NTNG2 |
| FUOM | GNG13 | NEUROG3 | GCGR | HAPLN4 | NTRK1 |
| FUS | GNN | NFIA | GCM2 | HAUS2 | NTRK2 |
| FXYD2 | GOLGA3 | NFIC | GDE1 | HBM | NXPH4 |
| FXYD5 | GOLGA7B | NFIX | GDF6 | HBZ | O3FAR1 |
| FXYD7 | GPAM | NGF | GDF7 | HCFC2 | OAF |
| FZD10 | GPR101 | NGFR | GDNF | HCN4 | OCA2 |
| FZD10-AS1 | GPR139 | NIM1 | GDNF-AS1 | HCRTR2 | OLFML2B |
| GAB3 | GPR149 | NIN | GET4 | HCST | OLIG2 |
| GABPA | GPR158 | NKAIN2 | GFI1 | HDAC9 | OLIG3 |
| GABRA1 | GPR26 | NKPD1 | GFI1B | HDHD2 | ONECUT1 |
| GABRA2 | GPR27 | NKX2-1 | GFOD1 | HDLBP | ONECUT2 |
| GABRA4 | GPR50 | NKX2-2 | GFRA1 | HECW1 | OPRD1 |
| GABRB2 | GPR64 | NKX2-3 | GFRA4 | HELT | OSBP2 |
| GABRE | GPR78 | NKX2-5 | GGT8P | HERC4 | OSR1 |
| GAD2 | GPR88 | NKX2-8 | GHR | HERC5 | OSR2 |
| GADD45G | GRAP2 | NKX3-1 | GHRL | HES2 | OTOP1 |
| GAGE12F | GRB7 | NKX3-2 | GHSR | HES3 | OTOP2 |
| GAGE12I | GREM1 | NKX6-1 | GIMAP4 | HEY2 | OTOP3 |

Fig. 16-16

| | | | | | |
|---|---|---|---|---|---|
| GINS3 | HHEX | OTP | GRM4 | HPGD | PITX2 |
| GIPC1 | HHIP-AS1 | OTX1 | GRM6 | HPN-AS1 | PITX3 |
| GIPC2 | HHLA1 | OTX2 | GRM7 | HPSE | PKNOX2 |
| GJA3 | HIST1H1C | OVOL1 | GRM8 | HPSE2 | PKP1 |
| GJB2 | HIST1H1E | OXCT2 | GRP | HR | PLEC |
| GJB3 | HIST1H2AC | P2RX5 | GSC | HRC | PLLP |
| GJB4 | HIST1H2AE | PABPC1LA | GSC2 | HRH1 | PLP1 |
| GJB6 | HIST1H2BC | PADI2 | GSDMC | HRH2 | PLXNA2 |
| GJD2 | HIST1H2BG | PAPL | GSG1L | HRH3 | PLXNC1 |
| GLB1L | HIST1H3J | PAPPA | GSG2 | HRK | PMP22 |
| GLB1L3 | HLA-J | PARD3B | GSTA3 | HS3ST2 | PODN |
| GLIS1 | HLF | PARM1 | GSTZ1 | HS3ST3A1 | POLE |
| GLP1R | HLX | PARP8 | GSX1 | HS3ST3B1 | POLR3GL |
| GLYAT | HMBS | PAX1 | GSX2 | HS3ST4 | POMC |
| GMFB | HMGA2 | PAX2 | H1F0 | HS3ST6 | POU3F1 |
| GNAL | HMGCS1 | PAX3 | H1FX | HS6ST3 | POU3F2 |
| GNAS | HMGCS2 | PAX5 | H1FX-AS1 | HSF4 | POU3F4 |
| GNE | HMHA1 | PAX6 | H2AFX | HSP90AA1 | POU4F1 |
| GNG13 | HMX1 | PAX7 | H3F3B | HSP90B1 | POU4F2 |
| GNN | HMX2 | PAX8 | HAGH | HSP81 | POU4F3 |
| GOLGA3 | HMX3 | PAX9 | HAND1 | HSPH1 | PPM1E |
| GOLGA7B | HNRNPA1L2 | PCDH17 | HAND2 | HTR1A | PPP1R13B |
| GPAM | HOPX | PCDH8 | HAND2-AS1 | HTR1B | PPP1R14C |
| GPR101 | HOTAIRM1 | PCDHGC4 | HAP1 | HTR4 | PRAC |
| GPR139 | HOXA1 | PCGF5 | HAPLN4 | HTR6 | PRDM12 |
| GPR149 | HOXA11-AS | PCSK2 | HAUS2 | ICAM1 | PRDM13 |
| GPR158 | HOXA2 | PDE10A | HBA1 | ICAM5 | PRKAG2 |
| GPR26 | HOXA4 | PDE1B | HBA2 | ICOSLG | PRKCB |
| GPR27 | HOXA5 | PDE4DIP | HBM | ID3 | PRKCE |
| GPR4 | HOXA6 | PDE8A | HBZ | ID4 | PRKCH |
| GPR50 | HOXB3 | PDE8B | HCFC2 | IDO2 | PRKD1 |
| GPR64 | HOXB7 | PDGFRA | HCK | IFIH1 | PRKG1 |
| GPR78 | HOXB8 | PDX1 | HCN4 | IFITM10 | PRLHR |
| GPR88 | HOXB9 | PDZD2 | HCRTR2 | IFNG | PROK2 |
| GRAP2 | HOXC10 | PENK | HCST | IFNL4 | PRR18 |
| GRB7 | HOXC6 | PGM5 | HDAC9 | IFT27 | PRRT1 |
| GREM1 | HOXC9 | PGR | HDHD2 | IGF2-AS | PRSS12 |
| GRIA2 | HOXC-AS1 | PHLDB1 | HDLBP | IGFBP3 | PRUNE2 |
| GRID1 | HOXD11 | PHOX2A | HECW1 | IGFL1 | PSD2 |
| GRIK3 | HOXD13 | PHOX2B | HELT | IHH | PTF1A |
| GRIN1 | HOXD8 | PHYHIPL | HEMGN | IKZF1 | PTGDR |
| GRIN2C | HOXD9 | PIGZ | HERC4 | IKZF3 | PTGER2 |
| GRIN3A | HOXD-AS1 | PIP5K1B | HERC5 | IL10RA | PTGER3 |
| GRIN3B | HOXD-AS2 | PIR | HES2 | IL15RA | PTGER4 |
| GRM1 | HPCA | PITX1 | HES3 | IL17REL | PTGFR |

Fig. 16-17

| | | | | | |
|---|---|---|---|---|---|
| HEY2 | IL1F10 | PTH2 | HOXA9 | KCNA1 | RPRML |
| HHEX | IL1RAPL2 | PTHLH | HOXA-AS3 | KCNA10 | RPS6KA2 |
| HHIP-AS1 | IL20RA | PTPRN2 | HOXA-AS4 | KCNA2 | RPS6KA6 |
| HHLA1 | IL22RA2 | PTPRT | HOXB1 | KCNA5 | RSPO1 |
| HIST1H1A | IL6R | PTPRU | HOXB13 | KCNA7 | RSPO2 |
| HIST1H1C | IL7 | PXMP2 | HOXB2 | KCNAB1 | RSPO3 |
| HIST1H1D | IL9R | PYY | HOXB3 | KCNAB2 | RTBDN |
| HIST1H1E | ILF2 | RAB11FI3 | HOXB4 | KCNB2 | RTN4RL2 |
| HIST1H2AC | IMP3 | RAB33A | HOXB5 | KCNC4 | RUNX2 |
| HIST1H2AE | IMPACT | RAB40B | HOXB6 | KCNE2 | RXRG |
| HIST1H2BC | INCA1 | RAB6C | HOXB7 | KCNH2 | RYR3 |
| HIST1H2BG | INSL5 | RAB9B | HOXB8 | KCNH4 | SAMD11 |
| HIST1H3J | INSM1 | RAMP1 | HOXB9 | KCNH5 | SATB2 |
| HIST2H2AA3 | INSRR | RAPGEF4 | HOXB-AS1 | KCNIP2-AS1 | SCD5 |
| HIST2H2AA4 | INTS4L2 | RARA | HOXB-AS3 | KCNIP3 | SCIN |
| HIST2H2BC | INTS6 | RARRES2 | HOXC10 | KCNIP4 | SCN4B |
| HLA-J | INTS6-AS1 | RASGEF1C | HOXC11 | KCNJ12 | SCNN1G |
| HLF | INTS7 | RASGRF1 | HOXC12 | KCNJ5 | SCTR |
| HLX | IQGAP2 | RASL10A | HOXC13 | KCNK1 | SCUBE3 |
| HMBS | IQSEC2 | RASSF5 | HOXC4 | KCNK10 | SECTM1 |
| HMGA2 | IQSEC3 | RAX | HOXC5 | KCNK12 | SEMA3B |
| HMGCS1 | IRF5 | RBBP7 | HOXC6 | KCNK13 | SEMA4F |
| HMGCS2 | IRF8 | RBP4 | HOXC8 | KCNK15 | SEMA6D |
| HMHA1 | IRX1 | RBP7 | HOXC9 | KCNK17 | SERTM1 |
| HMX1 | IRX2 | RCSD1 | HOXC-AS1 | KCNK2 | SEZ6 |
| HMX2 | IRX3 | REEP1 | HOXC-AS2 | KCNK4 | SFRP1 |
| HMX3 | IRX5 | REPS2 | HOXC-AS5 | KCNK6 | SFRP4 |
| HNF1B | IRX6 | RFX4 | HOXD1 | KCNK9 | SFRP5 |
| HNRNPA1L2 | ISL1 | RFX6 | HOXD10 | KCNMA1 | SFTPC |
| HOPX | ISLR2 | RGAG4 | HOXD11 | KCNMB4 | SGPP2 |
| HOTAIR | ISM1 | RGS10 | HOXD12 | KCNN2 | SH3GL2 |
| HOTAIRM1 | ITGA11 | RGS20 | HOXD13 | KCNQ1 | SHC4 |
| HOTTIP | ITGA4 | RGS9 | HOXD3 | KCNQ3 | SHH |
| HOXA1 | ITGA8 | RGS9BP | HOXD4 | KCNS2 | SHISA6 |
| HOXA10 | ITGB2-AS1 | RIMBP3 | HOXD8 | KCNS3 | SHOX |
| HOXA10-HOXA9 | ITIH5 | RIMBP3B | HOXD9 | KCNV1 | SHOX2 |
| | | | HOXD-AS1 | KDM1A | SIDT1 |
| HOXA11 | ITPKA | RIMBP3C | HOXD-AS2 | KDM3B | SIM1 |
| HOXA11-AS | ITPR3 | RIMKLA | HPCA | KDM4A | SIM2 |
| HOXA13 | ITPRIPL1 | RIMS4 | HPGD | KDM4D | SIX1 |
| HOXA2 | IVNS1ABP | RIPK3 | HPN-AS1 | KIAA0087 | SIX2 |
| HOXA3 | JPH3 | RIPPLY2 | HPSE | KIAA0226L | SIX3 |
| HOXA4 | JUND | RNF128 | HPSE2 | KIAA1009 | SIX6 |
| HOXA5 | KANK4 | RNF2 | HR | KIAA1024 | SKAP1 |
| HOXA6 | KBTBD12 | RNPEPL1 | HRC | KIAA1211L | SLC10A4 |
| HOXA7 | KBTBD13 | ROBO3 | | | |

Fig. 16-18

| | | | | | |
|---|---|---|---|---|---|
| HRH1 | KIAA1244 | SLC16A11 | IL17REL | LASP1 | SOX17 |
| HRH2 | KIAA1324 | SLC17A6 | IL1F10 | LBH | SOX7 |
| HRH3 | KIF1C | SLC17A7 | IL1RAPL2 | LBX1 | SOX8 |
| HRK | KIF5B | SLC1A2 | IL20RA | LBX1-AS1 | SOX9 |
| HS3ST1 | KIRREL3 | SLC1A4 | IL22RA2 | LBX2-AS1 | SPAG6 |
| HS3ST2 | KIRREL3-AS3 | SLC22A3 | IL6R | LDB2 | SPOCK3 |
| HS3ST3A1 | KISS1R | SLC24A4 | IL7 | LEF1 | SPON1 |
| HS3ST3B1 | KIT | SLC25A27 | IL9R | LEF1-AS1 | SPON2 |
| HS3ST4 | KL | SLC26A4 | ILF2 | LEPR | SPTB |
| HS3ST6 | KLF1 | SLC26A5 | IMP3 | LFNG | SPTBN4 |
| HS6ST3 | KLF4 | SLC27A2 | IMPACT | LGALS4 | SRD5A2 |
| HSF4 | KLF6 | SLC30A10 | INCA1 | LGI1 | SRRM4 |
| HSP90AA1 | KLHDC9 | SLC30A2 | INSL5 | LGI3 | SSBP4 |
| HSP90B1 | KLHL24 | SLC30A3 | INSM1 | LGR5 | SSTR1 |
| HSPA5 | KLHL30 | SLC30A4 | INSRR | LGR6 | SSTR2 |
| HSPA6 | KLHL32 | SLC32A1 | INTS4L2 | LHFPL3 | ST8SIA2 |
| HSPB1 | KLHL35 | SLC35D3 | INTS6 | LHFPL4 | ST8SIA4 |
| HSPH1 | KLK1 | SLC35F3 | INTS6-AS1 | LHX1 | ST8SIA5 |
| HTR1A | KLK10 | SLC35G1 | INTS7 | LHX2 | STC2 |
| HTR1B | KLK13 | SLC40A1 | IQGAP2 | LHX3 | STK32B |
| HTR2C | KLK4 | SLC6A1 | IQSEC2 | LHX4 | STMN2 |
| HTR4 | KLK9 | SLC6A11 | IQSEC3 | LHX5 | STX1A |
| HTR6 | KLRG2 | SLC6A2 | IRF4 | LHX9 | STXBP6 |
| ICAM1 | KMT2A | SLC6A20 | IRF5 | LIAS | SUSD4 |
| ICAM4 | KNTC1 | SLC6A3 | IRF8 | LIF | SV2B |
| ICAM5 | KPNA4 | SLC6A5 | IRX1 | LILRA6 | SYNE1 |
| ICOSLG | KRT1 | SLC9A2 | IRX2 | LIMS2 | SYT12 |
| ID3 | KRT19 | SLC9A3 | IRX3 | LIN28A | SYT6 |
| ID4 | KRT19P2 | SLCO2A1 | IRX4 | LIN28B | SYT7 |
| IDO2 | KRT25 | SLCO3A1 | IRX5 | LINC00114 | T |
| IFIH1 | KRT36 | SLCO5A1 | IRX6 | LINC00115 | TAC1 |
| IFITM10 | KRT7 | SLFN11 | ISL1 | LINC00210 | TACR1 |
| IFNG | KRT71 | SLIT1 | ISL2 | LINC00221 | TACSTD2 |
| IFNL4 | KRT78 | SLIT2 | ISLR2 | LINC00222 | TAL1 |
| IFT27 | KRT83 | SLIT3 | ISM1 | LINC00261 | TAP1 |
| IGF2 | KRTAP13-1 | SLITRK1 | ITGA11 | LINC00273 | TBR1 |
| IGF2-AS | KRTAP5-9 | SLITRK3 | ITGA4 | LINC00461 | TBX1 |
| IGFBP3 | KRTCAP2 | SMOC2 | ITGA8 | LINC00466 | TBX2 |
| IGFL1 | L1CAM | SMPD3 | ITGB2 | LINC00473 | TBX20 |
| IGSF21 | LACE1 | SNAI2 | ITGB2-AS1 | LINC00475 | TBX21 |
| IHH | LAD1 | SNCAIP | ITIH5 | LINC00485 | TBX3 |
| IKZF1 | LAMB1 | SNTB1 | ITPKA | LINC00599 | TBX5 |
| IKZF3 | LAMP5 | SORCS1 | ITPR3 | LINC00608 | TBXAS1 |
| IL10RA | LARP1B | SORCS3 | ITPRIPL1 | LINC00617 | TCEA3 |
| IL15RA | LARS | SOX14 | IVNS1ABP | LINC00629 | TCEAL1 |

Fig. 16-19

| | | | | | |
|---|---|---|---|---|---|
| JPH3 | LINC00643 | TCEAL8 | KIAA0087 | LOC100506810 | TWIST1 |
| JUND | LINC00682 | TCF21 | KIAA0226L | LOC100653046 | UCN |
| KANK4 | LINC00693 | TCTE1 | KIAA1009 | LOC100996485 | UCP1 |
| KBTBD12 | LINC00707 | TET2 | KIAA1024 | LOC101054525 | ULBP1 |
| KBTBD13 | LINC00940 | TFAP2B | KIAA1211L | LOC145474 | ULBP2 |
| KCNA1 | LINC00943 | TFAP2D | KIAA1217 | LOC145845 | UNC5B |
| KCNA10 | LINC00951 | TFAP2E | KIAA1239 | LOC146513 | UNC5C |
| KCNA2 | LINC00960 | TGFA | KIAA1244 | LOC152578 | USH1G |
| KCNA5 | LINC00966 | THBD | KIAA1324 | LOC153684 | VASH1 |
| KCNA7 | LINC01024 | THBS2 | KIF1C | LOC283299 | VAV3 |
| KCNAB1 | LINC01081 | TIGD3 | KIF5B | LOC283731 | VAX1 |
| KCNAB2 | LINGO2 | TLE2 | KIRREL3 | LOC284395 | VAX2 |
| KCNB2 | LIPI | TLL1 | KIRREL3-AS3 | LOC284412 | VDR |
| KCNC4 | LIPJ | TLX1 | KISS1 | LOC284801 | VGLL2 |
| KCNE2 | LMTK3 | TLX2 | KISS1R | LOC285084 | VSX1 |
| KCNH2 | LMX1A | TLX3 | KIT | LOC285547 | VSX2 |
| KCNH4 | LMX1B | TMEFF2 | KL | LOC285548 | WNT1 |
| KCNH5 | LNX1 | TMEM106C | KLF1 | LOC340017 | WNT10A |
| KCNIP2-AS1 | LOC100128770 | TMEM132E | KLF14 | LOC348761 | WNT10B |
| KCNIP3 | LOC100129148 | TMEM151A | KLF4 | LOC375295 | WNT11 |
| KCNIP4 | LOC100129175 | TMEM163 | KLF6 | LOC388242 | WNT16 |
| KCNJ12 | LOC100129917 | TMEM185A | KLHDC9 | LOC389023 | WNT2 |
| KCNJ5 | LOC100130476 | TMEM27 | KLHL24 | LOC389895 | WNT3A |
| KCNK1 | LOC100130539 | TMEM30B | KLHL30 | LOC392232 | WNT5B |
| KCNK10 | LOC100130992 | TMEM54 | KLHL32 | LOC399829 | WNT6 |
| KCNK12 | LOC100131320 | TMEM59L | KLHL35 | LOC400043 | WNT7A |
| KCNK13 | LOC100132111 | TMEM88 | KLK1 | LOC400456 | WRAP73 |
| KCNK15 | LOC100132215 | TMOD2 | KLK10 | LOC401463 | WSCD1 |
| KCNK17 | LOC100132891 | TNFRSF1B | KLK13 | LOC402160 | WT1 |
| KCNK2 | LOC100134391 | TNFSF9 | KLK4 | LOC440461 | WT1-AS |
| KCNK4 | LOC100144602 | TP73 | KLK9 | LOC440896 | XYLT1 |
| KCNK6 | LOC100190940 | TPPP3 | KLRG2 | LOC440925 | YAF2 |
| KCNK9 | LOC100240734 | TRADD | KMT2A | LOC493754 | ZACN |
| KCNMA1 | LOC100240735 | TRH | KNTC1 | LOC613038 | ZADH2 |
| KCNMB4 | LOC100268168 | TRIM28 | KPNA2 | LOC63930 | ZBTB16 |
| KCNN2 | LOC100288069 | TRIM36 | KPNA4 | LOC642366 | ZBTB7A |
| KCNQ1 | LOC100288637 | TRIM67 | KRT1 | LOC643201 | ZCCHC16 |
| KCNQ3 | LOC100288748 | TRIM7 | KRT19 | LOC643837 | ZEB2 |
| KCNS2 | LOC100288842 | TRIM9 | KRT19P2 | LOC643923 | ZFHX3 |
| KCNS3 | LOC100288866 | TRPC5 | KRT25 | LOC648987 | ZFPM1 |
| KCNV1 | LOC100288911 | TSLP | KRT36 | LOC654342 | ZFYVE28 |
| KDM1A | LOC100505622 | TTLL7 | KRT7 | LOC728463 | ZIC1 |
| KDM3B | LOC100505782 | TTLL9 | KRT71 | LOC728739 | ZIC4 |
| KDM4A | LOC100506127 | TTPA | KRT76 | LOC728989 | ZMYND15 |
| KDM4D | LOC100506551 | TTYH1 | KRT78 | LOC729911 | ZNF436 |

Fig. 16-20

| | | | | |
|---|---|---|---|---|
| KRT83 | LONRF3 | ZNF503 | LIN28B | MECOM |
| KRTAP13-1 | LOR | | LINC00114 | MECR |
| KRTAP5-9 | LPIN1 | | LINC00115 | MED1 |
| KRTCAP2 | LPL | | LINC00210 | MED8 |
| L1CAM | LPPR4 | | LINC00221 | MEFV |
| L1TD1 | LRG1 | | LINC00222 | MEIS1 |
| LACE1 | LRRC18 | | LINC00261 | MEIS1-AS3 |
| LAD1 | LRRC38 | | LINC00273 | MEIS2 |
| LAMA3 | LRRC57 | | LINC00461 | MEOX2 |
| LAMB1 | LRRC71 | | LINC00466 | MEPCE |
| LAMP5 | LRRK1 | | LINC00473 | MESP1 |
| LARP1B | LSR | | LINC00475 | MET |
| LARS | LTA4H | | LINC00485 | METTL12 |
| LASP1 | LTBP2 | | LINC00489 | METTL25 |
| LBH | LTK | | LINC00554 | MFSD4 |
| LBX1 | LUZP2 | | LINC00599 | MGC12916 |
| LBX1-AS1 | LYSMD1 | | LINC00608 | MGC39584 |
| LBX2 | LYSMD2 | | LINC00617 | MGEA5 |
| LBX2-AS1 | MAB21L1 | | LINC00629 | MGME1 |
| LDB2 | MAB21L2 | | LINC00643 | MICAL2 |
| LEF1 | MAFB | | LINC00682 | MICB |
| LEF1-AS1 | MAGEC2 | | LINC00693 | MIR124-1 |
| LEPR | MAGED1 | | LINC00707 | MIR124-2 |
| LFNG | MAL | | LINC00910 | MIR124-3 |
| LGALS4 | MAL2 | | LINC00940 | MIR1247 |
| LGI1 | MANBAL | | LINC00943 | MIR1253 |
| LGI3 | MAP3K13 | | LINC00951 | MIR128-1 |
| LGR5 | MAPKAPK2 | | LINC00960 | MIR129-2 |
| LGR6 | MAPKAPK5 | | LINC00966 | MIR144 |
| LHFPL3 | MAPRE2 | | LINC01024 | MIR1469 |
| LHFPL4 | MAPT-AS1 | | LINC01081 | MIR183 |
| LHX1 | MAPT-IT1 | | LINGO2 | MIR188 |
| LHX2 | MATK | | LIPI | MIR190B |
| LHX3 | MBIP | | LIPJ | MIR203 |
| LHX4 | MBL2 | | LMF1 | MIR302F |
| LHX5 | MBNL3 | | LMTK3 | MIR3115 |
| LHX6 | MBP | | LMX1A | MIR3120 |
| LHX8 | MC5R | | LMX1B | MIR3188 |
| LHX9 | MCHR2 | | LNX1 | MIR3193 |
| LIAS | MCHR2-AS1 | | LOC100128770 | MIR3196 |
| LIF | MCIDAS | | LOC100129148 | MIR31HG |
| LILRA5 | MCOLN2 | | LOC100129175 | MIR34B |
| LILRA6 | MCOLN3 | | LOC100129917 | MIR34C |
| LIMS2 | MCRS1 | | LOC100130476 | MIR3545 |
| LIN28A | MDGA1 | | LOC100130539 | MIR3621 |

Fig. 16-21

| | | | | | |
|---|---|---|---|---|---|
| LOC100130992 | MIR3652 | LOC389895 | MKX | MAB21L2 | MYH10 |
| LOC100131320 | MIR3663 | LOC392232 | MLNR | MAFB | MYH11 |
| LOC100132111 | MIR3687 | LOC399829 | MLPH | MAGEC2 | MYH13 |
| LOC100132215 | MIR375 | LOC400043 | MLST8 | MAGED1 | MYO5B |
| LOC100132891 | MIR378D2 | LOC400456 | MLXIPL | MAL | MYOCD |
| LOC100134391 | MIR378E | LOC401463 | MME | MAL2 | MYOD1 |
| LOC100144602 | MIR424 | LOC402160 | MMP25 | MANBAL | MYRIP |
| LOC100190940 | MIR4287 | LOC440461 | MMP9 | MAP3K13 | MYT1 |
| LOC100240734 | MIR4297 | LOC440896 | MNAT1 | MAPKAPK2 | NAGK |
| LOC100240735 | MIR4304 | LOC440925 | MNX1-AS1 | MAPKAPK5 | NAGS |
| LOC100268168 | MIR4436A | LOC493754 | MOGAT3 | MAPRE2 | NAT10 |
| LOC100288069 | MIR4453 | LOC613038 | MOS | MAPT-AS1 | NAT16 |
| LOC100288637 | MIR4471 | LOC63930 | MOSPD2 | MAPT-IT1 | NAV1 |
| LOC100288748 | MIR4515 | LOC642366 | MOXD1 | MARCH11 | NBEA |
| LOC100288842 | MIR4520A | LOC643201 | MPP2 | MAST4 | NBEAP1 |
| LOC100288866 | MIR4520B | LOC643837 | MPP5 | MATK | NCCRP1 |
| LOC100288911 | MIR4634 | LOC643923 | MPZ | MBIP | NCLN |
| LOC100505622 | MIR4638 | LOC648987 | MPZL2 | MBL2 | NCOA7 |
| LOC100505782 | MIR4645 | LOC654342 | MRPL13 | MBNL3 | NCR1 |
| LOC100506127 | MIR4656 | LOC728463 | MRPL18 | MBP | NCR2 |
| LOC100506551 | MIR4700 | LOC728739 | MRPL22 | MC5R | NDP |
| LOC100506810 | MIR4732 | LOC728989 | MRPL33 | MCHR2 | NDRG1 |
| LOC100507003 | MIR4752 | LOC729911 | MRPL35 | MCHR2-AS1 | NEFH |
| LOC100653046 | MIR4770 | LONRF3 | MRPS14 | MCIDAS | NEFL |
| LOC100996485 | MIR4781 | LOR | MRTO4 | MCOLN2 | NELL1 |
| LOC101054525 | MIR4785 | LPAR3 | MRVI1-AS1 | MCOLN3 | NEUROD2 |
| LOC145474 | MIR4787 | LPIN1 | MSC | MCRS1 | NEUROG1 |
| LOC145845 | MIR4792 | LPL | MSMO1 | MDGA1 | NEUROG2 |
| LOC146513 | MIR483 | LPPR4 | MSX1 | MECOM | NEUROG3 |
| LOC152578 | MIR503 | LRG1 | MSX2 | MECR | NEXN |
| LOC153684 | MIR503HG | LRRC18 | MT1A | MED1 | NFE2L3 |
| LOC283299 | MIR5091 | LRRC26 | MT1B | MED8 | NFRKB |
| LOC283731 | MIR532 | LRRC38 | MT1DP | MEFV | NGB |
| LOC284395 | MIR548AO | LRRC57 | MT1E | MEIS1 | NGF |
| LOC284412 | MIR548N | LRRC71 | MT1F | MEIS1-AS3 | NGFR |
| LOC284801 | MIR5580 | LRRK1 | MT1H | MEIS2 | NHLH2 |
| LOC285084 | MIR598 | LSR | MT1JP | MEOX2 | NID2 |
| LOC285547 | MIR615 | LTA4H | MT1M | MEPCE | NKAIN4 |
| LOC285548 | MIR622 | LTBP2 | MTBP | MESP1 | NKX1-2 |
| LOC285696 | MIR632 | LTF | MTUS1 | MET | NKX2-1 |
| LOC340017 | MIR9-1 | LTK | MUC17 | METTL12 | NKX2-1-AS1 |
| LOC348761 | MIR933 | LUZP2 | MUSTN1 | METTL25 | NKX2-2 |
| LOC375295 | MIR936 | LYSMD1 | MXRA5 | MFSD4 | NKX2-3 |
| LOC388242 | MIR944 | LYSMD2 | MYCNOS | MGC12916 | NKX2-4 |
| LOC389023 | MIR96 | MAB21L1 | MYCT1 | MGC39584 | NKX2-5 |

Fig. 16-22

| | | | | | |
|---|---|---|---|---|---|
| MGEA5 | NKX2-6 | MIR4304 | NTF3 | MME | OR9I1 |
| MGME1 | NKX2-8 | MIR4436A | NTN4 | MMP25 | OSBPL10 |
| MICAL2 | NKX3-1 | MIR4453 | NTNG2 | MMP9 | OSR1 |
| MICB | NKX3-2 | MIR4471 | NTRK1 | MNAT1 | OSR2 |
| MIR10A | NKX6-1 | MIR4515 | NTSR1 | MNX1 | OTOP1 |
| MIR10B | NKX6-2 | MIR4520A | NUDT22 | MNX1-AS1 | OTOP2 |
| MIR124-1 | NMNAT3 | MIR4520B | NUFIP2 | MOGAT3 | OTOP3 |
| MIR124-2 | NMUR2 | MIR4634 | NUPL2 | MOS | OTP |
| MIR124-3 | NOC4L | MIR4638 | NUSAP1 | MOSPD2 | OTX1 |
| MIR1247 | NODAL | MIR4645 | NXPH1 | MOXD1 | OTX2 |
| MIR1253 | NOL3 | MIR4656 | NXPH2 | MPP2 | OVOL1 |
| MIR1258 | NOL7 | MIR4700 | NXPH3 | MPP5 | OXTR |
| MIR128-1 | NOS1 | MIR4727 | NXPH4 | MPZ | P2RX2 |
| MIR129-2 | NOTCH2NL | MIR4732 | NXT2 | MPZL2 | P4HA1 |
| MIR144 | NOTUM | MIR4752 | OIP5 | MRPL13 | PABPC1L2A |
| MIR1469 | NPAS1 | MIR4770 | OLFML2A | MRPL18 | PABPC1L2B |
| MIR183 | NPAS4 | MIR4781 | OLIG2 | MRPL22 | PADI2 |
| MIR188 | NPBWR1 | MIR4785 | OLIG3 | MRPL33 | PAK3 |
| MIR190B | NPHP4 | MIR4787 | ONECUT1 | MRPL35 | PANK3 |
| MIR196A1 | NPHS2 | MIR4792 | ONECUT2 | MRPS14 | PAPPA |
| MIR196A2 | NPNT | MIR4801 | ONECUT3 | MRTO4 | PAQR5 |
| MIR196B | NPPB | MIR483 | OPA1 | MRVI1-AS1 | PARP10 |
| MIR203 | NPPC | MIR503 | OPCML | MSC | PARP11 |
| MIR302F | NPR1 | MIR503HG | OPN1LW | MSMO1 | PARP2 |
| MIR3115 | NPR3 | MIR5091 | OPRD1 | MSX1 | PATE4 |
| MIR3120 | NPTX1 | MIR5188 | OPRK1 | MSX2 | PAX1 |
| MIR3131 | NPTX2 | MIR532 | OPRL1 | MSX2P1 | PAX2 |
| MIR3185 | NPW | MIR548AO | OPRM1 | MT1A | PAX4 |
| MIR3188 | NPY | MIR548N | OR10A6 | MT1B | PAX8 |
| MIR3193 | NPY5R | MIR5580 | OR10G2 | MT1DP | PAX9 |
| MIR3196 | NR0B1 | MIR598 | OR13C3 | MT1E | PCDH11X |
| MIR31HG | NR2E1 | MIR615 | OR13C5 | MT1F | PCDH11Y |
| MIR34B | NR2F2 | MIR622 | OR1F2P | MT1G | PCDH19 |
| MIR34C | NR2F2-AS1 | MIR632 | OR1G1 | MT1H | PCDH8 |
| MIR3545 | NR3C2 | MIR663A | OR2W5 | MT1JP | PCDH9 |
| MIR3621 | NR5A2 | MIR9-1 | OR4D1 | MT1M | PCED1B-AS1 |
| MIR3652 | NRG2 | MIR933 | OR4D2 | MTBP | PCP4L1 |
| MIR3663 | NRG3 | MIR936 | OR4D5 | MTUS1 | PCSK2 |
| MIR3687 | NRIP3 | MIR944 | OR4F15 | MUC12 | PCSK9 |
| MIR375 | NRK | MIR96 | OR5B12 | MUC17 | PDE1C |
| MIR378D2 | NRN1 | MKX | OR5H15 | MUSTN1 | PDE2A |
| MIR378E | NRSN1 | MLNR | OR6B2 | MXRA5 | PDE4B |
| MIR424 | NRXN1 | MLPH | OR6C68 | MYCNOS | PDE4D |
| MIR4287 | NRXN3 | MLST8 | OR6C76 | MYCT1 | PDGFA |
| MIR4297 | NT5E | MLXIPL | OR7D2 | MYH10 | PDGFB |

Fig. 16-23

| | | | | | |
|---|---|---|---|---|---|
| MYH11 | PDGFRA | NKX2-3 | POM121L2 | NRG3 | PRPF31 |
| MYH13 | PDLIM5 | NKX2-4 | POMC | NRIP3 | PRPH |
| MYO5B | PDP1 | NKX2-5 | POMT2 | NRK | PRR15 |
| MYOCD | PDX1 | NKX2-6 | POP4 | NRN1 | PRR21 |
| MYOD1 | PDX1-AS1 | NKX2-8 | POU1F1 | NRSN1 | PRRG1 |
| MYRIP | PDYN | NKX3-1 | POU2F2 | NRXN1 | PRRX1 |
| MYT1 | PENK | NKX3-2 | POU2F3 | NRXN3 | PRSS45 |
| NAGK | PEPD | NKX6-1 | POU3F4 | NSG1 | PRUNE2 |
| NAGS | PET117 | NKX6-2 | POU4F1 | NT5E | PSAP |
| NAT10 | PEX5L | NMNAT3 | POU4F2 | NTF3 | PSD2 |
| NAT16 | PGCP1 | NMUR2 | POU4F3 | NTN4 | PTAR1 |
| NAV1 | PGLS | NOC4L | PP12613 | NTNG2 | PTF1A |
| NBEA | PGM5 | NODAL | PPAPDC1A | NTRK1 | PTGDR |
| NBEAP1 | PGM5P2 | NOL3 | PPARG | NTSR1 | PTGER2 |
| NCCRP1 | PGR | NOL7 | PPFIBP2 | NUBPL | PTGER3 |
| NCLN | PGS1 | NOS1 | PPM1D | NUDT22 | PTGER4 |
| NCOA7 | PHOX2A | NOTCH2NL | PPM1J | NUFIP2 | PTGER4P2-CDK2AP2P2 |
| NCR1 | PID1 | NOTO | PPM1N | | |
| NCR2 | PIGV | NOTUM | PPP1R12B | NUPL2 | PTGS2 |
| NDP | PIK3CD | NPAS1 | PPP1R14C | NUSAP1 | PTH2 |
| NDRG1 | PIK3R1 | NPAS3 | PPP1R15A | NXPH1 | PTHLH |
| NDRG4 | PIK3R5 | NPAS4 | PPP6R3 | NXPH2 | PTK2B |
| NEFH | PINX1 | NPBWR1 | PRAC1 | NXPH3 | PTPN1 |
| NEFL | PIP4K2A | NPFFR1 | PRDM12 | NXPH4 | PTPN23 |
| NELL1 | PITX3 | NPHP4 | PRDM13 | NXT2 | PTPN3 |
| NEUROD1 | PKP2 | NPHS2 | PRDM6 | OIP5 | PTPN5 |
| NEUROD2 | PLA2G10 | NPNT | PRDM8 | OLFM3 | PTPRN |
| NEUROD4 | PLA2G2A | NPPB | PRDX3 | OLFML2A | PTPRT |
| NEUROG1 | PLAGL1 | NPPC | PRG2 | OLIG2 | PTRF |
| NEUROG2 | PLB1 | NPR1 | PRICKLE2-AS1 | OLIG3 | PUM1 |
| NEUROG3 | PLCG2 | NPR3 | PRIMA1 | ONECUT1 | PURA |
| NEXN | PLD1 | NPTX1 | PRKAB2 | ONECUT2 | PYDC1 |
| NFE2L3 | PLD5 | NPTX2 | PRKCB | ONECUT3 | PYY |
| NFIX | PLEKHA8 | NPW | PRKCH | OPA1 | QRFPR |
| NFRKB | PLEKHD1 | NPY | PRKCQ-AS1 | OPCML | QRSL1 |
| NGB | PLS3 | NPY5R | PRKG2 | OPN1LW | RAB37 |
| NGF | PLXDC1 | NR0B1 | PRKRIR | OPRD1 | RAB3B |
| NGFR | PMP22 | NR2E1 | PRLHR | OPRK1 | RAB6B |
| NHLH2 | PNOC | NR2F1 | PRMT3 | OPRL1 | RAB6C |
| NID2 | PNPLA5 | NR2F1-AS1 | PRMT8 | OPRM1 | RABGAP1L |
| NKAIN4 | POC1B | NR2F2 | PROK2 | OR10A6 | RACGAP1P |
| NKX1-2 | POC1B-GALNT4 | NR2F2-AS1 | PROKR1 | OR10G2 | RAD1 |
| NKX2-1 | POLR2A | NR3C2 | PROKR2 | OR13C3 | RAD51AP2 |
| NKX2-1-AS1 | POLR3A | NR5A2 | PROM1 | OR13C5 | RAD54B |
| NKX2-2 | POLR3E | NRG2 | PROX1 | OR1F2P | RAET1K |
| | | | | OR1G1 | RAI14 |

Fig. 16-24

| | | | | | |
|---|---|---|---|---|---|
| OR1I1 | RAI2 | PAX4 | RGS9BP | PID1 | RUNX1 |
| OR1L3 | RAPSN | PAX5 | RHOU | PIGV | RUNX1T1 |
| OR2W5 | RARB | PAX6 | RIPK1 | PIK3CD | RUNX3 |
| OR4B1 | RASEF | PAX7 | RIPK3 | PIK3R1 | RYR2 |
| OR4D1 | RASGEF1A | PAX8 | RIPK4 | PIK3R5 | S100A12 |
| OR4D2 | RASGRF1 | PAX9 | RNASE4 | PINX1 | S100A14 |
| OR4D5 | RASGRF2 | PAXBP1 | RND1 | PIP4K2A | S100A7 |
| OR4F15 | RASL11B | PCDH11X | RNF141 | PITX1 | S100A7A |
| OR5B12 | RASSF10 | PCDH11Y | RNF207 | PITX2 | S100A8 |
| OR5H15 | RASSF5 | PCDH19 | RNF220 | PITX3 | SAE1 |
| OR6B2 | RAX | PCDH8 | RNF6 | PKD2L1 | SALL1 |
| OR6C68 | RBFOX1 | PCDH9 | RNMT | PKP2 | SALL2 |
| OR6C76 | RBKS | PCED1B-AS1 | RNU11 | PLA2G10 | SAMD11 |
| OR7D2 | RBM11 | PCP4L1 | ROCK1P1 | PLA2G2A | SART1 |
| OR9I1 | RBM14 | PCSK2 | ROR1 | PLAGL1 | SATB1 |
| OSBPL10 | RBM14-RBM4 | PCSK9 | ROR2 | PLB1 | SATB2-AS1 |
| OSR1 | RBM20 | PDCL | RPF1 | PLCG2 | SCAMP5 |
| OSR2 | RBM4 | PDE1C | RPH3A | PLD1 | SCARNA10 |
| OTOP1 | RBM42 | PDE2A | RPL10A | PLD5 | SCGN |
| OTOP2 | RBMS1 | PDE4A | RPL23 | PLEKHA8 | SCN5A |
| OTOP3 | RBP4 | PDE4B | RPL26L1 | PLEKHD1 | SCNM1 |
| OTP | RBP7 | PDE4D | RPL27 | PLS3 | SCNN1B |
| OTX1 | RBPJ | PDE4DIP | RPL29 | PLXDC1 | SCP2 |
| OTX2 | RC3H2 | PDGFA | RPL31 | PMP22 | SCRIB |
| OTX2-AS1 | RDH13 | PDGFB | RPL34 | PNOC | SCRT1 |
| OVOL1 | RDH8 | PDGFRA | RPL34-AS1 | PNPLA5 | SCRT2 |
| OVOL2 | RDM1 | PDLIM5 | RPL5 | POC1B | SCTR |
| OXTR | REEP1 | PDP1 | RPL9 | POC1B-GALNT4 | SDE2 |
| P2RX2 | RELN | PDX1 | RPP25 | | |
| P4HA1 | RESP18 | PDX1-AS1 | RPPH1 | POLR2A | SDF2L1 |
| PABPC1L2A | RET | PDYN | RPRD2 | POLR3A | SEC16B |
| PABPC1L2B | RFC1 | PENK | RPS12 | POLR3E | SEC22A |
| PADI2 | RFPL2 | PEPD | RPS26 | POM121L2 | SEMA3F |
| PAK3 | RFPL4B | PET117 | RPS27 | POMC | SENP7 |
| PANK3 | RFTN2 | PEX5L | RPUSD4 | POMT2 | SERPINA7 |
| PAPL | RFX3 | PGCP1 | RRAS2 | POP4 | SERPINB6 |
| PAPPA | RFX6 | PGLS | RRP1 | POU1F1 | SERTAD4 |
| PAQR5 | RFX7 | PGM5 | RSPO2 | POU2F2 | SERTAD4-AS1 |
| PARP10 | RFXAP | PGM5-AS1 | RSPO3 | POU2F3 | SEZ6 |
| PARP11 | RGCC | PGM5P2 | RSRC1 | POU3F4 | SFMBT2 |
| PARP2 | RGL3 | PGR | RSRC2 | POU4F1 | SFRP1 |
| PATE4 | RGS10 | PGS1 | RTBDN | POU4F2 | SFRP5 |
| PAX1 | RGS6 | PHACTR3 | RTN2 | POU4F3 | SFTA3 |
| PAX2 | RGS7 | PHOX2A | RTN4IP1 | PP12613 | SFTPC |
| PAX3 | RGS7BP | PHOX2B | RTN4RL1 | PPAPDC1A | SGPP2 |
| | | | | PPARG | SH2D1B |

Fig. 16-25

| | | | | | |
|---|---|---|---|---|---|
| PPFIBP2 | SH2D3A | PRUNE2 | SLC26A5 | RASGRF1 | SNORA21 |
| PPIP5K1 | SH2D3C | PSAP | SLC30A2 | RASGRF2 | SNORA57 |
| PPM1D | SH3BP5 | PSD2 | SLC30A3 | RASL11B | SNORA76 |
| PPM1J | SH3GL2 | PTAR1 | SLC32A1 | RASSF10 | SNORD101 |
| PPM1N | SH3RF3 | PTF1A | SLC35D3 | RASSF5 | SNORD114-3 |
| PPP1R12B | SH3RF3-AS1 | PTGDR | SLC35F3 | RAX | SNORD114-4 |
| PPP1R14C | SHE | PTGER2 | SLC35F4 | RBFOX1 | SNORD116-28 |
| PPP1R15A | SHF | PTGER3 | SLC35F5 | RBKS | SNORD1A |
| PPP2R2C | SHH | PTGER4 | SLC38A3 | RBM11 | SNORD1B |
| PPP6R3 | SHISA2 | PTGER4P2-CDK2AP2P2 | SLC38A4 | RBM14 | SNTB1 |
| PRAC1 | SHISA3 | PTGS2 | SLC38A6 | RBM14-RBM4 | SNTG2 |
| PRAC2 | SHISA6 | PTH2 | SLC4A1 | RBM20 | SNX31 |
| PRDM12 | SHISA7 | PTHLH | SLC4A8 | RBM4 | SNX5 |
| PRDM13 | SHISA8 | PTK2B | SLC5A8 | RBM42 | SOCS2 |
| PRDM14 | SHISA9 | PTPN1 | SLC6A1 | RBMS1 | SOCS2-AS1 |
| PRDM6 | SHOX | PTPN23 | SLC6A11 | RBP4 | SORBS2 |
| PRDM8 | SHOX2 | PTPN3 | SLC6A17 | RBP7 | SORCS1 |
| PRDX3 | SIDT1 | PTPN5 | SLC6A3 | RBPJ | SORCS3 |
| PRG2 | SIGIRR | PTPRD | SLC6A4 | RC3H2 | SOWAHA |
| PRICKLE2-AS1 | SIGLEC14 | PTPRN | SLC6A5 | RDH13 | SOWAHB |
| PRIMA1 | SIGMAR1 | PTPRT | SLC7A10 | RDH8 | SOX1 |
| PRKAB2 | SIM2 | PTRF | SLC7A14 | RDM1 | SOX14 |
| PRKCB | SIX1 | PUM1 | SLC7A2 | REEP1 | SOX17 |
| PRKCH | SIX2 | PURA | SLC7A5P2 | RELN | SOX3 |
| PRKCQ-AS1 | SIX3 | PVALB | SLC8A3 | RESP18 | SOX7 |
| PRKCZ | SIX3-AS1 | PYDC1 | SLC9A2 | RET | SP5 |
| PRKG2 | SKAP1 | PYY | SLC9A3 | REXO1L2P | SP7 |
| PRKRIR | SKAP2 | QRFPR | SLCO4A1 | RFC1 | SP9 |
| PRLHR | SKOR1 | QRSL1 | SLCO5A1 | RFPL2 | SPAG6 |
| PRMT3 | SLC12A4 | RAB37 | SLFN11 | RFPL4B | SPATA2 |
| PRMT8 | SLC15A1 | RAB3B | SLFN12L | RFTN2 | SPATA31C1 |
| PROK2 | SLC16A12 | RAB6B | SLFN14 | RFX3 | SPATA31D4 |
| PROKR1 | SLC16A6 | RAB6C | SLIT3 | RFX6 | SPCS2 |
| PROKR2 | SLC17A6 | RABGAP1L | SLITRK3 | RFX7 | SPHKAP |
| PROM1 | SLC17A7 | RACGAP1P | SMAD5 | RFXAP | SPINT1 |
| PROX1 | SLC18A3 | RAD1 | SMDT1 | RGCC | SPNS2 |
| PRPF31 | SLC1A2 | RAD51AP2 | SMEK2 | RGL3 | SPOCK1 |
| PRPH | SLC22A31 | RAD54B | SMIM14 | RGS10 | SPON1 |
| PRR15 | SLC24A2 | RAET1K | SMOC2 | RGS6 | SPON2 |
| PRR21 | SLC24A3 | RAI14 | SNAP25 | RGS7 | SRC |
| PRRG1 | SLC24A4 | RAI2 | SNAP25-AS1 | RGS7BP | SRD5A2 |
| PRRX1 | SLC25A18 | RAPSN | SNAR-B1 | RGS9BP | SRGAP2-AS1 |
| PRSS16 | SLC25A48 | RARB | SNAR-B2 | RHOU | SRP68 |
| PRSS22 | SLC26A10 | RASEF | SND1-IT1 | RIPK1 | SRSF3 |
| PRSS45 | SLC26A4-AS1 | RASGEF1A | SNED1 | RIPK3 | SST |

Fig. 16-26

| | | | | | | |
|---|---|---|---|---|---|---|
| RIPK4 | SSTR2 | RTN2 | TBX1 | SFMBT2 | TMEM176B |
| RNASE4 | ST3GAL6-AS1 | RTN4IP1 | TBX18 | SFRP1 | TMEM18 |
| RND1 | ST6GAL1 | RTN4RL1 | TBX2 | SFRP5 | TMEM215 |
| RNF128 | ST6GAL2 | RUNX1 | TBX20 | SFTA3 | TMEM229A |
| RNF141 | ST6GALNAC1 | RUNX1T1 | TBX3 | SFTPC | TMEM229B |
| RNF207 | ST6GALNAC2 | RUNX3 | TC2N | SGPP2 | TMEM233 |
| RNF220 | ST8SIA5 | RYR2 | TCEAL6 | SH2D1B | TMEM235 |
| RNF6 | ST8SIA6 | S100A12 | TCERG1L | SH2D3A | TMEM30B |
| RNMT | STAC | S100A14 | TCF15 | SH2D3C | TMEM38B |
| RNPS1 | STAM | S100A7 | TCF24 | SH3BP5 | TMEM59 |
| RNU11 | STC2 | S100A7A | TCP1 | SH3GL2 | TMEM59L |
| ROBO3 | STK16 | S100A8 | TDGF1 | SH3RF3 | TMEM61 |
| ROCK1P1 | STK3 | SAE1 | TDP2 | SH3RF3-AS1 | TMEM66 |
| ROR1 | STMN2 | SALL1 | TDRD10 | SHE | TMEM79 |
| ROR2 | STX11 | SALL2 | TECTA | SHF | TMOD1 |
| RPF1 | STX8 | SAMD11 | TERF2 | SHH | TMOD2 |
| RPH3A | SUPT5H | SART1 | TESK1 | SHISA2 | TMPRSS2 |
| RPL10A | SURF6 | SATB1 | TEX10 | SHISA3 | TMX1 |
| RPL23 | SUSD4 | SATB2 | TFAP2A-AS1 | SHISA6 | TNFRSF11A |
| RPL26L1 | SUSD5 | SATB2-AS1 | TFAP2C | SHISA7 | TNFRSF19 |
| RPL27 | SUV420H2 | SCAMP5 | TFCP2L1 | SHISA8 | TNFRSF8 |
| RPL29 | SV2B | SCARNA10 | TFPT | SHISA9 | TNFSF9 |
| RPL31 | SV2C | SCGN | TGFA | SHOX | TNK1 |
| RPL34 | SYCP2L | SCN5A | TGFBI | SHOX2 | TOP1P2 |
| RPL34-AS1 | SYK | SCNM1 | TGFBR3L | SIDT1 | TP73 |
| RPL5 | SYMPK | SCNN1B | THBD | SIGIRR | TPBG |
| RPL9 | SYN3 | SCP2 | THRB | SIGLEC14 | TPR |
| RPP25 | SYNDIG1 | SCRIB | THRB-AS1 | SIGMAR1 | TPRKB |
| RPPH1 | SYNE1 | SCRT1 | THSD7B | SIM1 | TRABD2A |
| RPRD2 | SYNPR | SCRT2 | TIA1 | SIM2 | TRABD2B |
| RPS12 | SYT15 | SCTR | TIFAB | SIX1 | TRADD |
| RPS26 | SYT2 | SDE2 | TLE6 | SIX2 | TRH |
| RPS27 | SYT3 | SDF2L1 | TLL1 | SIX3 | TRHDE-AS1 |
| RPSAP52 | SYT6 | SEC16B | TLR2 | SIX3-AS1 | TRIM34 |
| RPUSD4 | SZT2 | SEC22A | TLX1 | SIX6 | TRIM35 |
| RRAD | T | SELL | TLX1NB | SKAP1 | TRIM36 |
| RRAS2 | TACR1 | SEMA3A | TLX2 | SKAP2 | TRIM41 |
| RRP1 | TARBP2 | SEMA3F | TLX3 | SKOR1 | TRIM46 |
| RSPO1 | TARS | SENP7 | TMEM132C | SKOR2 | TRIM54 |
| RSPO2 | TBC1D1 | SEPT2 | TMEM132D | SLC12A4 | TRIM67 |
| RSPO3 | TBC1D21 | SERPINA7 | TMEM132E | SLC15A1 | TRIM72 |
| RSPO4 | TBC1D30 | SERPINB6 | TMEM155 | SLC16A12 | TRMT5 |
| RSRC1 | TBC1D8B | SERTAD4 | TMEM163 | SLC16A6 | TRPC5 |
| RSRC2 | TBCCD1 | SERTAD4-AS1 | TMEM171 | SLC17A6 | TRPC6 |
| RTBDN | TBR1 | SEZ6 | TMEM176A | SLC17A7 | TRPM4 |

Fig. 16-27

| | | | | | |
|---|---|---|---|---|---|
| SLC18A2 | TRPT1 | SLCO4A1 | VRK3 | SNTB1 | ZFYVE28 |
| SLC18A3 | TSC22D2 | SLCO5A1 | VSIG2 | SNTG2 | ZIC1 |
| SLC1A2 | TSGA13 | SLFN11 | VSTM2B | SNX16 | ZIC2 |
| SLC22A31 | TSLP | SLFN12L | VTRNA2-1 | SNX31 | ZIC3 |
| SLC24A2 | TSPEAR | SLFN14 | VWA2 | SNX5 | ZIC4 |
| SLC24A3 | TTC39A | SLIT3 | VWA5B2 | SOCS2 | ZIC5 |
| SLC24A4 | TTLL6 | SLITRK3 | VWC2 | SOCS2-AS1 | ZMYND15 |
| SLC25A18 | TUBA4A | SMAD5 | VWC2L-IT1 | SORBS2 | ZNF106 |
| SLC25A48 | TUBA4B | SMDT1 | WASH2P | SORCS1 | ZNF207 |
| SLC26A10 | TWIST1 | SMEK2 | WBSCR17 | SORCS3 | ZNF259 |
| SLC26A4 | UBASH3B | SMIM14 | WDR16 | SOWAHA | ZNF385B |
| SLC26A4-AS1 | UBE2D3 | SMOC2 | WDR33 | SOWAHB | ZNF436 |
| SLC26A5 | UBE2F | SMUG1 | WDR4 | SOX1 | ZNF471 |
| SLC27A6 | UBE2F-SCLY | SNAP25 | WIF1 | SOX14 | ZNF473 |
| SLC30A2 | UBE4A | SNAP25-AS1 | WLS | SOX17 | ZNF484 |
| SLC30A3 | UBTD2 | SNAR-A1 | WNT1 | SOX18 | ZNF503 |
| SLC32A1 | UCN | SNAR-A10 | WNT10A | SOX3 | ZNF503-AS2 |
| SLC35D3 | UCP1 | SNAR-A11 | WNT11 | SOX5 | ZNF546 |
| SLC35F3 | UG0898H09 | SNAR-A14 | WNT2 | SOX7 | ZNF706 |
| SLC35F4 | ULBP1 | SNAR-A2 | WNT2B | SOX8 | ZNF77 |
| SLC35F5 | ULBP2 | SNAR-A3 | WNT3 | SP5 | ZNF775 |
| SLC38A3 | UNC5A | SNAR-A4 | WNT3A | SP6 | ZNF804B |
| SLC38A4 | UNC5B-AS1 | SNAR-A5 | WNT6 | SP7 | ZNF827 |
| SLC38A6 | UNC5C | SNAR-A6 | WNT7A | SP8 | ZNF830 |
| SLC4A1 | UNC5D | SNAR-A7 | WNT7B | SP9 | ZNF860 |
| SLC4A11 | UNCX | SNAR-A8 | WNT9B | SPAG6 | ZSCAN5B |
| SLC4A8 | UPB1 | SNAR-A9 | WRAP73 | SPATA2 | ZSWIM6 |
| SLC5A7 | UQCRC2 | SNAR-B1 | WTH3DI | SPATA31C1 | |
| SLC5A8 | USH1G | SNAR-B2 | XIRP1 | SPATA31D4 | |
| SLC6A1 | USP42 | SNAR-C1 | XKR7 | SPCS2 | |
| SLC6A11 | USP50 | SNAR-C2 | XRRA1 | SPHKAP | |
| SLC6A17 | UTF1 | SNAR-C5 | YBX3P1 | SPINT1 | |
| SLC6A2 | UTRN | SND1-IT1 | YWHAE | SPNS2 | |
| SLC6A20 | VAV3-AS1 | SNED1 | ZACN | SPOCK1 | |
| SLC6A3 | VAX1 | SNHG7 | ZBTB4 | SPON1 | |
| SLC6A4 | VAX2 | SNORA21 | ZCCHC16 | SPON2 | |
| SLC6A5 | VDR | SNORA57 | ZCWPW1 | SRC | |
| SLC6A7 | VENTX | SNORA76 | ZDHHC22 | SRD5A2 | |
| SLC7A10 | VGF | SNORD101 | ZDHHC5 | SRGAP2-AS1 | |
| SLC7A14 | VGLL4 | SNORD114-3 | ZFAND5 | SRP68 | |
| SLC7A2 | VIPR1 | SNORD114-4 | ZFHX3 | SRSF3 | |
| SLC7A5P2 | VIPR2 | SNORD116-28 | ZFP91 | SRSF7 | |
| SLC8A3 | VMA21 | SNORD1A | ZFP91-CNTF | SST | |
| SLC9A2 | VPS33A | SNORD1B | ZFPL1 | SSTR1 | |
| SLC9A3 | VPS51 | SNRPA1 | ZFPM2 | SSTR2 | |

Fig. 16-28

| | | | | | | |
|---|---|---|---|---|---|---|
| SSTR5 | TBC1D21 | THRB-AS1 | TP73 | UNC5A | WNT10A | |
| ST14 | TBC1D3 | THSD7B | TPBG | UNC5B-AS1 | WNT10B | |
| ST3GAL6-AS1 | TBC1D30 | TIA1 | TPM3 | UNC5C | WNT11 | |
| ST5 | TBC1D3C | TIFAB | TPR | UNC5D | WNT16 | |
| ST6GAL1 | TBC1D3F | TLE6 | TPRKB | UNCX | WNT2 | |
| ST6GAL2 | TBC1D3H | TLL1 | TRABD2A | UPB1 | WNT2B | |
| ST6GALNAC1 | TBC1D8B | TLR2 | TRABD2B | UQCRC2 | WNT3 | |
| ST6GALNAC2 | TBCCD1 | TLX1 | TRADD | USH1G | WNT3A | |
| ST8SIA5 | TBR1 | TLX1NB | TRH | USP42 | WNT6 | |
| ST8SIA6 | TBX1 | TLX2 | TRHDE-AS1 | USP44 | WNT7A | |
| STAC | TBX15 | TLX3 | TRIM34 | USP50 | WNT7B | |
| STAM | TBX18 | TMEM132C | TRIM35 | USPL1 | WNT8B | |
| STC2 | TBX2 | TMEM132D | TRIM36 | UTF1 | WNT9B | |
| STK16 | TBX20 | TMEM132E | TRIM41 | UTRN | WRAP73 | |
| STK3 | TBX3 | TMEM155 | TRIM46 | VAV3-AS1 | WT1 | |
| STMN2 | TBX4 | TMEM163 | TRIM54 | VAX1 | WT1-AS | |
| STX11 | TBX5 | TMEM171 | TRIM67 | VAX2 | WTH3DI | |
| STX6 | TBX5-AS1 | TMEM176A | TRIM72 | VDR | XIRP1 | |
| STX8 | TC2N | TMEM176B | TRMT5 | VENTX | XKR7 | |
| SUPT5H | TCEAL6 | TMEM18 | TRPA1 | VGF | XRRA1 | |
| SURF6 | TCERG1L | TMEM215 | TRPC5 | VGLL2 | YBX3P1 | |
| SUSD4 | TCF15 | TMEM229A | TRPC6 | VGLL4 | YWHAE | |
| SUSD5 | TCF21 | TMEM229B | TRPM4 | VIPR1 | ZACN | |
| SUV420H2 | TCF24 | TMEM233 | TRPT1 | VIPR2 | ZBTB4 | |
| SV2B | TCP1 | TMEM235 | TSC22D2 | VMA21 | ZCCHC16 | |
| SV2C | TDGF1 | TMEM30B | TSGA13 | VPS33A | ZCWPW1 | |
| SYCP2L | TDP2 | TMEM38B | TSLP | VPS51 | ZDHHC22 | ZNF436 |
| SYK | TDRD10 | TMEM45B | TSPEAR | VRK3 | ZDHHC5 | ZNF462 |
| SYMPK | TECTA | TMEM59 | TTC39A | VSIG2 | ZFAND5 | ZNF471 |
| SYN3 | TERF2 | TMEM59L | TTLL6 | VSTM2B | ZFHX3 | ZNF473 |
| SYNDIG1 | TESK1 | TMEM61 | TUBA4A | VSX1 | ZFP91 | ZNF484 |
| SYNE1 | TEX10 | TMEM66 | TUBA4B | VSX2 | ZFP91-CNTF | ZNF503 |
| SYNPR | TFAP2A | TMEM79 | TWIST1 | VTRNA2-1 | ZFPL1 | ZNF503-AS2 |
| SYT15 | TFAP2A-AS1 | TMOD1 | UBASH3B | VWA2 | ZFPM2 | ZNF546 |
| SYT2 | TFAP2B | TMOD2 | UBC | VWA5B2 | ZFYVE28 | ZNF555 |
| SYT3 | TFAP2C | TMPRSS2 | UBE2D3 | VWC2 | ZIC1 | ZNF706 |
| SYT6 | TFAP2D | TMX1 | UBE2F | VWC2L-IT1 | ZIC2 | ZNF77 |
| SZT2 | TFCP2L1 | TNFRSF11A | UBE2F-SCLY | WASH2P | ZIC3 | ZNF775 |
| T | TFPT | TNFRSF19 | UBE4A | WBSCR17 | ZIC4 | ZNF804B |
| TAC1 | TGFA | TNFRSF8 | UBTD2 | WDR16 | ZIC5 | ZNF827 |
| TACR1 | TGFBI | TNFSF11 | UCN | WDR33 | ZMYND15 | ZNF830 |
| TAL1 | TGFBR3L | TNFSF9 | UCP1 | WDR4 | ZNF106 | ZNF860 |
| TARBP2 | TGM5 | TNK1 | UG0898H09 | WIF1 | ZNF207 | ZSCAN5B |
| TARS | THBD | TNS4 | ULBP1 | WLS | ZNF259 | ZSWIM6 |
| TBC1D1 | THRB | TOP1P2 | ULBP2 | WNT1 | ZNF385B | |

Fig. 16-29

| Name | IC50 (-log mM) | | |
|---|---|---|---|
| | Normal | P5K | Δ |
| MI-2 (hydrochloride) | 2.18 | 3.81 | 1.64 |
| Sinefungin | <1.5 | 2.43 | 0.93 |
| CAY10591 | 1.95 | 2.55 | 0.60 |
| MS-275 | 1.87 | 2.46 | 0.59 |
| Tubastatin A (trifluoroacetate salt) | 1.61 | 2.07 | 0.46 |
| Tenovin-6 | 2.53 | 2.82 | 0.30 |
| Decitabine | <1.5 | 1.80 | 0.30 |
| (−)-Neplanocin A | <1.5 | 1.68 | 0.18 |
| UNC0224 | 2.49 | 2.61 | 0.12 |
| 4-iodo-SAHA | 2.31 | 2.41 | 0.10 |
| HC Toxin | 3.07 | 3.17 | 0.09 |
| AGK2 | 2.06 | 2.12 | 0.06 |
| UNC0638 | 2.54 | 2.59 | 0.05 |
| CAY10398 | 2.47 | 2.49 | 0.02 |
| Piceatannol | 1.94 | 1.94 | 0.00 |
| Apicidin | 2.90 | 2.89 | -0.01 |
| SB 939 | 2.73 | 2.71 | -0.02 |
| Trichostatin A | 2.75 | 2.68 | -0.08 |
| M 344 | 2.50 | 2.40 | -0.10 |
| Suberohydroxamic Acid | 2.18 | 2.07 | -0.11 |
| SAHA | 2.38 | 2.23 | -0.15 |
| Chidamide | 2.51 | 2.28 | -0.23 |
| 2,4-Pyridinedicarboxylic Acid | 1.75 | <1.5 | -0.25 |
| (S)-HDAC-42 | 2.58 | 2.32 | -0.27 |
| Ellagic Acid | 2.07 | <1.5 | -0.57 |
| Mirin | 2.65 | 2.07 | -0.58 |
| Oxamflatin | 2.10 | <1.5 | -0.60 |
| Pyroxamide | 2.13 | <1.5 | -0.63 |
| Tenovin-1 | 2.14 | <1.5 | -0.64 |
| (−)-JQ1 | <1.5 | <1.5 | NA |
| (+)-JQ1 | <1.5 | <1.5 | NA |
| 2',3',5'-triacetyl-5-Azacytidine | <1.5 | <1.5 | NA |
| 2,4-DPD | <1.5 | <1.5 | NA |
| 2-PCPA (hydrochloride) | <1.5 | <1.5 | NA |
| 3-amino Benzamide | <1.5 | <1.5 | NA |
| 3-Deazaneplanocin A | <1.5 | <1.5 | NA |
| 5-Azacytidine | <1.5 | <1.5 | NA |
| AG-014699 | <1.5 | <1.5 | NA |
| AMI-1 (sodium salt) | <1.5 | <1.5 | NA |

Fig. 17

| | | | |
|---|---|---|---|
| Anacardic Acid | <1.5 | <1.5 | NA |
| BSI-201 | <1.5 | <1.5 | NA |
| C646 | <1.5 | <1.5 | NA |
| CAY10433 | <1.5 | <1.5 | NA |
| CAY10603 | <1.5 | <1.5 | NA |
| CBHA | <1.5 | <1.5 | NA |
| Cl-Amidine | <1.5 | <1.5 | NA |
| Daminozide | <1.5 | <1.5 | NA |
| Delphinidin chloride | <1.5 | <1.5 | NA |
| DMOG | <1.5 | <1.5 | NA |
| EX-527 | <1.5 | <1.5 | NA |
| F-Amidine (trifluoroacetate salt) | <1.5 | <1.5 | NA |
| Garcinol | <1.5 | <1.5 | NA |
| Gemcitabine | <1.5 | <1.5 | NA |
| GSK-J1 (sodium salt) | <1.5 | <1.5 | NA |
| GSK-J4 (hydrochloride) | <1.5 | <1.5 | NA |
| HNHA | <1.5 | <1.5 | NA |
| IOX1 | <1.5 | <1.5 | NA |
| Isoliquiritigenin | <1.5 | <1.5 | NA |
| JGB1741 | <1.5 | <1.5 | NA |
| Lomeguatrib | <1.5 | <1.5 | NA |
| MI-nc (hydrochloride) | <1.5 | <1.5 | NA |
| Nicotinamide | <1.5 | <1.5 | NA |
| N-Oxalylglycine | <1.5 | <1.5 | NA |
| PCI 4051 | <1.5 | <1.5 | NA |
| PFI-1 | <1.5 | <1.5 | NA |
| Phthalazinone pyrazole | <1.5 | <1.5 | NA |
| Pimelic Diphenylamide 106 | <1.5 | <1.5 | NA |
| RG-108 | <1.5 | <1.5 | NA |
| S-Adenosylhomocysteine | <1.5 | <1.5 | NA |
| Salermide | <1.5 | <1.5 | NA |
| Scriptaid | <1.5 | <1.5 | NA |
| Sirtinol | <1.5 | <1.5 | NA |
| Sodium Butyrate | <1.5 | <1.5 | NA |
| Splitomicin | <1.5 | <1.5 | NA |
| Suramin (sodium salt) | <1.5 | <1.5 | NA |
| trans-Resveratrol | <1.5 | <1.5 | NA |
| UNC0321 (trifluoroacetate salt) | <1.5 | <1.5 | NA |
| UNC1215 | <1.5 | <1.5 | NA |
| Valproic Acid (sodium salt) | <1.5 | <1.5 | NA |
| Zebularine | <1.5 | <1.5 | NA |

Fig. 17 (Continued)

shRNA target sequences

| Name | Target Sequence | SEQ ID NO: |
| --- | --- | --- |
| shLuc | CTTACGCTGAGTACTTCGA | 1 |
| sh-p53 | GACTCCAGTGGTAATCTACT | 2 |
| sh-p53#2 | GTAATCTACTGGGACGGAA | 3 |
| shLIN28B#1 | GCAGGCATAATAAGCAAGTTA | 4 |
| shLIN28B#3 | GGATTCATCTCCATGATAAAC | 5 |
| shPLAG1#1 | GGAAGAAGCACATTCTTCTGT | 6 |
| shPLAG1#2 | GCAAGAACTACAATACCAAGC | 7 |
| shPLAGL1#1 | GAGAAGACGTTCAACCGGAAA | 8 |
| shPLAGL1#2 | GTCAGTTACAATATGAGAAAG | 9 |
| shMEN1#1 | GATCTACAAGGAGTTCTTTGA | 10 |
| shMEN1#2 | GAGTACAGTCTGTATCAAACC | 11 |

Primer sequences

| Name | Sequence | SEQ ID NO: |
| --- | --- | --- |
| LIN28BFw | GAAGACCCAAAGGGAAGACAC | 12 |
| LIN28BRv | TTCTTTGGCTGAGGAGGTAGA | 13 |
| PLAG1Fw | ATTGTGATCGCCGGTTCTAC | 14 |
| PLAG1_Rv | ATCCTTTCGCCCAAATCTCT | 15 |
| PLAGL1Fw | CAGACCGGAGACCTTCTGAG | 16 |
| PLAGL1Rv | TCTGGGCAGAAGCTCCTAAA | 17 |
| Nkx2-2_Fw | AGTACCCTGCACGGTCTG | 18 |
| Nkx2-2Rv | GGGTCTCCTTGTCATTGTCC | 19 |
| MBPFw | CCCACATGTAGTAAGCCACTC | 20 |
| MBPRv | TGTCCTTCTCTCACCTCCTAAA | 21 |
| ActinFw | ACCCATCGAGCACGGCATCG | 22 |
| ActinRv | GTCACCGGAGTCCATCACGATG | 23 |
| MEN1Fw | TCCAGTCCCTCTTCAGCTTC | 24 |
| MEN1Rv | ACCACAGCAAAGGCCACAC | 25 |

Fig. 18

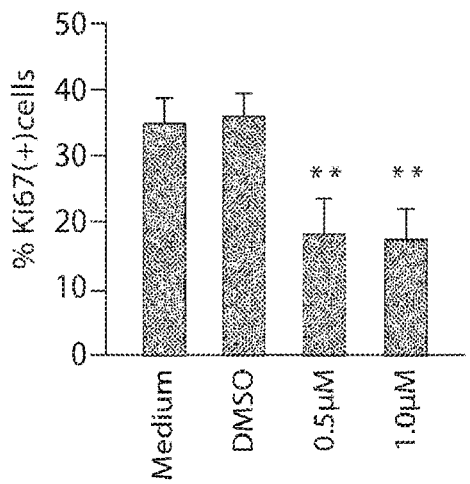
Fig. 27E
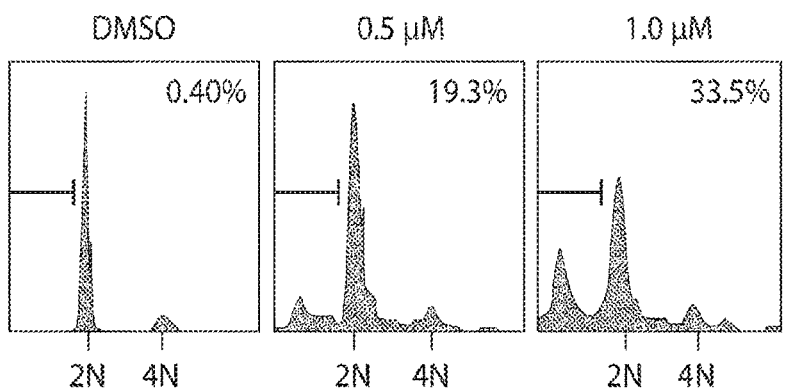
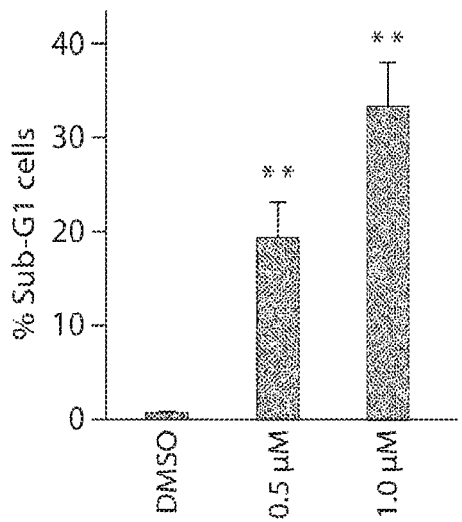
Fig. 27F

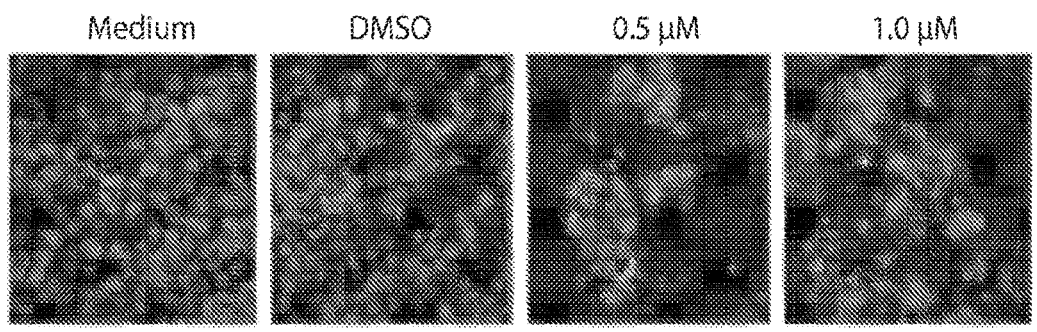
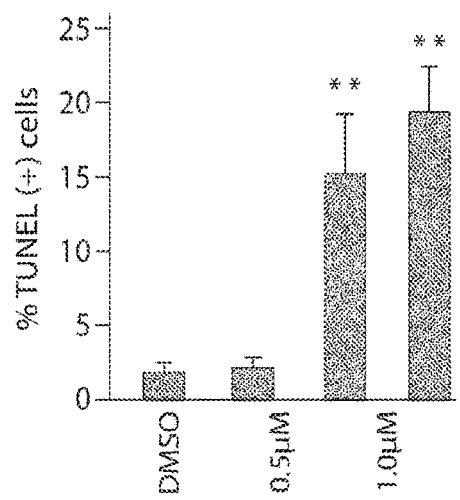
Fig. 27G
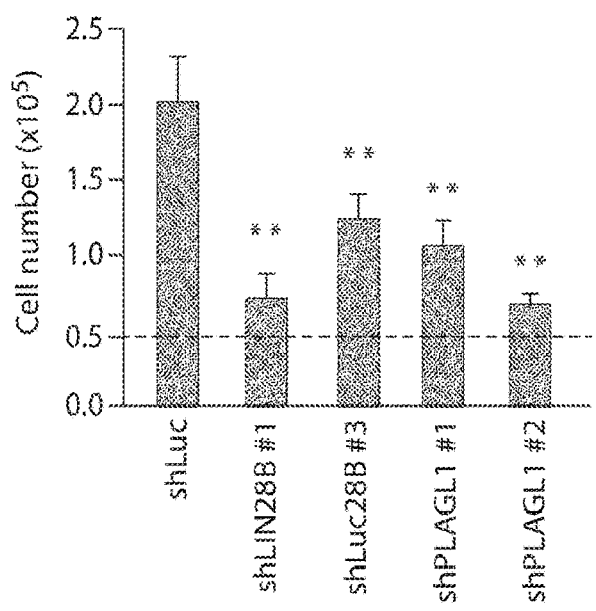
Fig. 27H

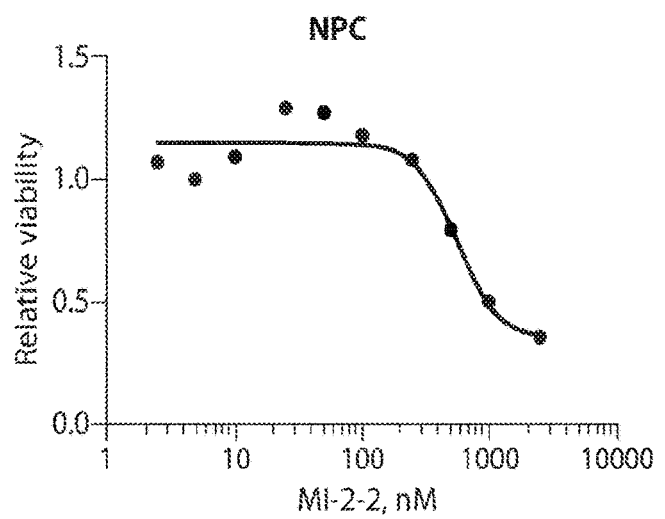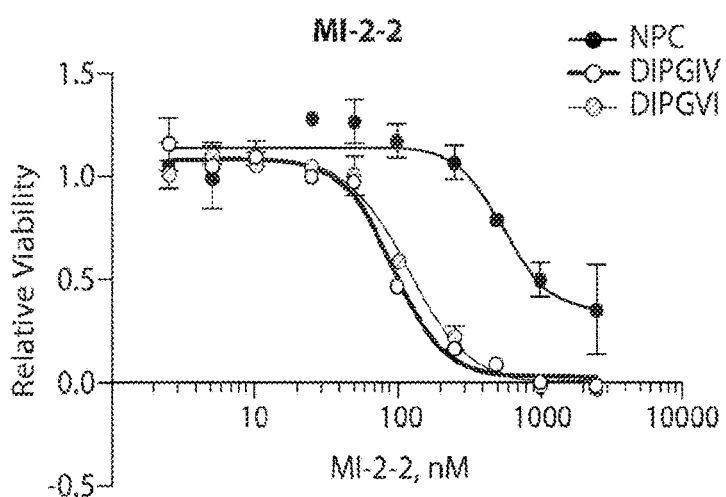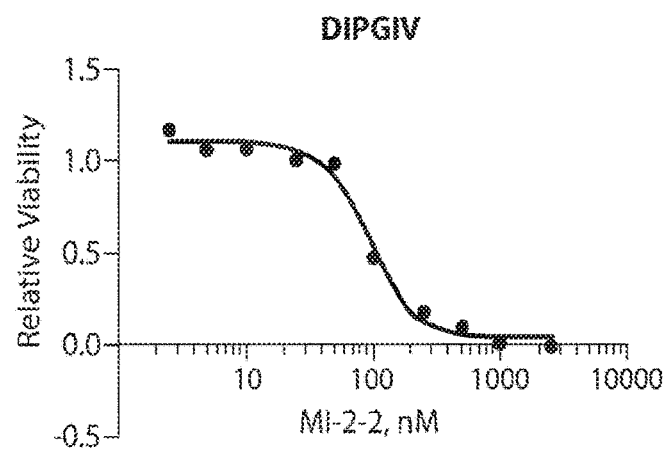
Fig. 29

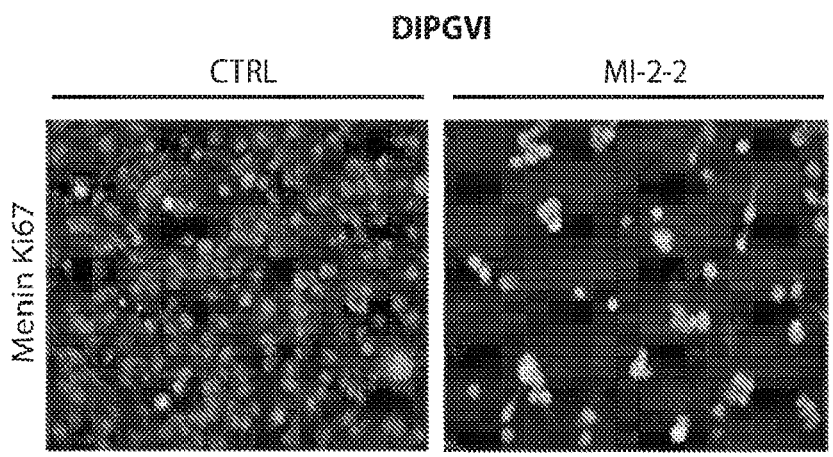
Fig. 30A
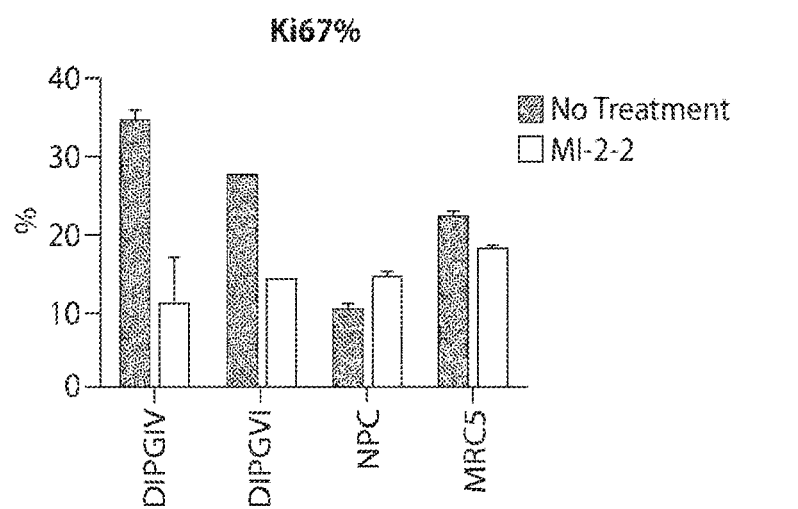
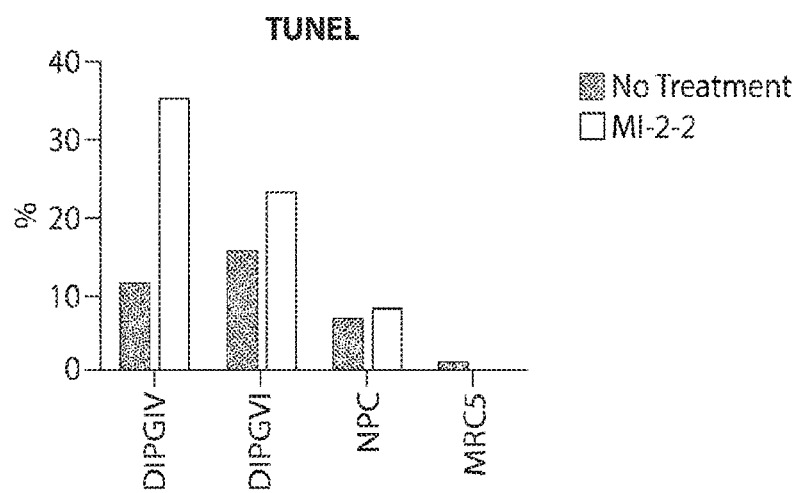
Fig. 30B

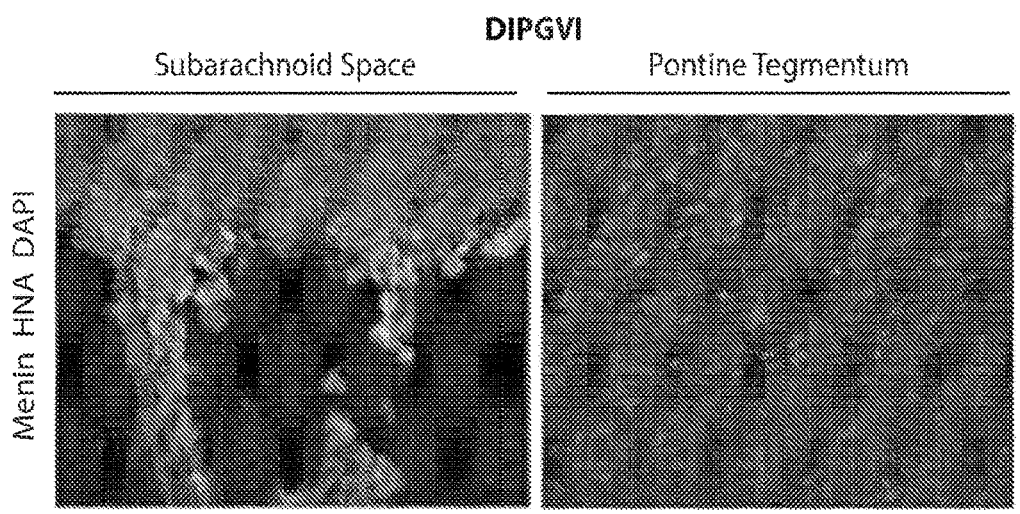
Fig. 36A
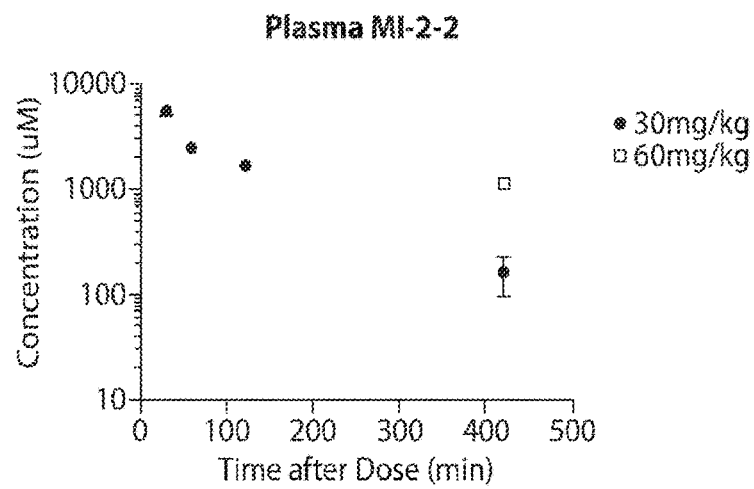
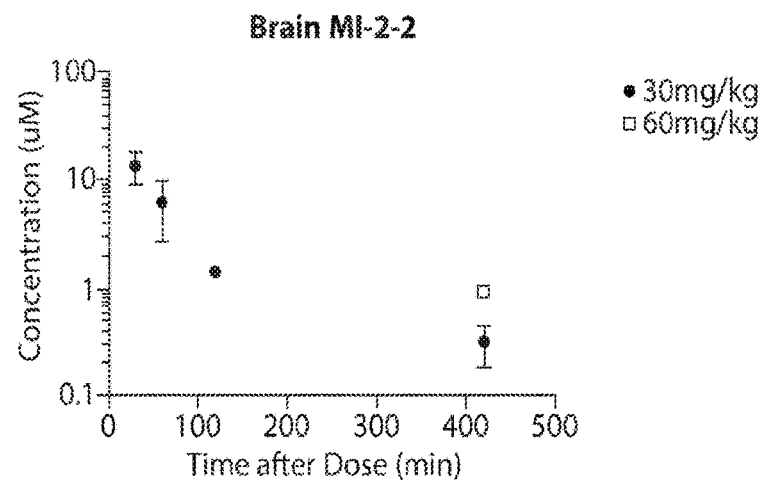
Fig. 36B

THIENOPYRIMIDINES AND USES THEREOF

RELATED APPLICATIONS

The present application is a national stage filing under 35 U.S.C. § 371 of international PCT application, PCT/US2015/061594, filed Nov. 19, 2015, which claims priority under 35 U.S.C. § 119(e) to U.S. provisional patent application, U.S. Ser. No. 62/081,984, filed Nov. 19, 2014, each of which is incorporated herein by reference.

BACKGROUND OF THE INVENTION

A brain tumor is an abnormal growth occurring in any tissue contained within the cranium, including the brain, cranial nerves, meninges, skull, pituitary gland, and pineal gland (Kabitha, *Int. J. Pharm. Chem. Bio. Sci.* 2013, 1165-1171). These tumors are inherently difficult to cure because of their protected location in the brain, with surgery, radiation and chemotherapy options carrying potentially lasting morbidity for patients and incomplete cure of the tumor. Brain tumors are life threatening because the space inside the skull is limited, their growth increases intracranial pressure, and may cause edema, reduced blood flow, and displacement with consequent degeneration of healthy tissue that controls vital functions. Brain tumors are, in fact, the second leading cause of cancer-related deaths in children and young adults. Diffuse Intrinsic Pontine Gliomas (DIPGs) are highly aggressive tumors of childhood, often located in the pons. Their impact is devastating in view of their anatomic location and poor outcome. Recent DIPG exome sequencing revealed frequent mutations (>70%) in the H3F3A or HIST1H3B genes encoding histone H3.3 and H3.1, respectively (1-3). Mutated tumors are associated with poorer prognosis and diminished survival, compared to "wild type" DIPG tumors. Accordingly, there is an urgent need to develop new therapies to treat brain tumors.

SUMMARY OF THE INVENTION

Brain tumors account for 85% to 90% of all primary central nervous system (CNS) tumors (Mehta, *Principles and Practice of Oncology.* 9th ed., 2011, pp 1700-49). Brain tumors represent a unique challenge in that each area of the brain serves a different but vital function (Kabitha, *Int. J. Pharm. Chem. Bio. Sci.* 2013, 1165-1171). The therapy that is most effective for other cancers—surgical removal of either the entire organ or the tumor with a generous amount of surrounding normal tissue—cannot be used to treat brain tumors. Therefore, the present invention provides new therapies for treating brain tumors (e.g., DIPGs).

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The inventive compounds have been found to be useful for the treatment of cancers, such as brain cancer (e.g., DIPG), in a subject.

In one aspect, the present invention provides compounds of Formula (I):

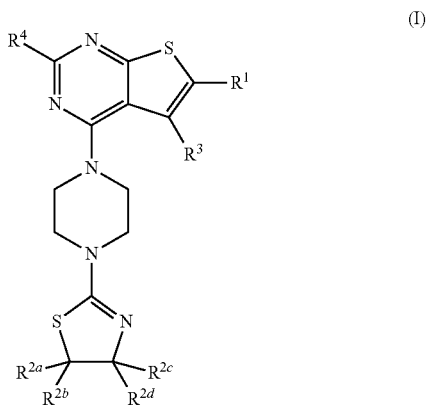

and pharmaceutically acceptable salts, solvates, hydrates, polymorphs, co-crystals, tautomers, stereoisomers, isotopically labeled derivatives, and prodrug thereofs, wherein $R^1$, $R^{2a}$, $R^{2b}$, $R^{2c}$, $R^{2d}$, $R^3$, and $R^4$ are as defined herein.

In another aspect, the present invention provides pharmaceutical compositions comprising a compound of Formula (I), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, polymorph, co-crystal, tautomer, stereoisomer, isotopically labeled derivative, or prodrug thereof. The pharmaceutical composition may be useful for treating and/or preventing brain tumors.

In another aspect, the present invention provides methods for treating and/or preventing a cancer such as brain tumors.

In another aspect, the invention relates to methods of inhibiting the activity of menin in a biological sample or subject.

In another aspect, the invention relates to methods of inhibiting cell growth in a biological sample or subject.

In another aspect, the invention relates to methods of inducing apoptosis of a cell in a biological sample or subject.

In another aspect, the invention relates to a platform assay useful in identifying candidate compounds for treating prolierative diseases such as cancer (e.g., brain tumor). This platform assay involves a genetically engineered precursor cell, for example, neural precursor cell (NPC), which is derived from embryonic stem cells (e.g., human embryonic stem cells) and comprises one or more oncogenes. In some embodiments, the genetically engineered precursor cell is a NPC that comprises a first oncogene encoding a mutant histone H3 (e.g., the K27M mutant), a second oncogene encoding a constitutively active form of PDGFRA (e.g., the D842V mutant), or a combination thereof. Alternatively or in addition, the genetically engineered precursor cell has a reduced p53 activity as compared to a wild-type counterpart. For example, the genetically engineered precursor cell may express a small intering RNA (e.g., a small hairpin RNA) that targets p53.

Any of the genetically engineered precursor cells described herein can be used in screening for drug candidates for treating a prolierative disease, such as cancer. Such a screening method may comprise (i) contacting the genetically engineered precursor cell as described herein with a test agent; and (ii) identifying the test agent as an agent for treating cancer (e.g., brain tumor) if the test agent inhibits growth of the genetically engineered precursor cell. In certain embodiments, the cancer is brain tumor.

In another aspect, the invention relates to a method of identifying a compound for treating cancer (e.g., brain tumor) comprising providing a sample comprising menin; contacting a test agent with the sample; and identifying the test agent as an agent for treating cancer if the test agent inhibits the activity of menin. In certain embodiments, the cancer is a brain tumor.

In another aspect, the present invention provides kits comprising a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment of cancer (e.g., a brain tumor). In certain embodiments, the kits described herein further include instructions for administering the compound of Formula (I), or the pharmaceutically acceptable salt, solvate, hydrate, polymorph, co-crystal, tautomer, stereoisomer, isotopically labeled derivative, or prodrug thereof, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is unspecified (e.g., —CH=CHCH₃ or

)

may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "carbocyclyl" or "carbocyclic" refers to a radical of a nonaromatic cyclic hydrocarbon group having from 3 to 14 ring carbon atoms ("$C_{3-14}$ carbocyclyl") and zero heteroatoms in the nonaromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b] pyranyl, 5,7-dihydro-4H-thieno[2,3-c]pyranyl, 2,3-dihydro-1H-pyrrolo[2,3-b]pyridinyl, 2,3-dihydrofuro[2,3-b] pyridinyl, 4,5,6,7-tetrahydro-1H-pyrrolo[2,3-b]pyridinyl, 4,5,6,7-tetra-hydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6,10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_{2OR}$$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-m}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, hetero C$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)

$SR^{aa}$, —OC(=O)$R^{aa}$, —OCO$_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)$R^{aa}$, —OSO$_2R^{aa}$, —OSi($R^{aa}$)$_3$, —OP($R^{cc}$)$_2$, —OP($R^{cc}$)$_3$, —OP(=O)$_2R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$X$^-$, wherein $R^{bb}$ and X$^-$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_{2OR}^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_{2OR}^{cc}$, —SO$R^{aa}$, —C(=S)N($R^{cc}$)$_2$, —C(=O)S$R^{cc}$, —C(=S)S$R^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBDTmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DBtBOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (tBumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxolcyclohexenyl)amine, N-borane derivative, N-diphenylborinic acid derivative, N-[phenyl(pentaacylchromium or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, onitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (pAOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxylnapththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrates, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2$H_2O$) and hexahydrates (R.6$H_2O$)).

As used herein, the term "tautomer" includes two or more interconvertable forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable minor images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds which have cleavable groups and become by solvolysis or under physiological conditions the compounds of Formula (I) which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middleaged adult, or senior adult)) and/or other nonhuman animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A nonhuman animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I) refers to an amount sufficient to elicit a desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" of a compound of Formula (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrm's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g.,bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

As used herein "inhibition", "inhibiting", "inhibit" and "inhibitor", and the like, refer to the ability of a compound to reduce, slow, halt, or prevent the activity of a particular biological process involving a protein, enzyme, or pathway in a cell relative to vehicle.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

BRIEF DESCRIPTION OF THE DRAWINGS

FIG. 1A is a schematic representation of the strategy to transform human ESC-derived neural precursors (NPC), using a combination of lentiviral vectors that express H3.3 WT or K27M, PDGFRA and shp53. FIG. 1B depicts the immunohistochemistry of NPCs that were transduced with different vector combinations and demonstrate maintenance of SOX2 and Nestin expression. Expression of K27M is associated with significantly reduced H3K27 trimethylation mark (H3K27me3). Ki67 immunopositivity depicts proliferation and is most elevated in the K27M, PDGFRA, and sh-p53 conditions. Scale bar, 50 µm. FIG. 1C shows the western blot of transduced NPCs. Total lysates and acid-extracted histones were separated by SDS-PAGE and blotted with the indicated antibodies. *, higher bands indicate hemagglutinin (HA)-tagged histone H3.3 transgene. FIG. 1D shows the quantification of Ki67 immunostaining in NPCs transfected with K27M+/−PDGFRA and sh-p53. FIG. 1E illustrates Ki67 levels in NPCs transfected with the K27M, G34R, or G34V mutations. FIG. 1F shows the impact of the K27M mutation on the proliferation index of various indicated cell lines. Error bars in FIGS. 1D and 1F indicate mean±S.D. (n=4~5 in each). *, p<0.05; **, p<0.01.

FIGS. 2A-2N show the synergistic effect of K27M and oncogenes in inducing transformation and tumorigenicity of NPCs. FIGS. 2A and 2B show the bright phase microscopy of transduced NPCs grown at very low density for 4 weeks and stained with crystal violet (B, insert). P5, P5W, and P5K indicate PDGFRA (D842V)+sh-p53, P5+WT histone H3.3 and P5+K27M mutant, respectively. The number of viable cells was counted by trypan-blue staining. Bars indicate mean±S.D. (n=4). FIG. 2I shows that the transcranial injection of P5K cells into the brainstem of mice led to tumor formation, while P5W cells gave rise to isolated cell clusters. Low magnification immunofluorescence images of representative sections labeled for human specific nuclear antigen (HNA) and counter-stained with DAPI. FIG. 2J is a summary of transplantation and tumor formation. FIG. 2K shows the light microscopy of H&E representative sections taken from the pons of a mouse bearing P5K tumors demonstrate encasement of the basilar artery (arrow) by tumor cells, microcystic change and infiltration in the pons. Scale bar, 500 µm (left panel), 100µ (right panel). FIGS. 2L-2N show the immunophenotyping of transplanted animals. Immunofluorescence images and quantification for HNA, Ki67 (FIGS. 2L and 2M), SOX2 (FIGS. 2L and 2N), and human-specific Nestin (FIG. 2L). Bars in FIGS. 2M and 2N indicate mean±S.E.M. *, p<0.05; **, p<0.01. NS, Not Significant. ND, Not Detected.

FIGS. 3A-3B show the unsupervised hierarchical clustering and principal component analysis (PCA) of microarray data. FIG. 3C depicts a hierarchical clustering of microarray data from P5K cells and reported patient tumor samples bearing the K27M or G34R/V mutations (GSE34824) obtained from Schwartzentruber et al. "Driver mutations in histone H3.3 and chromatin remodeling genes in paediatric glioblastoma", Nature 2012, 482, 226-231. FIG. 3D shows RT-qPCR demonstrating increased expression levels of LIN28B, PLAG1 and PLAGL1 in the P5K cells. Bars indicate mean±S.E.M. (n=4-6). FIG. 3E is a boxplot showing the expression levels of the indicated genes in patient tumor samples. FIG. 3F illustrates that a knockdown of LIN28B and PLAGL1 reduced the number of viable cells in P5K cells. P5W and P5K cells were infected with the indicated shRNA-expressing lentiviruses. Viability was assayed by trypan-blue following 6 days in vitro. Values are normalized to control shRNA (shLuc) and log transformed. Bars indicate mean±S.E.M. (n=3~6). FIGS. 3G-3I show the chromatin landscape of transformed cells. P5K cells showed evidence of global decrease in H3K27M, but enrichment at the gene body or promoter regions of select genes as shown in representative profiles in (FIG. 3G, H3K4me3 in red and H3K27me3 in blue). In FIG. 3H, profiles of H3K4me3 and H3K27me3 marks over the upregulated (91 genes) or downregulated (80 genes) by K27M (FIG. 14) are shown. Blue, P5W cells; red, P5K cells. Arrows indicate the peak of signal intensity. FIG. 3I shows the levels of H3K4me3 and H3K27me3 marks at the promoter region (+1 kb~500 bp) of the genes differentially regulated by K27M. P-values were calculated by the Wilcoxon rank-sum test. FIG. 3J shows Venn diagrams comparing genes that are marked by H3K27me3 or bound by PRC2. *, p<0.05; **, p<0.01. NS, Not Significant.

FIGS. 4A-I show a chemical screen of the transformed NPCs. FIG. 4A presents a schematic representation of the screening strategy. A mixture of GFP-labeled normal NPCs and RFP-labeled P5K cells in a 1:3 ratio were plated into 96-well plates and each compound in the library was added in a 2-fold serial dilution for a total of 8 doses. FIG. 4B depicts the IC50 calculated for each compound after 6 days in vitro, using a fluorescence plate reader. FIG. 4C shows representative dose response curves in normal NPCs (Mock, blue), P5W (green) and P5K (red) cells treated with Sunitinib, MI-2 or MI-nc (MI-2 analog) show selectivity of MI-2, a menin inhibitor. Error bars indicate S.D. (n=4). Viability (FIG. 4D) and proliferation (FIG. 4E) assays demonstrate a significant effect of MI-2 on P5K cells, with no impact on normal or P5W cells. Bars indicate mean±S.D. (n=4). FIG. 4F illustrates that MI-2 treatment induced cell death in P5K cells. After 6 days of treatment, the percentage of sub-G1 fraction was measured by FACS analysis. FIGS. 4G and 4H show that the silencing of menin via shRNA also decreased the proliferation of P5K cells. Menin knockdown was confirmed by western blotting (FIG. 4G), and proliferation was assessed by Ki67 staining (FIG. 4H). FIG. 4I shows that the knockdown of menin suppressed in vivo growth of P5K cells. Intracranial growth of Luciferase-labeled P5K cells, transduced with control or menin shRNA-expressing (shMEN1) lentivirus, was measured by quantitative in vivo bioluminescence imaging (IVIS). *, $p<0.05$; **, $p<0.01$. NS, Not Significant. Structures of MI-2 and MI-nc are as follows:

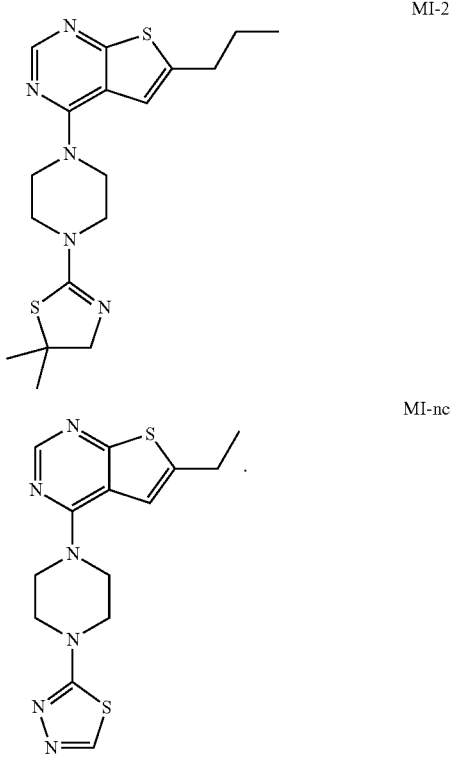

Figure 5A:
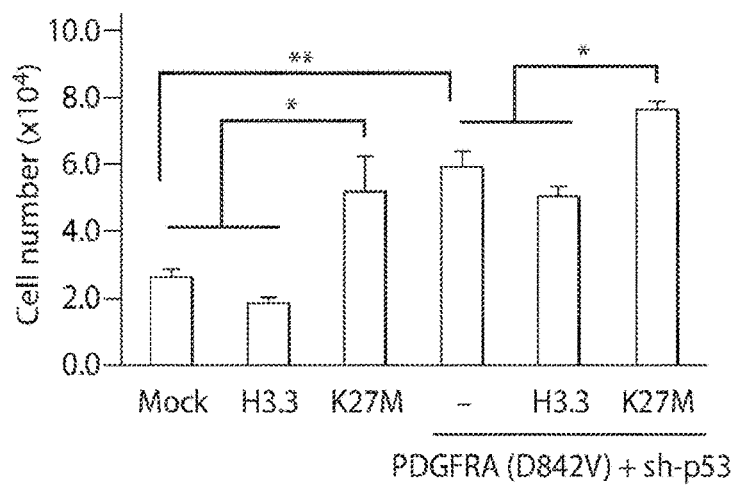
Figure 5B:
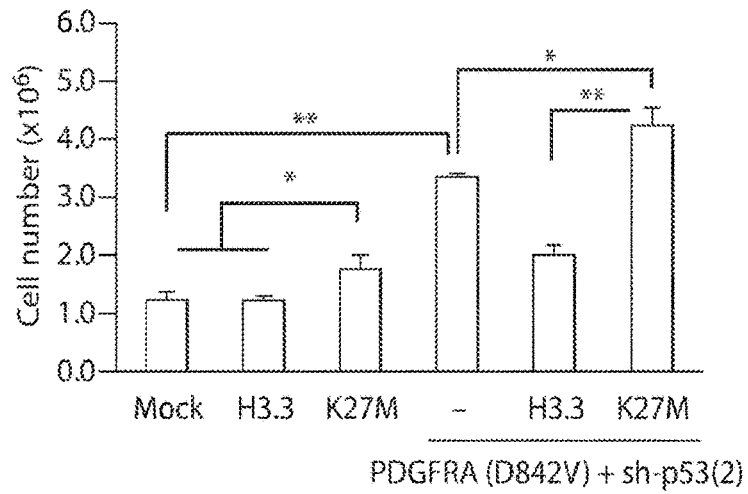
Figure 5C:
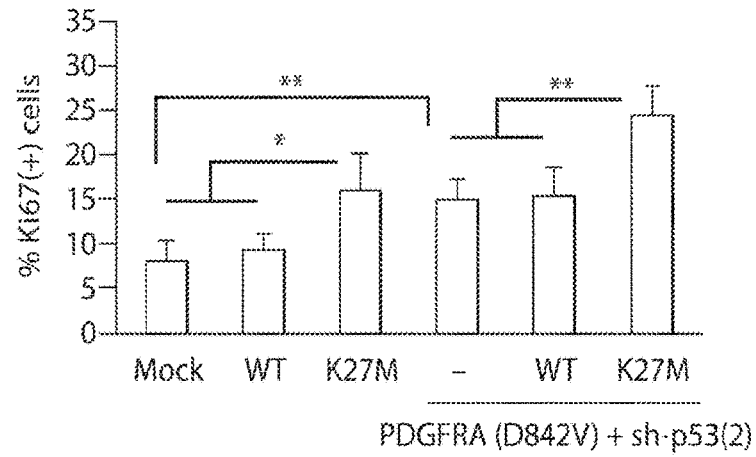
Figure 5D:
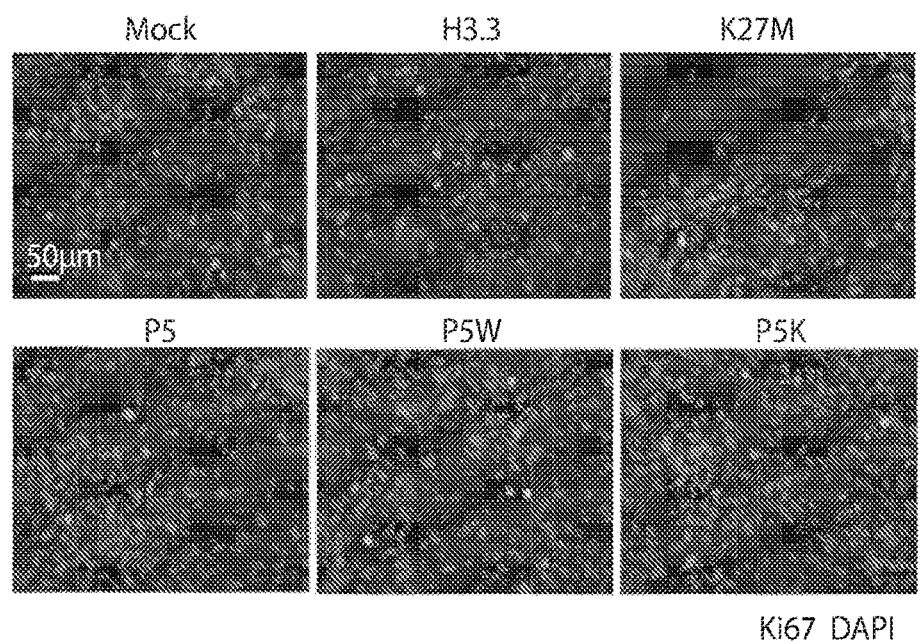

FIGS. 5A and 5B show the quantification of cell viability (trypan blue) following incubation for 5 days in vitro. A second shRNA against p53 was used in 5B, leading to similar results. FIG. 5C shows the quantification of proliferation via Ki67 upon transduction of oncogene combinations and using the second shRNA-p53. FIG. 5D represents the immunohistochemistry for Ki67 in the different cell groups. Bars indicate mean±S.D. (n=4~5). *, $p<0.05$; **, $p<0.01$.

Figure 6A:
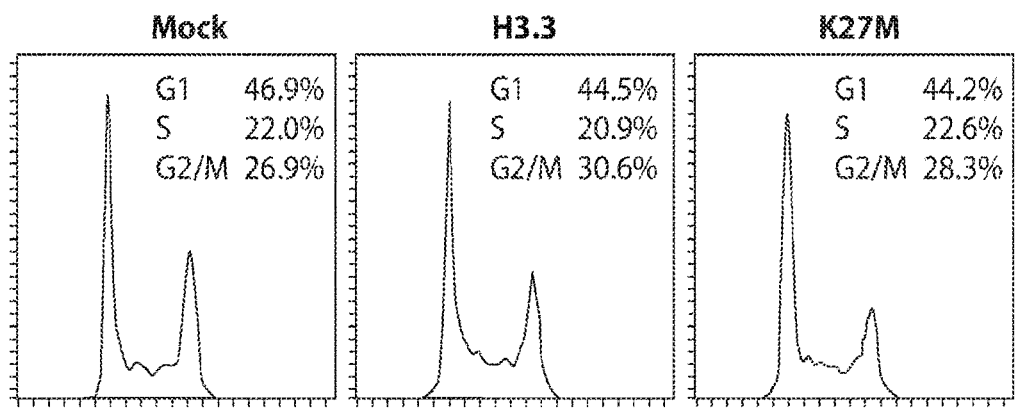
Figure 6B:
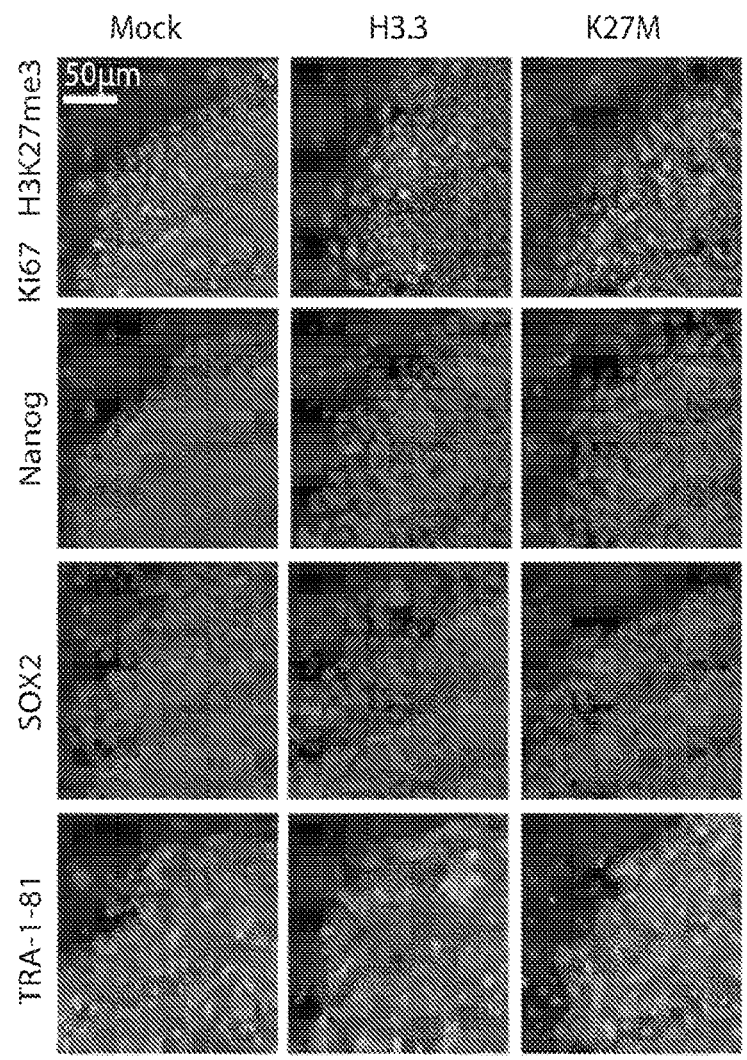
Figure 6C:
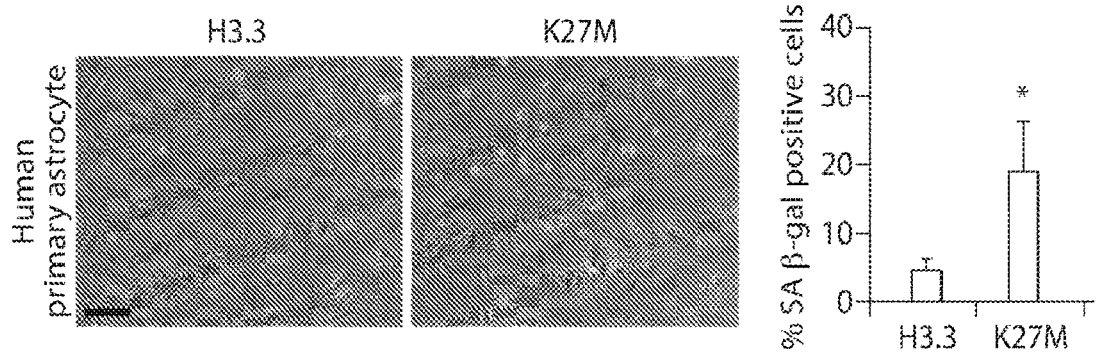
Figure 6D:
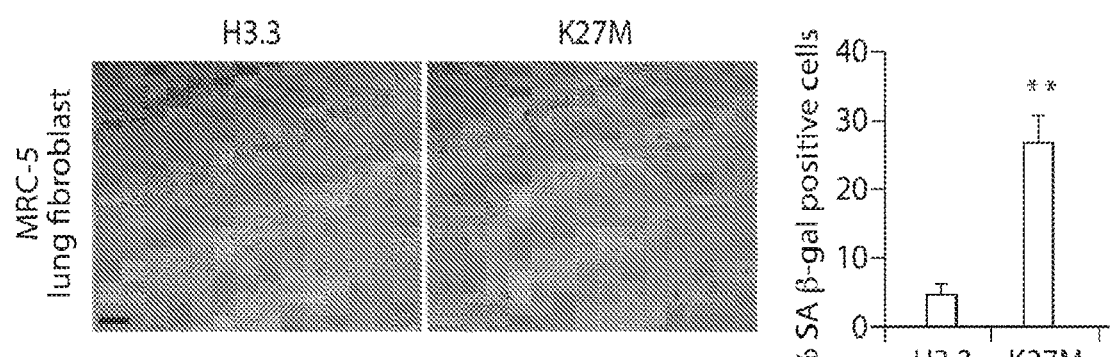

FIG. 6A shows the FACS-based cell cycle analysis of human ES cells transduced with the WT or K27M mutant form of histone H3.3. In FIG. 6B, human ES cells expressing WT histone H3.3 or K27M mutant were immunostained with the indicated antibodies, demonstrating absence of H3K27me3 marks, and unchanged expression of pluripotency markers Nanog and TRA1-81 as well as the early transcription factor SOX2. Sporadic expression of H3K27me3 is likely localized to the feeder layer. FIGS. 6C and 6D show that the expression of K27M is associated with a decrease in proliferation and increased senescence in differentiated cells, such as astrocytes (FIG. 6C) and fibroblasts (FIG. 6D). Quantification of senescent cells was performed via analysis of senescence-associated β-galactosidase activity (SA β-gal). Bars indicate mean±S.D. (n=4~5). Scales: 100 μm. *, $p<0.05$; **, $p<0.01$.

Figure 7A:
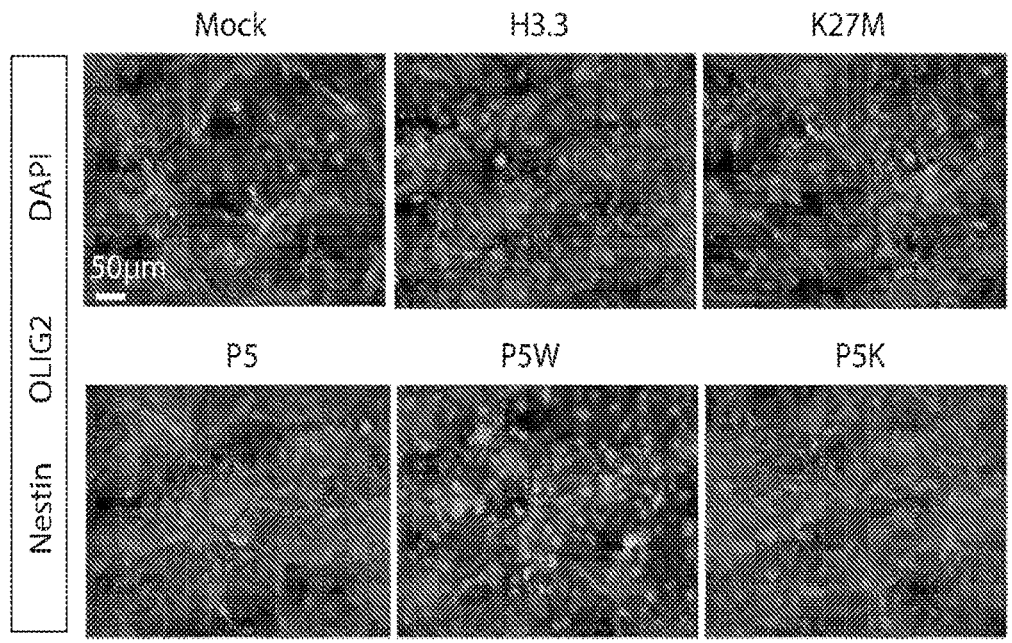
Figure 7B:
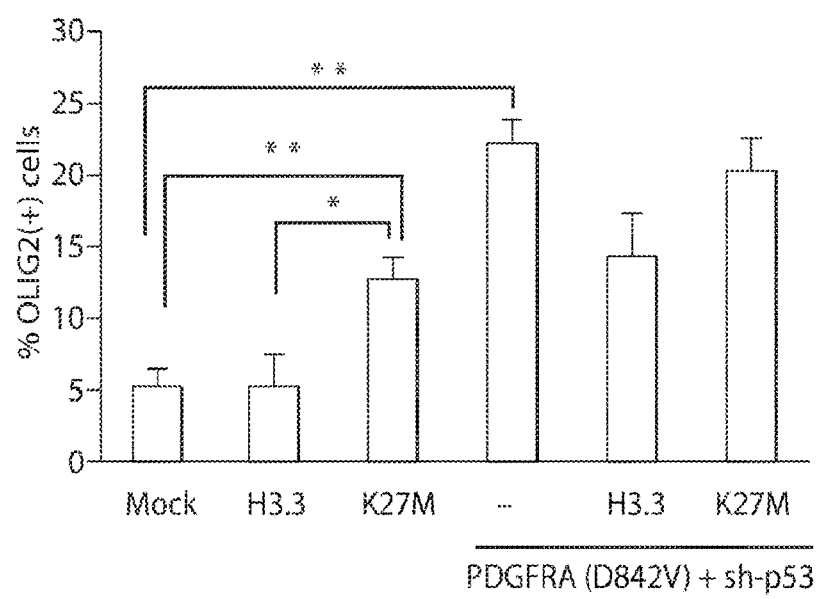

FIG. 7A shows that NPCs transduced with the indicated lentiviruses were immunostained for Nestin and Olig2. FIG. 7B presents the quantification of immunofluorescent cells for Olig2. Bars indicate mean±S.D. (n=4~5). *, $p<0.05$; **, $p<0.01$.

Figure 8A:
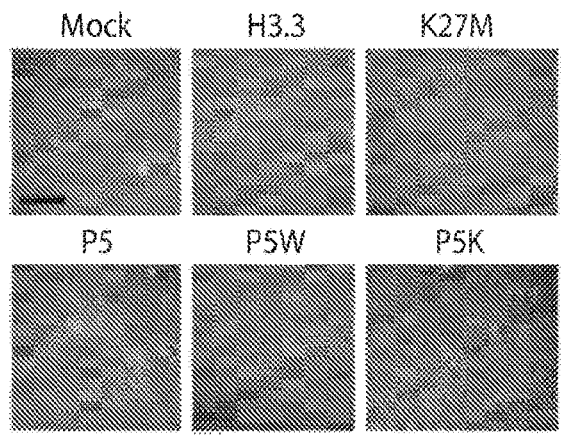
Figure 8B:
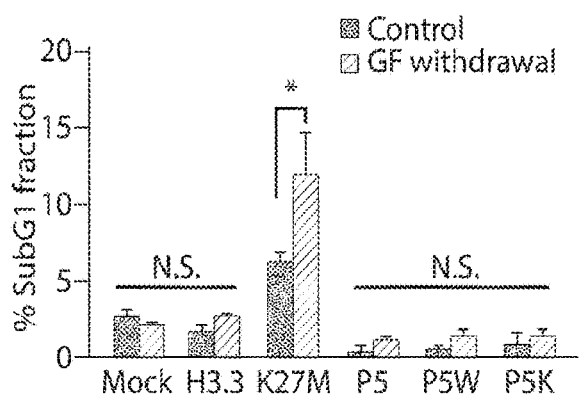
Figure 8C:
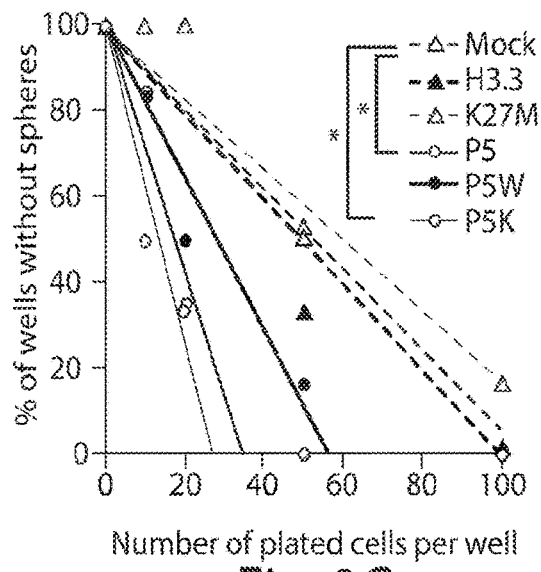
Figure 8D:
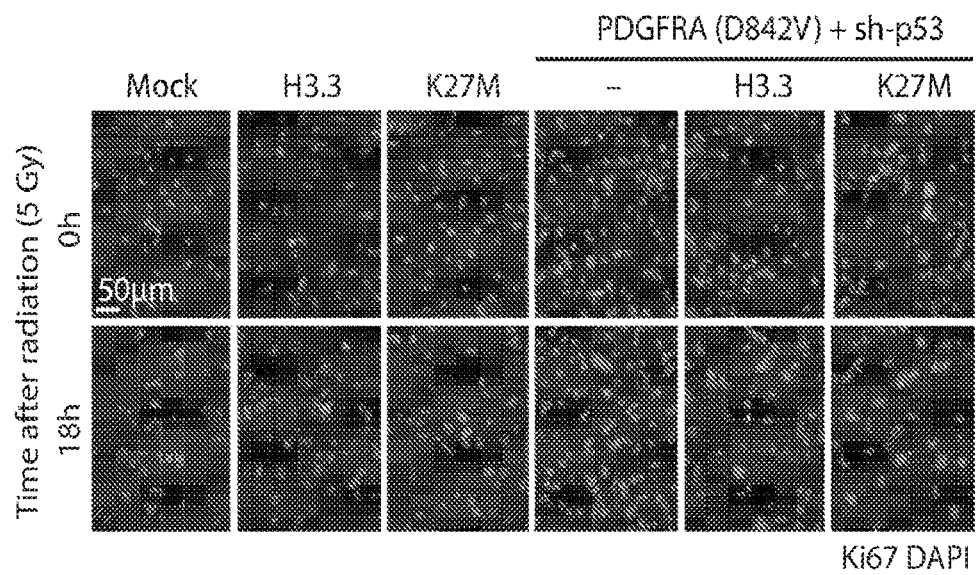
Figure 8E:
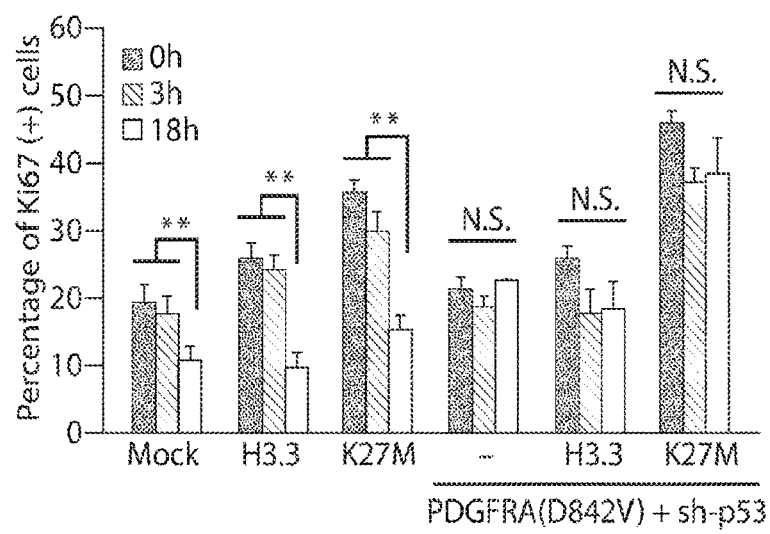
Figure 8F:
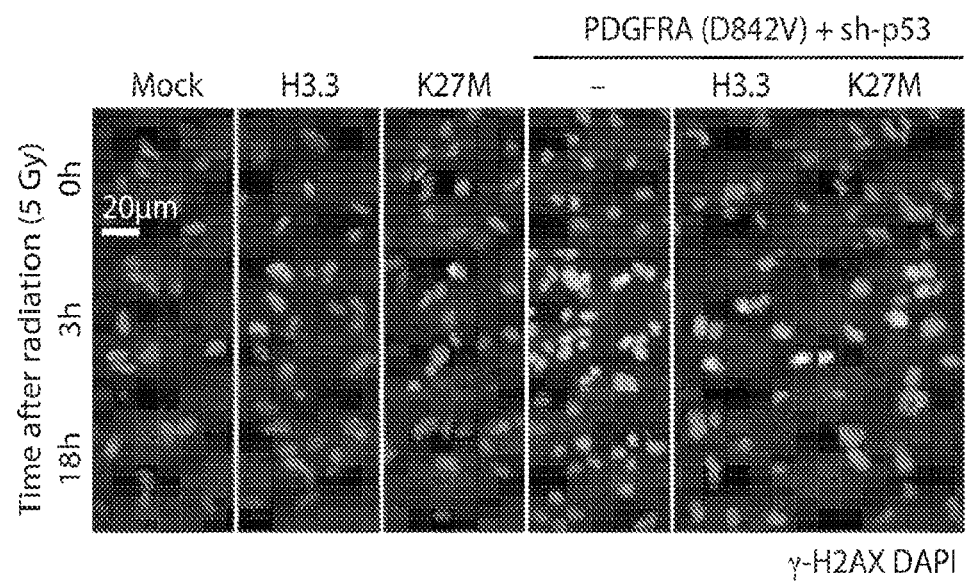
Figure 8G:
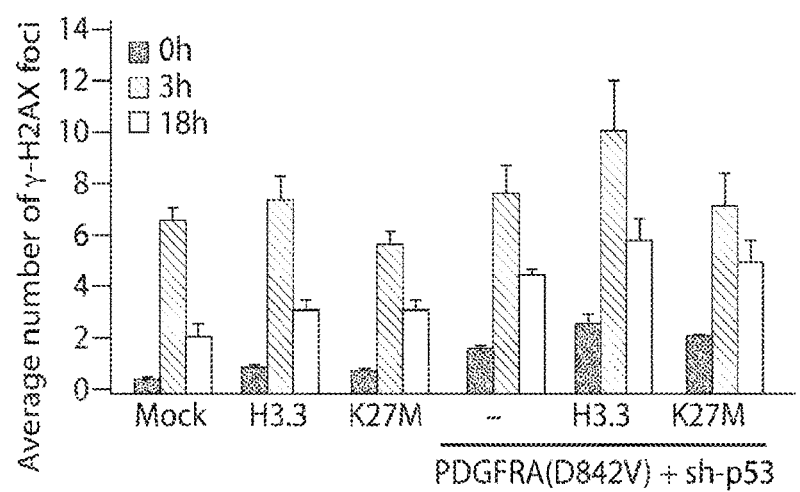
Figure 8H:
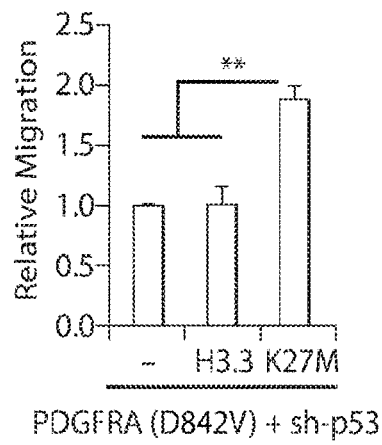
Figure 8I:
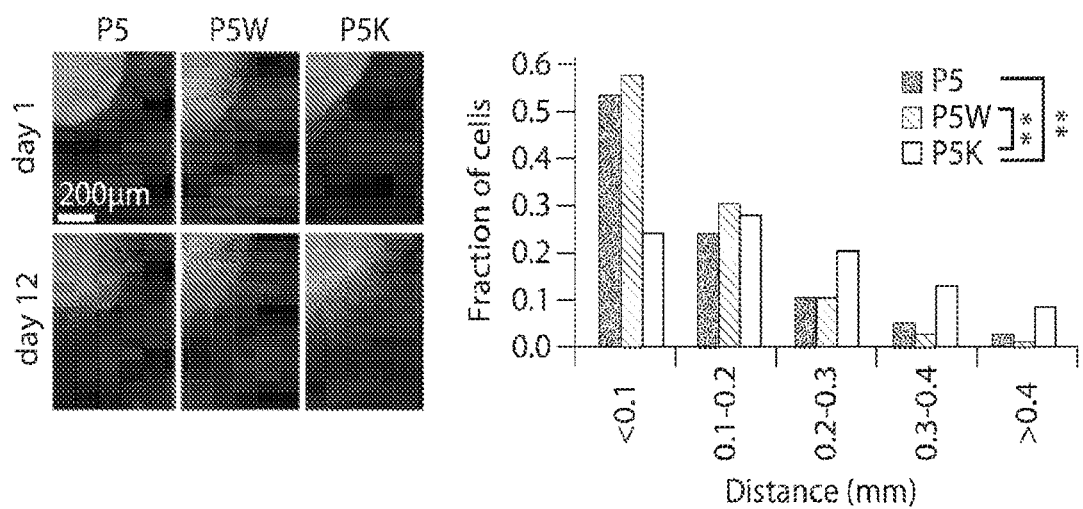

FIG. 8A shows the bright phase microscopy of transduced NPCs grown at very low density for 4 weeks. FIG. 8B depicts the FACS analysis for the sub-G1 fraction (apoptotic cells) in transduced NPCs under control conditions and 24 hours following growth factor withdrawal. Error bars indicate mean±S.D. (n=3). FIG. 8C shows that sphere-forming capacity was assessed by limiting dilution assay. 10~100 cells were plated into a 96-well low-attachment plate. After 12 days of incubation, spheres with more than 5 cells were counted. In FIGS. 8D and 8E, the proliferation of normal and transformed NPCs was assessed following a single dose of radiation (5 Gy) at the indicated time point, by Ki67 staining. Bars in (FIG. 8C) indicate mean±S.D. (n=4~5). FIGS. 8F and 8G depict DNA repair kinetics following radiation. Cells were immune-stained for phospho-γ-H2A.X at 0, 3 hours, and 18 hours following a dose of 5 Gy. The number of positive foci was counted. FIG. 8H shows cell migration assessed by the Boyden chamber assay. 3,000 cells were plated in the top chamber and the number of cells that migrated to the bottom chamber was counted by fluorescence microscopy of DAPI stained cells. Bars indicate mean±S.D. (n=4). FIG. 8I shows low magnification immunofluorescence microscopy of RFP-labeled transduced NPCs embedded as spheres in Matrigel. Cells migrating from the spheres were analyzed on day 12 and the distance travelled from the sphere edge was measured. *, $p<0.05$; **, $p<0.01$. NS, Not Significant.

Figure 9:
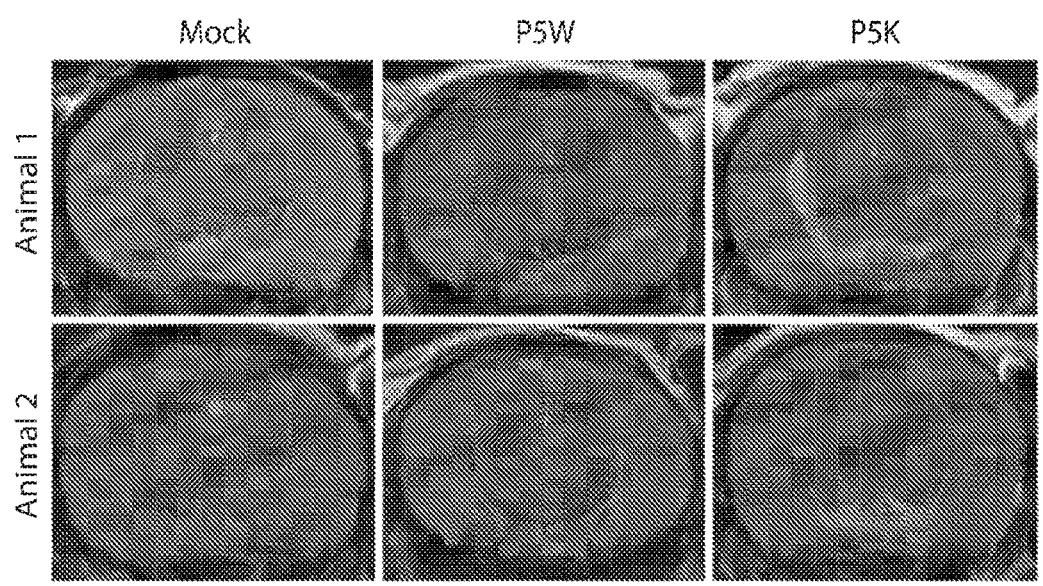

FIG. 9 shows representative MRI (T2 sequence) coronal images of mouse brains at the level of the pons, transplanted with normal NPCs, P5W, or P5K cells, respectively.

Figure 10C:
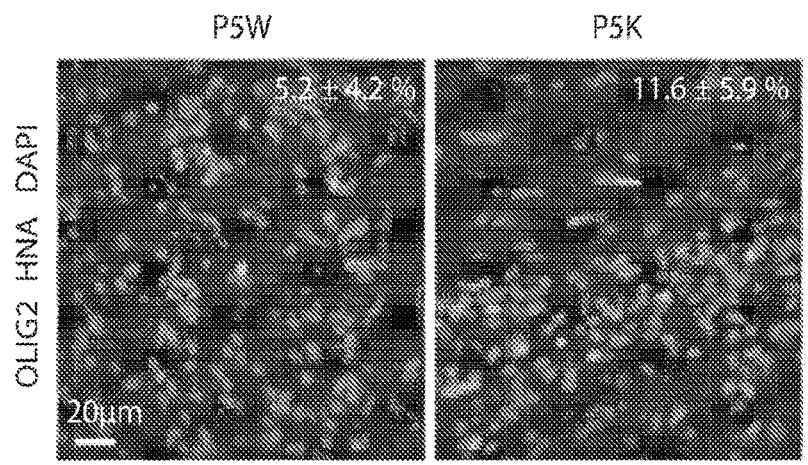
Figure 10D:
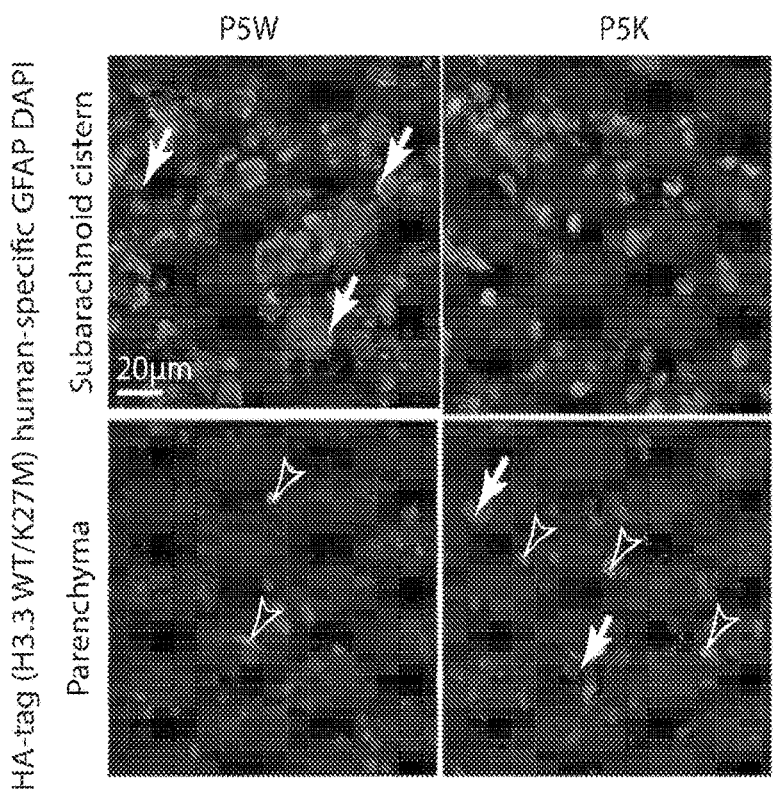

FIGS. 10A-10D show the immunophenotyping of transplanted cells. In FIGS. 10A-10D frozen sections of mouse brains transplanted with P5W or P5K cells were immunostained for the indicated antibodies. Expression of H3.3 WT or K27M was coupled to hemagglutinin (HA) epitope tag, while sh-p53 was associated with a RFP reporter. In FIG. 10A, immunostaining for the HA-tag showed that the majority of the cells retained the histone transgenes. Numbers indicate the percentage of HA-stained cells relative to HNA-stained cells (mean±S.E.M., n=3~4). In FIG. 10B, silencing of the histone transgene and/or sh-p53 expression in transplanted P5K cells was evaluated by immunostaining for the HA-tag and RFP expression, respectively. FIG. 10C shows immunohistochemistry for Olig2 demonstrating an increased percentage in the P5K tumors, compared to P5W. Numbers indicate the percentage of Olig2-stained cells relative to HNA-stained cells (mean±S.E.M., n=3~4). In FIG. 10D, astrocytic differentiation of transplanted cells was assessed by immunostaining for human-specific GFAP and the HA-tag. White arrows indicate astrocytes of human origin. Yellow arrowheads indicate transplanted cells that retain histone transgenes. Quantification of the staining is shown in the table below (mean±S.E.M., n=4~6). **, p<0.01.

Figure 11F:
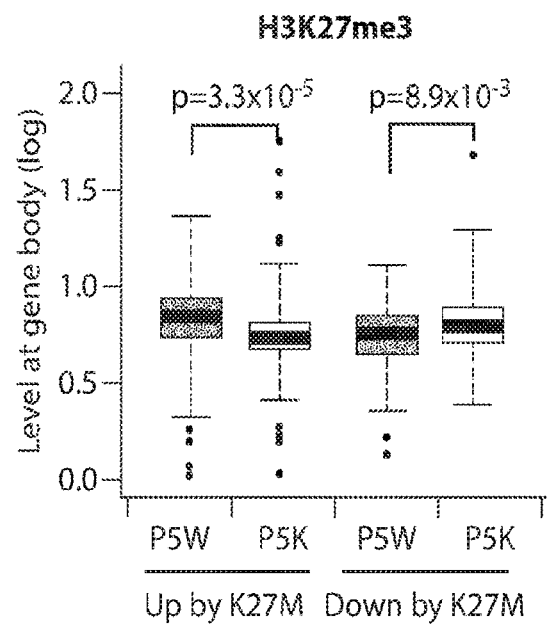
Figure 11G:
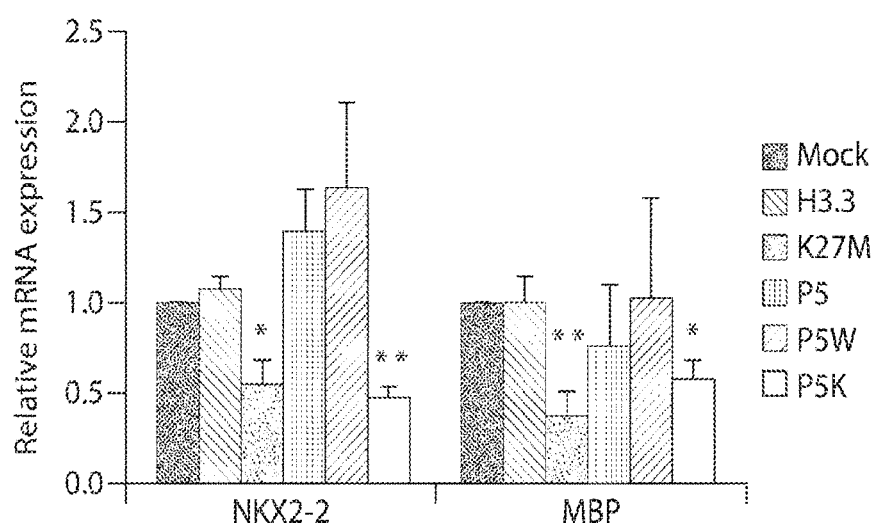

FIG. 11A shows overlap of indicated transcript sets in Venn diagrams. Transcripts that are up or down-regulated for more than 3 folds by K27M ('K27M up' and 'K27M down') were compared with the transcripts that are upregulated in early-stage NPCs ('Rosette'), late-stage NPCs ('Late-NPCs') or shared between early-stage NPCs and undifferentiated ES cells ('ES/Rosette shared'), respectively. P-values were calculated by hyper-geometric test. FIG. 11B shows confirmation of silencing by real-time RT-qPCR. FIG. 11C shows that the knockdown of LIN28B decreased the proliferation of P5K cells. P5W and P5K cells were transduced with control (shLuc) or LIN28B-shRNA expressing (shLIN28B#3) lentiviral vectors, respectively, and immunostained for Ki67. Bars indicate mean±S.D. (n=4~5). FIGS. 11D and 11E show the chromatin landscape of selected genes. H3K4me3 (red) and H3K27me3 (blue) marks are shown for P5W and P5K cells. FIG. 11F depicts the levels of H3K27me3 marks at gene-body region of the genes upregulated or downregulated by K27M. P-values were calculated by the Wilcoxon rank-sum test. In FIG. 11G, the decreased expression of the indicated genes was confirmed by RT-qPCR. Bars indicate mean±S.E.M. (n=3~5). *, p<0.05; **, p<0.01.

Figure 12A:
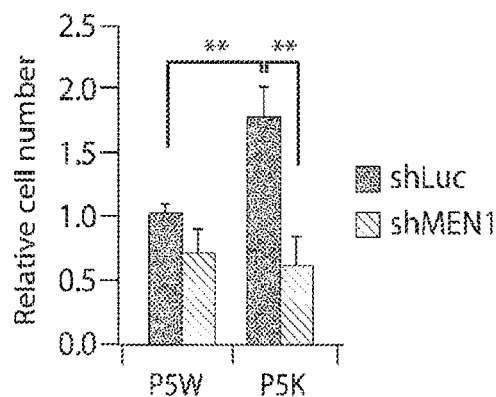
Figure 12B:
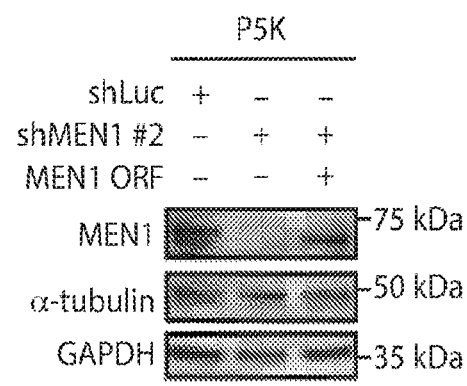
Figure 12C:
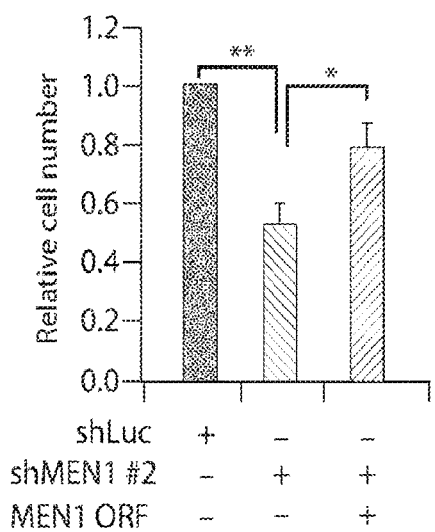
Figure 12D:
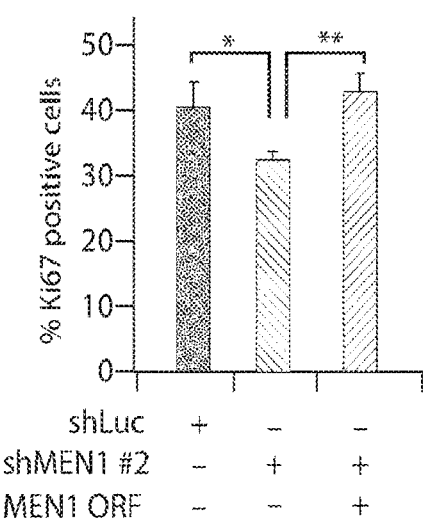

FIG. 12A shows that the knockdown of menin decreased the proliferation of P5K cells. The number of viable cells was counted by trypan-blue staining. Bars indicate mean±S.D. (n=4). FIG. 12B shows the confirmation of menin knockdown and rescue by western blotting. The expression of menin was suppressed by the shRNA targeting 3' UTR of menin (shMEN1 #2) and rescued by the overexpression of menin ORF (MEN1 ORF) in P5K cells. FIGS. 12C and 12D show the proliferation of P5K cells was decreased by menin knockdown and rescued by the overexpression of menin ORF. Viability and proliferation were assessed by trypan-blue staining (FIG. 12C) and Ki67 staining (FIG. 12D). Bars indicate mean±S.D. (n=4~5). FIG. 12E shows that the menin knockdown restored astrocytic differentiation in P5K cells. Bars indicate mean±S.D. (n=4~5). Scale, 20 µm; *, p<0.05; **, p<0.01.

FIG. 13 is a table showing the genes upregulated in cells expressing the H3.3 K27M mutation (K27M+P5K vs all other conditions).

FIG. 14 is a table showing the genes downregulated in cells expressing the H3.3 K27M mutation (K27M+P5K vs all other conditions).

FIG. 15 is a table showing the levels of H3K4me3 and H3K27me3 at the promoter regions of genes that are upregulated or downregulated by K27M.

FIG. 16 is a table listing the target genes by H3K27me3 marks or by PRC2 complex.

FIG. 17 is a table of the $IC_{50}$ of compounds (selected from an epigenetic chemical library from Cayman Chemicals (cat. No. 11076)) used in the chemical screen.

FIG. 18 is a table of the target and primer oligonucleotide sequences.

Figure 4A:
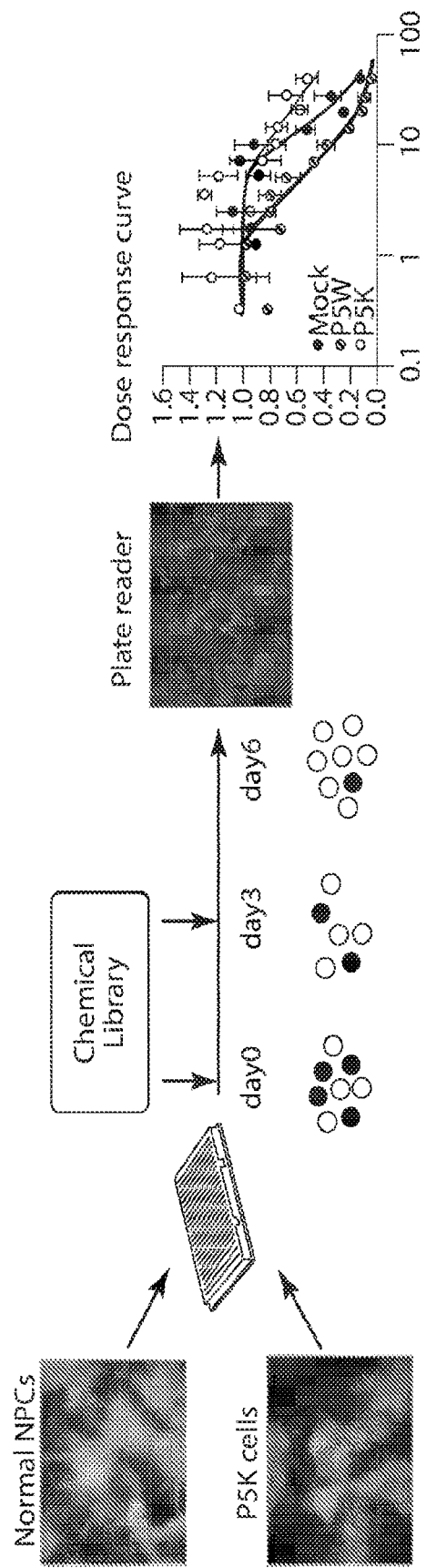
Figure 4B:
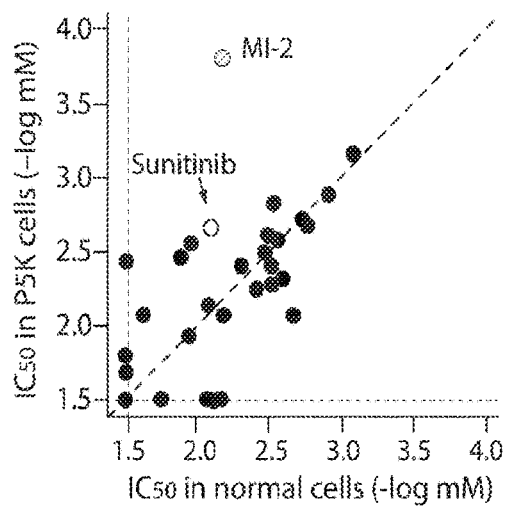
Figure 4C:
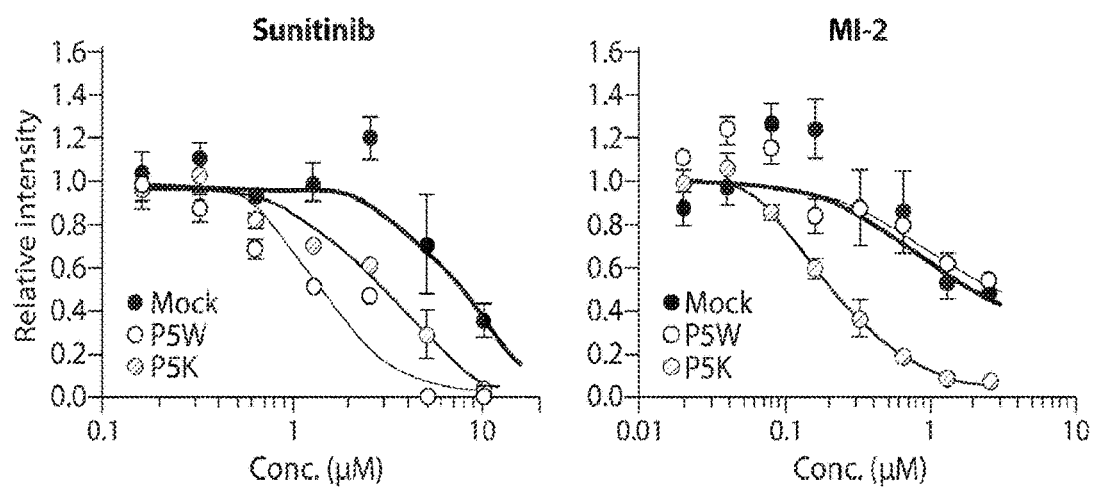
Figure 4D:
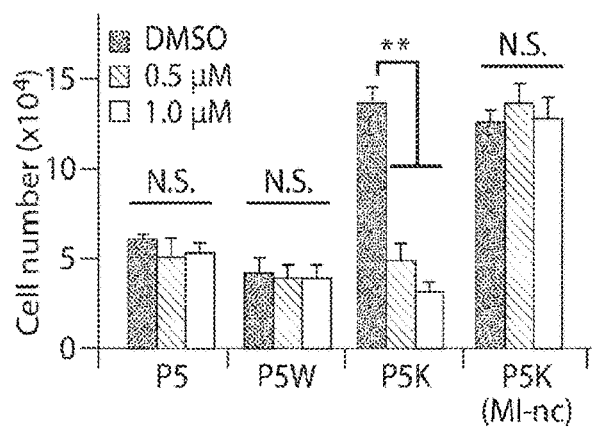

FIG. 19 depicts the chemical screen of the transformed NPCs. FIG. 19A is a schematic representation of the screening strategy. A mixture of GFP-labeled normal NPCs and RFP-labeled P5K cells in a 1:3 ratio were plated into 96-well plates and each compound in the library was added in a 2-fold serial dilution for a total of 8 doses. FIG. 19B shows the $IC_{50}$ calculated for each compound after 6 days in vitro, using a fluorescence plate reader. FIG. 19C presents representative dose response curves in normal NPCs (Mock, blue), P5W (green) and P5K (red) cells treated with MI-2 or MI-nc (MI-2 analog), demonstrating the selectivity of MI-2, a menin inhibitor. Error bars indicate S.D. (n=4). FIG. 4D depicts a viability assay demonstrating a significant effect of MI-2 on P5K cells, with no impact on normal or P5W cells (n=4). FIG. 19E shows that silencing menin via shRNA also decreases the proliferation of P5K cells. FIG. 19F demonstrates that the administration of MI-2 suppresses in vivo growth of P5K cells. Intracranial growth of Luciferase-labeled P5K cells was measured by quantitative in vivo bioluminescence imaging. Values indicate fold change of luminescence before and after the treatment. FIG. 19G shows that MI-2 treatment suppresses the proliferation of a patient DIPG-derived cell line. Cells were treated with MI-2 for 7 days and the number of viable cells was counted by trypan-blue staining (n=4). Error bars in panels C-D, E, F and G indicate mean±S.D. *, p<0.05; **, p<0.01. NS, Not Significant. FIG. 19H represents a dose-response curve of MI-2-2. $IC_{50}$ for the DIPG line is 10 nM, while normal precursors (NPC) and fibroblasts (MRCS) are highly resistant even at several fold higher drug doses.

Figure 20:
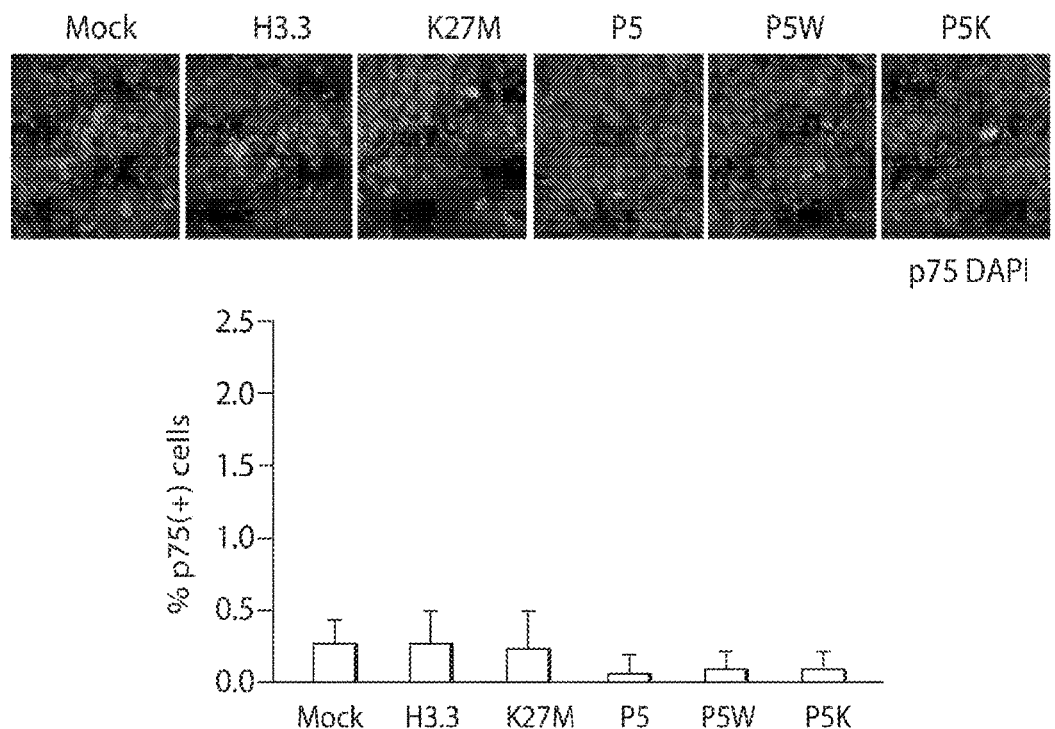

FIG. 20 shows spontaneous differentiation to mesenchymal cells analyzed by p75 immunostaining. *, p<0.05; **, p<0.01.

Figure 21:
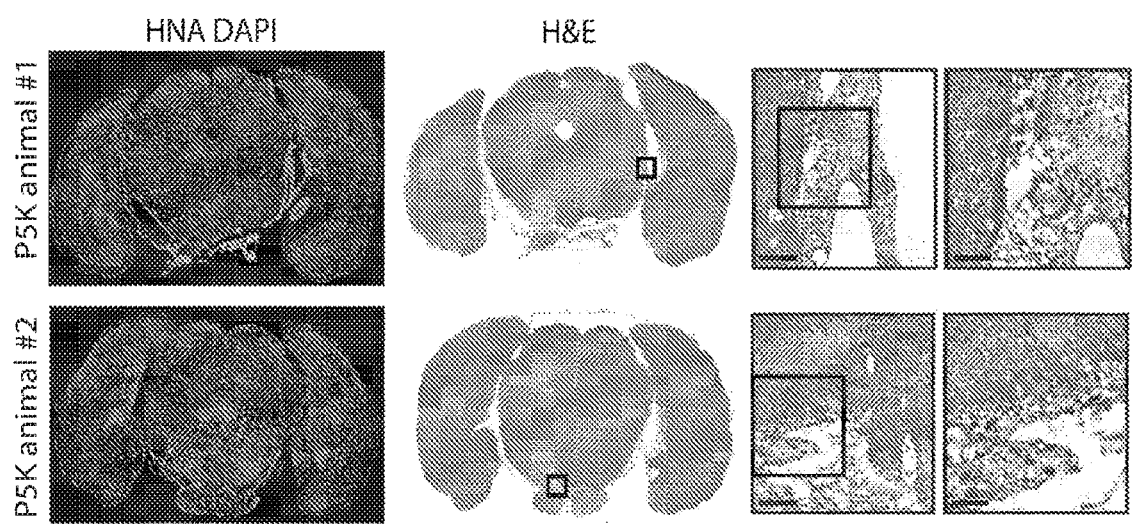

FIG. 21 presents representative images of mouse brains transplanted with P5K cells. Low magnification immunofluorescence images of representative sections labeled for human specific nuclear antigen (HNA) and counter-stained with DAPI are shown in the left panel. The consecutive sections were stained with H&E (right panel). Scale bar, 100 µm (left), 50 µm (right). Note the presence of hydrocephalus secondary to subarachnoidal disease, as well as intraventricular tumor (animal #2).

Figure 22A:
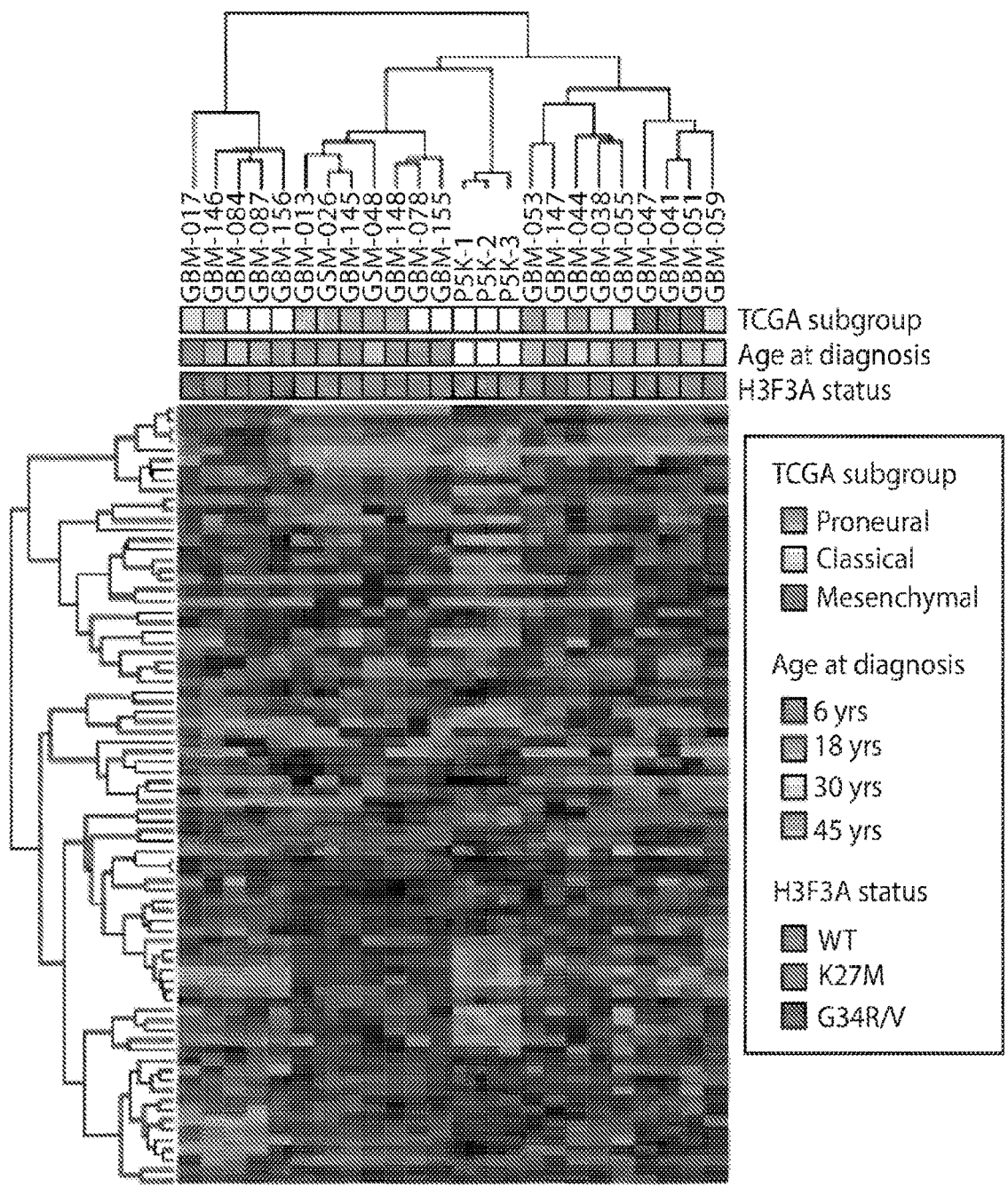
Figures 22B, 22C:
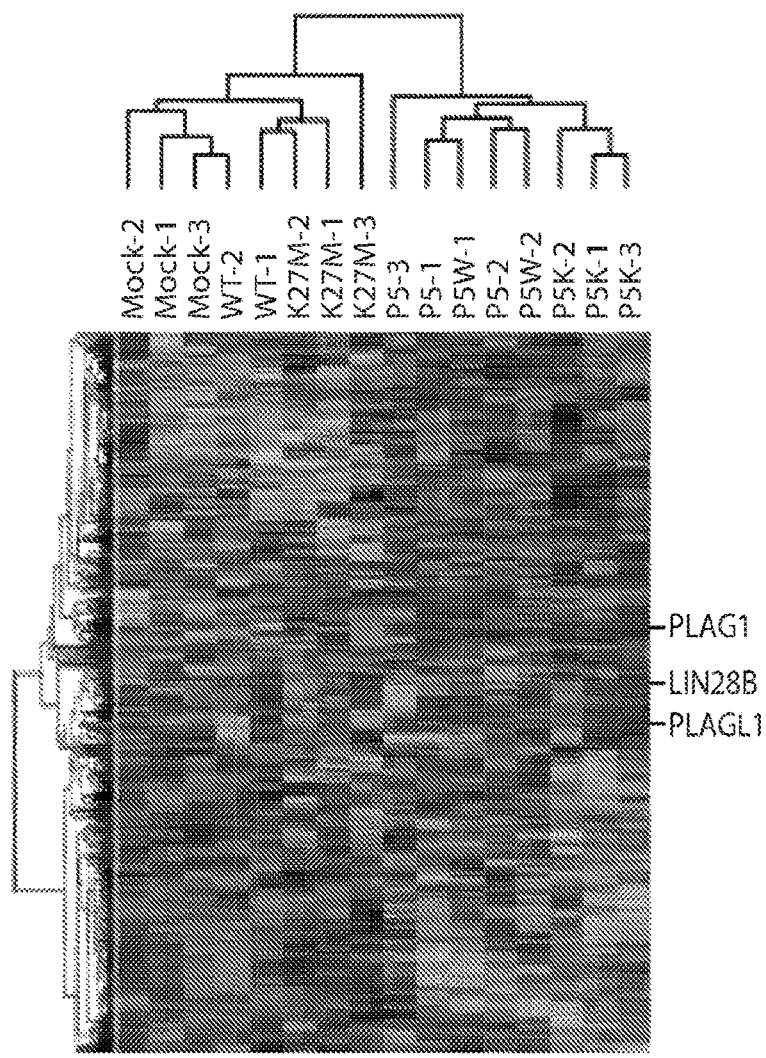
Figure 22D:
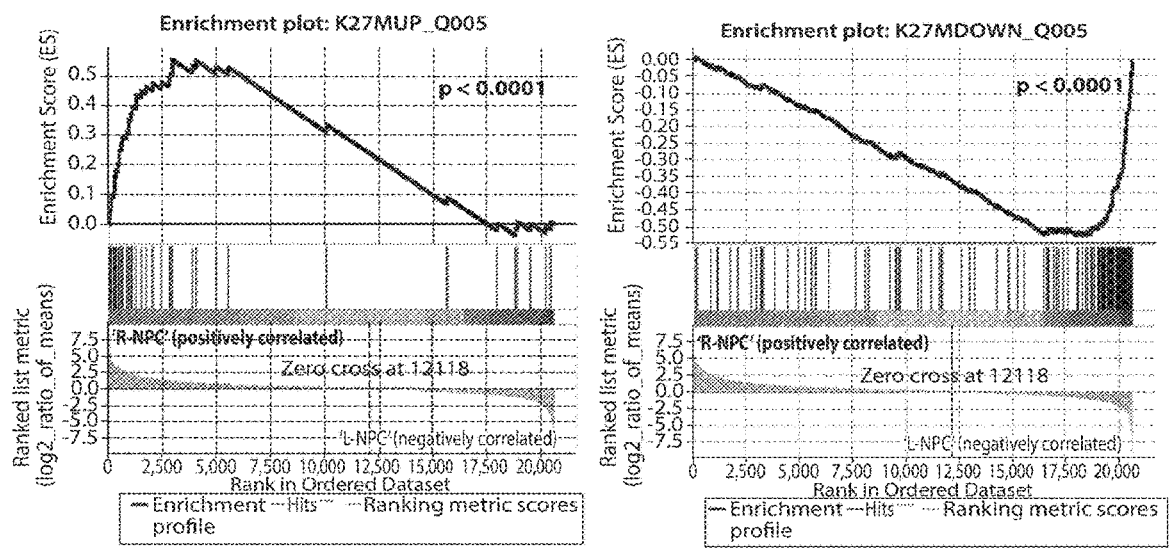
Figure 22F:
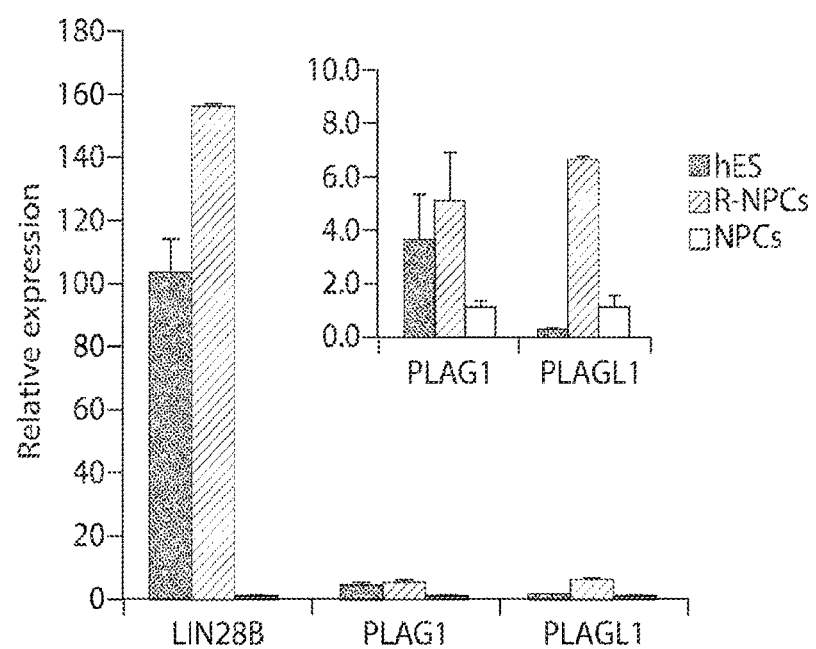

FIG. 22A shows the hierarchical clustering of microarray data from P5K cells and patient tumor samples bearing the H3.3K27M or G34R/V mutations (GSE36245) obtained from Sturm et al."Hotspot Mutations in H3F3A and IDH1 Define Distinct Epigenetic and Biological Subgroups of Glioblastoma", *Cancer Cell* 2012, 22, 425-437. FIG. 22B shows an analysis of Pearson's correlation between the two groups. FIG. 22C presents an unsupervised hierarchical clustering of microarray data obtained from NPCs transduced with the different H3.3 and oncogene combinations. FIG. 22D presents a Gene Set Enrichment Analysis (GSEA) that indicates an enrichment of the gene sets that are up or down-regulated by H3.3K27M in the expression profile of early-stage (rosette-stage) NPCs compared with late-stage NPCs. FIG. 22F shows RT-qPCR demonstrating the increased expression levels of LIN28B, PLAG1 and PLAGL1 in human ES cells and rosette-stage NPCs. Error bars indicate mean±S.E.M. (n=3~4).

Figure 23A:
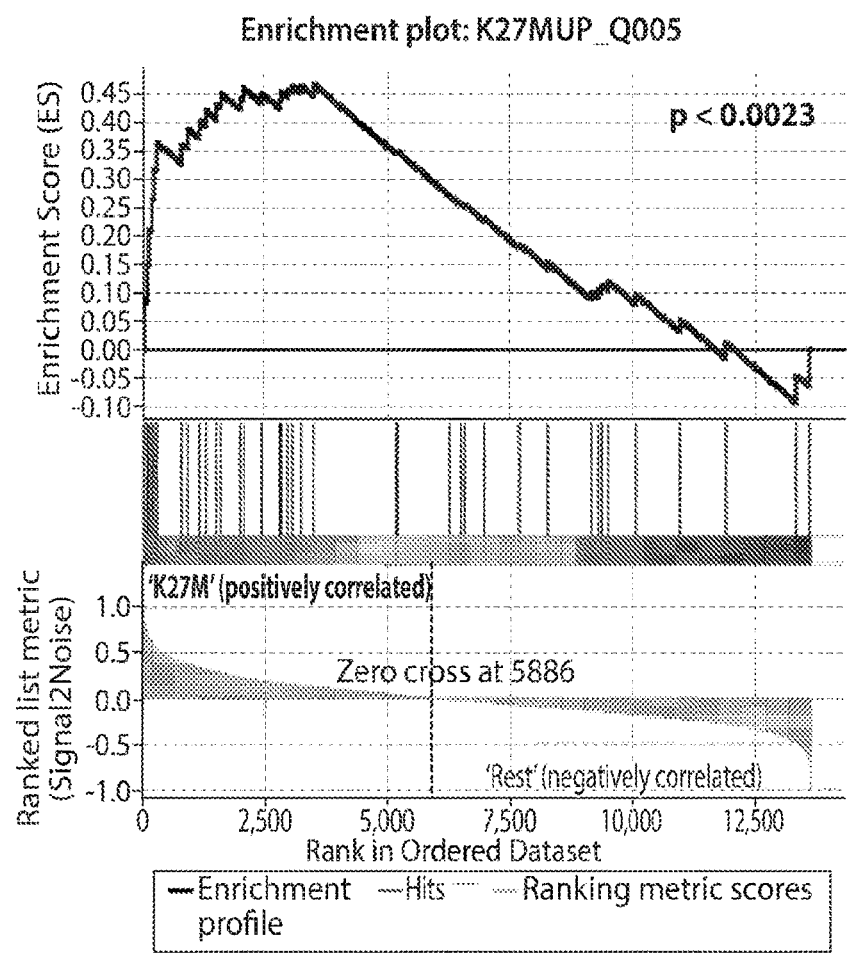
Figure 23B:
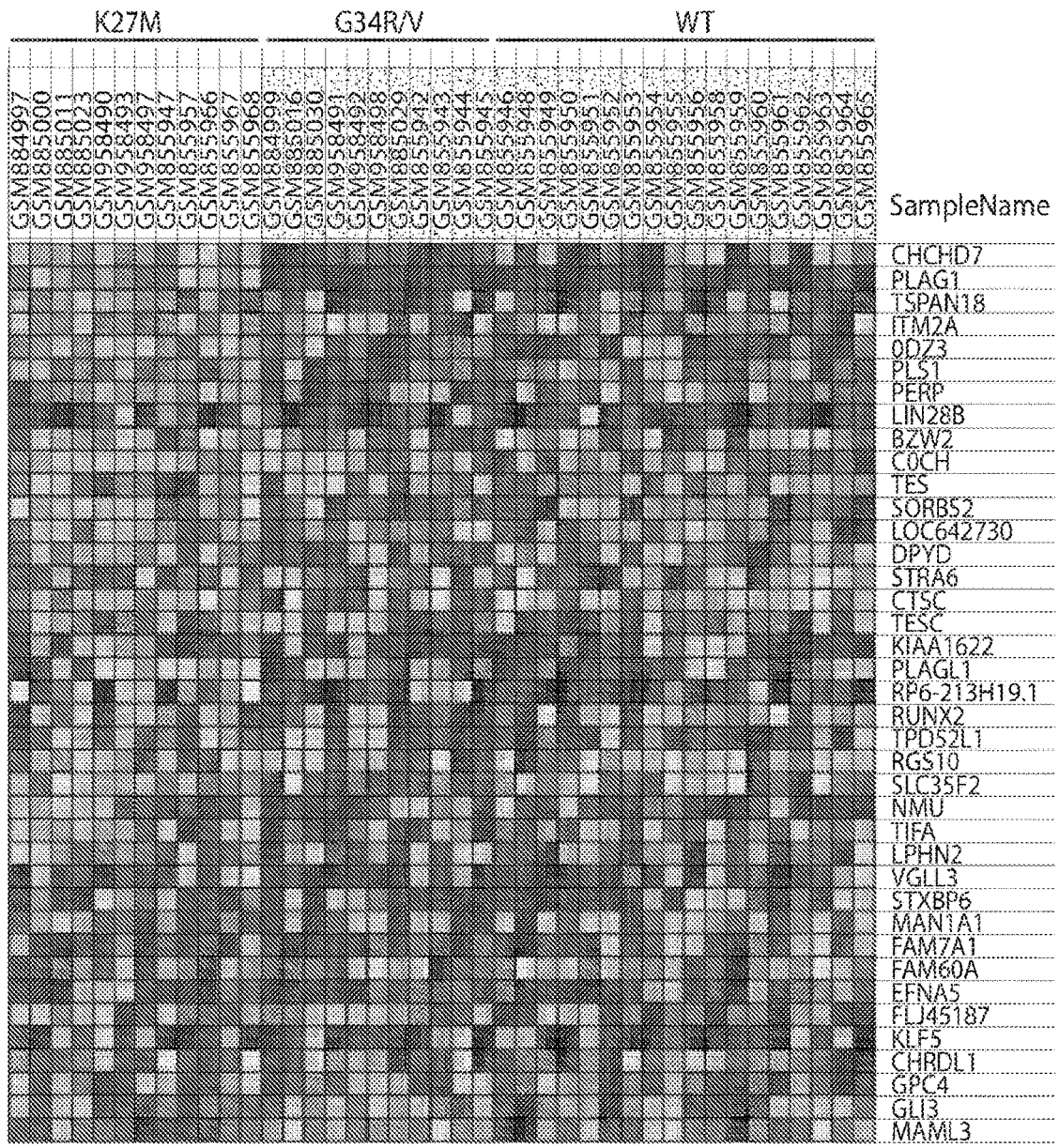

FIGS. 23A and 23B show Gene Set Enrichment Analysis (GSEA) that indicates an enrichment of the gene set that is upregulated by H3.3K27M in the gene expression profile of patient tumor samples with H3K27M mutation, compared to G34R/V mutations, and non-histone mutated GBMs.

Figure 24A:
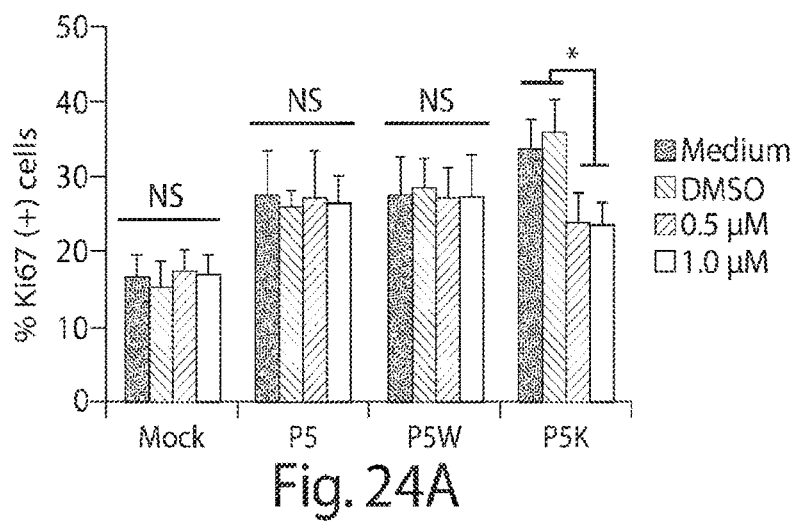
Figure 24B:
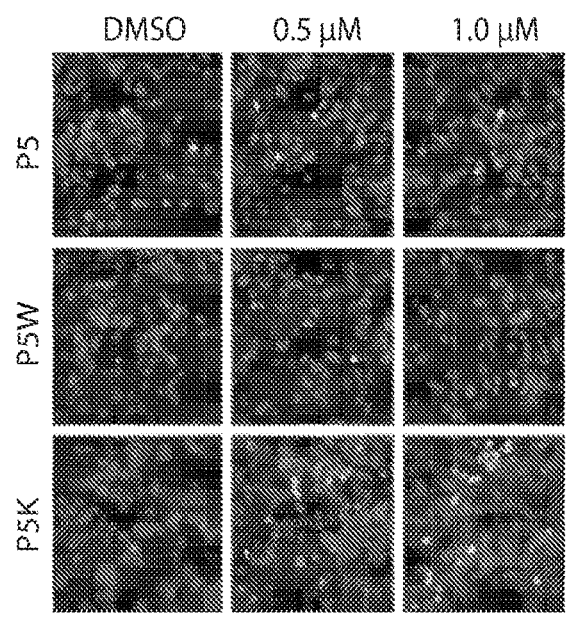
Figure 24C:
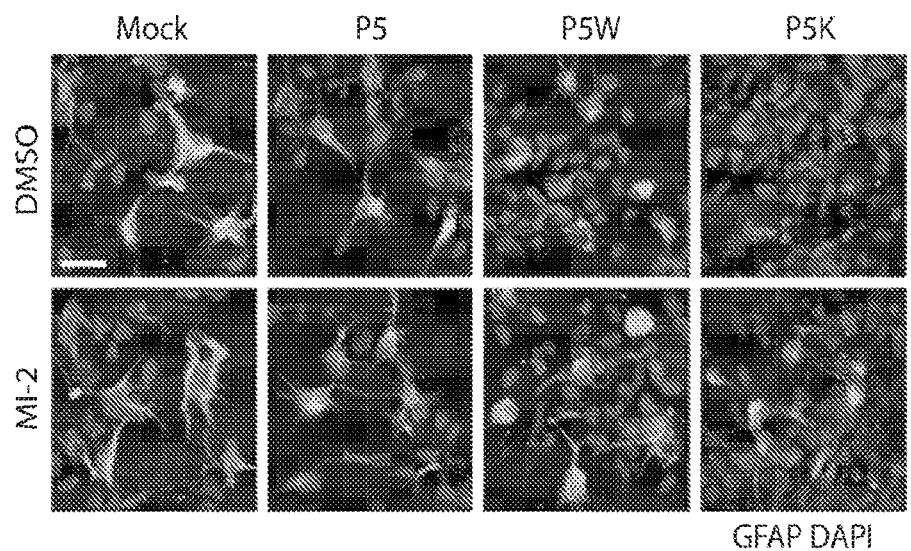
Figure 24D:
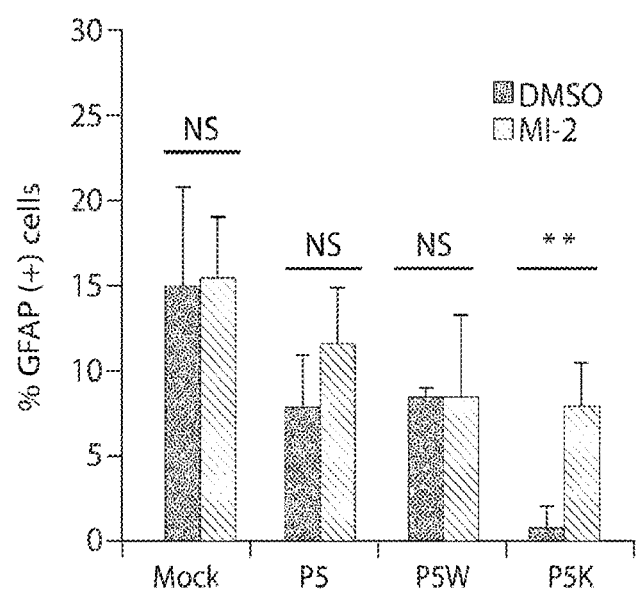

FIG. 24A shows a proliferation assay demonstrating a significant effect of MI-2 on P5K cells, with no impact on normal or P5W cells. Bars indicate mean±S.D. (n=4). FIG. 24B shows MI-2 treatment induced cell death in P5K cells. After 6 days of treatment, the percentage of dead cells was measured by TUNEL staining. FIG. 24C shows that the suppression of menin restored astrocytic differentiation in P5K cells. P5K cells transduced with control or menin shRNA-expressing lentiviruses (shMEN #1 and shMEN #2), were cultured under the differentiation condition. Cells were cultured under the differentiation condition with or without MI-2 (0.5 μM) for 14 days. Error bars indicate mean±S.D. (n=4~5). Scale, 20 μm. *, p<0.05; **, p<0.01. NS, Not Significant.

Figure 25A:
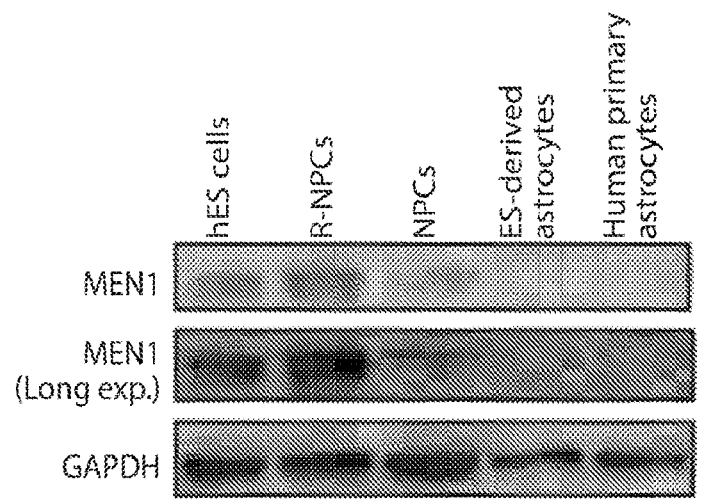
Figure 25B:
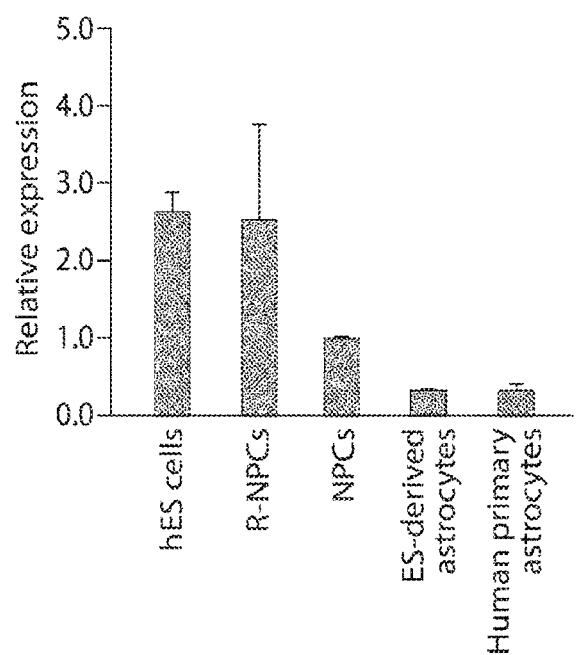
Figure 25C:
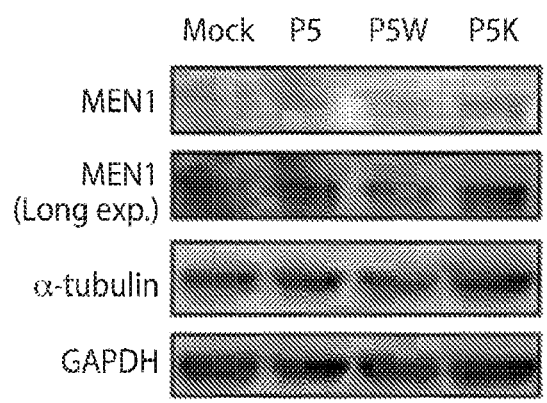
Figure 25D:
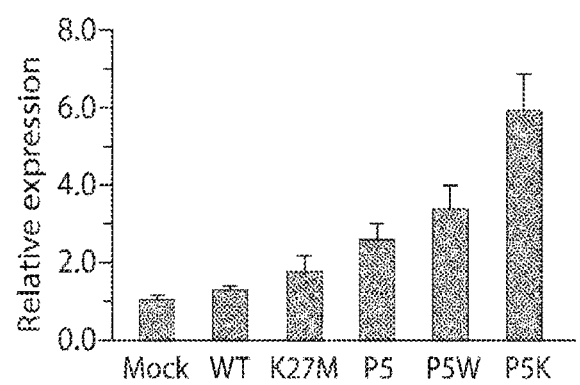
Figure 25E:
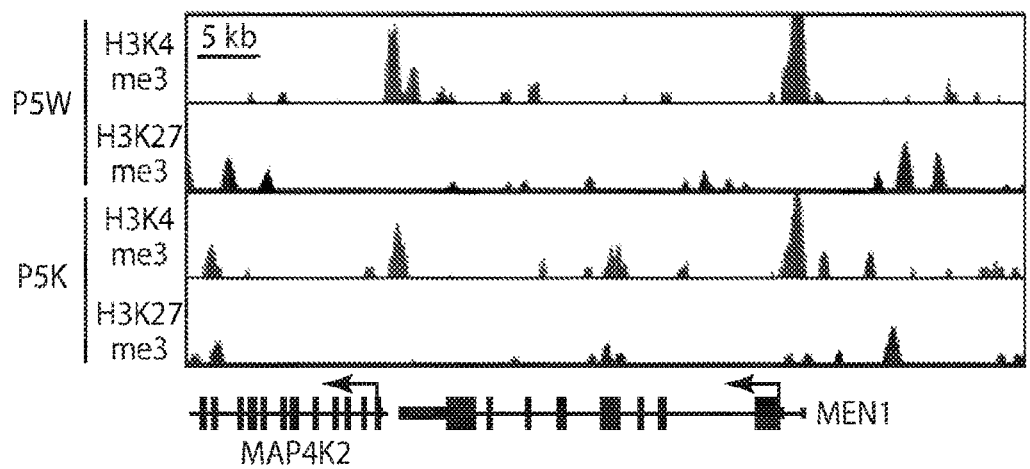
Figure 25F:
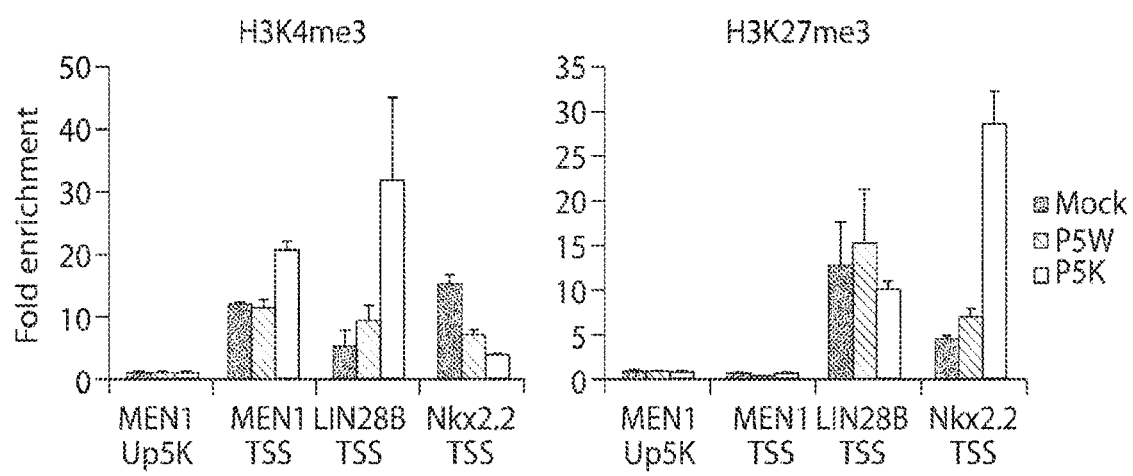

FIGS. 25A and 25B show the increased expression of menin in P5K cells by western blotting (FIG. 25A) and RT-qPCR (FIG. 25B). FIGS. 25C and 25D show that the expression level of menin is upregulated in human ES cells and rosette-stage NPCs (R-NPCs), whereas downregulated in astrocytes. Bars in FIGS. 25B and 25D indicate mean±S.E.M. (n=3~5). FIGS. 25E and 25F present the chromatin landscape of MEN1 locus in P5W and P5K cells. ChIP-seq data for H3K4me3 (red) and H3K27me3 (blue) (FIG. 25E), and validation by ChIP—PCR (FIG. 25F). Error bars indicate mean±S.D. (n=3).

Figure 26A:
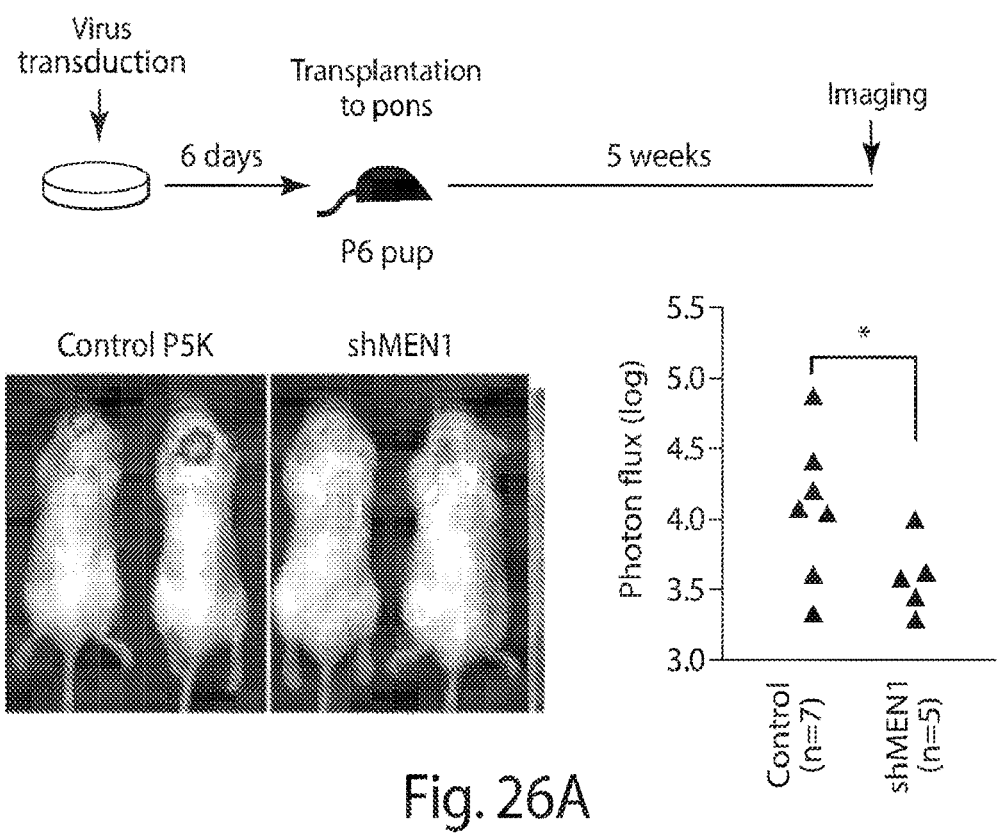
Figure 26B:
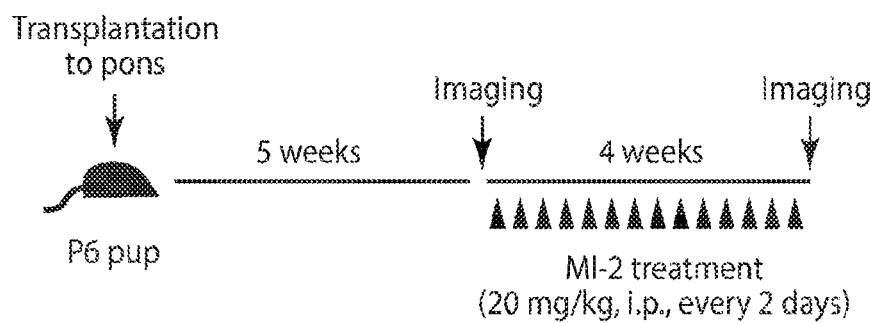

FIG. 26A shows that the knockdown of menin suppresses in vivo growth of P5K cells. Intracranial growth of Luciferase-labeled P5K cells, transduced with control or menin shRNA-expressing (shMEN1) lentiviruses, was measured by quantitative in vivo bioluminescence imaging (IVIS). FIG. 26B is a schematic representation of the drug treatment experiment shown in FIG. 19G. *, p<0.05.

Figure 27A:
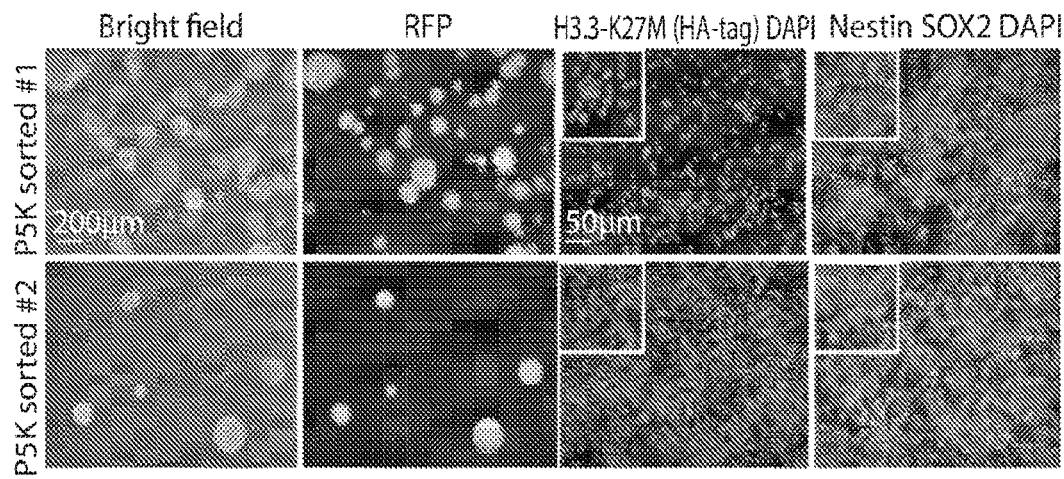
Figure 27B:
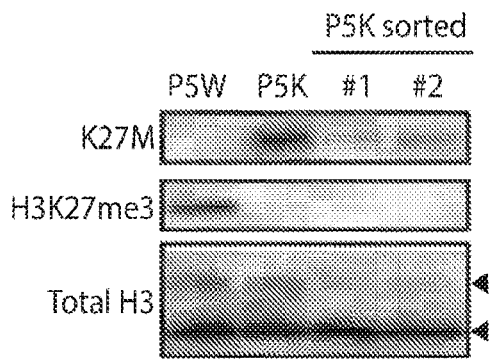
Figure 27C:
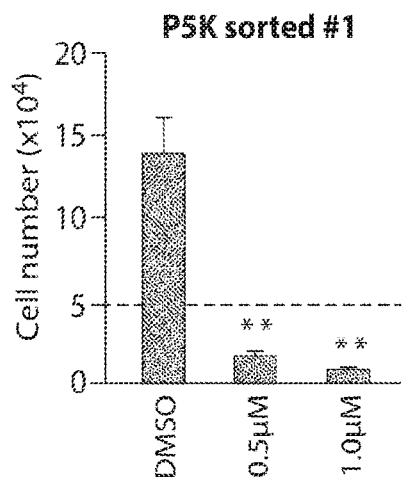
Figure 27D:
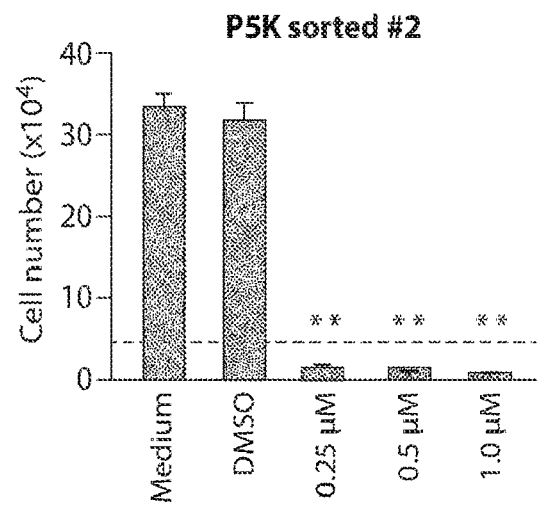

FIG. 27A shows the characterization of P5K cells sorted from mouse xenografts. Cells can be grown in both sphere (left panels) and adherent-culture (right panels). Immunohistochemistry demonstrates maintenance of SOX2 and Nestin expression as well as H3.3K27M transgene. FIG. 27B is a western blot of xenograft-derived P5K cells showing the expression of H3.3K27M and loss of H3K27 trimethylation mark (H3K27me3). Higher bands in the total H3 blot indicate hemagglutinin (HA)-tagged H3.3 transgene. FIGS. 27C and 27D show sorted P5K cells treated with MI-2 for 7 days and the number of viable cells counted by trypan-blue staining. Error bars indicate mean±S.D. (n=4). FIG. 27E illustrates that MI-2 treatment suppresses the proliferation of sorted P5K cells. Cells were treated with MI-2 at various concentrations for 5 days and immunostained for Ki67. Error bars indicate mean±S.D. (n=4~5). FIGS. 27F and 27G show that MI-2 treatment induced cell death in sorted P5K cells. Following 6 days of treatment, the percentage of dead cells was measured by Sub-G1 assay (FIG. 27F) and TUNEL staining (FIG. 27G). Error bars indicate indicate mean±S.D. (n=4). FIG. 27H shows that the knockdown of LIN28B and PLAGL1 reduced the number of viable cells in sorted P5K cells. Cells were infected with the indicated shRNA-expressing lentiviruses. Viability was assayed by trypan-blue following 6 days in vitro. Error bars indicate mean±S.D. (n=4). **, p<0.01.

Figure 28A:
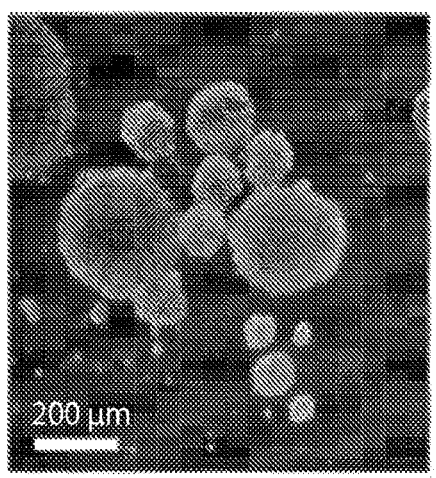
Figure 28B:
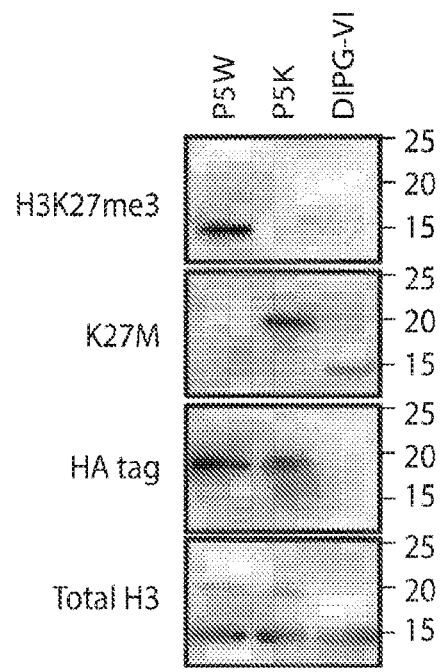
Figure 28C:
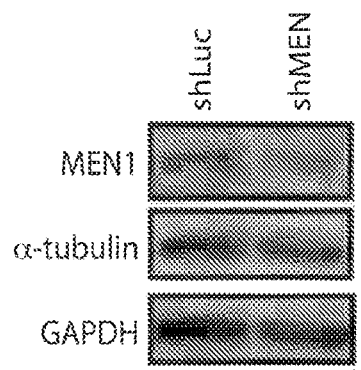
Figure 28D:
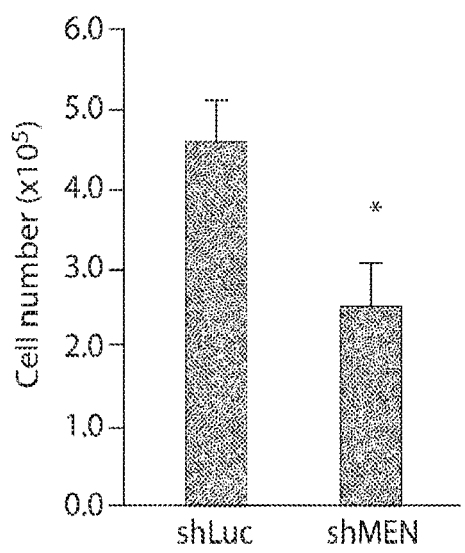

FIG. 28A shows bright phase microscopy of a patient-derived DIPG cell line. FIG. 28B shows western blotting indicating the presence of H3.3K27M mutation and significant reduction of H3K27 trimethylation mark (H3K27me3) in the DIPG cell line (DIPG-VI). FIGS. 28C and 28D show that the knockdown of menin suppresses the proliferation of DIPG cell line. Cells were transduced with control or menin shRNA-expressing (shMEN) lentiviruses. Following 7 days in vitro, knockdown of menin was confirmed by western blotting (FIG. 28D) and the number of viable cells was counted by trypan-blue staining (FIG. 28E). Error bars indicate indicate mean±S.D. (n=4). *, p<0.05; **, p<0.01.

Figure 29:
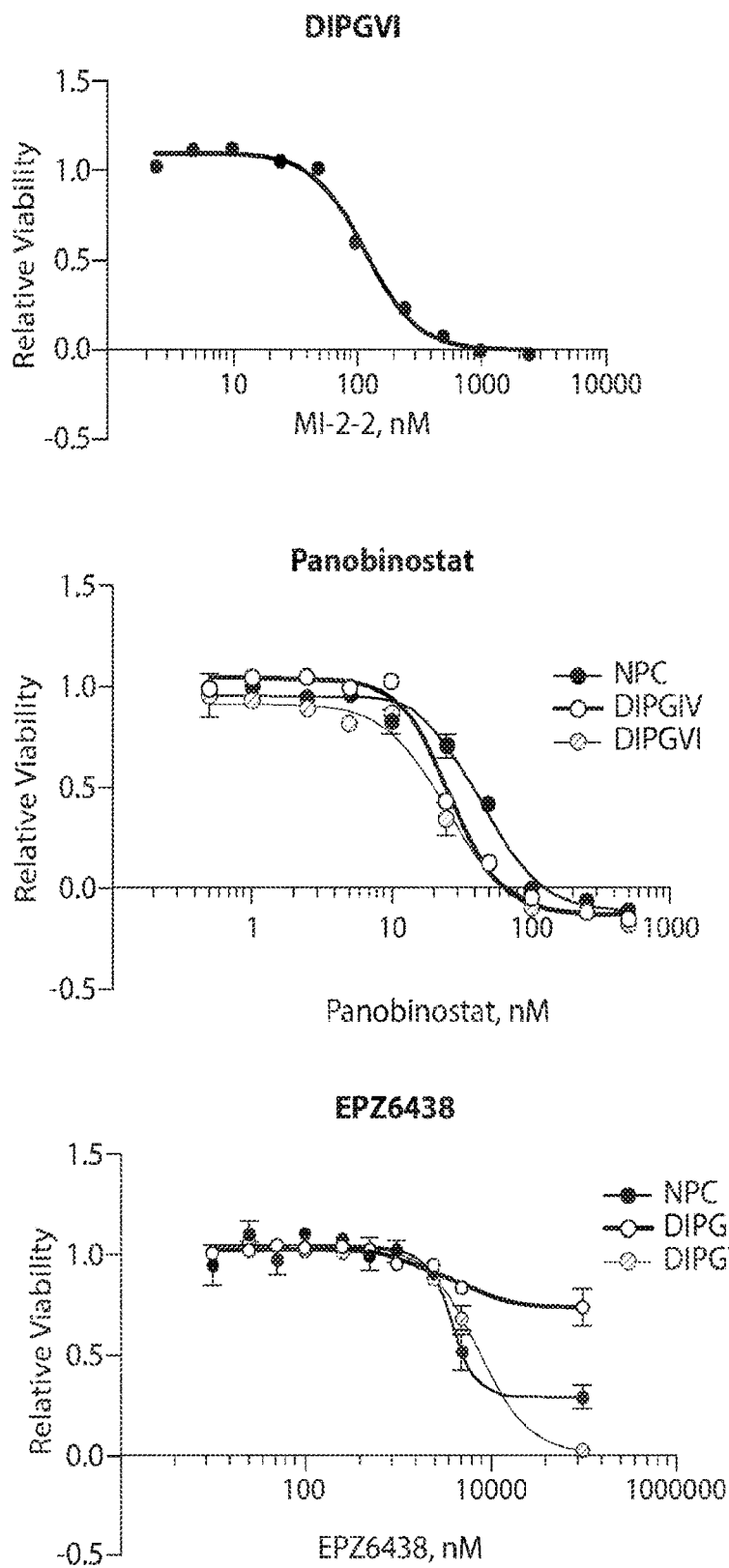

FIG. 29 shows MI-2-2 depletes patient-derived DIPG cells in vitro. Dose-response curves for the treatment of NPC, DIPGIV, and DIPGVI cell lines with MI-2-2, Panobinostat, and EPZ6438 are shown.

FIGS. 30A-30B show that MI-2-2 treatment decreases DIPG proliferation and increases apoptosis in vitro.

Figure 31A:
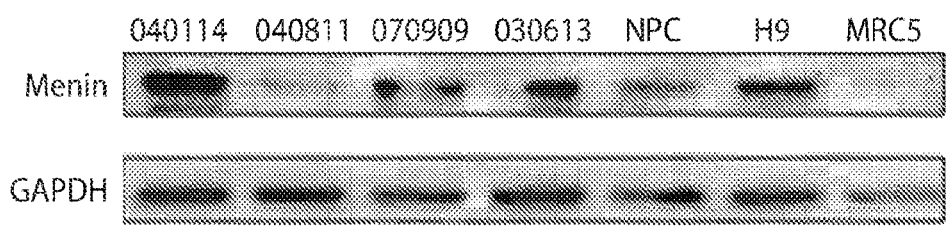
Figure 31B:
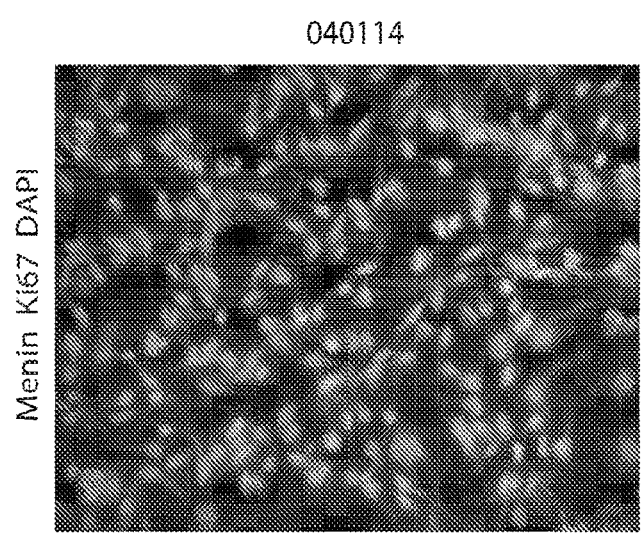

FIGS. 31A-31B show Menin is expressed in patient-derived glioblastoma cell lines.

Figure 32A:
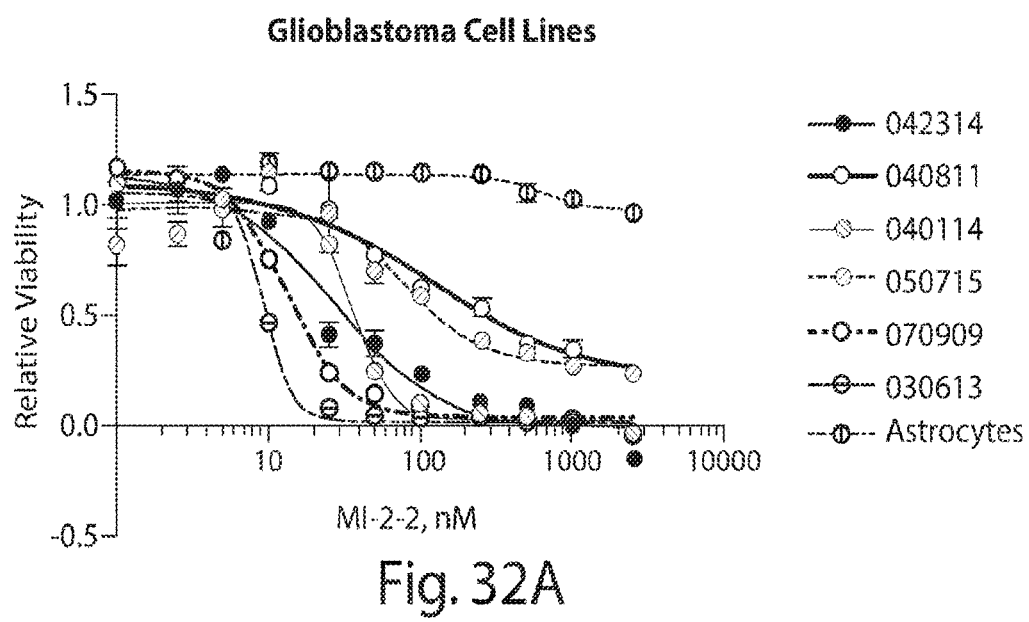
Figure 32B:
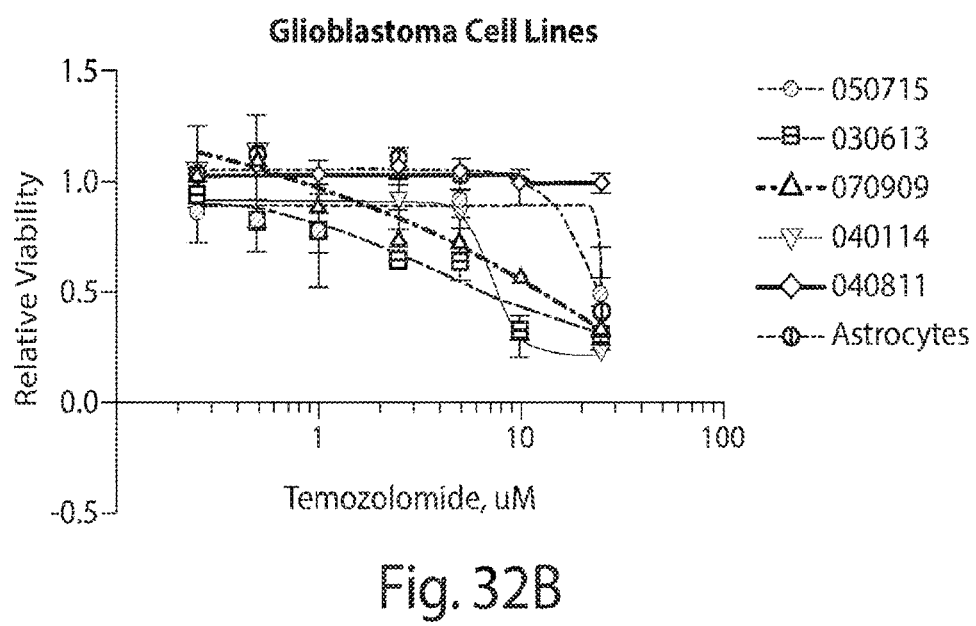
Figure 32C:
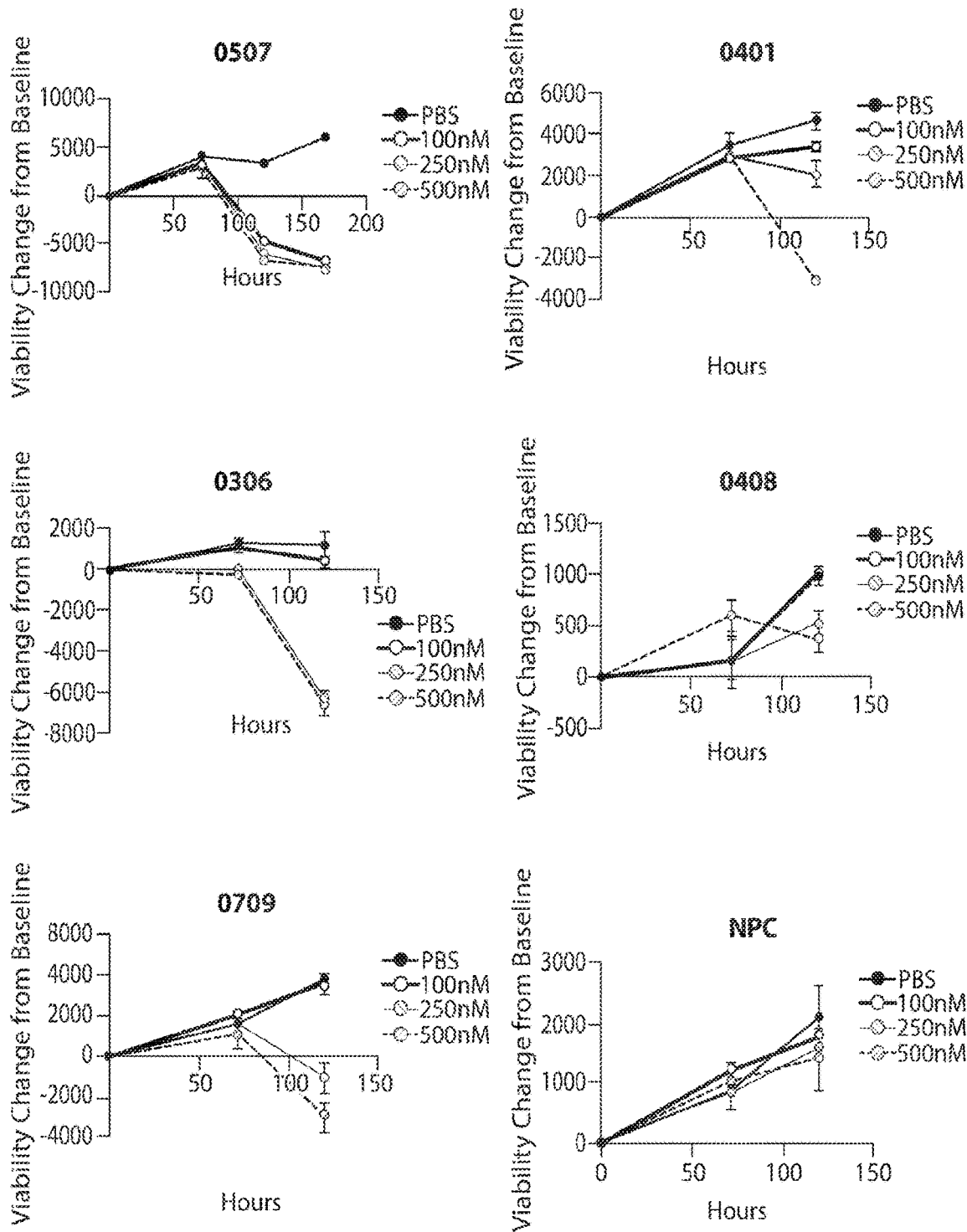

FIGS. 32A-32C show glioblastoma cell lines demonstrate sensitivity to MI-2-2 in vitro. Dose-response curves for the treatment of several glioblastoma cell lines with MI-2-2 and temozolomide are shown.

Figure 33A:
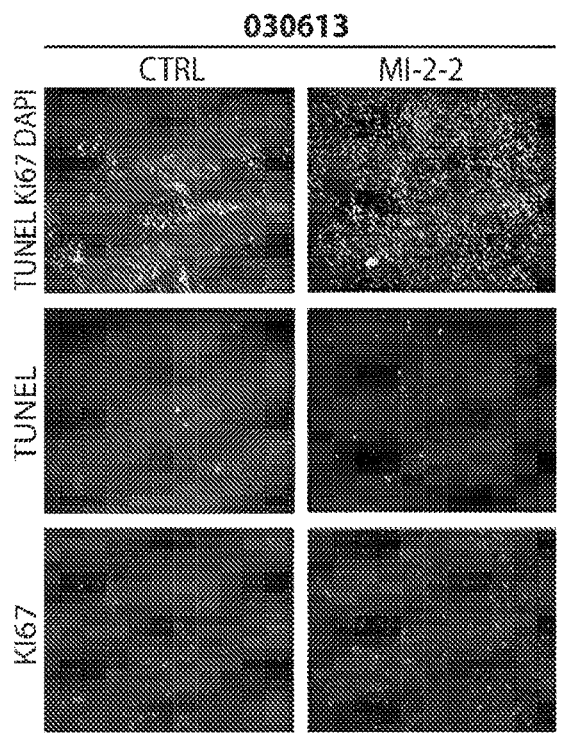
Figure 33B:
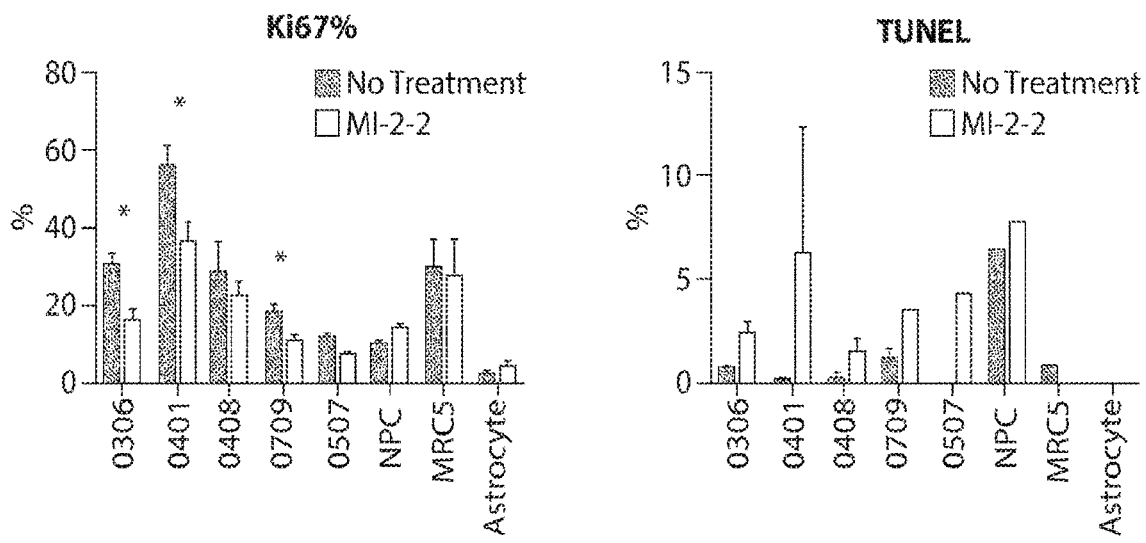
Figure 34A:
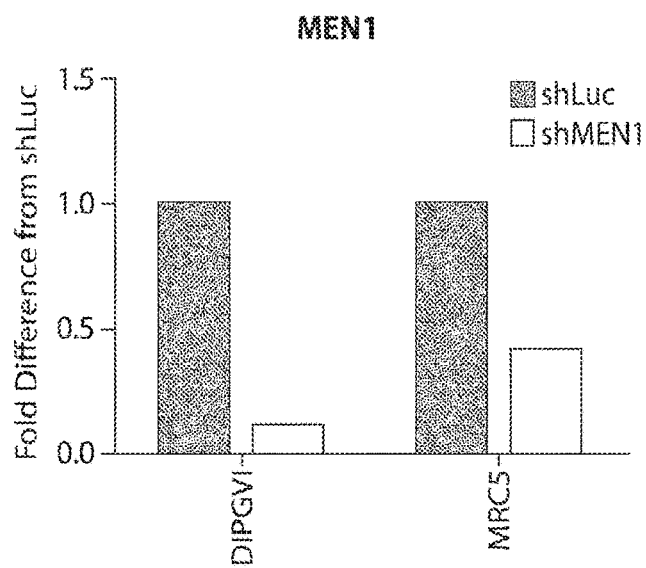
Figure 34B:
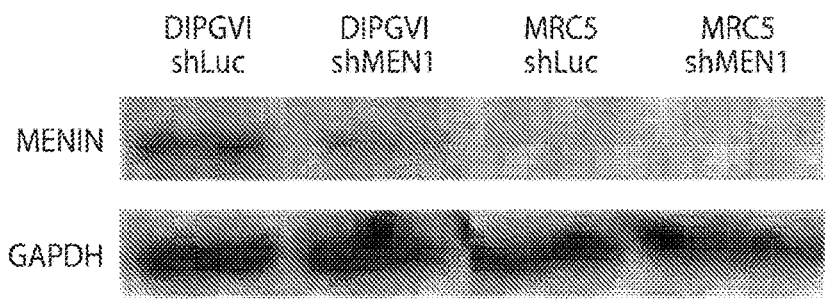
Figure 34C:
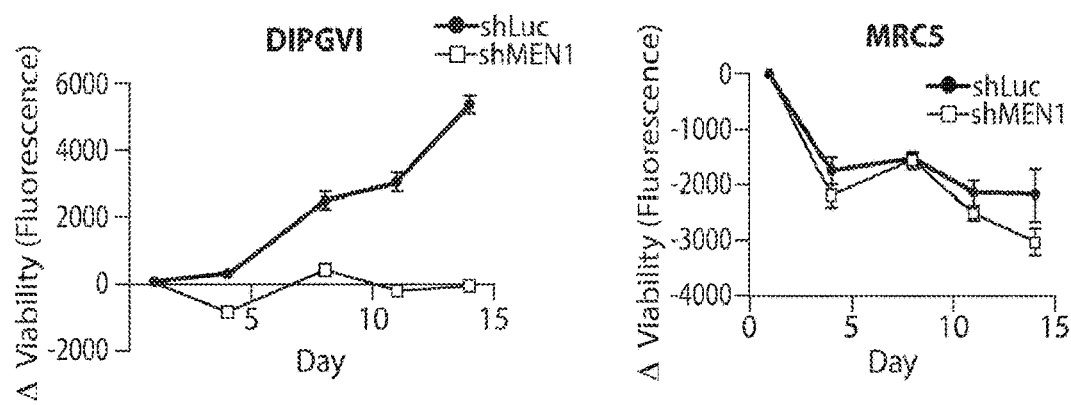
Figure 34D:
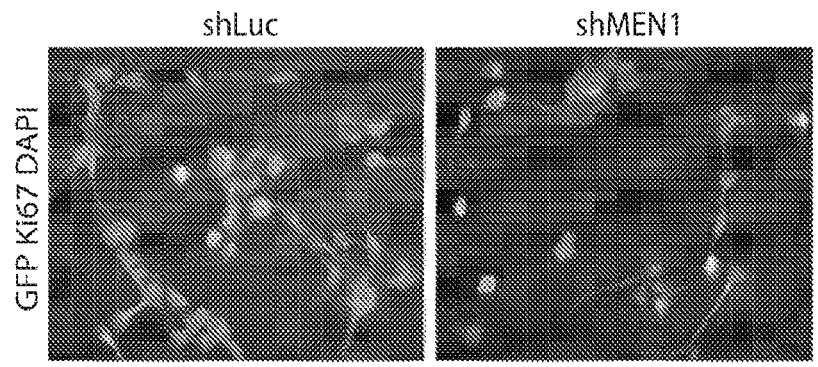
Figure 34E:
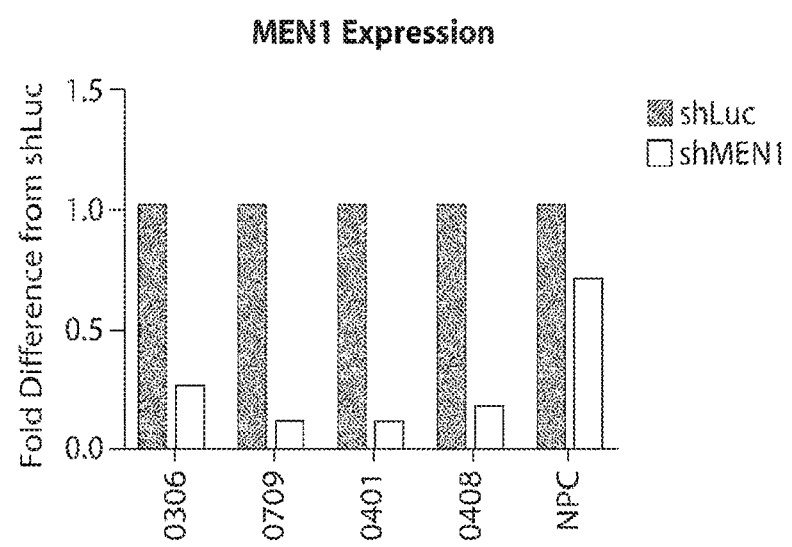
Figure 34F:
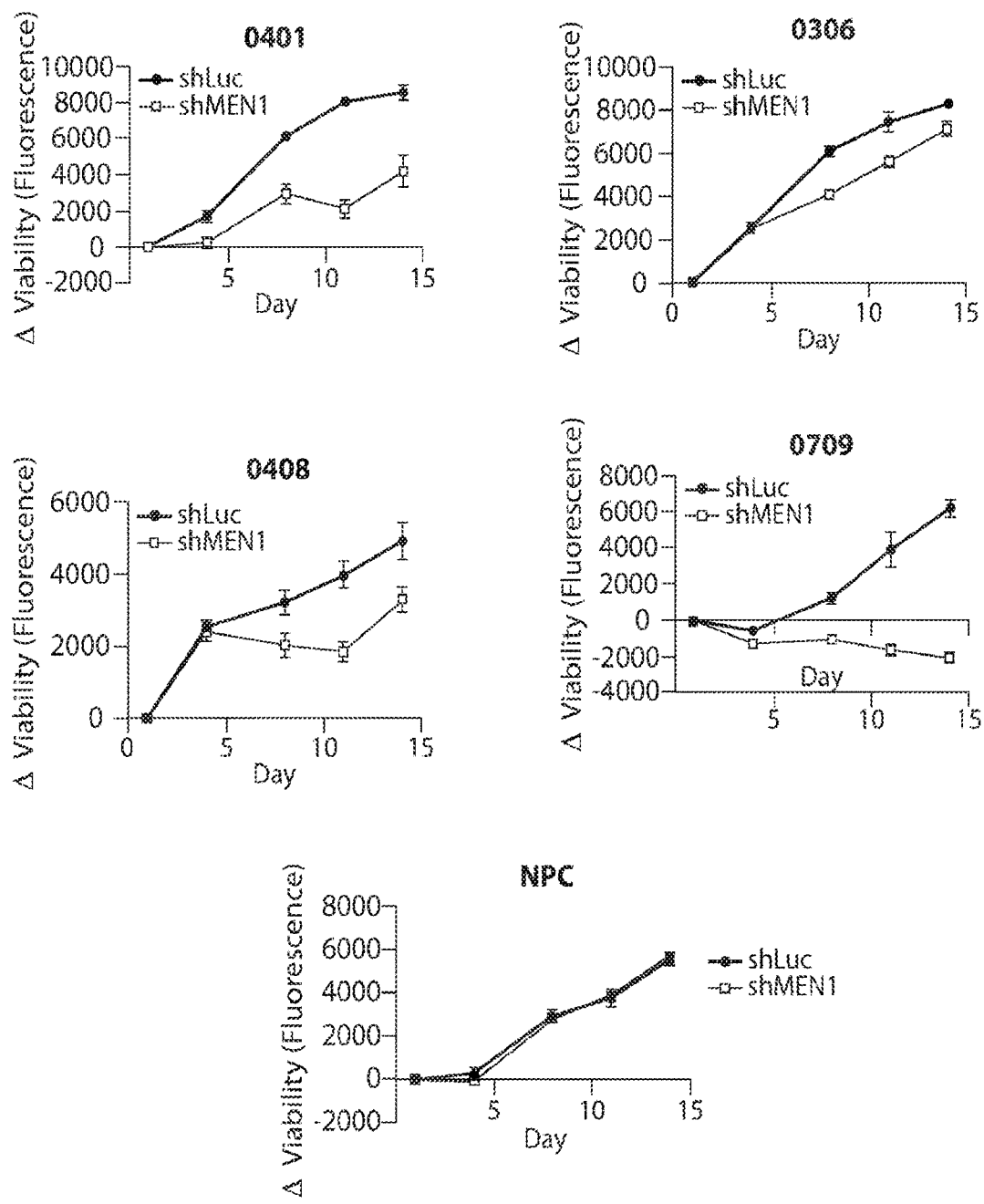

FIGS. 33A-33B show MI-2-2 decreases proliferation in glioblastoma lines. Proliferation assay for glioblastoma cell line 030613 is shown in FIG. 33A.

FIGS. 34A-34F show shRNA-driven MEN1 knockdown recapitulates MI-2-2 effects on cell viability.

Figure 35:
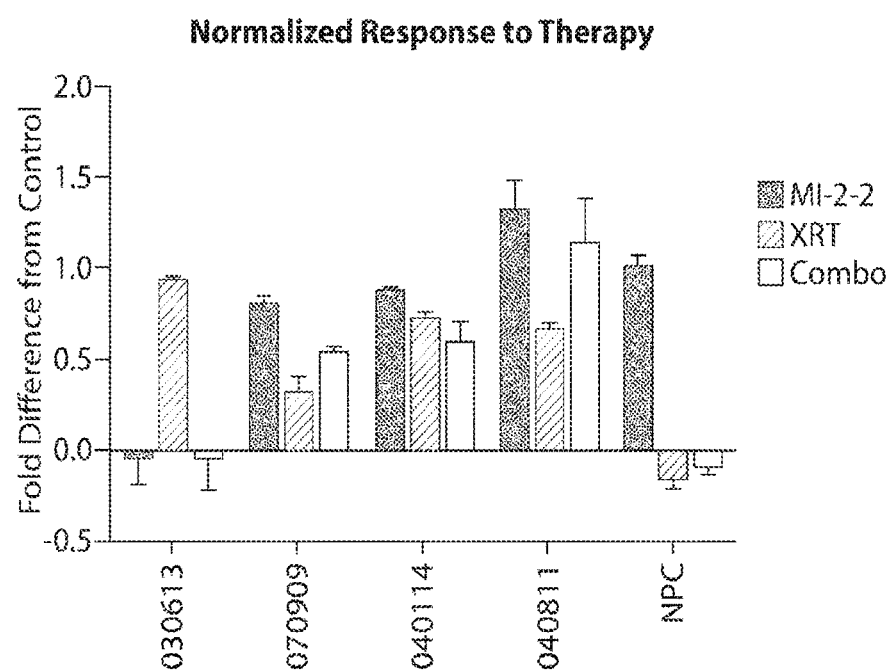

FIG. 35 shows normalized response of glioblastoma cell lines to MI-2-2 and radiation combination therapy.

Figure 36C:
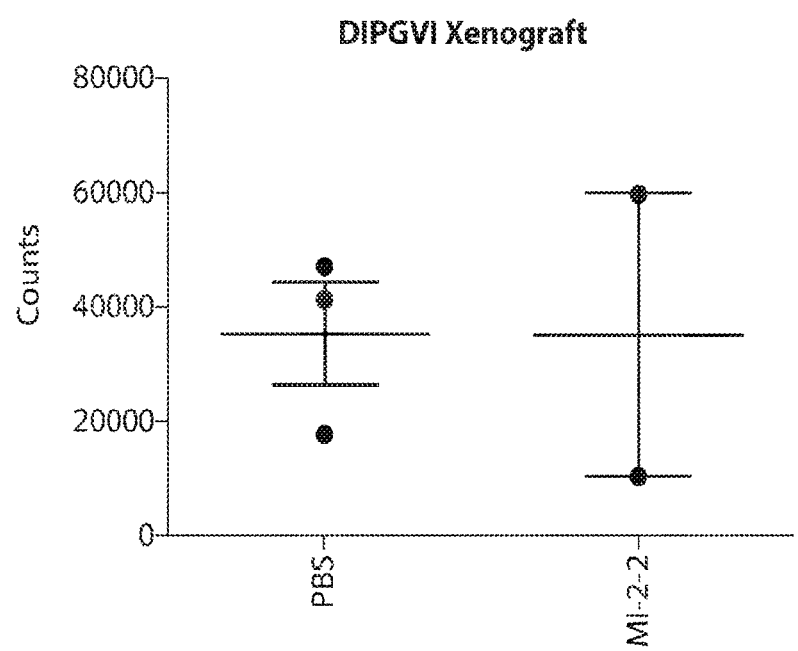

FIGS. 36A-36C show treatment of DIPGVI xenografts with MI-2-2.

Figure 37:
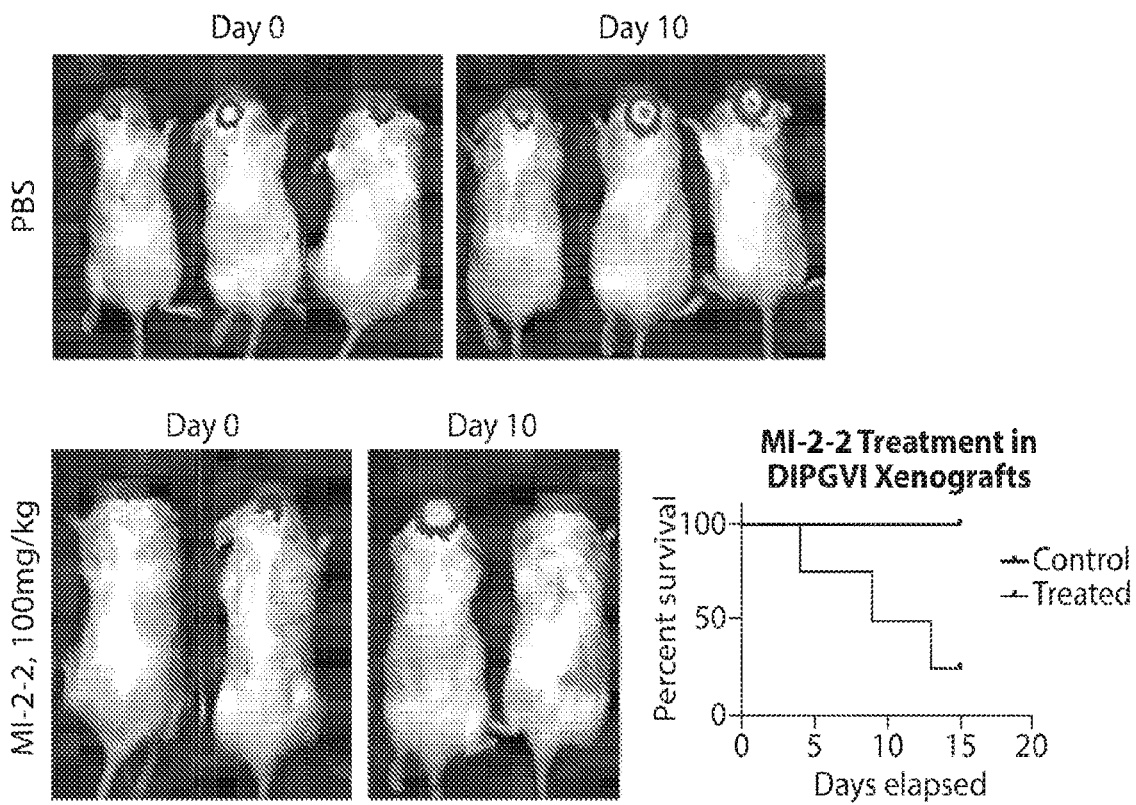

FIG. 37 shows MI-2-2 treatment in DIPGVI xenografts.

Figure 38:
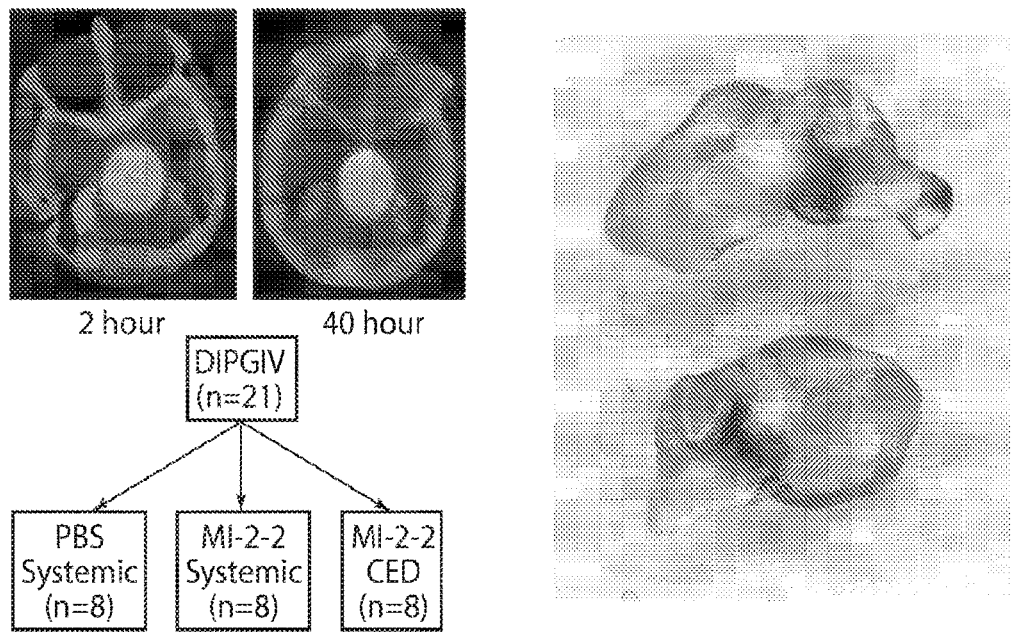

FIG. 38 shows that Convection Enhanced Delivery (CED) helps bypass the blood-brain barrier (BBB).

Figure 39:
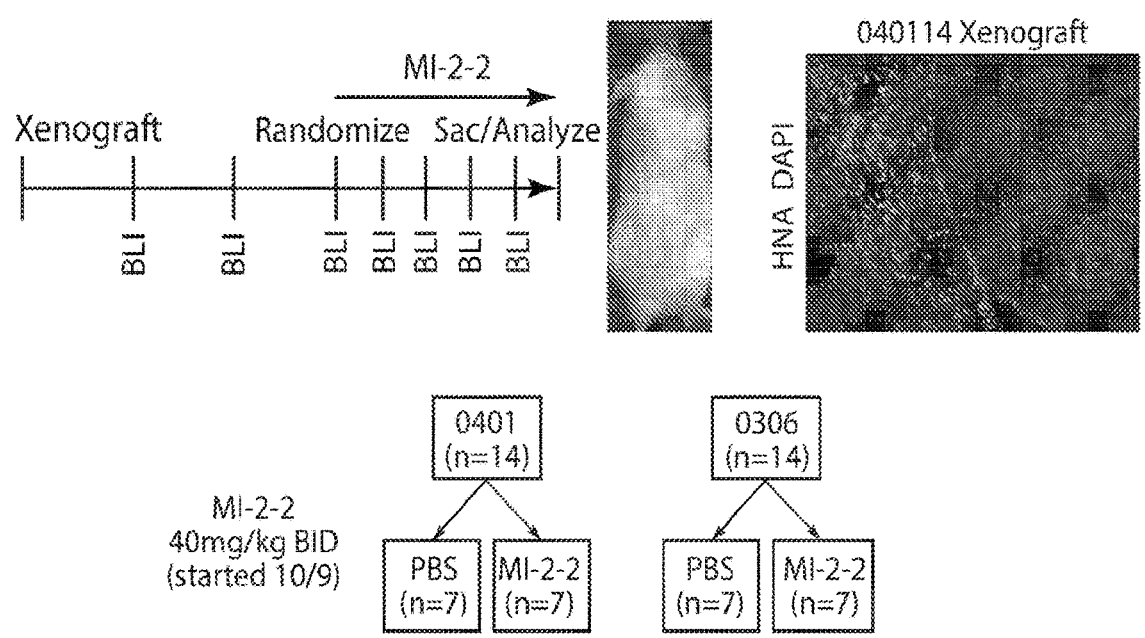

FIG. 39 shows MI-2-2 testing in vivo on gliblastoma xenografts.

Figure 40A:
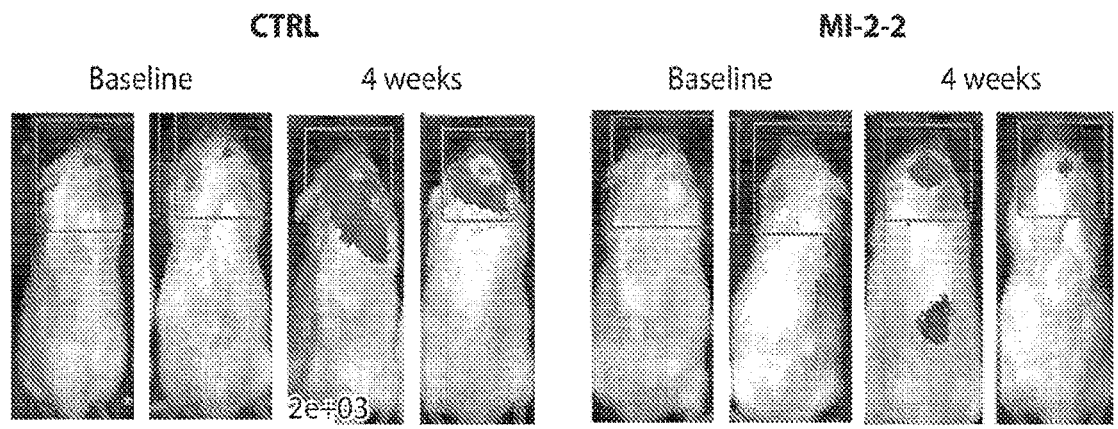
Figure 40B:
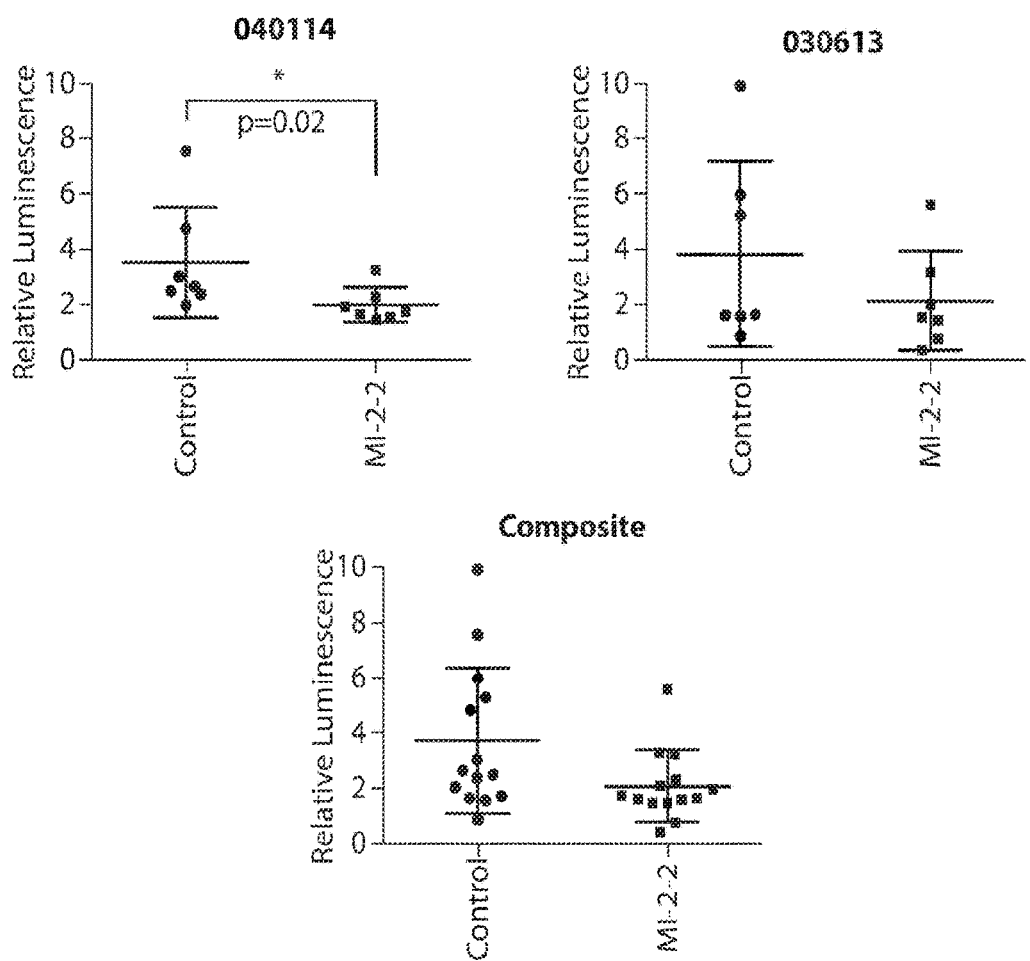

FIGS. 40A-40B shows efficacy of MI-2-2 in glioblastoma xenografts.

DETAILED DESCRIPTION OF CERTAIN EMBODIMENTS OF THE INVENTION

The present invention provides compounds of Formula (I), for the prevention and/or treatment of cancer. Exemplary cancers include, but are not limited to, brain cancer, lung cancer, large bowl cancer, pancreas cancer, biliary tract cancer, and endometrial cancer. In certain embodiments, the cancer is brain tumor. In certain embodiments, the brain tumor is DIPG. In certain embodiments, the cancer is pediatric brain tumor. In certain embodiments, the brain tumor is pediatric DIPG. In certain embodiments, the brain tumor is K27M-mutated DIPG.

Compounds

As generally described above, provided herein are compounds of Formula (I). In certain embodiments, the present disclosure provides compounds of Formula (I):

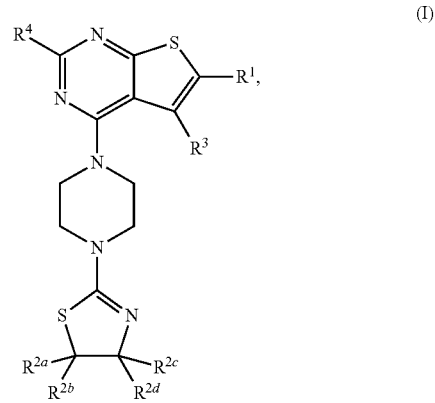

and pharmaceutically acceptable salts thereof,
wherein
each of $R^1$, $R^3$, and $R^4$ is independently hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, or —N(R$^B$)$_2$;

or R$^1$ and R$^3$ taken together with the intervening atoms form optionally substituted heterocyclyl or optionally substituted carbocyclyl each of R$^{2a}$, R$^{2b}$, R$^{2c}$, and R$^{2d}$ is independently hydrogen, halogen, optionally substituted C$_{1-6}$ alkyl, optionally substituted alkenyl, optionally substituted alkynyl, optionally substituted carbocyclyl, optionally substituted aryl, optionally substituted heterocyclyl, optionally substituted heteroaryl, —OR$^A$, or —N(R$^B$)$_2$; and each instance of R$^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

In certain embodiments, the compound of Formula (I) is of Formula (I-a):

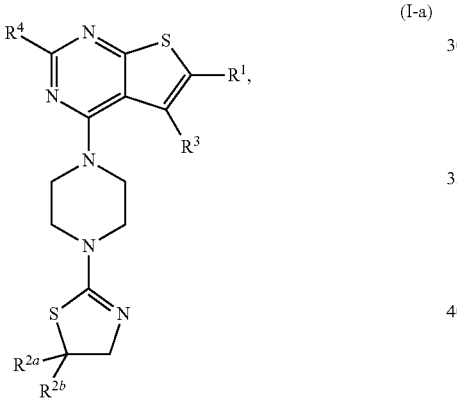

(I-a)

or a pharmaceutically acceptable salt thereof.

In certain embodiments, the compound of Formula (I) is of Formula (I-b):

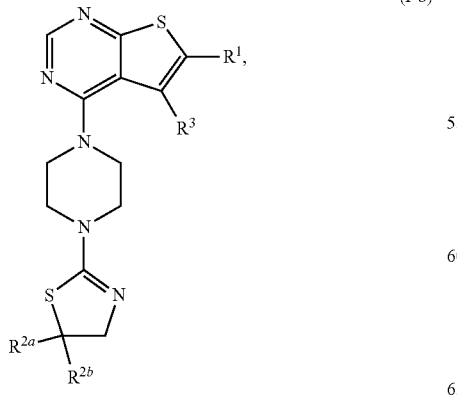

(I-b)

or a pharmaceutically acceptable salt thereof.

In certain embodiments, the compound of Formula (I) is of Formula (I-c):

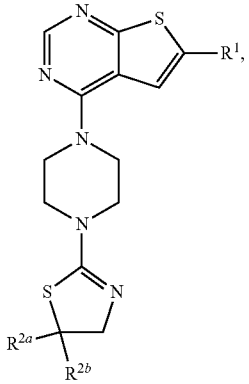

(I-c)

or a pharmaceutically acceptable salt thereof.

In certain embodiments, the compound of Formula (I) is of Formula (I-c1):

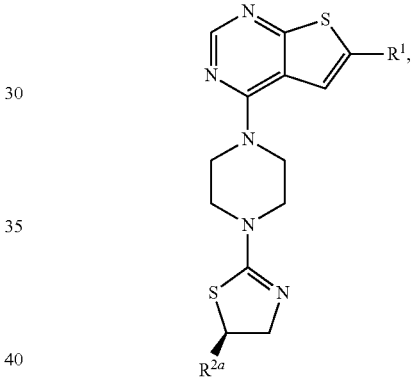

(I-c1)

or a pharmaceutically acceptable salt thereof.

In certain embodiments, the compound of Formula (I) is of Formula (I-c2):

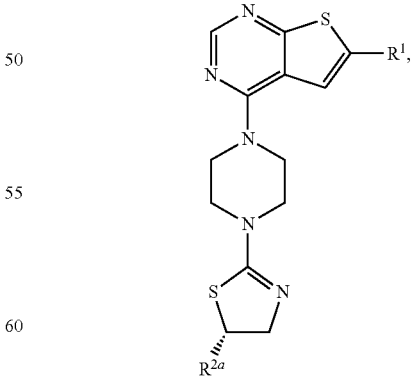

(I-c2)

or a pharmaceutically acceptable salt thereof.

In certain embodiments, R$^1$ is hydrogen, halogen, —NO$_2$, —N$_3$, —CN, or optionally substituted alkyl. In certain embodiments, R$^1$ is hydrogen. In certain embodiments, R$^1$ is halogen. In certain embodiments, $R^1$ is F. In certain embodiments, $R^1$ is Cl. In certain embodiments, $R^1$ is Br. In certain embodiments, $R^1$ is I. In certain embodiments, $R^1$ is optionally substituted $C_{1-6}$ alkyl. In certain embodiments, $R^1$ is optionally substituted $C_{1-6}$ alkyl. In certain embodiments, $R^1$ is unsubstituted $C_{1-6}$ alkyl (e.g., methyl, ethyl, n-propyl, or iso-propyl). In certain embodiments, $R^1$ is substituted $C_{1-6}$ alkyl. In certain embodiments, $R^1$ is optionally substituted $C_{1-6}$ haloalkyl. In certain embodiments, $R^1$ is —$C_{1-5}$alkylene-$CF_3$. In certain embodiments, $R^1$ is —$(CH_2)_{1-5}$—$CF_3$. In certain embodiments, $R^1$ is —$CH_2$—$CF_3$. In certain embodiments, $R^1$ is —$(CH_2)_2$—$CF_3$. In certain embodiments, $R^1$ is —$(CH_2)_3$—$CF_3$. In certain embodiments, $R^1$ is —$(CH_2)_4$—$CF_3$. In certain embodiments, $R^1$ is —$(CF_2)_{1-5}$—$CF_3$. In certain embodiments, $R^1$ is —$CF_2$—$CF_3$. In certain embodiments, $R^1$ is —$(CHCH_3)_{1-5}$—$CF_3$. In certain embodiments, $R^1$ is —$CHCH_3$—$CF_3$. In certain embodiments, $R^1$ is —$(CH_2)_{1-4}$-alkoxy. In certain embodiments, $R^1$ is —$(CH_2)_3$—$OCH_3$. In certain embodiments, $R^1$ is —$(CH_2)_{1-6}$-Ph. In certain embodiments, $R^1$ is —$CH_2$-Ph. In certain embodiments, $R^1$ is —$(CH_2)_2$-Ph. In certain embodiments, $R^1$ is —$(CH_2)_3$-Ph. In certain embodiments, $R^1$ is —$(CH_2)_4$-Ph. In certain embodiments, $R^1$ is optionally substituted carbocyclyl. In certain embodiments, $R^1$ is cyclohexyl. In certain embodiments, $R^1$ is optionally substituted aryl. In certain embodiments, $R^1$ is unsubstituted phenyl. In certain embodiments, $R^1$ is substituted phenyl.

In certain embodiments, $R^{2a}$ is hydrogen, halogen, or optionally substituted alkyl. In certain embodiments, $R^{2a}$ is hydrogen. In certain embodiments, $R^{2a}$ is halogen. In certain embodiments, $R^{2a}$ is F. In certain embodiments, $R^{2a}$ is Cl. In certain embodiments, $R^{2a}$ is Br. In certain embodiments, $R^{2a}$ is I. In certain embodiments, $R^{2a}$ is optionally substituted alkyl. In certain embodiments, $R^{2a}$ is optionally substituted $C_{1-6}$ alkyl. In certain embodiments, $R^{2a}$ is unsubstituted $C_{1-6}$ alkyl (e.g., methyl, ethyl, n-propyl, or iso-propyl). In certain embodiments, $R^{2a}$ is substituted $C_{1-6}$ alkyl.

In certain embodiments, $R^{2b}$ is hydrogen, halogen, or optionally substituted alkyl. In certain embodiments, $R^{2b}$ is hydrogen. In certain embodiments, $R^{2b}$ is halogen. In certain embodiments, $R^{2b}$ is F. In certain embodiments, $R^{2b}$ is Cl. In certain embodiments, $R^{2b}$ is Br. In certain embodiments, $R^{2b}$ is I. In certain embodiments, $R^{2b}$ is optionally substituted alkyl. In certain embodiments, $R^{2b}$ is optionally substituted $C_{1-6}$ alkyl. In certain embodiments, $R^{2b}$ is unsubstituted $C_{1-6}$ alkyl (e.g., methyl, ethyl, n-propyl, or iso-propyl). In certain embodiments, $R^{2b}$ is substituted $C_{1-6}$ alkyl.

In certain embodiments, $R^{2c}$ is hydrogen, halogen, or optionally substituted alkyl. In certain embodiments, $R^{2c}$ is hydrogen. In certain embodiments, $R^{2c}$ is halogen. In certain embodiments, $R^{2c}$ is F. In certain embodiments, $R^{2c}$ is Cl. In certain embodiments, $R^{2c}$ is Br. In certain embodiments, $R^{2c}$ is I. In certain embodiments, $R^{2c}$ is optionally substituted alkyl. In certain embodiments, $R^{2c}$ is optionally substituted $C_{1-6}$ alkyl. In certain embodiments, $R^{2c}$ is unsubstituted $C_{1-6}$ alkyl (e.g., methyl, ethyl, n-propyl, or iso-propyl). In certain embodiments, $R^{2c}$ is substituted $C_{1-6}$ alkyl.

In certain embodiments, $R^{2d}$ is hydrogen, halogen, or optionally substituted alkyl. In certain embodiments, $R^{2d}$ is hydrogen. In certain embodiments, $R^{2d}$ is halogen. In certain embodiments, $R^{2d}$ is F. In certain embodiments, $R^{2d}$ is Cl. In certain embodiments, $R^{2d}$ is Br. In certain embodiments, $R^{2d}$ is I. In certain embodiments, $R^{2d}$ is optionally substituted alkyl. In certain embodiments, $R^{2d}$ is optionally substituted $C_{1-6}$ alkyl. In certain embodiments, $R^{2d}$ is unsubstituted $C_{1-6}$ alkyl (e.g., methyl, ethyl, n-propyl, or iso-propyl). In certain embodiments, $R^{2d}$ is substituted $C_{1-6}$ alkyl.

In certain embodiments, $R^{2c}$ and $R^{2d}$ are each independently hydrogen or optionally substituted $C_{1-6}$ alkyl. In certain embodiments, $R^{2c}$ and $R^{2d}$ are hydrogen.

In certain embodiments, $R^3$ is hydrogen, halogen, —$NO_2$, —$N_3$, —CN, or optionally substituted alkyl. In certain embodiments, $R^3$ is hydrogen. In certain embodiments, $R^3$ is halogen. In certain embodiments, $R^3$ is F. In certain embodiments, $R^3$ is Cl. In certain embodiments, $R^3$ is Br. In certain embodiments, $R^3$ is I. In certain embodiments, $R^3$ is optionally substituted alkyl. In certain embodiments, $R^3$ is optionally substituted $C_{1-6}$ alkyl. In certain embodiments, $R^3$ is unsubstituted $C_{1-6}$ alkyl (e.g., methyl, ethyl, n-propyl, or iso-propyl). In certain embodiments, $R^3$ is substituted $C_{1-6}$ alkyl. In certain embodiments, $R^3$ is optionally substituted carbocyclyl. In certain embodiments, $R^3$ is cyclohexyl. In certain embodiments, $R^3$ is optionally substituted aryl. In certain embodiments, $R^3$ is unsubstituted phenyl.

In certain embodiments, $R^4$ is hydrogen, halogen, —$NO_2$, —$N_3$, —CN, or optionally substituted $C_{1-6}$ alkyl. In certain embodiments, $R^4$ is hydrogen. In certain embodiments, $R^4$ is halogen. In certain embodiments, $R^4$ is F. In certain embodiments, $R^4$ is Cl. In certain embodiments, $R^4$ is Br. In certain embodiments, $R^4$ is I. In certain embodiments, $R^4$ is optionally substituted $C_{1-6}$ alkyl. In certain embodiments, $R^4$ is unsubstituted $C_{1-6}$ alkyl (e.g., methyl, ethyl, n-propyl, or iso-propyl). In certain embodiments, $R^4$ is substituted $C_{1-6}$ alkyl. In certain embodiments, $R^4$ is optionally substituted carbocyclyl. In certain embodiments, $R^4$ is cyclohexyl. In certain embodiments, $R^4$ is optionally substituted aryl. In certain embodiments, $R^3$ is unsubstituted phenyl.

In certain embodiments, $R^3$ and $R^4$ are hydrogen. In certain embodiments, $R^3$ and $R^4$ are hydrogen; and $R^1$ is halogen or optionally substituted $C_{1-6}$ alkyl. In certain embodiments, $R^3$ is optionally substituted carbocyclyl; $R^4$ is hydrogen; and $R^1$ is halogen or optionally substituted $C_{1-6}$ alkyl.

In certain embodiments, $R^A$ is independently hydrogen, optionally substituted alkyl, or an oxygen protecting group. In certain embodiments, $R^A$ is hydrogen. In certain embodiments, $R^A$ is optionally substituted alkyl. In certain embodiments, $R^A$ is an oxygen protecting group such as Ac or Boc.

In certain embodiments, $R^B$ is independently hydrogen, optionally substituted alkyl, or a nitrogen protecting group. In certain embodiments, $R^B$ is hydrogen. In certain embodiments, $R^B$ is optionally substituted alkyl. In certain embodiments, $R^B$ is a nitrogen protecting group such as Ac or Fmoc.

Synthesis of the provided compounds can be carried out using the schemes and methods as disclosed in Grembecka et al. *Nat. Chem. Biol.* 2012, 12(8): 277-284, which is incorporated by reference by entirety herein.

Pharmaceutical Compositions, Kits, and Administration

The present invention provides pharmaceutical compositions comprising a compound of Formula (I), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the compound of Formula (I), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating cancer (e.g., brain tumors). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating cancer in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat cancer.

Methods of Treatment and Uses

The present invention also provides methods of using the compounds of Formula (I) or a pharmaceutically acceptable salt, solvate, hydrate, polymorph, co-crystal, tautomer, stereoisomer, isotopically labeled derivative, and prodrug thereof, or a pharmaceutical composition thereof, for the treatment or prevention of cancer (e.g., brain cancer) in a subject. In some embodiments, a provided compound is useful to delay the onset of, slow the progression of, or ameliorate the symptoms of, cancer. In some embodiments, a provided compound is administered in combination with other compounds, drugs, or therapeutics to treat cancer.

In some embodiments, compounds described herein are useful for treating a cancer such as brain tumor. In certain embodiments, the cancer is brain tumor. In certain embodiments, the cancer is pediatric brain tumor. In certain embodiments, the brain tumor is medulloblastoma, supratentorial medulloblastoma, pineoblastomas, gliomas, brain stem glioma, astrocytoma, oligodendroglioma, meningioma, ependymoma, germ cell tumors, or choroid plexus tumors (e.g., papillomas and carcinomas). In certain embodiments, the brain tumor is medulloblastoma. In certain embodiments, the brain tumor is supratentorial medulloblastoma. In certain embodiments, the brain tumor is pineoblastomas. In certain embodiments, the brain tumor is glioma. In certain embodiments, the brain tumor is brain stem glioma. In certain embodiments, the brain tumor is oligodendroglioma. In certain embodimetns, the brain tumor is meningioma. In certain embodiments, the brain tumor is ependymoma. In certain embodiments, the brain tumor is germ cell tumors. In certain embodiments, the brain tumor is choroid plexus tumors. In certain embodiments, the brain tumor is papillomas. In certain embodiments, the brain tumor is carcinomas. In certain embodiments, the brain tumor is a meningioma, astrocytoma (e.g., glioblastoma), or medulloblastoma. In certain embodiments, the brain tumor is glioblastoma. In certain embodiments, the brain tumor is Diffuse Intrinsic Pontine Gliomas (DIPGs). In certain embodiments, the brain tumor is wild-type DIPGs. In certain embodiments, the brain tumor is mutated DIPG. In certain embodiments, the brain tumor is K27M-mutated DIPG. In certain embodiments, the brain cancer is pediatric DIPG. In certain embodiments, the brain cancer is human mutated DIPG. In certain embodiments, the brain cancer is human child mutated DIPG. In certain embodiments, the brain cancer is human K27M-mutated DIPG. In certain embodiments, the brain cancer is human child K27M-mutated DIPG. As it is generally understood, the point mutation such as K27M can be determined by the genome mapping. In certain embodiments, the brain cancer is H3F3A-mutated DIPG. In certain embodiments, the brain cancer is HIST1H3B-mutated DIPG. In certain embodiments, the brain cancer is human H3F3A-mutated DIPG. In certain embodiments, the brain cancer is human HIST1H3B-mutated DIPG. In certain embodiments, the brain cancer is human child H3F3A-mutated DIPG. In certain embodiments, the brain cancer is human child HIST1H3B-mutated DIPG.

In certain embodiments, the present invention provides methods for treating tumors of the central nervous system. Examples of tumors of the central nervous system include, but are not limited to, astrocytic tumours (i.e., astrocytomas) (e.g., pilocytic astrocytoma (e.g., pilomyxoid astrocytoma), subependymal giant cell astrocytoma, pleomorphic xanthoastrocytoma, diffuse astrocytoma, anaplastic astrocytoma, glioblastoma, (e.g., giant cell glioblastoma, gliosarcoma), gliomatosis cerebri), oligodendroglial tumours (e.g., oligodendroglioma, anaplastic oligodendroglioma), oligoastrocytic tumours (e.g., oligoastrocytoma, anaplastic oligoastrocytoma), ependymal tumours (e.g., subependymoma, myxopapillary ependymoma, ependymoma, anaplastic ependymoma), choroid plexus tumours (e.g., choroid plexus papilloma, atypical choroid plexus papilloma, choroid plexus carcinoma), other neuroepithelial tumours (e.g., astroblastoma, chordoid glioma of the third ventricle, angiocentric glioma), neuronal and mixed neuronal-glial tumours (e.g., dysplastic gangliocytoma of cerebellum, desmoplastic infantile astrocytoma/ganglioglioma, dysembryoplastic neuroepithelial tumour, gangliocytoma, ganglioglioma, anaplastic ganglioglioma, central neurocytoma, extraventricular neurocytoma, cerebellar liponeurocytoma, papillary glioneuronal tumour, rosette-forming glioneuronal tumour of the fourth ventricle, paraganglioma), tumours of the pineal region (e.g., pineocytoma, pineal parenchymal tumour of intermediate differentiation, pineoblastoma, papillary tumors of the pineal region), embryonal tumours (e.g., medulloblastoma (e.g., medulloblastoma with extensive nodularity, anaplastic medulloblastoma), CNS Primitive neuroectodermal tumour (e.g., CNS Neuroblastoma, atypical teratoid/rhabdoid tumour), schwannoma, neurofibroma, perineurioma, malignant peripheral nerve sheath tumour (MPNST), tumours of meningothelial cells (e.g., meningioma, atypical meningioma, anaplastic meningioma), mesenchymal tumours (e.g., lipoma, angiolipoma, hibernoma, liposarcoma, solitary fibrous tumour, fibrosarcoma, malignant fibrous histiocytoma, leiomyoma, leiomyosarcoma, rhabdomyoma, rhabdomyosarcoma, chondroma, chondrosarcoma, osteoma, osteosarcoma, osteochondroma, haemangioma, epithelioid hemangioendothelioma, haemangiopericytoma, anaplastic haemangiopericytoma, angiosarcoma, kaposi sarcoma, ewing sarcoma), primary melanocytic lesions (e.g., diffuse melanocytosis, melanocytoma, malignant melanoma, meningeal melanomatosis), haemangioblastoma, malignant lymphomas, plasmocytoma, granulocytic sarcoma, germinoma, embryonal carcinoma, yolk sac tumour, choriocarcinoma, teratoma, mixed germ cell tumours, craniopharyngioma, granular cell tumour, pituicytoma, and spindle cell oncocytoma of the adenohypophysis.

In certain embodiments, the compound useful for the treatment of cancer (e.g., brain tumor) is selected from one of the following formulae:

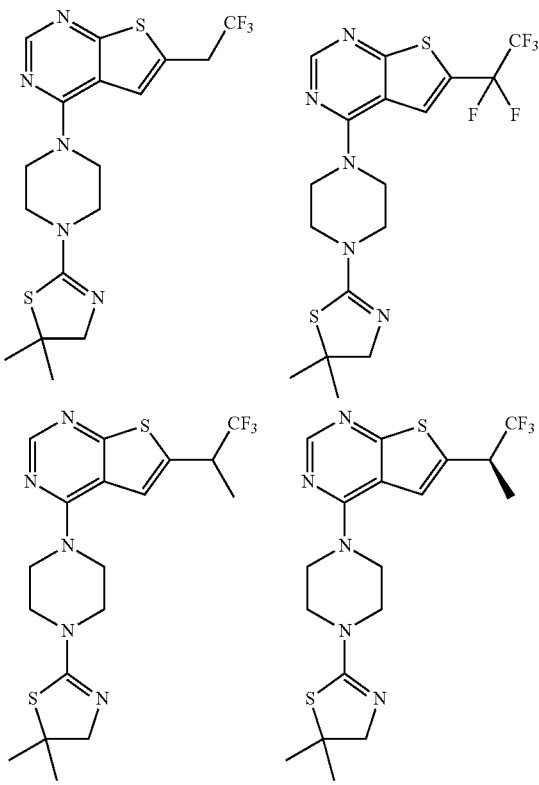

-continued

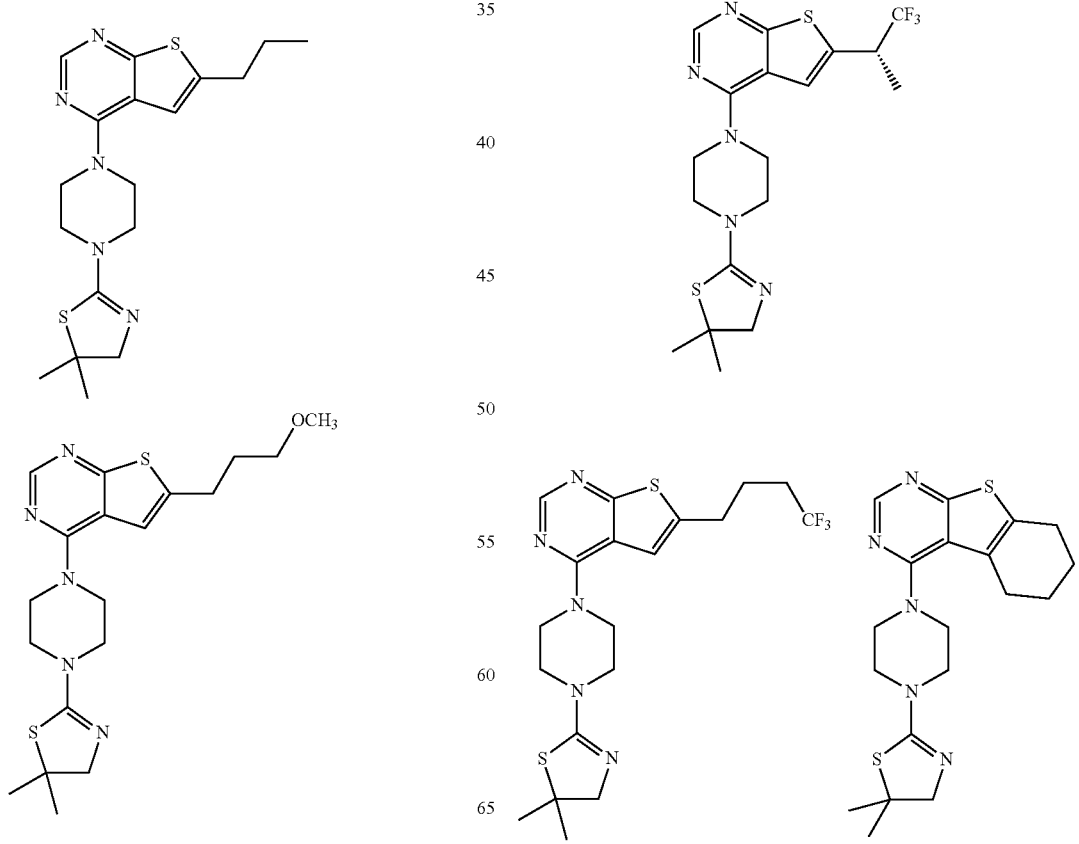

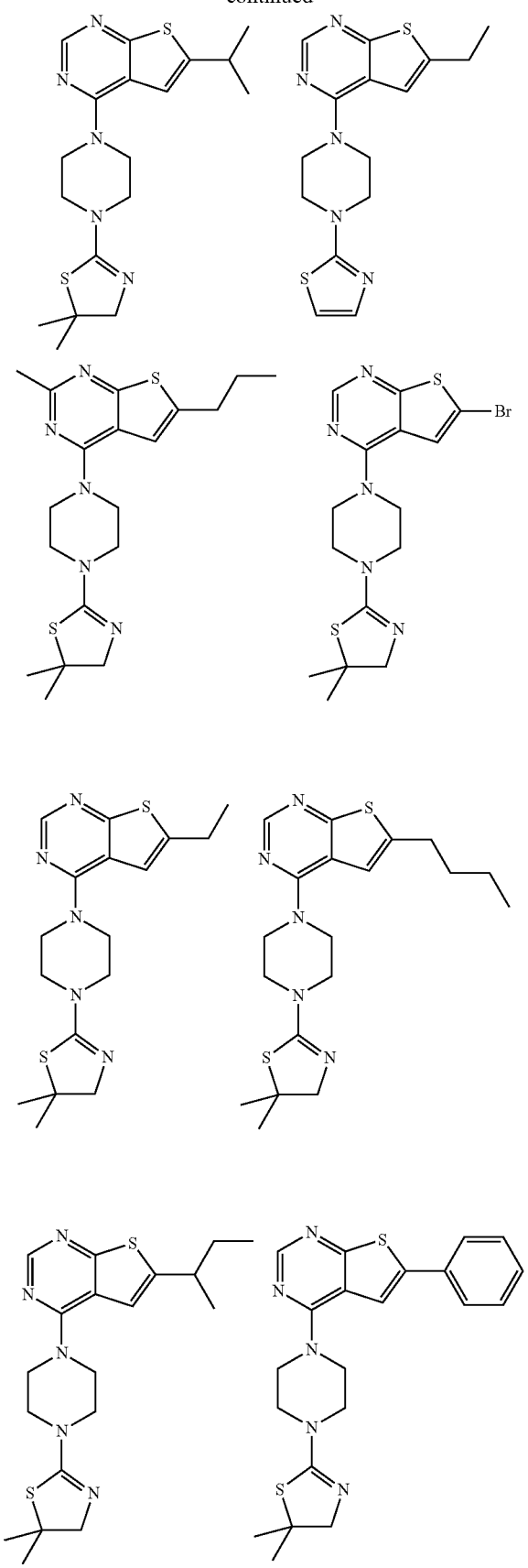
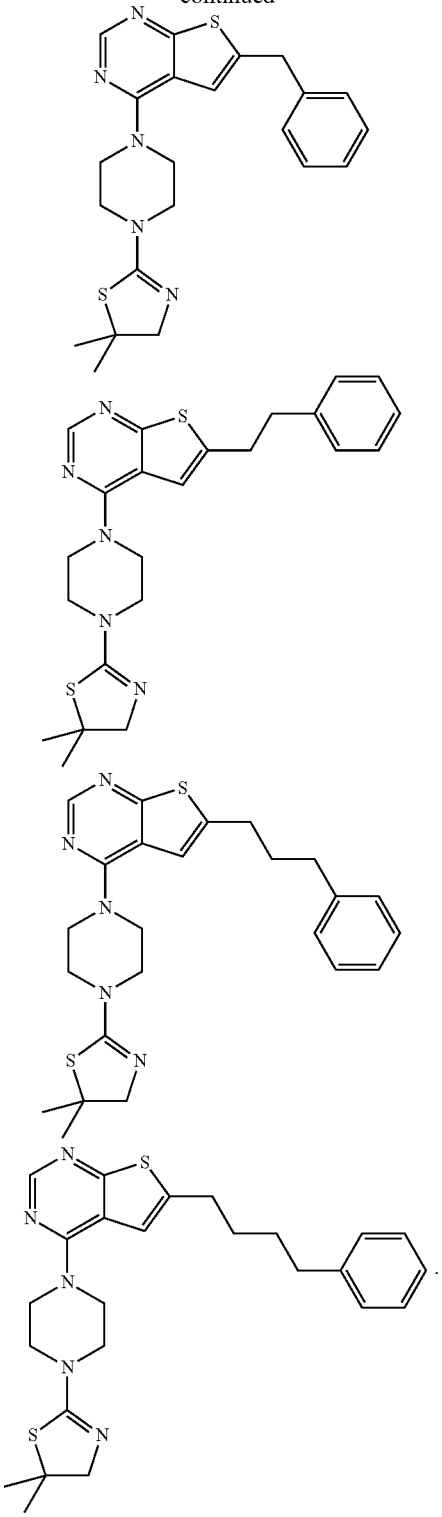

In certain embodiments, the subject is a mammal. In certain embodiments, the subject is a human. In certain embodiments, the subject is a human of any age. In certain embodiments, the subject is a human child. In certain embodiments, the subject is a human adult. In certain embodiments, the subject is under age 15. In certain embodiments, the subject is age 15 or over. In certain embodiments, the subject is between 5-8 years old. In certain embodiments, the subject has cancer cells carrying the K27M mutation in histone H3. In certain embodiments, the subject is a human having diffuse intrinsic pontine glioma (DIPG). In certain embodiments, the subject is a human child having diffuse intrinsic pontine glioma (DIPG). In certain embodiments, the subject is a human adult having diffuse intrinsic pontine glioma (DIPG).

The cell described herein may be an abnormal cell. The cell may be in vitro or in vivo. In certain embodiments, the cell is a proliferative cell. In certain embodiments, the cell is a stem cell. In certain embodiments, the cell is a blood cell. In certain embodiments, the cell is a lymphocyte. In certain embodiments, the cell is a cancer cell. In certain embodiments, the cell is a brain tumor cell. In certain embodiments, the cell is a meningioma cell. In certain embodiments, the cell is an astrocytoma cell. In certain embodiments, the cell is a glioblastoma cell. In certain embodiments, the cell is a medulloblastoma cell. In certain embodiments, the cell is a glioma cell. In certain embodiments, the cell is a diffuse intrinsic pontine glioma (DIPG) cell. In certain embodiments, the cancer cells carry the K27M mutation in histone H3. In certain embodiments, the cells carry the H3F3A mutation in histone H3.3. In certain embodiments, the cells carry the HIST1H3B mutation in histone H3.1. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

As used herein, Histone H3 refers to one of the five main histone proteins involved in the structure of chromatin in eukaryotic cells (Bhasin et al., *J. Comput. Biol.* 2006, 13(1): 102-12). Mammalian cells have three known sequence variants of histone H3. These are denoted as Histone H3.1, Histone H3.2 and Histone H3.3. In certain embodiments, the histone H3 is H3.1. In certain embodiments, the histone H3 is H3.2. In certain embodiments, the histone H3 is H3.3.

The present invention also provides methods of inhibiting cell growth in a biological sample or subject.

In still another aspect, the present invention provides methods of inducing apoptosis in a cell in a biological sample or a subject.

In still another aspect, the present invention provides methods of inhibiting the interaction of menin and MLL fusion protein in a biological sample or a subject.

In certain embodiments, the methods described herein include administering to a subject or contacting a biological sample with an effective amount of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound of Formula (I), or a pharmaceutically acceptable salt thereof, or a pharmaceutical composition thereof. In certain embodiments, the methods described herein include administering to a subject or contacting a biological sample with an effective amount of a pharmaceutically acceptable salt of a compound of Formula (I). In certain embodiments, the pharmaceutically acceptable salt is a salt of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, or valerate salts.

In certain embodiments, the compound is administered in combination with one or more additional therapeutic agents described herein. In certain embodiments, the additional therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunomodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib ORES SA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentie), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin aminopterin, and hexamethyl melamine.

In certain embodiments, the therapeutic agent is a receptor tyrosine kinase inhibitor. In certain embodiments, the tyrosine kinase inhibitor is selected from the group consisting of axitinib, bortezomib, bosutinib, carfilzomib, crizotinib, dabrafenib, dasatinib, erlotinib, gefitinib, Ibrutinib, imatinib, lapatinib, nilotinib, nazopanib, pegaptanib, ponatinib, ruxolitinib, sunitinib, trametinib, vandetanib, vemurafenib, and vismodegib.

In certain embodiments, the compound is administered in combination with an additional therapeutic treatment such as radiation. In certain embodiments, the subject is undergoing radiation therapy.

Embrynoic Stem Cell-Based Tumor Model and Uses Thereof

The present disclosure also provides an embryonic stem cell-based tumor cell model, which can be used for drug screening and disease target identification. Such a tumor cell model may be a genetically engineered precursor cell derived from embryonic stem cells (ESCs), such as human embryonic stem cells. Embryonic stem cells are pluripotent stem cells derived from embryo. Embryonic stem cells are the most versatile cells and can be differentiated into all types of cell lineages under suitable culturing conditions. A precursor cell is a type of partially differentiated stem cell. It can be a unipotent cell that is determined to differentiate into one specific type of cells. Examples of the genetically engineered precursor cells for use as the tumor cell model include, but not limited to, neural precursor cells, liver precursor cells, bone marrow precursor cells, endothelial precursor cells, myeloid precursor cells, and oligodendrocyte precursor cells.

The genetically engineered precursor cell can comprise any types of oncogenes. As used herein, oncogenes refer to any genetic material, the expression of which contribute to tumorgenesis. In some embodiments, the oncogene is a wild-type gene that has the potential to induce to tumorgenesis. Any of the genetically engineered precursor cell may over-express such an oncogene, leading to tumorigenesis. In other embodimetns, the oncogene may be a mutated gene that contributes to tumor development. In some examples, the mutation(s) in the oncogene results in gaining a function, which lead to tumorgenesis. In some examples, the genetically engineered precursor cell may express a mutated tyrosine kinase gene. In certain embodiments, the genetically engineered precursor cell expresses a constitutively active form of PDGERA (e.g., the D842V mutant).

In other examples, the mutation(s) in the oncogene results in loss of a function, which lead of tumorgenesis. For example, the oncogene may be a mutated tumor suppressor gene (e.g., p53). As used herein, tumor suppressor genes refer to genes that protect a cell from one step on the path to cancer. Mutation of tumor suppressor genes would cause a loss or reduction in its function and the cell can progress to cancer. In certain embodiments, the tumor suppressor genes are selected from the group consisting of p53, PI3K, pVHL, APC, CD95, STS, YPEL3, ST7, and ST14. In certain embodimetns, the tumor suppressor gene is p53.

In some embodiments, the genetically engineered precursor cell may comprise a gene that express an antisense RNA or an interfering RNA (e.g., a small hairpin RNA) that targets a tumor suppressor gene so as to reduce the level of that tumor suppressor gene in the presurcor cell.

In certain embodiments, the oncogene is mutated H3 histone. In certain embodiments, the oncogenes are the K27M mutant of H3 histone.

In certain embodiments, the genetically engineered precursor cell is a neural precursor cell (NPC) that expresses a mutated H3 histon gene (e.g., a histone gene encoding the K27M H3 mutant), a constitutively active form of PDGERA (e.g., the D842V mutant), and/or exhibit a lower level of p53 as compared to a wild-type counterpart. In some embodiments, the reduced level of p53 can be achieved by expressing an interfering RNA molecule (e.g., a small hairpin RNA) that targets the p53 gene.

As used herein, PDGFRA is a gene encoding a cell surface tyrosine kinase receptor for members of the platelet-derived growth factor family. A constitutively active form of PDGFRA refers to a protein form encoded by PDGFRA with constant activity.

In some embodiments, precursor cells (e.g., NPCs) can be obtained by incubating embryonic stem cells under suitable conditions allowing for the differentiation of ESCs to form desired precursor cells such as NPCs, following methods known in the art or disclosed herein. Any of the oncogenes known in the art and/or disclosed herein can then be introduced into the precursor cells via conventional technology, e.g., electroporation or using a viral vector.

NPCs are self-renewing, multipotent cells that can differentiated into cells of the nervous system, including neurons, astrocytes, and oligodendrocytes. An expression cassettee encoding the K27M H3 histone can be introduced into the NPCs via methods known in the art, for example, by viral transfection (using a retroviral vector or a lentiviral vector), to produce genetically engineered NPCs, which may serve as a brain tumor (e.g., DIPG) model.

In some examples, the genetically engineered NPCs are further modified to express a constitutitively active form of PDGERA (e.g., the D842V mutant). For example, a nucleotide sequence encoding such a mutant can be introduced into the NPCs via a known method. The nucleotide sequence can be operatively linked to a suitable promoter, which controls the expression of the PDGERA mutant.

In some examples, the genetically engineered NPCs may have reduced p53 activity (p53 knockdown). This can be achieved by inhibiting the expression of endogenous p53 gene via, e.g., RNA interference.

To prepare any of the genetically engineered precursor cells as described herein, nucleic acids encoding any of the oncogenes described herein (e.g., the K27M H3 histone mutant and/or the D842V PDGERA mutant) or encoding an interfering RNA targeting p53, can be inserted into a suitable vector (e.g., a retroviral vector or a lentiviral vector) using methods known in the art. Sambrook et al. *Molecular Cloning, A Laboratory Manual,* 3rd Ed., Cold Spring Harbor Laboratory Press. An interfering RNA is an RNA molecule that mediates RNA interference (RNAi), a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. For example, the gene and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art. Sambrook et al. *Molecular Cloning, A Laboratory Manual,* 3rd Ed., Cold Spring Harbor Laboratory Press.

A "vector" refers to a nucleic acid molecule capable of transporting another nucleic acid to which it has been linked. The vector can be capable of autonomous replication or integrate into a host DNA. Examples of the vector include a plasmid, cosmid, or viral vector. The vectors for use in the methods described herein may include a nucleic acid in a form suitable for expression of the nucleic acid in a host cell. Preferably the vector includes one or more regulatory sequences operatively linked to the nucleic acid sequence to be expressed. The term "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of transcription of RNA desired, and the like.

Selection of a suitable vector may depend on the type of host cell, to which the vector is to be introduced. For example, a mammalian vector may be selected if it is to be introduced into a mammalian cell such as a human cell. In some examples, a viral vector may be used for introducing nucleic acids that encode a fusion polypeptide as described herein into a precursor cell such as NPCs. A "viral vector" as described herein refers to a recombinantly produced virus or viral particle that comprises a polynucleotide to be delivered into a host cell, either in vivo, ex vivo or in vitro. Examples of viral vectors include retroviral vectors such as lentiviral vectors, adenovirus vectors, adeno-associated virus vectors, and the like. In aspects where gene transfer is mediated by a retroviral vector, a vector construct refers to the polynucleotide comprising the retroviral genome or part thereof, and a gene of interest.

A variety of promoters can be used for expression of any of the proteins or RNAs of interest. Promoters include cytomegalovirus (CMV) intermediate early promoter, a viral LTR such as the Rous sarcoma virus LTR, HIV-LTR, HTLV-1 LTR, the simian virus 40 (SV40) early promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters (See, e.g., Brown et al. *Cell* 1987, 49:603-612), those using the tetracycline repressor (tetR) (See, e.g., Gossen et al. *Proc. Natl. Acad. Sci. USA* 1992, 89:5547-5551; Yao et al. *Human Gene Therapy* 1998, 9:1939-1950; Shockelt et al. *Proc. Natl. Acad. Sci. USA* 1995, 92:6522-6526). Other systems include FK506 dimer, VP16 or p65 using estradiol, RU486, diphenol murislerone or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters (See, e.g., Brown et al. *Cell* 1987, 49:603-612; Gossen et al. *Proc. Natl. Acad. Sci. USA* 1992, 89:5547-5551) combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells trans-activator or repressor fusion protein, which in some instances can be toxic to cells (Gossen et al. *Proc. Natl.*

*Acad. Sci. USA* 1992, 89:5547-5551; Shockett et al. *Proc. Natl. Acad. Sci. USA* 1995, 92:6522-6526), to achieve its regulatable effects.

The effectiveness of some inducible promoters can be increased over time. In such cases one can enhance the effectiveness of such systems by inserting multiple repressors in tandem. Alternatively, one can wait at least 3 days before screening for the desired function. While some silencing may occur, it can be minimized by using a suitable number of cells, preferably at least $1 \times 10^4$, more preferably at least $1 \times 10^5$, still more preferably at least $1 \times 10^6$, and even more preferably at least 1×107. One can enhance expression of desired proteins by known means to enhance the effectiveness of this system, for example, using the Woodchuck Hepatitis Virus Posttranscriptional Regulatory Element (WPRE). See, e.g., Loeb et al. *Human Gene Therapy* 1999, 10:2295-2305; Zufferey et al. *J. of Virol.* 1999, 73:2886-2892; Donello et al. *J. of Virol.* 1998, 72:5085-5092.

Examples of polyadenylation signals useful to practice the methods described herein include, but are not limited to, human collagen I polyadenylation signal, human collagen II polyadenylation signal, and SV40 polyadenylation signal.

Vectors comprising nucleic acid sequences encoding the fusion polypeptides described herein, which may be operably linked to regulatory elements, may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired transgene into the progenitor cells described herein. These marker genes can be under the control of any promoter or an inducible promoter. These are known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, and LacZ.

Screening Methods

Any of the embryonic stem cell-derived tumor cell model as described herein can be used in the screening of anti-proliferative disease drugs such as anti-brain tumor drugs (e.g., drug useful in the treatment of DIPG). To perform such a screening method, a population of any of the generically engineered presursor cells, such as NPC cells, can be incubated in the presence of a test agent under suitable conditions for a suitable period. The growth rate of the precursor cells such as NPCs can be monitored before, during, and/or after the incubation. If the test agent inhibits the growth of the precursor cells as compared to precursor cells incubated in the absence of the test agent, it indicates that the test agent is an anti-tumor candidate. In some instances, the growth rate of the precursor cells can be represented by cell viability. In other instances, the growth rate of the precursor cells can be represented by the proliferation level of the cells.

In any of the screening methods described herein, a test agent can be identified as a drug candidate if its half maximal inhibitory concentration ($IC_{50}$) value is lower tan 100 µM, e.g., 50 µM, 20 µM, 10 µM, 5 µM, 2 µM, 1 µM, 0.5 µM, or 0.1 µM. $IC_{50}$ refers to a measure of the effectiveness of a substance in inhibiting a specific biological or biochemical function. It represents the concentration of a test agent for 50% inhibition of in vitro, for example, 50% inhibition of cell growth or 50% inhibition of MLL-menin complex formation.

The provided screening method can be applied to selections of small molecules and/or macromolecules. In certain embodiments, the test agent is a small molecule. In certain embodiments, the test agent is a macromolecule (e.g., a DNA, an RNA, or a protein).

EXAMPLES

In order that the invention described herein may be more fully understood, the following examples are set forth. It should be understood that these examples are for illustrative purposes only and are not to be construed as limiting this invention in any manner.

Example 1 hES-Derived Model of DIPG

The first hES-derived model of DIPG was developed using expertise in differentiation and genetic modification of hES cells. This has facilitated study of this disease in vitro and in vivo and enabled screening and validation of drug candidates. Further details are provided in Example 4.

Neural progenitor cells (NPCs) are derived from hES cells via dual SMAD inhibition3 and subsequently transformed via a combination of lentiviral vectors to form P5K cells (constitutively active PDGFRA D842V mutant, p53 knockdown, H3.3K27M mutant), with in vitro biology mimicking DIPG. The cells exhibit a neoplastic phenotype in vitro, and the histone mutation proved to be highly dependent on cell context. Genome-wide studies on the transformed hES progeny demonstrate significant similarity to the profile of patient tissue samples bearing the H3.3K27M mutation. In addition, the transformed cells are capable of generating tumors upon injection in the pons of young immunocompromised mice. Histologically, the tumors resemble DIPGs in many respects, including widespread invasion, subependymal and subarachnoid spread and encasement of the basilar artery. The in vivo model includes a luciferase reporter, enabling bioluminescence imaging (BLI) and longitudinal follow-up of tumor growth.

Figure 19A:
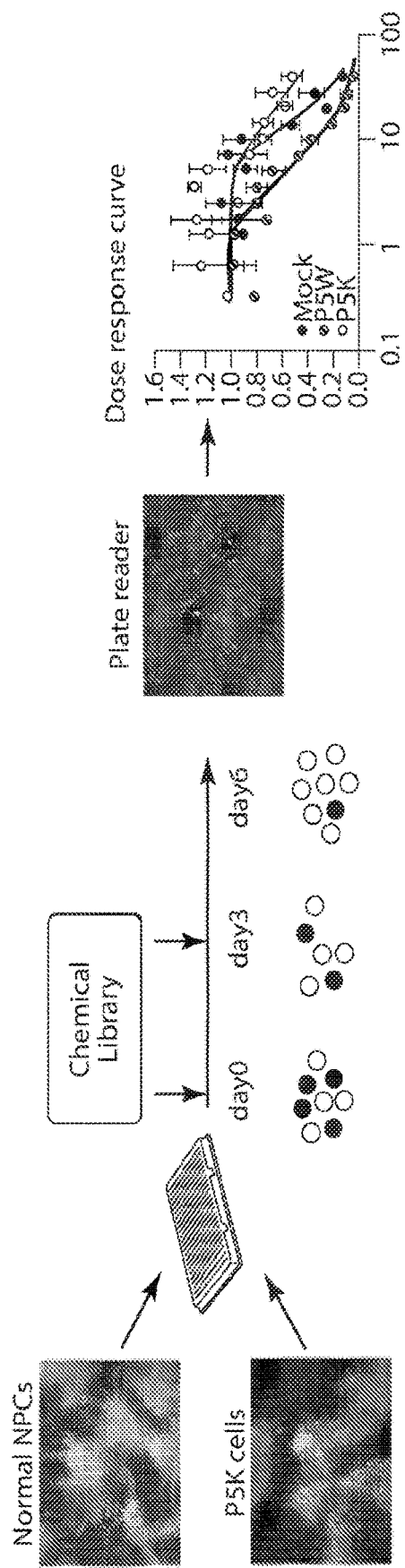
Figure 19B:
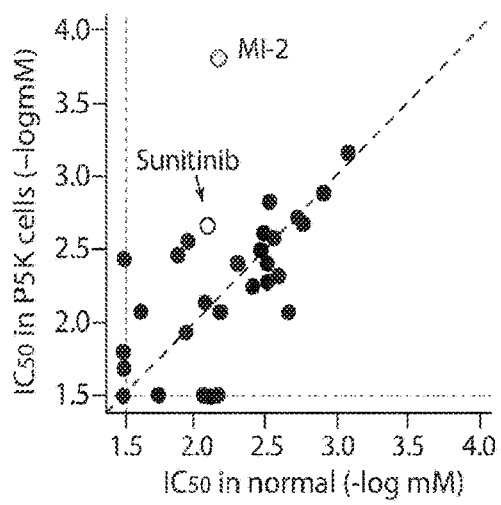
Figure 19C:
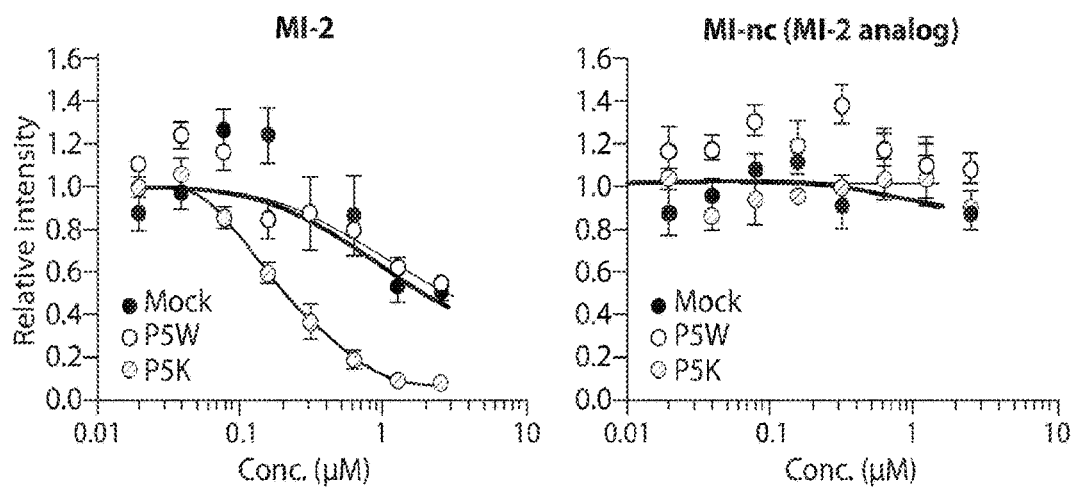
Figure 19D:
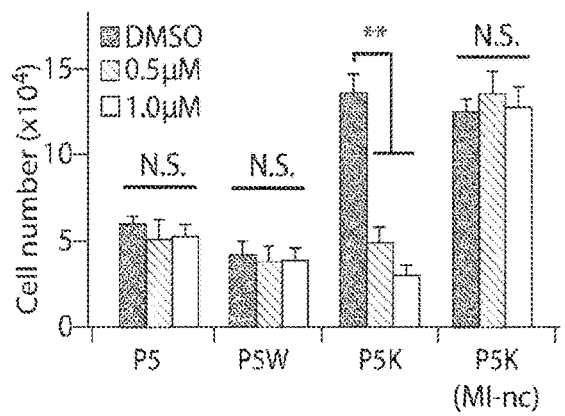
Figure 19E:
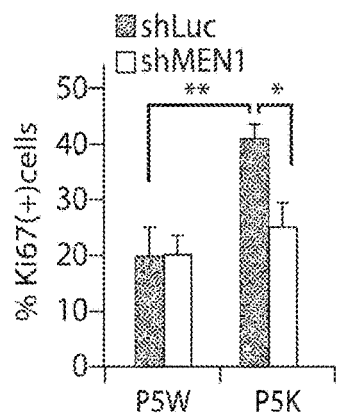
Figure 19F:
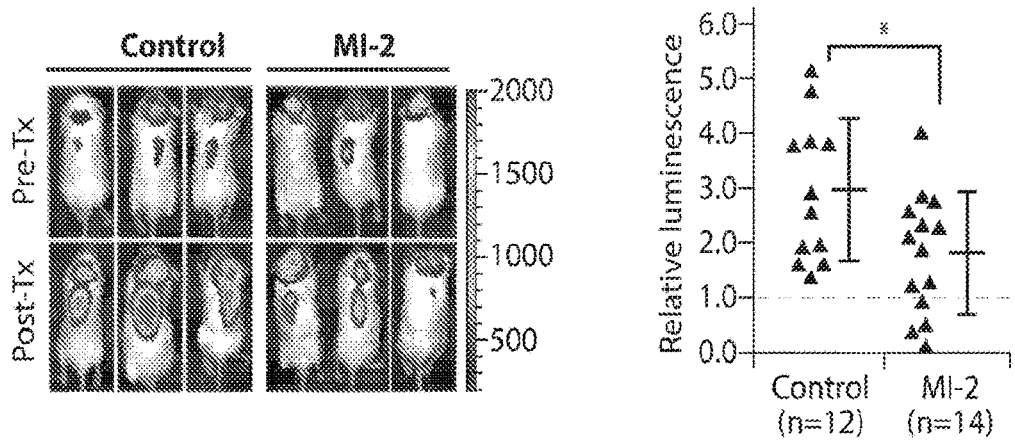
Figure 19G:
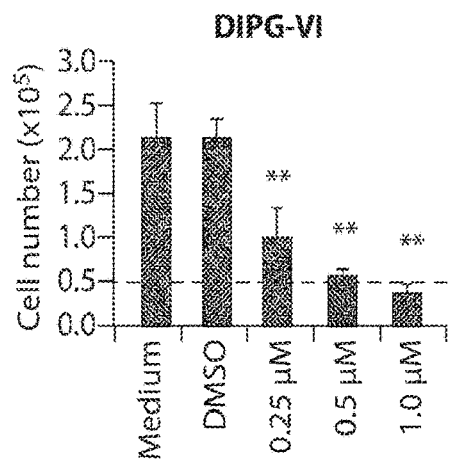
Figure 19H:
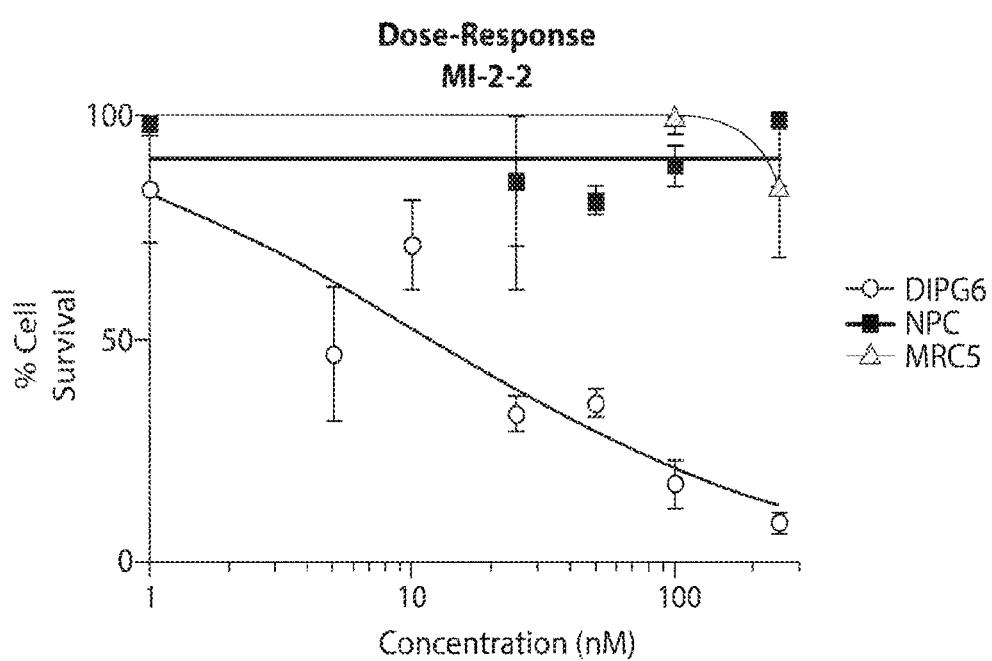

Following in vitro and in vivo studies demonstrating biological similarity between human DIPG and P5K cell populations, a competitive drug screening assay was developed that involved exposing a mix of GFP-labeled normal neural precursors and RFP-labeled transformed cells to a library of epigenetic modifier drugs. The screen identified a single major hit: MI-2, a small-molecule inhibitor of the menin protein. It was found that MI-2 selectively inhibits proliferation while increasing apoptotic activity and differentiation of the transformed cells, suggesting that it could represent a biologically active agent in DIPG. The drug hit was validated by genetically silencing menin via shRNA. In fact, cells expressing shRNA against menin are incapable of generating tumors in vivo. More importantly, mice were injected with transformed cells and monitored for tumor development by BLI. Once tumors were established, the mice were treated with intraperitoneal MI-2 at 20 mg/kg every other day. The data show statistically significant regression of tumors after one month of treatment (FIG. 19H)

More recently, a H3.3K27M mutated human xenograft line was obtained. The line was successfully propagated in vitro and its response to MI-2 was tested. The patient-derived line (DIPG6) responded with a significant decrease in proliferation and cell viability at similar $IC_{50}$, in the nanomolar range (FIG. 19H).

There exists a slightly modified form of MI-2, named MI-2-2, which has greatly increased potency and a presumed improved ability to cross the blood brain barrier (25). Data has demonstrated that MI-2-2 has similar activity to MI-2 in tumor cells, but with greater potency. It exerts a significant impact on cell survival in the DIPG patient-derived tumor line at a low $IC_{50}$ (10 nM), but has minimal impact on the survival of normal neural precursors or fibroblasts. The normal neural precursors are being analyzed for proof of maintained phenotype and differentiation ability, in further support of the safety profile of the drug used.

Example 2

Assessment of Pharmokinetics and Toxicity Profile of MI-2-2 for the Treatment of Brainstem Gliomas In vitro studies can utilize P5K (transformed cells) and human DIPG cells from 2 different patient samples. Control cells can include neural precursors (NPC) and fibroblasts (MRCS). Treatment with MI-2-2 in solution at a range of concentrations flanking the $IC_{50}$ of the compound (i.e. 100 nm, 50 nm, 25 nm, 10 nm, 5 nm, 2.5 nm, 1 nm) can be used to assess potential effects on tumor versus normal cells. Treatment can be completed over short term (6 days, as in FIGS. 19F-H) and long-term (2-3 weeks). Experiments can be performed in independent triplicates. Cells can be analyzed by immunocytochemistry (ICC) and FACS for apoptosis (Annexin V and TUNEL assays), proliferation (Ki67 index), cell survival, maintenance of phenotype, and differentiation ability.

In vivo toxicology studies can be designed to identify the maximum tolerated dose (MTD) of MI-2-2 in order to select a well-tolerated dose for further pharmacokinetic and efficacy studies in vivo. MI-2-2 can be delivered via intraperitoneal injection to non-tumor-bearing mice daily at escalating doses with controls receiving injections of vehicle. Clinical signs—weight loss, coordination, posture, grooming, and activity can be recorded daily. After 14 days of treatment animals can be sacrificed and serum chemistry and hematology, as well as tissue specific histopathology of major organs can be assessed. Results can then be compared to normal ranges and vehicle controls. Long-term studies may involve treatment of intra-peritoneal injection to non-tumor-bearing mice daily at escalating doses over 4 and 8-week periods with assessment of the above parameters during treatment and post-mortem.

Pharmacokinetic studies can be performed in adult wild type NSG mice at six weeks of age—the approximate age of intended treatment for xenografted animals. Animals can be treated with doses below the maximum tolerated dose (MTD) identified in preliminary toxicology studies. Controls can include untreated NSG mice. Brain and plasma samples may be extracted from two animals each at progressive time points (zero, 30 min, 1, 2, 3, 4, 6, 8, 12 and 24 hours) after treatment with a single dose of MI-2-2 dissolved in sterile PBS with the zero time point serving as control. Samples can be flash-frozen in liquid nitrogen and subsequently analyzed for levels of MI-2-2 by liquid chromatography-mass spectroscopy (LC-MS) in order to generate pharmacokinetic curves and demonstrate in vivo BBB penetration. The same study design can be applied to a group of animals after receiving 2 weeks of daily MI-2-2 treatment in order to assess any additive effect of treatment on bioavailability.

Example 4

Biological Experiment

Figure 1A:
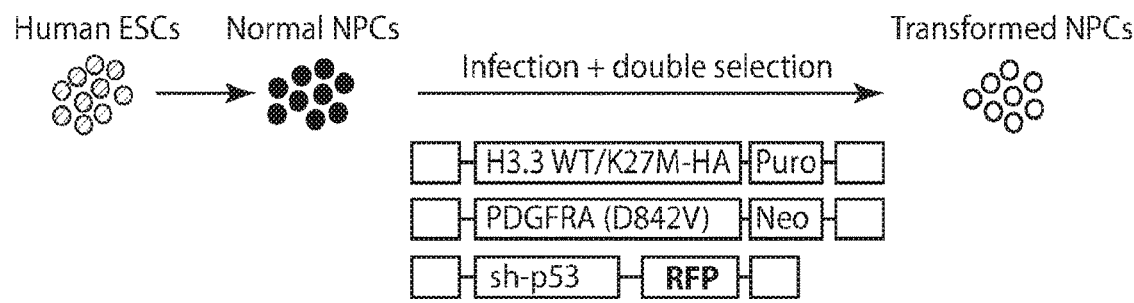
FIGS. 1A-1F show the impact of H3.3 K27M mutation on neural precursors.
Figure 1B:
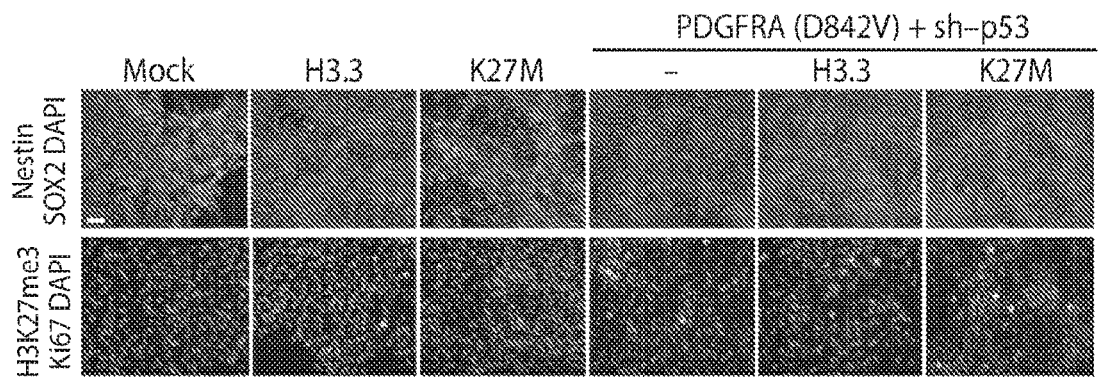
Figure 1C:
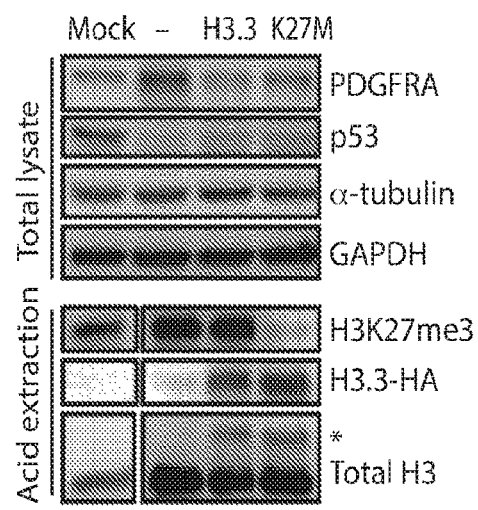
Figure 1D:
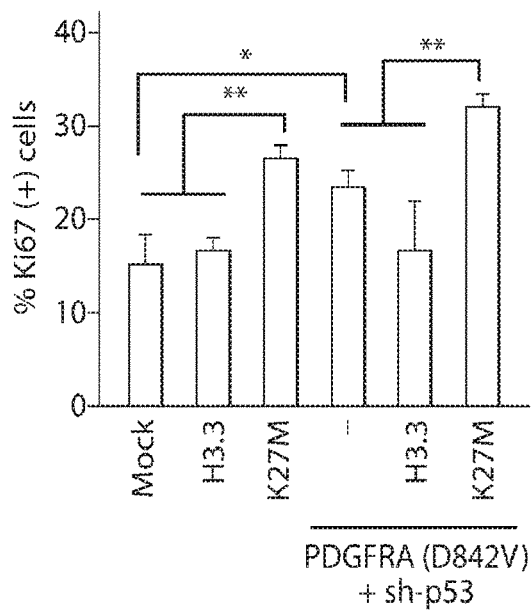
Figure 1E:
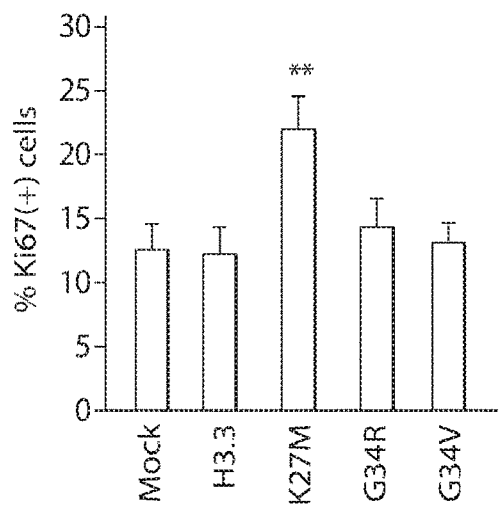
Figure 1F:
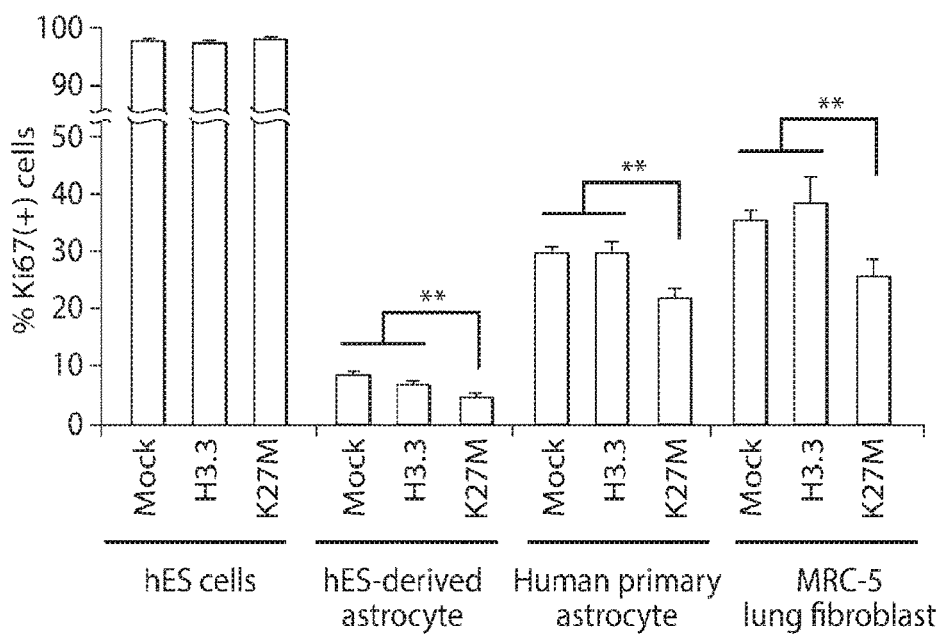
Figure 1G:
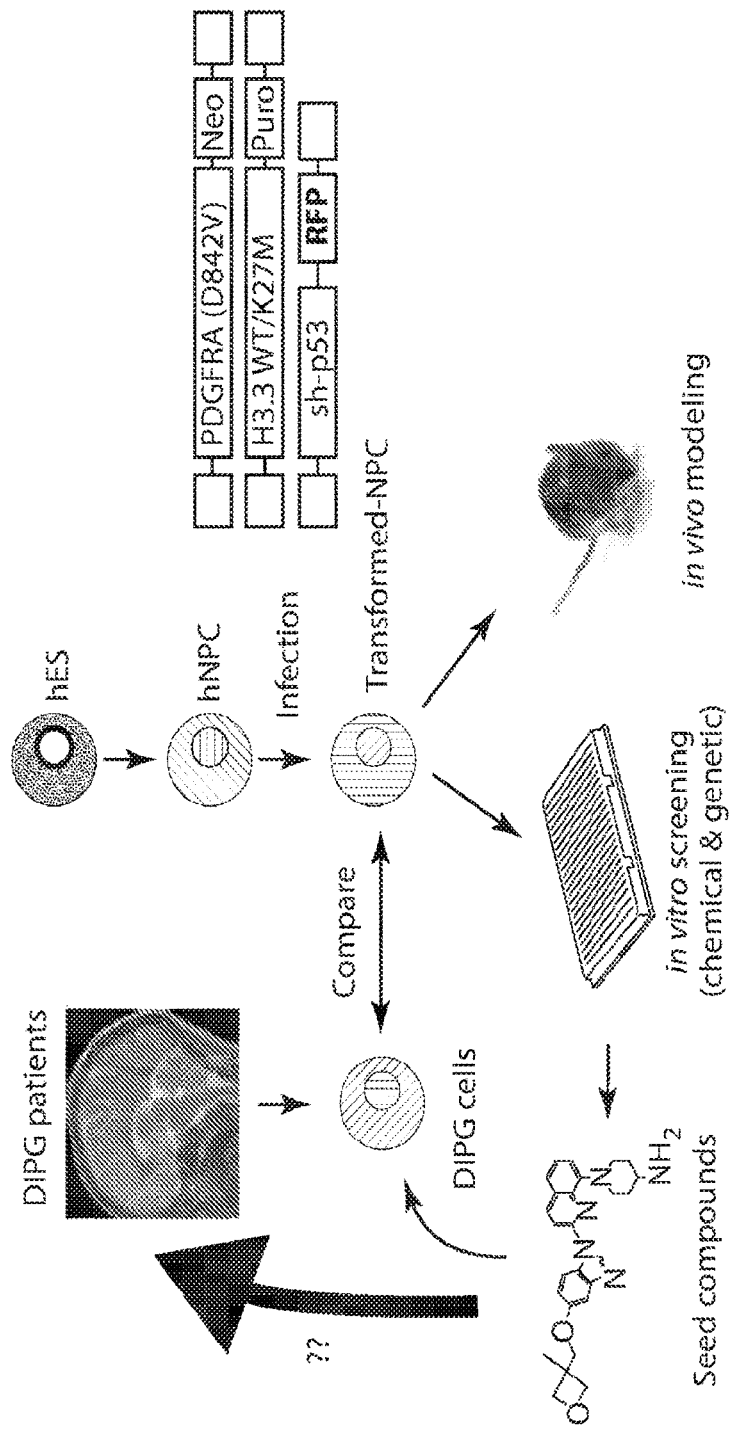
FIG. 1G provides the conceptual framework of previous studies, currently under revision. The goal of the present work is to establish whether the drug is suited for clinical testing (red arrow).

Human pluripotent stem cells (hPSC) (8) may be a valuable model for studying Diffuse Intrinsic Pontine Glioma (DIPG). These cells provide an attractive platform for functional analysis of oncogenic mutations in a genetically defined human background. In addition, neural differentiation protocols allow the derivation of relevant developmentally early neural stem cells that are often inaccessible; thus, tumorigenesis can be studied in the proper cell context. To mimic the cellular characteristics and oncogenic perturbations in DIPGs, early neural precursors (NPCs) were derived from human ESCs (H9, WA-09) using the previously published dual Smad inhibition protocol (9), followed by cotransduction with a combination of lentiviruses that separately encode (i) the constitutively active form of growth factor receptor A, PDGFRA (D842V); (ii) a small hairpin RNA (shRNA) against p53 tagged with RFP; and (iii) a hemagglutinin (HA)-tagged wild-type (WT) or K27M-mutant form of histone H3.3 (FIG. 1A). These oncogenes were selected based on their high frequency of expression and/or mutations in K27M-mutated DIPG (5, 10). Following transduction and double-selection under puromycin and G418, the cells maintained NPC-like morphology and expression of two NPC marker genes: Nestin and SOX2 (FIG. 1B). Overexpression of PDGFRA and histone H3.3, and knockdown of p53 were confirmed by immunoblotting (FIG. 1C). Consistent with previous reports (11-13), the expression of H3.3-K27M (hereafter referred to as K27M) led to a significant decrease in histone H3K27 trimethylation (H3K27me3) as shown by immunohistochemistry and western blotting (FIGS. 1B and 1C). Expression of H3.3K27M alone increased cell proliferation (Ki67 of 27% vs 15-17%) and total cell number, in comparison to WT H3.3 or mock (empty vector) conditions (FIGS. 1D and 5A). The combination of overexpression of constitutively active PDGFRA (D842V) and knockdown of p53 (hereafter referred to as P5) also increased the proliferation of NPCs. The combination of H3.3K27M and P5 was even more effective in increasing the proliferative capacity of the P5 cells, up to a Ki67 index >30%. This result was confirmed using a second independent shRNA against p53 (FIGS. 5B-5D). The proliferative effect on neural precursors is specific to H3.3K27M, and is not seen in the G34V/R mutations of H3.3, which are mostly reported in supratentorial glioblastomas (FIG. 1E). When K27M was expressed in undifferentiated human ES cells (hES) or in differentiated somatic cells such as hES-derived astrocytes, primary human astrocytes or MRC-5 human lung fibroblast cells, there was no evidence of a proliferative effect; in fact, some somatic cells experienced a decrease in proliferation as well as senescence, instead (FIGS. 1F and 6A-6D). It is also highly specific to the cell context, since H3.3K27M expression in undifferentiated human ES cells or in differentiated somatic cells such as hES-derived astrocytes, primary human astrocytes or MRC-5 human lung fibroblast cells, did not impact proliferation rates, and in some cases induced senescence (FIG. 1F and FIG. 6).

Concomitantly, the transduced neural precursors were analyzed for expression of Olig2, a transcription factor that is characteristic of neural progenitors and that is known to be expressed in DIPG tumors (4). Expression of Olig2 was increased in both the H3.3K27M and then P5 conditions (FIGS. 7A and 7B). The addition of K27M to the P5 condition did not result in further expansion of this cell population, implying some functional overlap in the gain of K27M and p53.

Figure 2A:
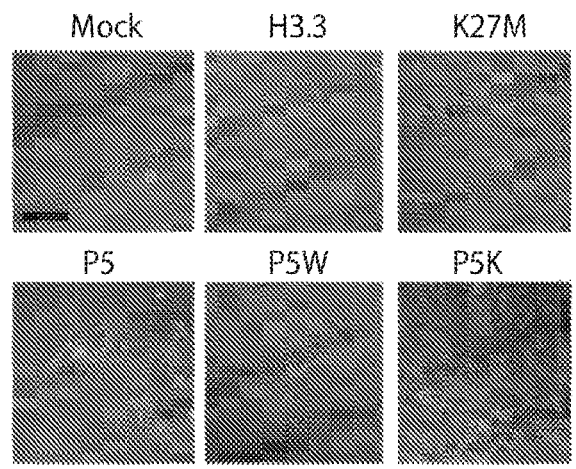
Figure 2B:
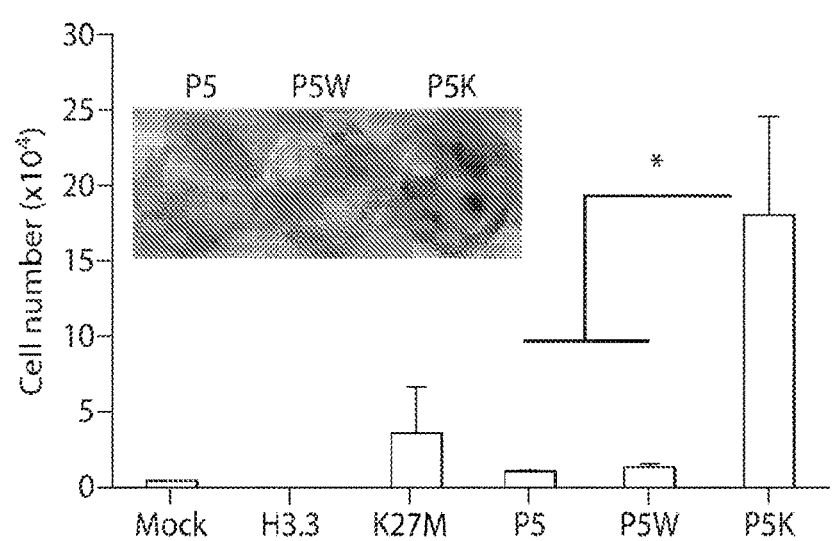
Figure 2C:
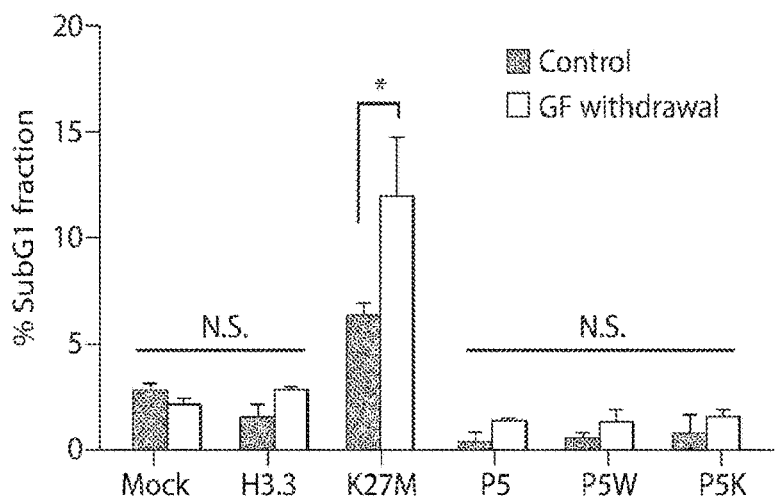
FIG. 2C depicts the FACS analysis for the sub-G1 fraction (apoptotic cells) in the transduced NPCs under control conditions and 24 hours following growth factor withdrawal. Bars indicate mean±S.D. (n=3).

A series of assays were then performed to ascertain whether the transduced NPCs have acquired features of neoplastic cells. Under low density culture conditions, all cell groups either survived poorly or completely failed to survive and proliferate, with the exception of the P5+K27M (P5K) cells which formed robust colonies that grew to confluence in the dish, supporting a neoplastic phenotype (FIGS. 2A and 2B, 8A). The combination of PDGFRA, sh-p53 and K27M was synergistic effect on cell survival (FIG. 2B). Survival following growth factor withdrawal was also tested. The percentage of sub-G1, or apoptotic cell fraction, was higher in the K27M-expressing cells in comparison with normal and WT H3.3-expressing NPCs, even in the presence of growth factors, and it was significantly increased by growth factor withdrawal (FIGS. 2C, 8B). This suggests that the proliferative effect of the histone mutation was balanced with an increased apoptotic rate, a phenomenon often described in premalignant states (14). The introduction of a p53 knockdown in the P5K condition abrogated the apoptotic response, possibly by encouraging genomic instability as the cells continued to proliferate. The P5 condition also conferred greater efficiency in neurosphere formation, in all groups, including the P5K combination, while cells expressing only H3.3K27M were similar to unperturbed NPCs (FIG. 8E). These results support a synergistic effect of H3.3K27M and P5 in the oncogenic transformation of NPCs, consistent with the high frequency of the co-mutation of H3.3K27M and mutated p53 in patient DIPGs (1, 4, 5). The sphere-forming capacity of the cells, a property often represented as a surrogate of stemness, was also evaluated. While NPCs are capable of growth as floating neurospheres, transformed cells exhibited a more robust phenotype under similar conditions. The data show that the P5 condition confers greater efficiency in sphere formation in all groups, including the P5K combination, while cells expressing only K27M were similar to control conditions (FIG. 8C).

The impact of radiation on mock and oncogene-transduced NPCs was tested next. Radiation is a mainstay of therapy for DIPGs, albeit it is not curative and often associated with tumor resistance and recurrence (15). After irradiation, cells transduced with the combination of H3.3K27M and P5 maintained a high proliferation rate despite significant DNA damage (FIGS. 8D-8F), a hallmark of cancer cells (16). Similar to the mock and WT H3.3 conditions, H3.3K27M-transduced NPCs showed a significant loss of proliferation in response to radiation, but expression of shp53 and PDGFRA led to significant protection from the anti-proliferative effect of radiation (FIGS. 8D and 8E). An analysis of radiation-induced foci of double-stranded DNA breaks, by phospho-γH2A.X staining, demonstrated a similar impact in all cell conditions thus suggesting minimal differences in the kinetics of DNA damage repair (FIGS. 8F and 8G). These results suggest that the combination of K27M and P5 leads to a significant imbalance in cell cycle kinetics under genotoxic stress, as it leads to the maintenance of a high proliferation rate despite significant DNA damage, a hallmark of cancer cells (16).

Figure 2D:
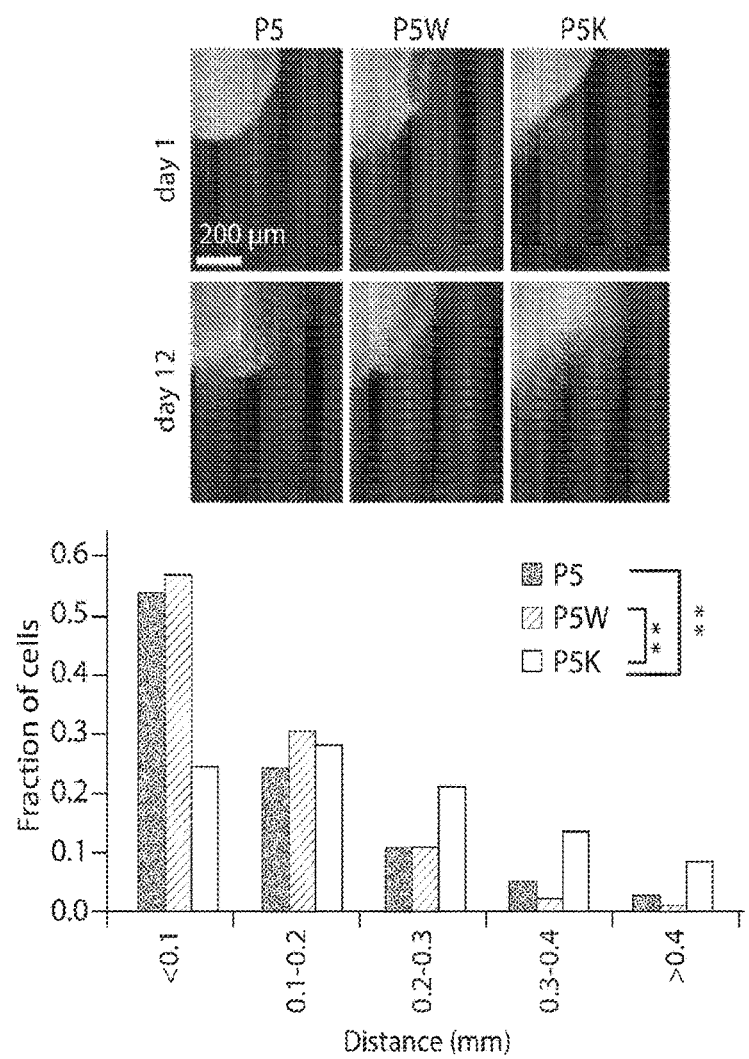
FIG. 2D shows the low magnification immunofluorescence microscopy of RFP-labeled transduced NPCs embedded as spheres in Matrigel. Cells migrating from the spheres were analyzed on day 12, and the distance travelled from the sphere edge was measured.

Extensive migration is a main feature of DIPGs, rendering the tumors unsuitable for surgical eradication. Using in vitro assays, the impact of K27M expression on the migratory properties of NPCs was investigated. Expression of H3.3K27M also increased cell migration (FIG. 8F) and invasion (FIGS. 2D and 8I) in in vitro assays. There was a near complete differentiation block in the astrocytic lineage in the P5K cells despite an extended culture period in vitro (normal NPCs acquire a capacity for robust differentiation into astrocytes (glial competence) only after several weeks in vitro) (FIG. 2B). Interestingly, neither the P5 nor the H3.3K27M condition alone inhibited differentiation, but the combination blocked differentiation into astrocytes and to some extent differentiation into oligodendrocytes (FIG. 8).

Figure 2E:
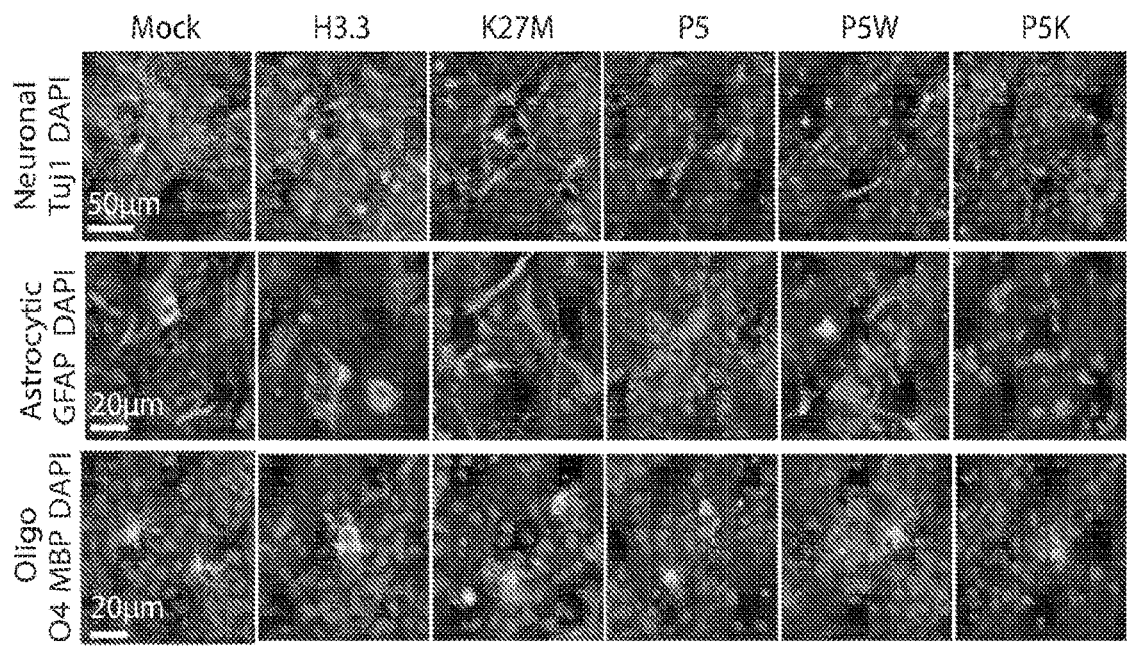
FIGS. 2E-2H depict transduced NPCs differentiated under neuronal, astrocytic and oligodendrocyte (oligo) conditions (FIG. 2E). Immunohistochemistry and quantification for the neuronal (TUJ1, FIG. 2F), glial (GFAP, FIG. 2G) and oligodendrocyte (O4 and MBP, FIG. 2H) markers, respectively. Error bars in panels G and H indicate mean±S.E.M. (n=3~6). Scale bar, 20 µm. *, p<0.05; **, p<0.01. NS, Not Significant. ND, Not Detected.
Figure 2F:
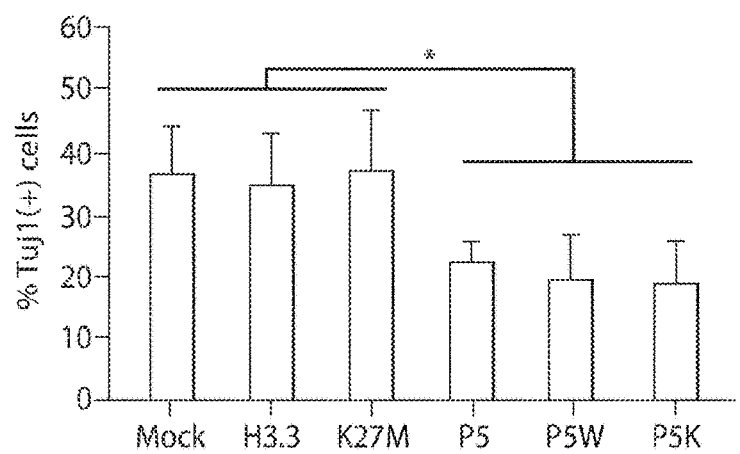
Figure 2G:
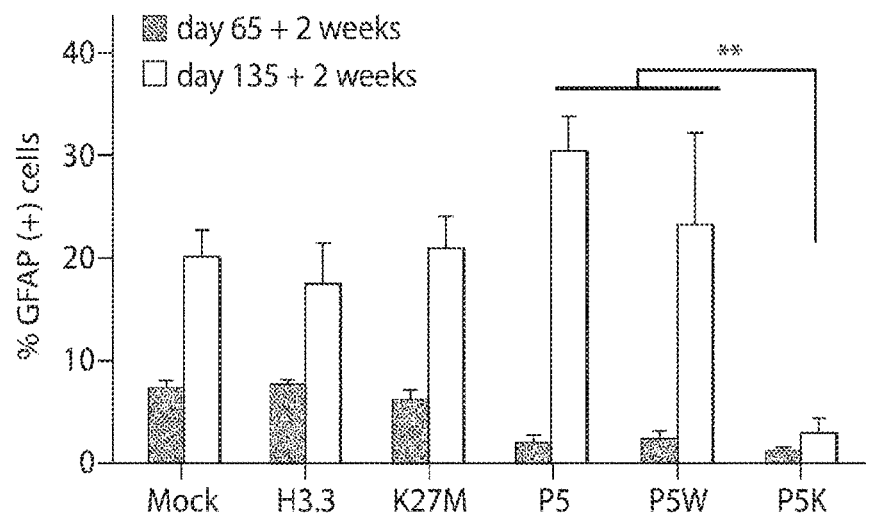
Figure 2H:
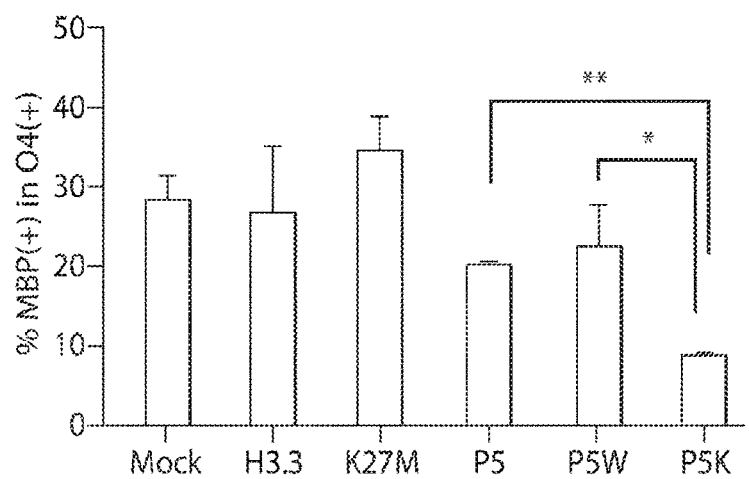

An investigation regarding whether this effect is associated with a capacity to evade differentiation, a common occurrence in malignant tumors, was undertaken (16). Accordingly, the cells were exposed to a set of standard differentiation conditions towards astrocytic, oligodendrocytic, or neuronal fates (17). Defined by morphology and TuJ1 expression, neuronal differentiation proceeded at a near normal rate, regardless of the H3.3 status, whereas the P5 condition resulted in a small decrease in efficiency (FIGS. 2E and 2F). Astrocytic differentiation was induced by transition to a serum-containing medium. At early time points (day 65+2 weeks of differentiation in vitro), normal glial differentiation is inefficient and was not impacted by K27M. However, when cells were allowed to reach glial competence after maintenance for 135+2 weeks of differentiation) in vitro, they were capable of expressing GFAP and undergoing an appropriate morphological change, with the remarkable exception of the P5K group, which exhibited a near complete differentiation block, with 2.6% of the cells expressing GFAP, compared to an average of 20-30% in the remaining conditions (FIGS. 2E and 2G). Neither P5 nor K27M could inhibit differentiation alone, but their combination was remarkably successful in blocking the astrocytic lineage. Oligodendrocytic differentiation and maturation was induced in oligodendrocyte-specific differentiation media (18). The combination of K27M and P5 conditions suppressed the maturation of O4-positive oligodendrocyte progenitor cells into myelin basic protein (MBP)-expressing oligodendrocytes, implying an additional synergistic effect of K27M and P5 in impairing the glial differentiation of NPCs (FIGS. 2E and 2H).

The transformed NPCs tumorigenic properties were investigated in vivo. Normal NPCs, P5W, or P5K cells were injected into the brainstem (pons) of immunocompromised NOD-SCID mice. Serial MRI imaging demonstrated massive brain tumor formation in the P5K group only, starting at 4-5 months (FIG. 9). Immunohistochemistry of the P5K animals demonstrated human cells infiltrating the pons, and frequently involving the subarachoidal spaces, encasing the basilar artery and at times resulting in hydrocephalus and the demise of the animals (FIG. 2I). Histological analysis demonstrated the presence of microcystic changes within the tumor tissue and features compatible with low grade DIPG, such as the absence of necrosis and microvascular proliferation (FIG. 2K) (19). Leptomeningeal spread of the tumor was also a common feature and is often seen in the human DIPG patient (19). Animals bearing P5W cells showed evidence of cell clusters and minimal infiltration in the pons while mock injections were associated with minimal cell survival (FIG. 2I). Tumor growth was relatively slow, with symptoms and/or significant tumor volume appearing 3 months after injection of 500,000 cells or 5 months after injection of 100,000 cells. Phenotypic analysis of the tumor cells confirmed expression of the H3.3K27M and sh-p53 constructs (HA and RFP tags in 78% and 76.4% of all human cells respectively; FIGS. 10A and 10B), as well as markers of immature NPCs (Nestin, Sox2, Olig2) and high proliferation rates in the P5K group compared to P5W cells or normal NPCs (10.4% vs 0.7% and 0%, (FIGS. 2F-2H and 10C)). Phenotypic analysis of the tumor cells demonstrated expression of Nestin, Sox2 (53.3%), Olig2 (11.6%) and GFAP (7.9%) (FIGS. 2L-2N, 10C and 10D). Glial fibrillary acidic protein (GFAP) expression co-labeled more often in the tumor cells that had downregulated H3K27M expression, perhaps compatible with the in vitro observation of impaired astrocytic differentiation (FIG. 10D). Pathologically, the tumors resembled lower grade DIPGs and not full blown glioblastomas (GBMs), as determined by the absence of necrosis and microvascular proliferation. It is thought that longer in vivo growth periods may be required for the accumulation of mutations leading to a more malignant phenotype. Animals bearing P5W cells showed evidence of a few cell clusters and minimal infiltration in the pons while mock cell injections were associated with minimal cell survival (FIG. 2C). There was no evidence of proliferation by the host cells. The efficiency of tumor formation reached 53.3% (8 out of 15) by 6 months in the P5K animals (FIG. 2J).

Figure 3A:
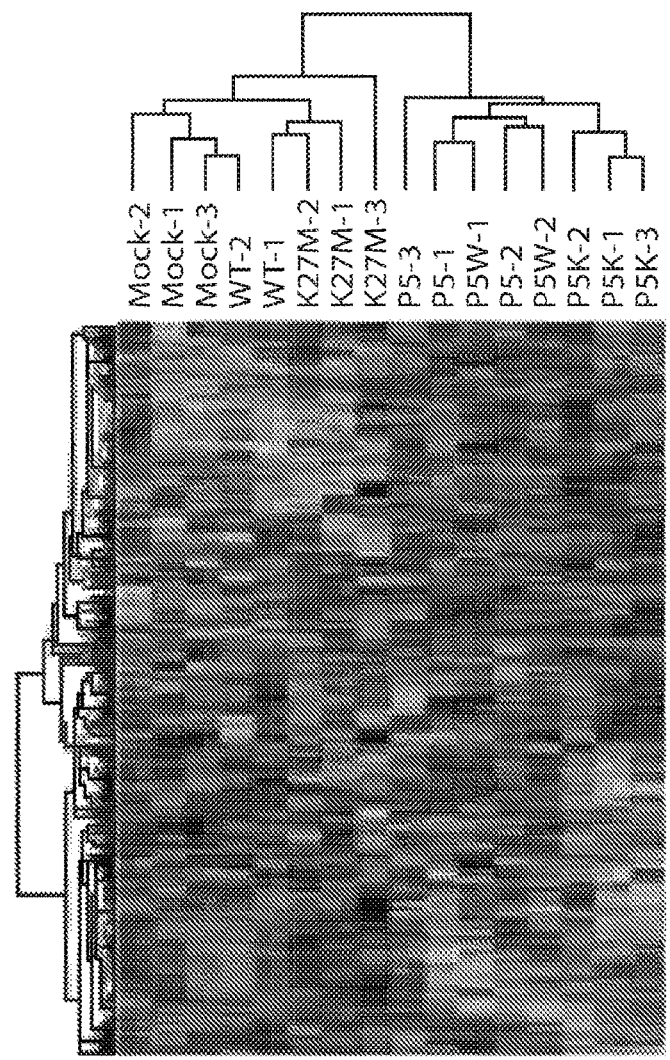
FIGS. 3A-3J present a genomewide analysis of the K27M transformed NPCs. Gene expression data was obtained from NPCs transduced with the different H3.3 and oncogene combinations.
Figure 3B:
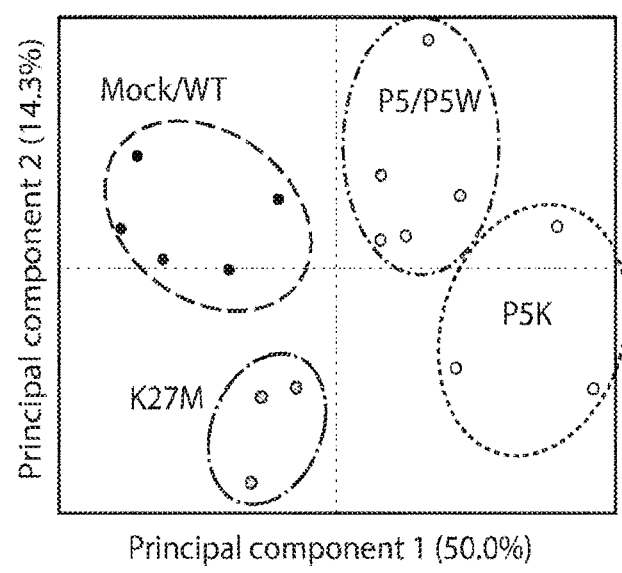
Figure 3C:
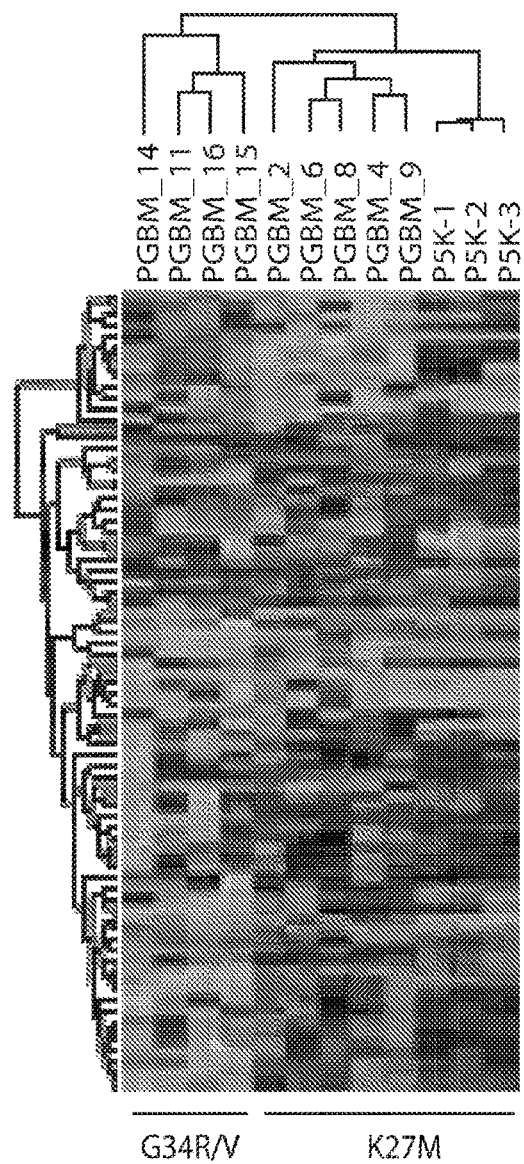
Figure 3D:
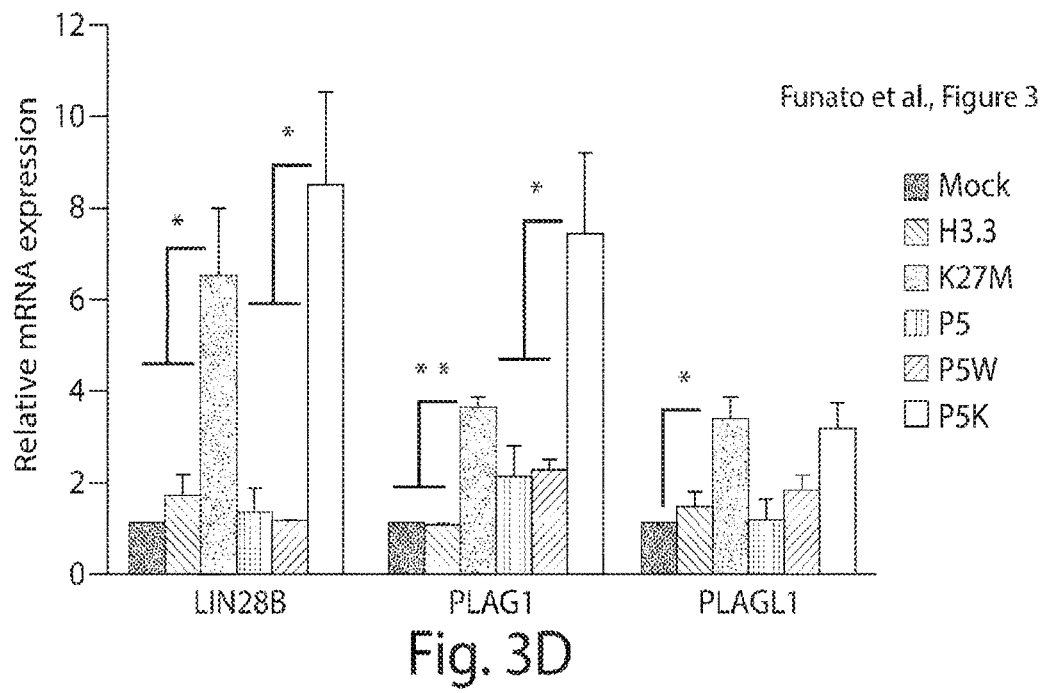
Figure 3E:
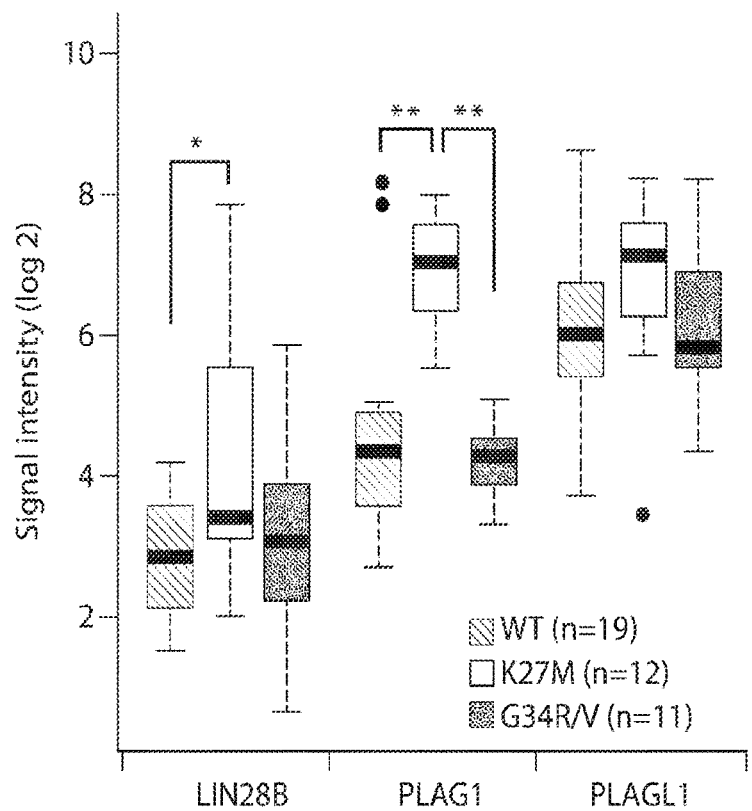
Figure 3F:
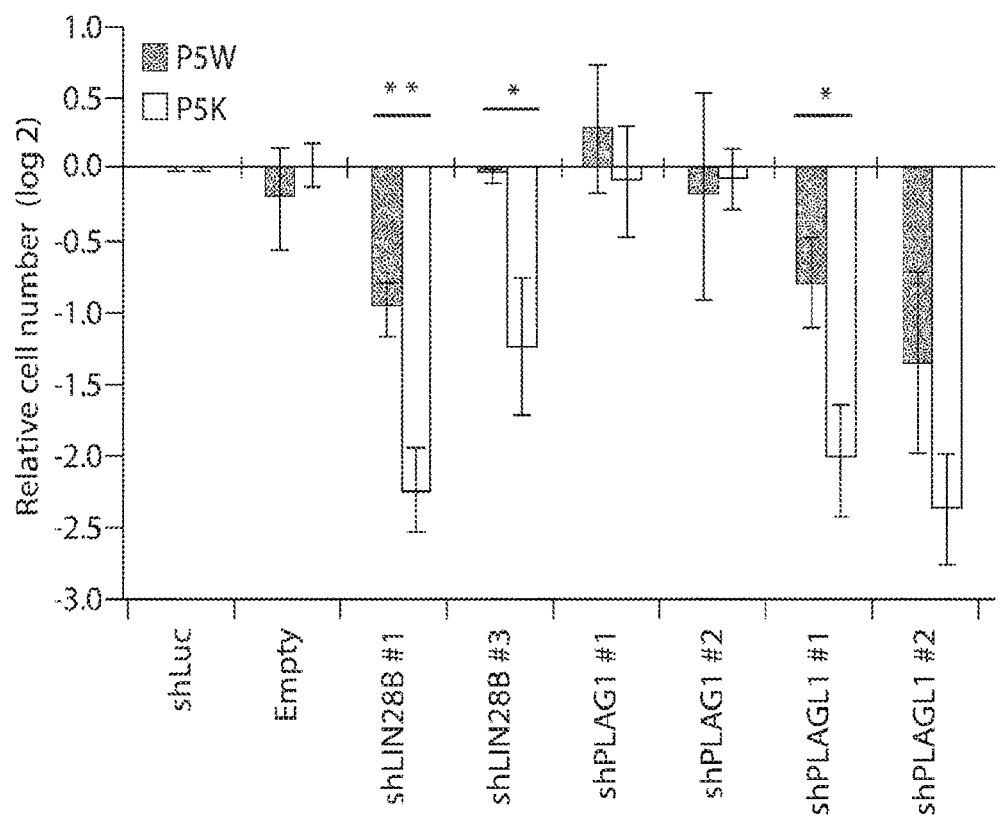

Given the demonstrated fundamental changes in the phenotype and functional status of the transformed NPCs in vitro and in vivo, gene expression profiling was subsequently conducted in an effort to better understand the molecular underpinnings of the neoplastic change (FIG. 3A). Principle component analysis indicated that the expression profile was shifted by the expression of K27M alone, as well as by the P5 and the combination of P5 and K27M (P5K) (FIG. 3B). The microarray data was compared to publically available profiles obtained from DIPG patient tumors that express K27M or G34R/V mutations (1). Upon unsupervised hierarchical clustering, the P5K cells from in vitro or in vivo sources clustered closer to the H3K27M group ($p<4.36\times10-8$ and $p<2.26\times10-4$) than the G34R/V or non-histone mutated GBMs (FIG. 3C Differentially expressed genes among the different NPC groups were analyzed (FIGS. 3B, 13 and 14). Among those, it was noted that the enrichment in the K27M expressing cells of a subset of transcripts known to be expressed in neuroepithelial cells at a very early developmental stage—i.e., the neural plate, which precedes the emergence of NPCs. To validate this finding, gene sets derived from public databases (GEO accession no: GSE9921) (20) gene sets that are uniquely expressed at the rosette (early neural plate) stage, the neural precursor stage (L-NSCs), as well as genes that are shared between rosette and undifferentiated ES cells (20-22) were used to compute overlaps with gene sets that were differentially regulated by K27M in the study cells. A gene set enrichment analysis revealed a significant correlation between H3.3K27M differentially regulated genes and genes enriched in rosette cells (R-NPCs), but not in normal NPCs (L-NPCs) (FIG. 11A). A highly significant intersection of genes that were upregulated in H3.3K27M cells with those in the Rosette or Rosette/human ES groups was found. In contrast, most of the genes that were differentially downregulated in the H3.3K27M cells were shared with those in the NPC group (FIG. 11A). Whether the rosette-associated genes could play a functional role in the phenotype of the K27M cells was next examined. Quantitative RT-PCR validated the increased expression of LIN28B, PLAG1 and PLAGL1 in hES cells and rosettes, and significant downregulation of all three genes in normal NPCs. Expression of H3.3K27M in NPCs upregulated expression levels of the same genes (FIG. 3D). Interestingly, analysis of patient samples revealed that these genes were expressed at higher levels in DIPGs with the H3K27M mutation than in DIPGs with the G34R/V mutation or without either mutation in histone H3.3 (1) (FIGS. 3E and 11). Knockdown of LIN28B or PLAG1 led to a significant decrease in cell number and proliferation in P5K cells (FIGS. 3F, 11B and 11C). These data suggest that expression of mutant H3.3K27M leads to a developmental resetting of neural precursors to a more primitive stem cell state, which in combination with growth factor signaling, results in the acquisition or consolidation of oncogenic features.

Figure 3G:
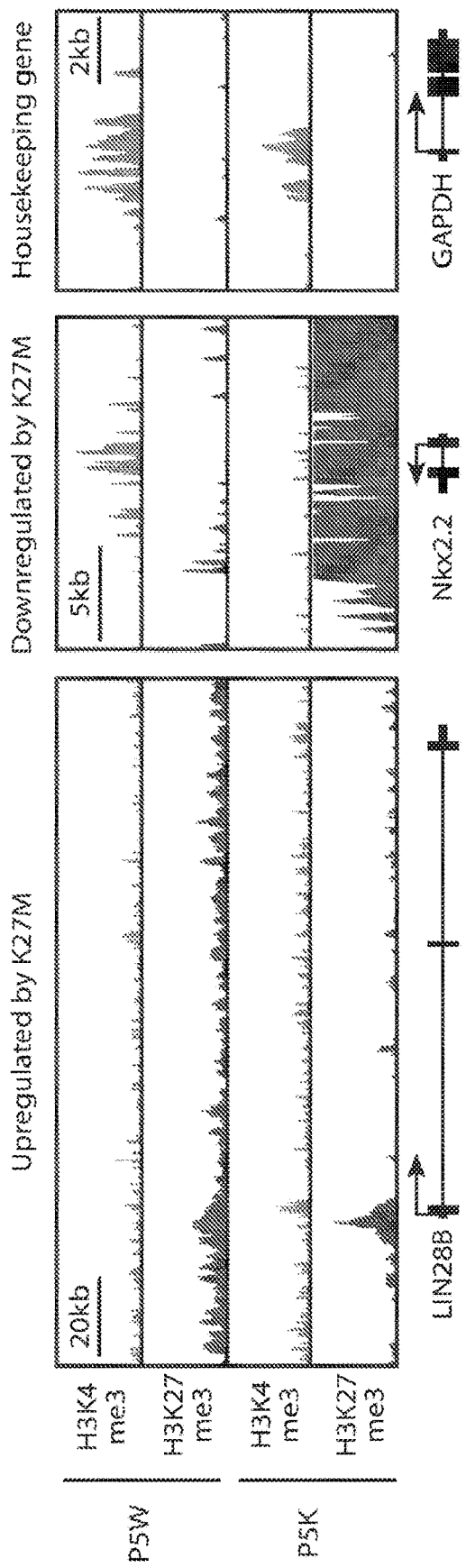
Figure 3H:
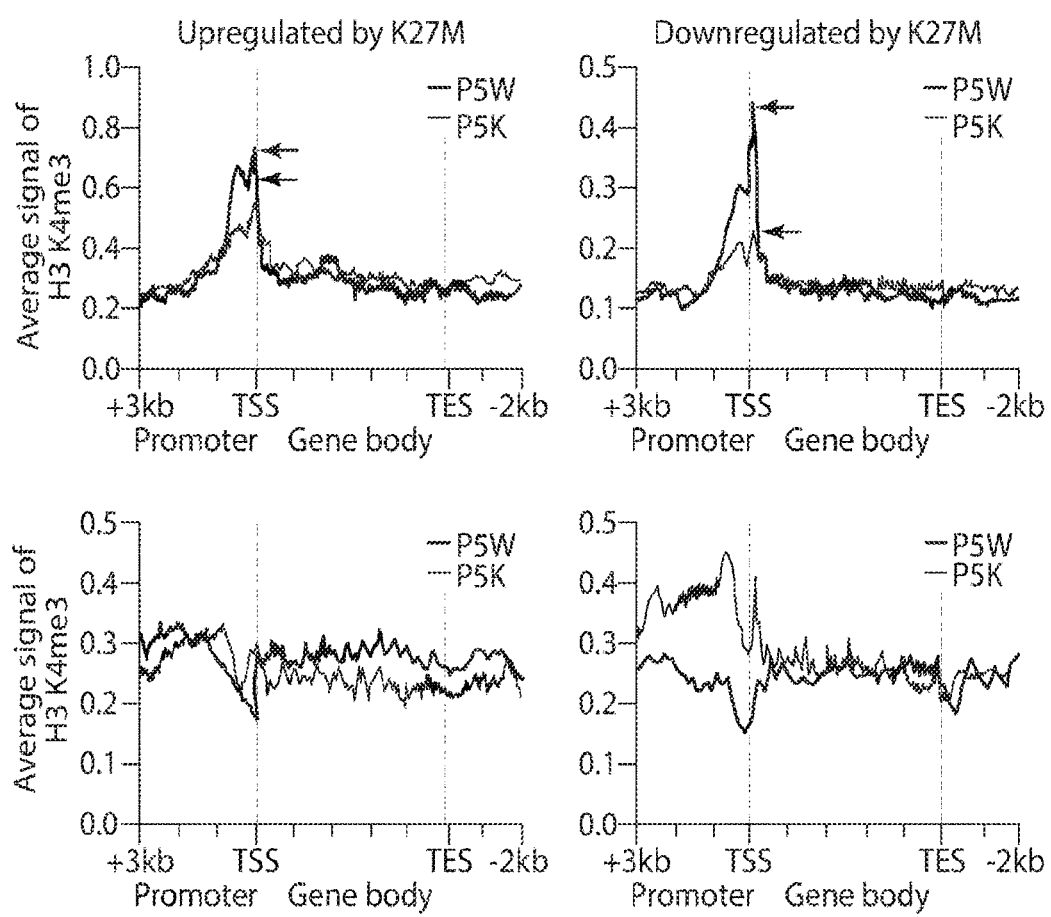
Figure 3I:
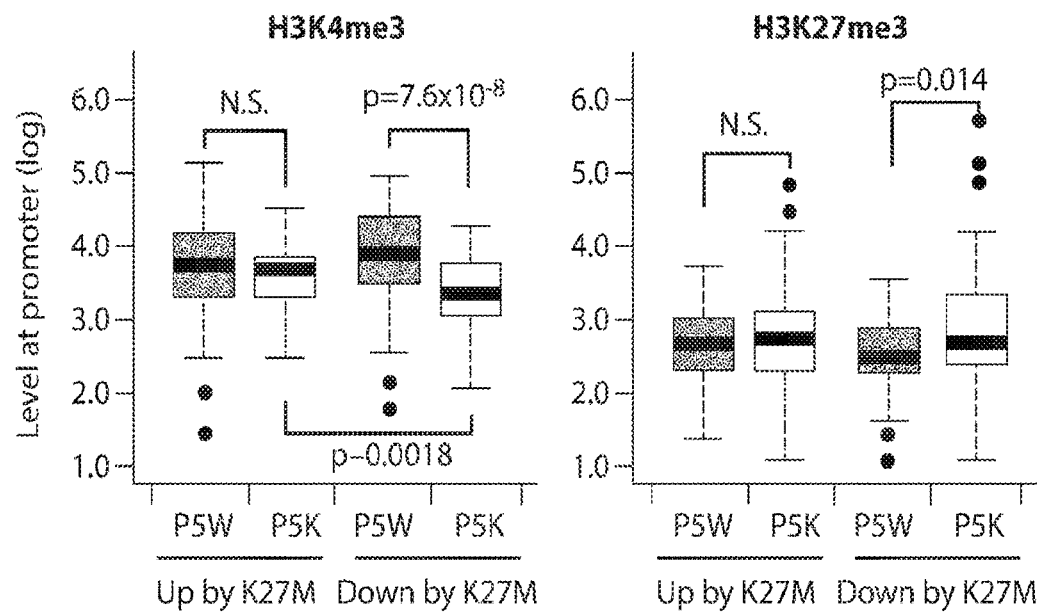
Figure 3J:
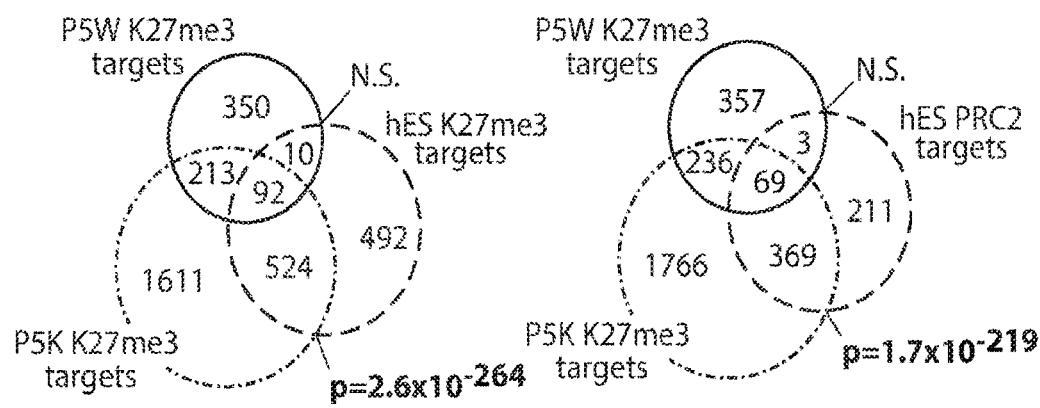

The transcriptional changes in the K27M groups were investigated to determine whether they were associated with well-known chromatin modifications indicative of changes in downstream "epigenetic landscapes". ChIP-seq analysis was performed to map active H3K4me3 and repressive H3K27me3 marks in the P5W and P5K cells. Consistent with previous reports (13, 23), H3K27me3 peaks undergo genomic redistribution in the P5K condition (FIG. 3G). Notably, the genes upregulated by K27M had significantly lower levels of H3K27me3 at their gene-body regions in P5K cells in comparison to P5W cells ($p<3.3\times10-5$, FIGS. 3G, 3H and 11D-11F). Concomitantly, H3K4me3 peaks remained stable at promoter regions, implying that K27M may release these genes from the poised state. On the other hand, the genes downregulated by K27M gained H3K27me3 and lost H3K4me3 marks in P5K cells at their promoter regions (FIGS. 3G-3I and 15). Of these, oligodendrocyte differentiation genes, Nkx2.2 and MBP were highly marked by H3K27me3 and their expression levels were decreased in the NPCs expressing K27M alone or the P5K combination (FIGS. 3G and 11G). Master genes that initiate acquisition of astrocyte cell fates are not fully elucidated in humans and could not be analyzed. A set of genes that gain H3K27me3 marks in P5K and P5W cells were further analyzed by comparing them with H3K27me3 or PRC2 target genes in undifferentiated human ES cells, as previously reported (24). There was a highly significant intersection of P5K-specific H3K27me3-target genes with H3K27me3-target genes as well as PRC2-target genes in ES cells ($p<2.6\times10-264$ and $p<1.7\times10-219$, FIGS. 3J and 16), whereas P5W-specific H3K27me3-target genes have no significant intersection. These data support the hypothesis that the expression of K27M leads to a resetting of neural precursors to a more primitive stem cell state.

Figure 4E:
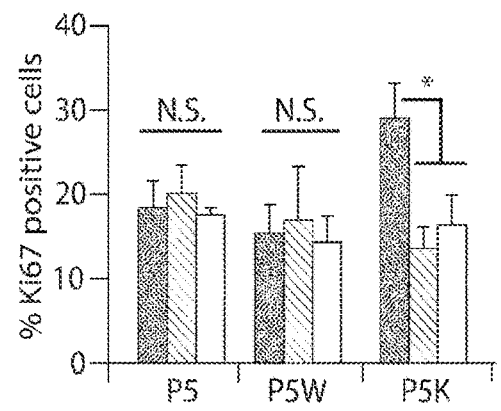
Figure 4F:
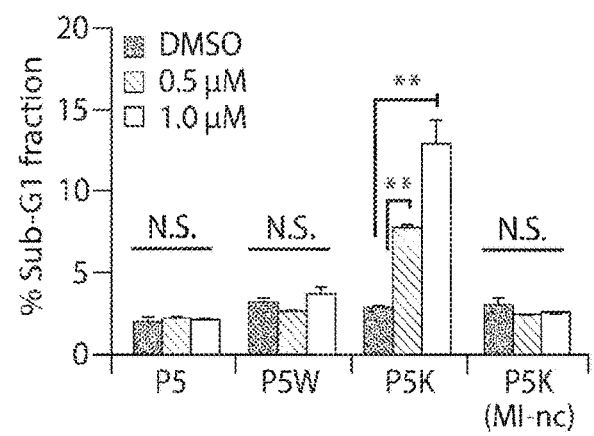

To further explore the relevance of the hES based tumor model to therapeutic target discovery, a chemical screen was performed using a small molecule library of compounds (n=80) that target epigenetic regulators, such as BET bromodomain inhibitors, deacetylase and demethylase inhibitors, including selective JMJD3 inhibitors (FIG. 17). Green fluorescent protein (GFP)-labeled normal NPCs and RFP-labeled P5K cells were mixed and seeded onto 96-well plates. Cells were then treated with each compound at 8 different concentrations for 6 days and GFP and RFP fluorescence was quantified by a plate reader (FIG. 4A). The top hit was the menin inhibitor MI-2 (25, 26) which reduced survival of P5K cells at submicromolar concentrations ($IC_{50}$: 155 nM), but had no effect on normal NPCs (FIGS. 4B and 17). In addition, P5W cells showed a similar dose-response-curve to normal NPCs, indicating that the effect of MI-2 treatment depends on the K27M mutation (FIG. 4C). Trypan-blue staining and Ki67 staining confirmed the decreased proliferation by MI-2 treatment in P5K cells but not in P5 or P5W cells (FIGS. 4D and 4E). Further validation demonstrated that MI-2 treatment led to a dose-dependent increase in cell death specifically in P5K cells (FIG. 4F). On the other hand, treatment of MI-nc, an ineffective analog of MI-2, had no effect on either proliferation or cell death (FIGS. 4C-4F). To confirm the specificity of the observed effect, the expression of the MEN1 gene that encodes the menin protein was silenced by shRNA (shMEN1), and decreased proliferation in P5K cells but not in normal NPCs or P5W cells was observed (FIGS. 4G and 22A). The effect of MEN1 knockdown was further confirmed by a second shRNA targeting the 3' UTR of the menin transcript and by a rescue experiment (FIGS. 12B-12D). Moreover, knockdown of menin appears to restore astrocytic differentiation in P5K cells (FIG. 12E), thus suggesting a common mechanism of the major transformation features, i.e. proliferation and impaired differentiation. Menin is expressed in undifferentiated hES cells and rosettes but its levels decrease in normal NPCs and astrocytes; however expression of the P5K combination in NPCs increases menin transcription by 6-fold (FIG. 12). Pontine injections of P5K cells transduced with shRNA against menin resulted in significantly reduced tumor formation in mice (FIG. 4I). Menin, a protein encoded by the MEN1 gene plays a tumor suppressor role in endocrine cancers (27) but is highly oncogenic in MLL-associated leukemias (28). It interacts with a wide range of proteins, including EZH2, the methyltransferase catalytic subunit in the PRC2 complex, however the role of menin in DIPG tumors has not been reported or explored previously. These data suggest that menin is a therapeutic target for pediatric gliomas harboring the K27M mutation.

The impact of systemic treatment with MI-2 on tumor growth in vivo was tested. To this end, P5K cells transduced with a Luciferase vector were injected in the brainstem of a large group of mice (n=26), monitored for tumor development via bioluminescence imaging (BLI), then started treatment with intraperitoneal injections of MI-2. Control mice received tumor cell injections in the brain but were treated with DMSO intraperitoneally. After four weeks of drug treatment, the MI-2 group demonstrated significantly smaller tumors by BLI (p=0.026, FIG. 19F and FIG. 26B) in comparison to the DMSO group. The P5K cells from mouse tumors were live sorted and their response to MI-2 was tested. The cells exhibited a decrease in cell survival and proliferation and increased apoptosis, similar to P5K cells that were never injected in mice (FIG. 27). P5K cells live sorted from mouse tumors also exhibited a decrease in cell survival upon silencing of LIN28B or PLAGL1 (FIG. 27H). Finally, MI-2 was tested on cell cultures derived from a patient sample. Cells from a human DIPG positive for the H3.3K27M mutation showed a robust anti-proliferative response, (FIG. 8G and FIG. 28). Menin plays a tumor suppressor role in endocrine cancers but is highly oncogenic in MLL-associated leukemias (27). It is a member of the trithorax family histone methyltransferase complex, but also interacts with a wide range of proteins and is thought to be involved in transcriptional regulation. The data suggest that it may be a potential therapeutic target for pediatric gliomas harboring the H3.3K27M mutation.

In summary, the data shown here demonstrate that a driver role of the H3.3 K27M mutation in the appropriate cell context and developmental window; the model also showed that the altered chromatin landscape induced by H3K27M facilitates the re-acquisition of an earlier developmental program with subsequent activation of factors crucial to reprogramming and oncogenesis, such as the micro-RNA binding protein LIN28B (30). A chemical screen identified the menin pathway as a contributor to tumor maintenance, thus providing a potential opportunity for therapeutic intervention. The cells are then poised to achieve oncogenic transformation upon the gain of additional events such as loss of p53 and activation of aberrant receptor tyrosine kinase pathways. None of these events seem sufficient on their own to efficiently induce neoplastic transformation in a normal cell. It was also demonstrated that the human embryonic stem cell platform is a useful approach for modeling cancer as it provides access to distinct and early developmental stages for modeling the tumor in a genetically defined and appropriate cell of origin. hES cells are useful in high throughput screens (31) to uncover novel potential therapeutic targets.

Example 5

Efficacy of MI-2-2 Against Gliomas and Glioblastoma In Vitro and In Vivo

It has been demonstrated that MI-2-2 depletes patient-derived DIPG cells in vitro. Sensitivity to MI-2-2 was assessed by a 12 point dose response curve calculated after seven days of drug exposure and alamarBlue cell viability assay. Multiple patient tumor-derived DIPG (DIPGIV, DIPGVI, MSK-1, Peds8) and Glioblastoma (070909, 030613, 050715, 042315, 040811, 040114) were tested, with fibroblasts (MRCS), hES derived NPCs and astrocytes serving as controls (see FIGS. 29-33). Dose-response curves for the treatment of NPC, DIPGIV, and DIPGVI cell lines with MI-2-2, Panobinostat, and EPZ6438 are shown in FIG. 29. FIGS. 30A-30B show that MI-2-2 treatment decreases DIPG proliferation and increases apoptosis in vitro.

Cell proliferation and apoptosis were assessed by immunofluorescence for Ki67 and TUNEL assays. After staining, Ki67 and TUNEL positive cells were manually counted to calculate a percentage of positive nuclei (see, e.g., FIG. 33). The pharmacokinetic profile of MI-2-2 was assessed by treating animals with 30 mg/kg and 60 mg/kg IP MI-2-2. Tail vein blood sampling and extraction of the pons was performed in animals at multiple time points and samples analyzed by LC-MS to generate a curve.

Menin is expressed in patient-derived glioblastoma cell lines (see FIGS. 31A-31B). It has been demonstrated that glioblastoma cell lines demonstrate sensitivity to MI-2-2 in vitro. Dose-response curves for the treatment of several glioblastoma cell lines with MI-2-2 and temozolomide are shown in FIGS. 32A-32C. FIGS. 33A-33B show MI-2-2 decreases proliferation in glioblastoma lines; a proliferation assay for glioblastoma cell line 030613 is shown in FIG. 33A. It has also been demonstrated that shRNA-driven MEN1 knockdown recapitulates MI-2-2 effects on cell viability (see FIGS. 34A-34F).

Treatment of cancer with compounds described herein may be performed in combination with radiotherapy. FIG. 35 shows normalized response of glioblastoma cell lines to MI-2-2 and radiation combination therapy.

DIPG and glioblastoma cell lines were used to generate xenografts in NSG immunocompromised mice for in vivo testing. All lines used for xenografting were transfected lentiviral vectors encoding firefly luciferase to enable bioluminescence imaging (BLI). For DIPG xenografts, 100,000 DIGIV or DIPGVI cells were stereotactically injected into the pons of cold anesthetized P6 pups by transcutaneous injection. For GBM xenografts, 500,000 cells (030613 and 040114) were injected stereotactically into the striatum of 6 week old mice anesthetized with ketamine/xylazine cocktail.

Animals were monitored every four weeks with BLI until >90% of animals demonstrated BLI signal, at which time they were randomized based on BLI signal and treated with daily 60 mg/kg intraperitoneal (IP) MI-2-2 for 4 weeks in DIPGVI xenografts, 40 mg/kg BID in GBM xenografts. BLI was performed every week during treatment.

BLI was performed using the IVIS Lumina II system. D-Luciferin (10 uL of 15 mg/mL solution was instilled by retro-orbital injection in mice under isopropanol anesthesia and 5 minute exposures were collected. Fold change over baseline pre-randomization imaging was calculated.

DIPG and Glioblastoma cell lines demonstrated a sensitivity in many lines (see Table 1). Astrocytes, NPCs and fibroblasts were not depleted at sub-micromolar doses. Ki67 staining demonstrated a significant reduction in proliferation in multiple lines.

TABLE 1

| Cell Line | IC50 (nM) | Ki67 % (pre- and post-treatment) | TUNEL % (pre- and post-treatment) |
|---|---|---|---|
| SU-DIPGIV | 93.44 | 34.9, 16.0* | 7.6, 21.4 |
| SU-DIPGVI | 121.4 | 26.5, 14.4* | 14.3, 17.9 |
| MSK-1 | N/A | | |
| Peds8 | N/A | | |
| 030613 | 9.51 | 30.4, 16.2* | |
| 070909 | 13.46 | 18.2, 10.8* | |
| 040114 | 36.44 | 56.0, 36.1* | |
| 050715 | 83.38 | 11.9, 7.8 | |
| 040811 | 112.8 | 28.4, 22.5 | |
| 042314 | 26.06 | | |
| NPC | N/A | 10.6, 12.1 | 3.8, 4.0 |
| Astrocytes | N/A | 2.4, 4.3 | |
| Fibroblasts | N/A | 29.6, 27.5 | 0.4, 0.0 |

*$p < 0.05$

In vivo blood-brain barrier (BBB) penetration was demonstrated with 30 mg/kg systemic MI-2-2 and maintenance of therapeutic levels for >6 hours. Initial testing of 60 mg/kg MI-2-2 in DIPGVI xenografts showed no significant difference in BLI signal at 4 weeks. DIPIV xenografts were generated and are monitored monthly for BLI signal prior to randomization into treatment groups. Upon treatment with 40 mg/kg BID MI-2-2 in 040114 xenografts, there was a significant reduction in signal fold change after three weeks.

MI-2-2 shows efficacy in cancer cell lines and xenograft models. FIGS. 36A-36C and 37 show treatment of DIPGVI xenografts with MI-2-2. MI-2-2 testing in vivo on gliblastoma xenografts is shown in FIGS. 39 and 40A-40B.

Materials and Methods
Cell Culture hESCs (WA-09; passages 35-45) were maintained at undifferentiated state on irradiated mouse embryonic fibroblasts (MEFs, Globalstem Inc.) in medium consisting of DMEM/F12 (Invitrogen) supplemented with 20% Knockout Serum Replacement (KSR, Invitrogen), 10 ng/ml basic fibroblast growth factor (bFGF, R&D Systems), 1 mM L-glutamine (Invitrogen), 100 µM non-essential amino acids and 0.1 mM β-mercaptoethanol (Sigma-Aldrich). The cells were fed daily and passaged weekly using 6 U/ml dispase. Human primary astrocytes (Sciencell) were maintained in Astrocyte Medium (Sciencell). MRC-5 lung fibroblasts (ATCC, CCL-171) were maintained in DMEM medium supplemented with 10% fetal bovine serum (FBS). Human patient-derived DIPG cells (DIPG-VI, kindly provided by Michelle Monje, Stanford University) were maintained in Neurobasal media (Invitrogen) supplemented with B27 without Vitamin A (Invitrogen), EGF (20 ng/ml), bFGF (20 ng/ml, R&D Systems), PDGF-AA and -BB (20 ng/ml, Peprotech) and heparin (10 ng/ml). The line was obtained in accordance with institutional guidelines for human subject research at Stanford University. Human ES cell work also follows institutional ESCRO (Embryonic Stem Cell Research Oversight) guidelines.

Neural Induction and Neural Subtype Specification

For neural induction, a modified version of the dual-SMAD inhibition was used (9). Undifferentiated hES-cells were disaggregated using Accutase (Innovative Cell Technology) and plated on Matrigel (BD)-coated dishes at a density of 40,000 cells/cm2 in MEF-conditioned ESC medium supplemented with 10 ng/ml of bFGF and ROCK inhibitor (Y-27632). When the cells reached the confluent state (2-3 days after plating), they were exposed for 9 days to LDN193189 (200 nM, Stemgent) and SB431542 (10 mM, Tocris) in KSR medium containing DMEM, 15% knockout serum replacement, 2 mM L-glutamine and 10 µM β-mercaptoethanol. KSR medium was gradually replaced with N2 medium (25%, 50%, 75%) starting on day 4 of differentiation as described previously. On day 12, cells were dissociated using Accutase and replated in high density conditions (300,000 cells per cm2) on dishes pre-coated with polyornithine (PO; 15 µg/ml), laminin (Lam; 1 µg/ml) and fibronectin (FN; 2 µg/ml) in N2 medium supplemented with BDNF (brain-derived neurotrophic factor, 20 ng/ml, R&D), ascorbic acid (0.2 mM, Sigma), Purmorphamine (1 mM, Stemgent) and FGF8 (100 mg/ml, R&D). They were patterned at P1 stage for two weeks and thereafter passaged by mechanical picking of the CNS clusters and re-plated on PO/Lam/FN coated dishes. Neural precursor cells (NPCs) were maintained in N2 medium supplemented with EGF (20 ng/ml), bFGF (20 ng/ml, R&D Systems) and B-27 supplement without vitamin A (1:50, Invitrogen). Medium was changed every 2 days while the cultures were passaged every two weeks. For the differentiation to astrocytes, NPCs (day 65-135) were exposed to N2 medium containing 5% FBS for an additional 14 days. For the differentiation to neurons, NPCs were cultured in N2 medium supplemented with BDNF (20 ng/ml) and ascorbic acid (AA, 0.2 mM) for 14 days. For the differentiation to oligodendrocytes, NPCs were cultured in N2 media supplemented with cAMP, triiodothyronine (T3), BDNF (20 ng/ml) and ascorbic acid (AA, 0.2 mM) for 21 days.

Immunostaining

Cells were fixed by incubation in 4% paraformaldehyde for 15 minutes and incubated in blocking buffer (10% fetal bovine serum or goat serum; 0.1% BSA; 0.3% Triton-X100 in PBS) for 1 hour. Cells were stained with primary (or conjugated) antibodies in blocking buffer at 4° C. overnight, washed and stained with secondary antibodies in PBS supplemented with 0.1% BSA for 30 minutes at room temperature, in the dark. Nestin (MAB5326; 1:400), SOX2 (AB5603; 1:200), TRA-1-81 (MAB4381; 1:100), Olig2 (AB9610; 1:100), O4 (MAB345; 1:50) and MBP (MAB386; 1:1000) antibodies were obtained from Milliopore, H3K27me3 (clone C36B11; 1:1500) and phospho-Histone H2A.X (Ser139; clone 20E3; 1:400) from Cell Signaling, Tuj 1 (PRB-435P; 1:500) from Covance, GFAP (1:5000) and Ki67 (clone MIB-1; 1:200) from Dako, Nanog (H-155; 1:200) from Santa Cruz. Nuclei were stained by DAPI (Invitrogen). Mice were perfused with 4% paraformaldehyde solution. The brains were extracted and fixed by incubation in 4% paraformaldehyde at 4° C. overnight. Following cryopreservation by incubation in 15% and 30% sucrose solutions, brains were frozen into OCT compound and cut by cryostat into 10 mm sections. For immunohistochemistry, sections were air-dried, washed by PBS and incubated in blocking buffer (10% fetal bovine serum or goat serum, 0.1% BSA and 0.3% Triton-X100 in PBS) for 1 hour. Cells were stained with primary antibodies in blocking buffer at 4° C. overnight, washed and stained with secondary antibodies in PBS supplemented with 0.1% BSA for 30 minutes at room temperature, in the dark, followed by nuclear staining by DAPI. Human specific GFAP antibody (STEM123; 1:1000) was obtained from StemCells Inc, HA-tag (clone 3F10; 1:200) from Roche, Ki67 (ab15580; 1:200) from Abcam, and human nuclear antigen (MAB1281; 1:200) from Millipore. Whole brain images are composed by stitching ~20 scan images. Hematoxylin and Eosin (H&E) staining was performed according to standard procedures.

Gamma-Radiation of Cells

Cells were plated onto 48-well plates and irradiated at the dose of 5 Gy (3.45 Gy/minute) using X-RAD 225C Biological X-ray irradiator (Precision X-ray, Inc). Following incubation for the indicated time period, cells were fixed and immunostained for Ki67 and g-H2A.X (phosphorylated at Ser139). The number of Ki67-positive cells and g-H2A.X foci per cell was counted manually or using ImageJ software.

Sub-G1 Assay

Cells were trypsinized, collected in PBS and fixed in cold 70% ethanol. Followed by RNase A (Ambion) treatment, cells were stained with propidium iodide (50 µg/ml, Invitrogen) in PBS and subjected to FACS analysis according to standard procedures.

Migration and Invasion Assay

Cell migration was assessed by the Boyden chamber assay. Briefly, the bottom chamber was coated with Lam/FN at 37° C. overnight and air-dried. 3,000 cells were plated on the top chamber and allowed to migrate for 4 hours. Following PBS wash, cells that migrated to the bottom chamber were fixed, stained with DAPI and counted by fluorescence microscopy. For invasion assay, spheres of RFP-labeled transduced NPCs (~1.5 mm in diameter) were embedded in Matrigel (BD). Following 12 days of incubation, invasion of cells into Matrigel was analyzed by measuring the distance travelled from the sphere edge. P-values were calculated by Chi-square test.

Low Density Culture 3,000 cells were evenly plated onto 24 well plates pre-coated with PO/Lam/FN and cultured in N2 medium supplemented with EGF (20 ng/ml), bFGF (20 ng/ml, R&D Systems) and B-27 supplement without vitamin A (1:50, Invitrogen) for 4 weeks. Medium was changed every 2-3 days. Crystal violet staining was performed according to standard procedures.

In Vitro Limiting Dilution Assay

Sphere-forming capacity was assessed by limiting dilution assay. 10-100 cells were plated into 96-well low-attachment plates. Following 12 days of incubation, spheres with more than 5 cells were counted. P-values were calculated using Extreme Limiting Dilution Analysis (ELDA) software (32).

Animal Surgery and Transplantation

All animal experiments were done in accordance with protocols approved by the Memorial Sloan Kettering Institutional Animal Care and Use Committee (IACUC, protocol no. 30-12-019) and following NIH guidelines for animal welfare. In vitro systems cannot substitute for the complexity for the in vivo environment, using current technology. This is particularly the case in this study, since the experiments test the ability of a drug to cross the blood-brain barrier and impact tumor growth. In vitro systems cannot substitute for animals for this purpose. Animals were monitored by a team including an experienced technician, as well as veterinary staff at the animal facility (RARC). Veterinary staff will assist with animal care, including analgesia, health and welfare monitoring and will respond to any emergency. Nude mice and all xenografted animals were housed separately in units that require gowning, mask and gloving prior to entry. The rate of opportunistic infections in this location has been very low and comparable to the general population. Procedures are designed to ensure that discomfort, distress, pain, and injury were limited. Animals were anesthetized for all procedures using Ketamine 100 mg/kg/Xylazine 10 mg/kg for the radiation and inhalational anesthesia for the grafting. Both anesthetic regimens have been tested and found to be successful in providing adequate periods of deep anesthesia. Animals received appropriate post-operative care and analgesics as needed (usually a single dose of buprenorphine 0.5 mg/kg subcutaneously). Animals were euthanized exclusively by subcutaneous injection of a barbiturate overdose, which results in instant deep coma and complete insensitivity to pain and distress.

Animals were used as hosts for tumor xenografts in some experiments. In others, 100,000 cells were injected intracranially into NOD-SCID mice (6-day-old pups, 3 mm posterior to lambda-suture and 3 mm deep). Hypothermia was used for anesthesia. Animals were monitored for 3-6 months with neurological assessments and MRI imaging. For evaluating in vivo growth of menin-knockdown cells, Luciferase-labeled P5K cells were transduced with control or sh-MEN1-expressing lentivirus. Following 6 days of incubation, cells were dissociated by Accutase and intracranially injected into immunocompromised mice as described above. The animals were monitored by bioluminescence imaging.

In Vivo Drug Treatment

MI-2 was purchased from Cayman Chemical and solubilized in DMSO. NOD SCID mice received intracranial P5K injections as described above. They were monitored for tumor growth using monthly in vivo bioluminescence imaging. Drug treatment started only after the animals showed evidence of tumor growth, usually at ~5 weeks following the intracranial injections (as described in the main text and in fig S14). MI-2 was administered intraperitoneally (IP) every other day at 20 mg/kg. The animals were sacrificed a month later.

In Vivo Imaging

Animals were anesthetized with isoflurane gas and injected with D-luciferin (Invitrogen; Pierce), followed by bioluminescent imaging by the IVIS imaging system (PerkinElmer) with a 5-minute exposure time (described in detail in (33). For MRI imaging, the mice were anesthetized using 1.5-2% isoflurane in a 70% N2O+30% O2 mixture. Imaging was performed on a Bruker Biospec 4.7-Tesla (200 MHz) 40 cm horizontal bore magnet. The system is equipped with a 300 mT/m gradient system. Examinations were conducted using a 32-mm quadrature birdcage resonator for excitation and detection.

Drug Screening

A chemical screen was performed using a limited small molecule library of compounds that target epigenetic regulators (80 compounds; Cayman Chemicals, Ann Arbor, Mich.; cat. No. 11076) along with DNA damage reagents (Camptothecin and Doxorubicin, Santa Cruz) and RTK inhibitors (Sunitinib and Imatinib, Selleck, Selleckchem.com) as controls. GFP-labeled normal NPCs and RFP-labeled P5K cells were mixed and seeded onto 96-well plates pre-coated with PO/Lam/FN. 24 hours after plating, cells were then treated with each compound at 8 different concentrations (2-fold serial dilution, typically from 10 mM to 78.125 nM) in duplicate wells for 6 days. Following PBS wash, GFP and RFP fluorescence was quantified by a multi-wavelength automated plate reader (Tecan Infinite M1000 Pro). For calculating $IC_{50}$ values, data were normalized by the values of vehicle-treated cells and fitted to Hill equation using the least squares method. The complete list of compounds in the library and their $IC_{50}$ values is provided in FIG. 17.

Microarray Analysis

Total RNA was extracted with Trizol reagent (Invitrogen). The RNA was then processed by the MSKCC Genomic core facility and hybridized with Affymetrix U133 Plus2.0 arrays. Gene expression analysis was carried out within the Gene-Pattern website (www.broadinstitute.org/cancer/software/genepattern). Briefly, background correction and quantile normalization was done with the Robust Multi-array Average (RMA) algorithm (34). Probes that passed the variation filter were subjected to PCA and hierarchical clustering with average linkage and Pearson correlation distance. For identifying differentially expressed genes between conditions, probes were ranked by signal-to-noise ratio and statistical significance was determined by permutation test (FIGS. 13 and 14). Microarray data of DIPG patients' samples was obtained from GSE34824/GSE36245 and early-stage NPCs was from GSE9921. Microarray data generated in this manuscript was deposited in GEO (GSE55541).

ChIP-Seq

Native ChIP was performed as previously described (36). Briefly, 10 million cells were washed, resuspended in digestion buffer (50 mM Tris-HCl, pH 7.6; 1 mM $CaCl2$; 0.2% Triton-X100) and treated with micrococcal nuclease from *Staphylococcus aureus* (MNase) for 5 min at 37° C. Nuclei were lysed by brief sonication and dialyzed into RIPA buffer (10 mM Tris-HCl, pH 7.6; 1 mM EDTA; 0.1% SDS; 0.1% Na-Deoxycholate; 1% Triton X-100) for 2 hours at 4° C. Soluble material was recovered and subjected to immunoprecipitation using antibody against H3K4me3 (Active Motif) or H3K27me3 (Millipore; Cell Signaling), and Dynabeads Protein A (Invitrogen). Following the final wash, chromatin was eluted with elution buffer (50 mM Tris-HCl, pH 8.0; 10 mM EDTA; 1% SDS) and digested by proteinase K (Roche). ChIP DNA and ChIP input DNA were then isolated using QIAGEN Qiaquick PCR purification kit. ChIPseq libraries were prepared according to the Illumina protocol and sequenced with either the Genome analyzer II or HiSeq 2000.

Data Analysis

Analysis of ChIP-seq data was carried out within the Galaxy website (http://galaxyproject.org/). Briefly, reads that passed the quality filter were mapped to the human genome (hg19) using Bowtie algorithm (36) with default setting. Peak calling was done by Model-based Analysis of ChIP-Seq (MACS) algorithm (37) with 500-bp window size. For comparing the level of histone modifications in different groups of promoters, the total number of reads in individual promoters (between +1 kb and −500 bp from transcription start site) was computed and normalized by total read counts. The level at gene-body regions was further normalized by the length of individual transcripts.

Western Blot

Cells were lysed in RIPA Buffer (50 mM Tris-HCl, pH 8.0; 120 mM NaCl; 5 mM EDTA; 0.5% NP-40). Following 30-minute centrifuge at 14000 rpm, supernatant was collected and protein concentration was measured by the Bradford Assay (Bio-Rad). Lysates were boiled for 5 minutes in Laemmli sample buffer and separated by electrophoresis on 4-12% Bis-Tris gel in SDS running buffer for 1.5-2 hours. Protein was transferred to nitrocellulose membrane using the iBlot gel transfer device (Invitrogen). Non-specific protein binding was prevented by blocking the membrane with 4% blocking reagent (Amersham) in TBST (0.1% Tween-20 in TBS buffer). Membrane was incubated at 4° C. overnight in the blocking buffer with primary antibodies: PDGFRA (1:1000; Cell Signaling), Trimethylated-H3K27 (1:1000; Cell Signaling), b-tubulin (clone DM1A; 1:1000; SantaCruz), GAPDH (1:1000; Cell Signaling), HA-tag (clone 3F10; 1:1000; Roche), H3 (clone 96C10; 1:1000; Cell Signaling), Menin (1:1000; Bethyl Laboratories). After four washes with TBS-T, the blot was incubated with respective secondary antibodies for mouse (1:5000) or rabbit (1:5000) at room temperature for 30 minutes. ECL prime Western Blotting Detection Kit was used for detection according to manufacturer's instruction (Amersham).

Quantitative Real-Time PCR

Total RNA was extracted using TRIzol (Invitrogen). For each sample, 1 mg of total RNA was reverse transcribed using the SuperScriptIII (Invitrogen). Amplified material was detected using Quantitect SYBR green probes and PCR kit (Qiagen) on a Mastercycler RealPlex2 (Eppendorf). All results were normalized to an Actin control. Sequences of primers are shown in FIG. 18.

Vectors and Mutagenesis

Human PDGFRA (Addgene #23892) (38) was cloned into pLenti PGK Neo DEST vector (Addgene #19067) (40). Mutagenesis was performed following the manufacturer's protocol (Promega). Cloning and mutagenesis of H3.3 transgenes were described previously (11). Luciferase-expressing vector (pLenti PGK Blast V5-LUC) was obtained from Addgene (#19166)(39), MEN1-expressing vector from Open Biosystems. For the construction of shRNA-expressing vectors, annealed oligos were cloned into H1 vector or pENTR-H1 vector. The shRNA expressing cassette in pENTR-H1 vector was transferred to lentiviral vectors by LR recombination according to manufacturer's instruction (Invitrogen). Target sequences of each shRNA are shown in FIG. 18.

Lentivirus Production

Lentiviruses were produced in 293T packaging cells, by a slightly modified version of a method described previously (40). Lentiviral vectors were transfected in 293T cells with packaging vectors (pCMV-dR8.2 and pCMV-VSV-G), in the presence of Polyethylenimine (Polysciences). Viral supernatants were collected 72 h after transfection and viral particles were concentrated by ultracentrifugation at 49,000 g for 1.5 h at 4° C.

Assessment of Senescence

Senescence-associated b-galactosidase activity was assessed using the staining kit from Invitrogen according to the manufacturer's instructions.

Statistical Analysis

Student's t-test and ANOVA were performed for statistical analysis, unless indicated otherwise.

REFERENCES

1. J. Schwartzentruber et al., Driver mutations in histone H3.3 and chromatin remodelling genes in paediatric glioblastoma, *Nature* 482, 226-31 (2012).
2. G. Wu et al., Somatic histone H3 alterations in pediatric diffuse intrinsic pontine gliomas and nonbrainstem glioblastomas, *Nat. Genet.* 44, 251-3 (2012).

3. J. Zhang et al., Whole-genome sequencing identifies genetic alterations in pediatric low-grade gliomas, *Nat. Genet.* 45, 602-12 (2013).
4. D. Sturm et al., Hotspot Mutations in H3F3A and IDH1 Define Distinct Epigenetic and Biological Subgroups of Glioblastoma *Cancer Cell* 22, 425-437 (2012).
5. D.-A. Khuong-Quang et al., K27M mutation in histone H3.3 defines clinically and biologically distinct subgroups of pediatric diffuse intrinsic pontine gliomas, *Acta Neuropathol.* 124, 439-47 (2012).
6. S. C. Zhang, M. Wernig, I. D. Duncan, O. Brüstle, J. A. Thomson, In vitro differentiation of transplantable neural precursors from human embryonic stem cells, *Nat. Biotechnol.* 19, 1129-33 (2001).
7. M. A. Cohen, P. Itsykson, B. E. Reubinoff, Neural differentiation of human ES cells, *Curr. Protoc. Cell Biol.* Chapter 23, Unit 23.7 (2007).
8. V. Tabar, L. Studer, Pluripotent stem cells in regenerative medicine: challenges and recent progress, *Nat. Rev. Genet.* 15, 82-92 (2014).
9. S. M. Chambers et al., Highly efficient neural conversion of human ES and iPS cells by dual inhibition of SMAD signaling, *Nat. Biotechnol.* 27, 275-80 (2009).
10. B. S. Paugh et al., Novel oncogenic PDGFRA mutations in pediatric high-grade gliomas, *Cancer Res.* 73, 6219-29 (2013).
11. P. W. Lewis et al., Inhibition of PRC2 activity by a gain-of-function H3 mutation found in pediatric glioblastoma, *Science* 340, 857-61 (2013).
12. K.-M. Chan et al., The histone H3.3K27M mutation in pediatric glioma reprograms H3K27 methylation and gene expression, *Genes Dev.* 27, 985-90 (2013).
13. S. Bender et al., Reduced H3K27me3 and DNA Hypomethylation Are Major Drivers of Gene Expression in K27M Mutant Pediatric High-Grade Gliomas, *Cancer Cell,* 660-672 (2013).
14. T. D. Halazonetis, V. G. Gorgoulis, J. Bartek, An oncogene-induced DNA damage model forcancer development, *Science* 319, 1352-5 (2008).
15. A. Chassot et al., Radiotherapy with concurrent and adjuvant temozolomide in children with newly diagnosed diffuse intrinsic pontine glioma, J. Neurooncol. 106, 399-407 (2012).
16. D. Hanahan, R. A. Weinberg, The Hallmarks of Cancer, Cell 100, 57-70 (2000).
17. S. M. Chambers, Y. Mica, L. Studer, M. J. Tomishima, Converting human pluripotent stem cells to neural tissue and neurons to model neurodegeneration, Methods Mol. Biol. 793, 87-97 (2011).
18. T. Major et al., D. L. Silver, Ed. Transgene Excision Has No Impact on In Vivo Integration of Human iPS Derived Neural Precursors, PLoS One 6, e24687 (2011).
19. R. Sethi et al., Prospective neuraxis MRI surveillance reveals a high risk of leptomeningeal dissemination in diffuse intrinsic pontine glioma, J. Neurooncol. 102, 121-7 (2011).
20. Y. Elkabetz et al., Human ES cell-derived neural rosettes reveal a functionally distinct early neural stem cell stage, Genes Dev. 22, 152-65 (2008).
21. T. M. Jessell, Neuronal specification in the spinal cord: inductive signals and transcriptional codes, Nat. Rev. Genet. 1, 20-9 (2000).
22. L. Conti, E. Cattaneo, Neural stem cell systems: physiological players or in vitro entities?, Nat. Rev. Neurosci. 11, 176-87 (2010).
23. P. W. Lewis, C. D. Allis, Poisoning the "histone code" in pediatric gliomagenesis, Cell Cycle 12, 3241-2 (2013).
24. I. Ben-Porath et al., An embryonic stem cell-like gene expression signature in poorly differentiated aggressive human tumors, Nat. Genet. 40, 499-507 (2008).
25. A. Shi et al., Structural insights into inhibition of the bivalent menin-MLL interaction by small molecules in leukemia. Blood (2012), doi:10.1182/blood-2012-05-429274.
26. J. Grembecka et al., Menin-MLL inhibitors reverse oncogenic activity of MLL fusion proteins in leukemia, Nat. Chem. Biol. 8, 277-84 (2012).
27. S. Matkar, A. Thiel, X. Hua, Menin: A scaffold protein that controls gene expression and cell signaling Trends Biochem. Sci. 38, 394-402 (2013).
28. A. Yokoyama et al., The menin tumor suppressor protein is an essential oncogenic cofactor for MLL-associated leukemogenesis, Cell 123, 207-18 (2005).
29. M. L. Suvà, N. Riggi, B. E. Bernstein, Epigenetic reprogramming in cancer, Science 339, 1567-70 (2013).
30. S. R. Viswanathan, G. Q. Daley, Lin28: A microRNA regulator with a macro role, Cell 140, 445-9 (2010).
31. G. Lee, E. Papapetrou, H. Kim, S. Chambers, M J, Modelling pathogenesis and treatment of familial dysautonomia using patient-specific iPSCs, Nature (2009), September 17; 461(7262):402-6.
32. Y. Hu, G. K. Smyth, ELDA: Extreme limiting dilution analysis for comparing depleted and enriched populations in stem cell and other assays, *J. Immunol. Methods* 347, 70-78 (2009).
33. M. S. Bradbury et al., Optical bioluminescence imaging of human ES cell progeny in the rodent CNSJ. *Neurochem.* 102, 2029-2039.
34. R. A. Irizarry et al., Exploration, normalization, and summaries of high density oligonucleotide array probe level data, *Biostatistics* 4, 249-264 (2003).
35. A. D. Goldberg et al., Distinct factors control histone variant H3.3 localization at specific genomic regions, *Cell* 140, 678-691 (2010).
36. B. Langmead, C. Trapnell, M. Pop, S. L. Salzberg, Ultrafast and memory-efficient alignment of short DNA sequences to the human genome, *Genome Biol* 10, R25 (2009).
37. Y. Zhang et al., Model-based analysis of ChIP-Seq (MACS), *Genome Biol.* 9, R137 (2008).
38. C. M. Johannessen et al., COT drives resistance to RAF inhibition through MAP kinase pathway reactivation, *Nature* 468, 968-72 (2010).
39. E. Campeau et al., A versatile viral system for expression and depletion of proteins in mammalian cells, *PLoS One* 4, e6529 (2009).
40. V. Tabar et al., Migration and differentiation of neural precursors derived from human embryonic stem cells in the rat brain, Nat. Biotechnol. 23, 601-606 (2005).
41. L. Li et al., Discovery of two aminoglycoside antibiotics as inhibitors targeting the menin-mixed lineage leukaemia interface, Bioorganic & Medicinal Chemistry Letters 24(9), 2090-2093 (2014).
42. C. L. Kulisa et al., Preparation of therapeutically active oxazoline derivatives, PCT Int. Appl. Publ. WO 2014053581 A1 (2014).
43. T. Cierpicki et al., Challenges and opportunities in targeting the menin-MLL interaction, Future Medicinal Chemistry 6(4), 447-462 (2014).
44. S. He et al., High-Affinity Small-Molecule Inhibitors of the Menin-Mixed Lineage Leukemia (MLL) Interaction Closely Mimic acNatural Protein—Protein Interaction, Journal of Medicinal Chemistry 57(4), 1543-1556 (2014).

45. Hans Robert Kalbitzer et al., Ras inhibitors screening and use as antitumor agents in Ras oncogenic mutation comprising tumors, Eur. Pat. Appl. Publ. EP 2671575 A1 (2013).
46. N. A. Kittan et al., Cytokine induced phenotypic and epigenetic signatures are key to establishing specific macrophage phenotypes, PLoS One 8(10), e78045 (2013).
47. A. T.; Thiel et al., The trithorax protein partner menin acts in tandem with EZH2 to suppress C/EBPa and differentiation in MLL-AF9 leukemia, Haematologica 98(6), 918-927 (2013).
48. R. V. Thakker, Multiple endocrine neoplasia type 1 (MEN1) and type 4 (MEN4), Molecular and Cellular Endocrinology 386(1-2), 2-15 (2014).
49. D. Charre et al., Preparation of dibenzodiazepines as inhibitors of cystathionine b-synthase to reduce the neurotoxic overproduction of endogenous hydrogen sulfide, PCT Int. Appl. Publ. WO 2013068592 A1 (2013).
50. A. Shi et al., Structural insights into inhibition of the bivalent menin-MLL interaction by small molecules in leukemia, Blood 120(23), 4461-4469 (2012).
51. N. McCarthy, Leukaemia: Targeting menin, Nature Reviews Cancer 12(3), 154-155 (2012).
52. J. Grembecka et al., Menin-MLL inhibitors reverse oncogenic activity of MLL fusion proteins in leukemia, Nature Chemical Biology 8(3), 277-284 (2012).
53. M. J. Murai et al., Crystal Structure of Menin Reveals Binding Site for Mixed Lineage Leukemia (MLL) Protein, Journal of Biological Chemistry 286(36), 31742-31748, S31742/1-S31742/2 (2011).
54. H. Zhang et al., Menin expression is regulated by transforming growth factor beta signaling in leukemia cells, Chinese Medical Journal (Beijing, China, English Edition) 124(10), 1556-1562 (2011).
55. J. Hess et al., Compositions and methods for treatment of leukemia, PCT Int. Appl. Publ. WO 2011029054 A1 (2011).
56. J. Grembecka et al., Molecular basis of the mixed lineage leukemia-menin interaction: implications for targeting mixed lineage leukemias, Journal of Biological Chemistry 285(52), 40690-40698 (2010).
57. X. Hua et al., Methods for inhibiting Menl gene encoded menin for prevention and treatment of type 1 and 2 diabetes mellitus, U.S. Pat. Appl. Publ. US 20090181917 A1 (2009).
58. M. J. Thirman, Therapeutic peptides to inhibit MLL-menin interaction for treating leukemia, PCT Int. Appl. Publ. WO 2008070303 A2 (2008).
59. [NO AUTHOR LISTED], Methods for inhibiting Menl gene encoded menin for prevention and treatment of type 1 and 2 diabetes mellitus, PCT Int. Appl. Publ. WO 2007139970 A2 (2007).
60. C. Caslini et al., Interaction of MLL Amino Terminal Sequences with Menin Is Required for Transformation, Cancer Research 67(15), 7275-7283 (2007).
61. A. Yokoyama et al., The menin tumor suppressor protein is an essential oncogenic cofactor for MLL-associated leukemogenesis, Cell (Cambridge, Mass., United States) 123(2), 207-218 (2005).
62. T. A. Milne, et al., Menin and MLL cooperatively regulate expression of cyclin-dependent kinase inhibitors, Proceedings of the National Academy of Sciences of the United States of America 102(3), 749-754 (2005).
63. T. Wu et al., Menin represses tumorigenesis via repressing cell proliferation, American journal of cancer research 1(6), 726-39 (2011).
64. M. J. Murai et al., Crystal structure of menin reveals binding site for mixed lineage leukemia (MLL) protein, The Journal of biological chemistry 286(36), 31742-8 (2011).

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating brain cancer in a subject in need thereof, the method comprising administering to the subject a therapeutically effective amount of a compound of Formula (I):

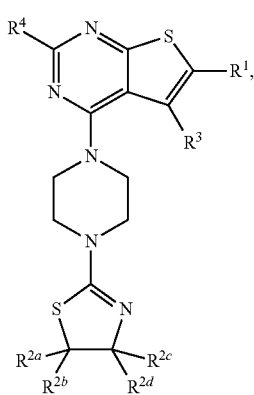

(I)

or a pharmaceutically acceptable salt thereof,
wherein:
  each of $R^1$, $R^3$, and $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, or —$N(R^B)_2$;
  or $R^1$ and $R^3$ taken together with the intervening atoms form optionally substituted heterocyclyl or optionally substituted carbocyclyl
  each of $R^{2a}$, $R^{2b}$, $R^{2c}$, and $R^{2d}$ is independently hydrogen, halogen, optionally substituted $C_{1-6}$ alkyl, optionally substituted alkenyl, optionally substituted alkynyl, optionally substituted carbocyclyl, optionally substituted aryl, optionally substituted heterocyclyl, optionally substituted heteroaryl, —$OR^A$, or —$N(R^B)_2$; and
  each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and
  each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
  wherein the brain cancer is meningioma, astrocytoma, medulloblastoma, or Diffuse Intrinsic Pontine Glioma (DIPGs).

2. The method of claim 1, wherein the compound is of Formula (I-c):

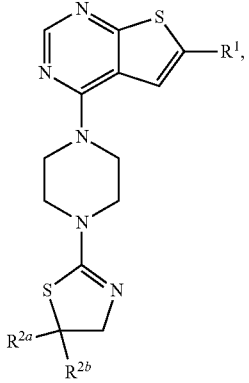

(I-c)

or a pharmaceutically acceptable salt thereof.

3. The method of claim 1, wherein $R^1$ is optionally substituted $C_{1-6}$ alkyl.

4. The method of claim 1, wherein $R^1$ is unsubstituted $C_{1-6}$ alkyl.

5. The method of claim 4, wherein $R^1$ is n-propyl.

6. The method of claim 1, wherein $R^1$ is substituted $C_{1-6}$ alkyl.

7. The method of claim 1, wherein $R^{2a}$ is optionally substituted $C_{1-6}$ alkyl.

8. The method of claim 7, wherein $R^{2a}$ is unsubstituted $C_{1-6}$ alkyl.

9. The method of claim 1, wherein $R^{2b}$ is optionally substituted $C_{1-6}$ alkyl.

10. The method of claim 9, wherein $R^{2b}$ is unsubstituted $C_{1-6}$ alkyl.

11. The method of claim 1, wherein $R^{2a}$ and $R^{2b}$ are each independently hydrogen or optionally substituted $C_{1-6}$ alkyl.

12. The method of claim 1, wherein the compound is of one of the following formulae:

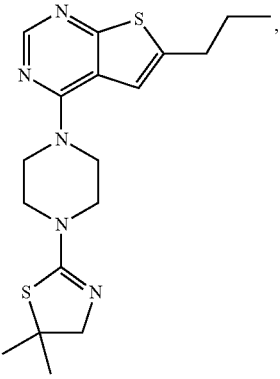

-continued
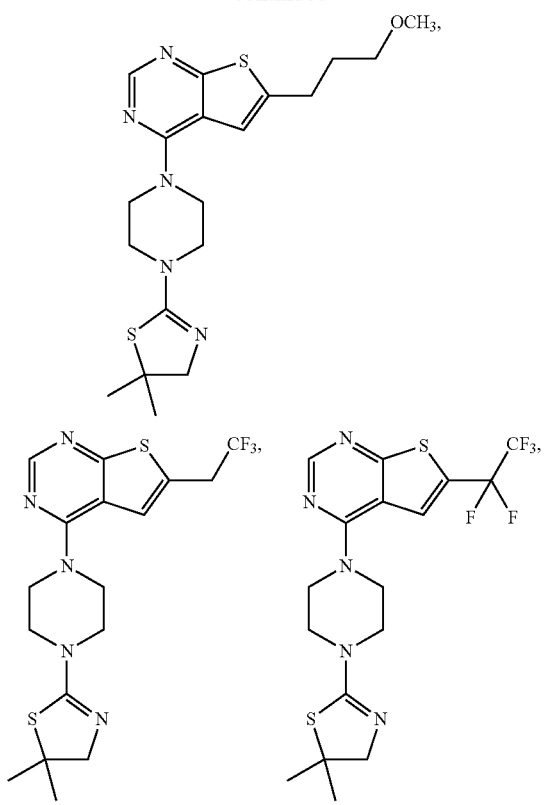
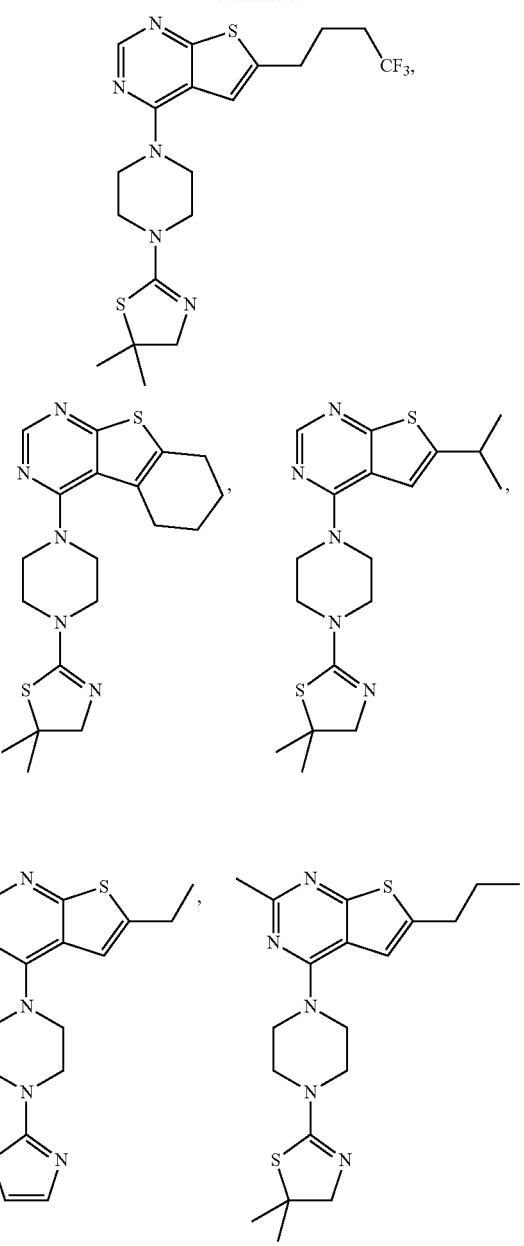
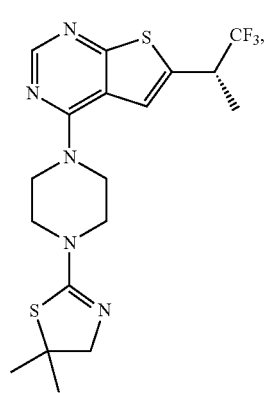
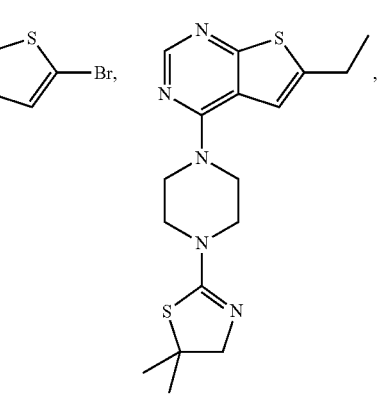

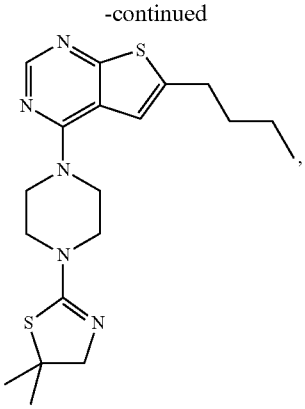
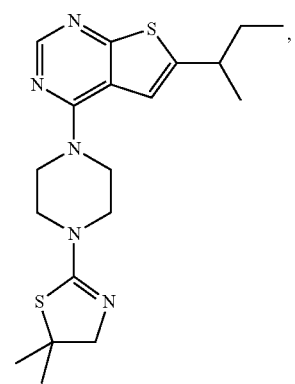
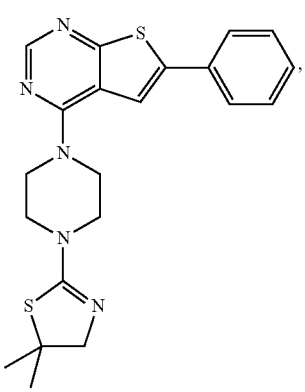
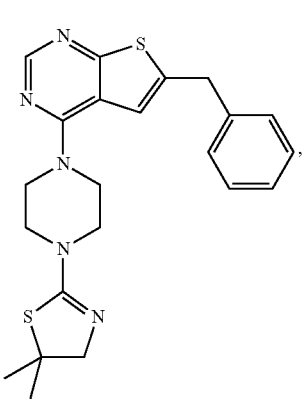
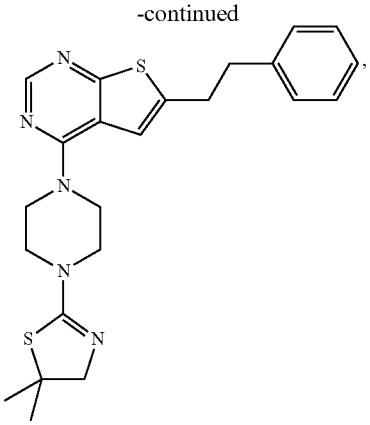
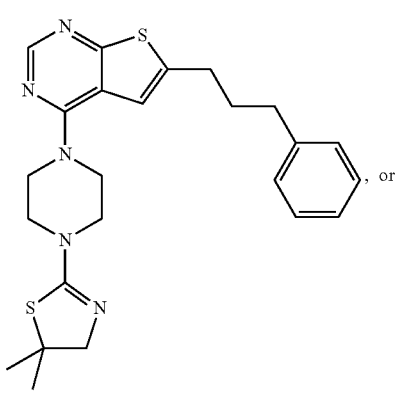
, or
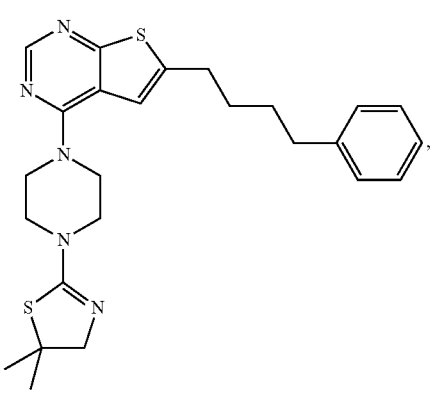
or a pharmaceutically acceptable salt thereof.
13. The method of claim 1, wherein the brain cancer is Diffuse Intrinsic Pontine Gliomas (DIPGs).
14. The method of claim 1, wherein the subject is a human child having Diffuse Intrinsic Pontine Glioma (DIPG).
15. The method of claim 1, wherein the subject has cancer cells carrying the K26M mutation in histone H3.

16. A compound selected from the group consisting of:
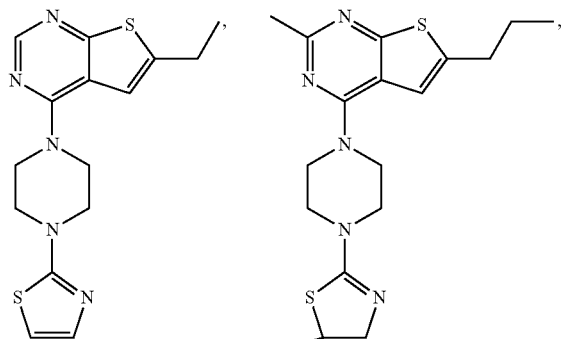
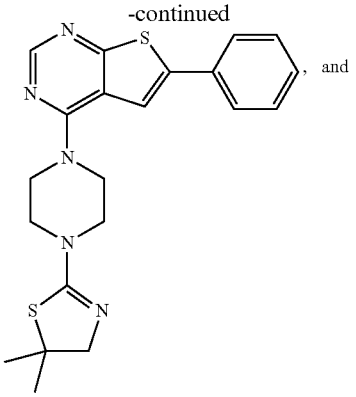
and pharmaceutically acceptable salts thereof.
17. A pharmaceutical composition comprising a compound of claim 16, or a pharmaceutically acceptable salt thereof, or a pharmaceutically acceptable excipient.
* * * * *